United States Patent
Pauls et al.

(10) Patent No.: US 12,114,693 B2
(45) Date of Patent: Oct. 15, 2024

(54) NON-ELECTRIC, NON-HEATED DEVICES FOR ORAL DELIVERY OF COMPOUNDS AND RELATED SYSTEMS AND METHODS

(71) Applicant: RDFN FUM Natural Products Ltd., Calgary (CA)

(72) Inventors: Braeden Pauls, Calgary (CA); Josiah Pauls, Herbert (CA); Chad Gothong, Calgary (CA); Joel Braun, Chestermere (CA); Hannah Loewen, Calgary (CA); Janai Whelan, Calgary (CA); Daniel Ogden, Chestermere (CA); Patrick Williams, Ontario (CA)

(73) Assignee: RDFN FUM Natural Products Ltd., Calgary (CA)

( * ) Notice: Subject to any disclaimer, the term of this patent is extended or adjusted under 35 U.S.C. 154(b) by 0 days.

(21) Appl. No.: 18/454,002

(22) Filed: Aug. 22, 2023

(65) Prior Publication Data
US 2024/0108060 A1      Apr. 4, 2024

Related U.S. Application Data

(60) Provisional application No. 63/407,701, filed on Sep. 18, 2022.

(51) Int. Cl.
*A61M 15/00*      (2006.01)
*A24D 3/17*       (2020.01)
(Continued)

(52) U.S. Cl.
CPC ............... *A24F 40/10* (2020.01); *A24D 3/17* (2020.01); *A24F 40/05* (2020.01); *A24F 40/40* (2020.01); *A24F 40/50* (2020.01); *A61M 15/003* (2014.02)

(58) Field of Classification Search
CPC ............... A61M 15/003; A61M 15/06; A61M 15/0021; A61M 11/04
See application file for complete search history.

(56) References Cited

U.S. PATENT DOCUMENTS

| 968,757 A | 8/1910 | Ferguson |
|---|---|---|
| 4,083,372 A | 4/1978 | Boden |

(Continued)

FOREIGN PATENT DOCUMENTS

| AT | 522111 B1 | 12/2020 |
|---|---|---|
| CN | 106858721 A | 6/2017 |

(Continued)

OTHER PUBLICATIONS

BreatheAura Etsy Canada website. Retrieved Sep. 18, 2023. https://www.etsy.com/ca/shop/BreatheAura?, Sep. 18, 2023, Breatheaura, Website.

(Continued)

*Primary Examiner* — Hae Moon Hyeon
(74) *Attorney, Agent, or Firm* — Len S. Smith; Denise M. Brown; Transformative Legal LLC

(57) ABSTRACT

The invention herein provides devices, e.g., non-electronic, non-heating, or both non-electronic and non-heating, devices for delivering volatile compound(s) to the mouth. In aspects devices comprise first and second components releasably held together by a selectively releasable attachment mechanism, such that the first and second components can be completely disengaged from one another. In aspects, devices further comprise an adjustable airflow control mechanism controlled by the rotation of the first and second components relative to one another. In aspects, rotation of the first and second components provides an audible, tactile, or audible and tactile indication of movement indicating a change in airflow control setting(s). Devices can further comprise one or more visual indicators indicating spatial (Continued)

Figure 1A:
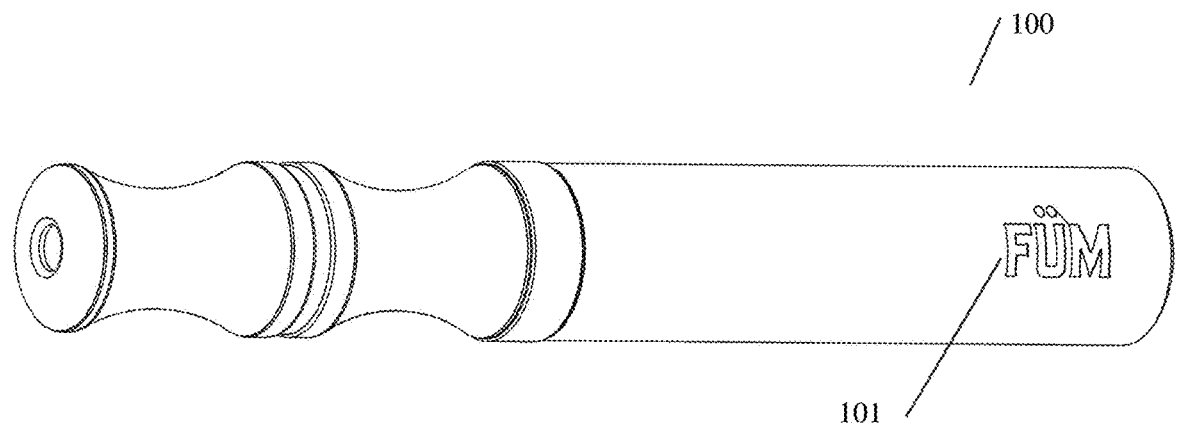

orientation of one or more device components, the status of the airflow control setting(s), or both. The invention further provides methods of using such devices in reducing one or more smoking habit-related cravings.

21 Claims, 32 Drawing Sheets

(51) Int. Cl.
*A24F 40/05* (2020.01)
*A24F 40/10* (2020.01)
*A24F 40/40* (2020.01)
*A24F 40/50* (2020.01)

(56) References Cited

U.S. PATENT DOCUMENTS

| | | | |
|---|---|---|---|
| 4,175,556 A | 12/1979 | Freezer | |
| 4,284,089 A | 8/1981 | Ray | |
| 4,429,703 A | 2/1984 | Haber | |
| 4,800,903 A | 1/1989 | Ray | |
| 9,700,691 B2 | 7/2017 | Watanabe | |
| 10,492,526 B2 | 12/2019 | Sampson | |
| 10,548,348 B2 | 2/2020 | Levilev | |
| 2006/0130857 A1 | 6/2006 | Roth | |
| 2008/0023003 A1* | 1/2008 | Rosenthal | A61M 15/06 |
| | | | 128/203.26 |
| 2011/0297166 A1 | 12/2011 | Takeuchi | |
| 2014/0238421 A1 | 8/2014 | Shapiro | |
| 2015/0122277 A1 | 5/2015 | Frobisher | |
| 2016/0279358 A1 | 9/2016 | Singer | |
| 2018/0207370 A1 | 7/2018 | Rowland | |
| 2020/0171266 A1* | 6/2020 | Trzecieski | A61M 11/041 |
| 2021/0052832 A1 | 2/2021 | Spadaro | |

FOREIGN PATENT DOCUMENTS

| | | |
|---|---|---|
| DE | 102018207543 | 11/2019 |
| EP | 2609822 B1 | 4/2018 |
| FR | 2654002 | 5/1991 |
| GB | 2412876 A | 10/2005 |
| KR | 649552 B1 | 11/2006 |
| KR | 20070020830 A | 2/2007 |
| KR | 20160066851 A | 6/2016 |
| RS | 20160590 A1 | 1/2018 |
| WO | WO2016026094 A1 | 2/2016 |
| WO | WO2020261540 A1 | 12/2020 |

OTHER PUBLICATIONS

Breth4life Etsy Canada website. Retrieved Sep. 18, 2023. https://www.etsy.com/ca/shop/breTH4life?ref=simple-shop-header-name&listing_id=1165024855, Sep. 18, 2023, Breth4life, Website.

Emitto Styx Facebook website. Retrieved Sep. 18, 2023. https://www.facebook.com/emittostyx/, Sep. 18, 2023, Emitto Styx, Website.

Grandview Research, "E-cigarette and Vape Market Size, Share & Trends Analysis Report by Product, by Distribution Channel, by Region, and Segment Forecasts, 2023-2030." Mar. 2022. https://www.grandviewresearch.com/industry-analysis/e-liquid-market, Mar. 1, 2022, Grandview, Research.

Holy Smokes Facebook website. Retrieved Sep. 18, 2023. https://www.facebook.com/manlyoiler/, Sep. 18, 2023, Holy Smokes, Website.

Kiff—Wooden Essential Oil Inhaler Kickstarter website. Retrieved Sep. 18, 2023. https://www.kickstarter.com/projects/kiff-story/kiff, Sep. 18, 2023, Kiff, Website.

Lung Love Etsy Canada store website. Retrieved Sep. 18, 2023. https://www.etsy.com/shop/LungLove?ref=seller-platform-mcnav, Sep. 18, 2023, Lung Love, Website.

Miech et al., "Trends in Use and Perceptions of Nicotine Vaping Among US Youth From 2017 to 2020." JAMA Pediatr. 2021;175(2):185-190. doi:10.1001/jamapediatrics.2020.5667. Published online Dec. 15, 2020, Dec.15, 2020, Miech, Richard.

Monq—Organic Hand-Held Essential Oil Diffusers website. Retrieved Sep. 18, 2023. https://monq.com/, Sep. 18, 2023, Monq Aromatherapy, Website.

Nicorette 15mg Inhalator Information page. EMC. last updated Sep. 1, 2021. https:www.medicines.org.uk/emc/product/4707/smpc#gref, Sep. 1, 2021, Nicorette, Website.

Oil and Bark Essential Oil Inhaler Website Home. Retrieved Sep. 18, 2023. https://oilandbark.com/, Sep. 18, 2023, Oil and Bark, Website.

Ripple+ zero nicotine plant powered puffs theripplestoreUSA website. Retrieved Sep. 18, 2023. https://www.therippleco.com/, Sep. 18, 2023, Ripple+, Website.

Alivape. "Vape Fidget Spinner Toy 510 Spinner Premium—Alivape." Bing image search and product page. Image in public domain on or before Nov. 2017. https://www.alivape.com/products/vape-fidget-spinner-toy-510-spinner-premium, Nov. 1, 2017, Alivape, Bing Image Search.

Non Final Office Action on Dec. 6, 2023 for U.S. Appl. No. 18/468,753, Dec. 6, 2023, Hyeon, Hae M.

International Search Report on Jan. 24, 2024 for PCT/IB2023/059217, Jan. 24, 2024, Search Report, International.

Written Opinion on Jan. 24, 2024 for PCT/IB2023/059217, Jan. 24, 2024, WO, Written Opinion.

* cited by examiner

NON-ELECTRIC, NON-HEATED DEVICES FOR ORAL DELIVERY OF COMPOUNDS AND RELATED SYSTEMS AND METHODS

RELATED APPLICATIONS/PRIORITY

This patent application claims priority to U.S. Provisional Patent Application No. 63/407,701, filed Sep. 18, 2022, entitled, "NON-ELECTRONIC, NON-HEATING INHALATION DEVICES FOR THE INHALATION OF NON-VOLATILE COMPOUNDS." This application claims the benefit of priority to, and incorporates by reference the entirety of, this above-referenced priority application.

FIELD OF THE INVENTION

The invention primarily relates to the field of inhalation devices, specifically non-electronic, non-heating, and e.g., non-medical inhalation devices for the delivery of one or more volatile compounds.

BACKGROUND OF THE INVENTION

Smoking tobacco in pipes and cigars has been a well-established practice for centuries. Evidence of the use of tobacco leaves for smoking has been traced as far back as the first century BC. The health risks associated with smoking are now well known. Nonetheless, 1 in 7 U.S. adults smoked cigarettes (13.7% of the US adult population), and many others used other forms of tobacco products (such as, e.g., cigars, cigarillos, or filtered little cigars (3.9% of the US adult population)).

Electronic cigarettes or "e-cigarettes" have been presented as an alternative to traditional tobacco products. E-cigarettes comprise a mouthpiece allowing a user to inhale an aerosol, the aerosol being created by atomization of a liquid housed within the device. The atomization is accomplished by the heating of the liquid, the heat generated by the incorporation of battery which powers the device. The term "vape" is often synonymous with e-cigarette (though vaping can also refer to administration of vaporized compounds via other means such as hookahs). The term vape refers to the vapor which is inhaled upon generation by the device. Such aerosolized compounds provided by e-cigarettes or other smokeless devices can include nicotine or other compounds, e.g., cannabinoid compounds, essential oils, and other volatile compounds. The liquid in an e-cigarette can include nicotine and when it does, such an e-cigarette is referred to as a "HANDS" device, HANDS being an acronym for "heated aerosolized nicotine delivery systems"; a handheld device that heat either nicotine-infused liquid or tobacco sticks, producing an aerosol that can be inhaled.

The market also has seen many non-nicotinic cigarette alternatives introduced, many delivering volatile compounds associated with aromatherapy and/or essential oils. Such products are marketed to those attempting to quit smoking, fulfilling the routine-related habits associated by smokers with cigarettes while excluding the provision of nicotine. Many such devices are non-electronic or "passive" devices, as heat is not required for the delivery of many non-nicotinic compounds.

For example, U.S. Pat. No. 4,083,372 to Boden ("'372") describes a non-electronic, cigarette-stimulating inhaler comprising a fluid-impermeable, resiliently flexible outer tubular sheath. The sheath is open at both ends. The '372 device comprises a wick within the sheath at one end and a soft, puncturable, liquid-containing capsule at the other, with an air chamber separating the two. The inhaler is activated by puncturing the end of the capsule closest to the wick and pinching the outer sheath at the location of the capsule to force the liquid contained therein into the air chamber prior to being absorbed by the wick. The empty capsule is then discarded.

French patent publication number FR2654002 to Laurens ("'002") describes an inhalation device in the general form of a cigarette, cigar, pipe, or cigarette holder, for applying aromatherapy by inhalation. The device comprises a support for a volatile substance positioned within the body of the device. The device further comprises a mechanism making it possible to control the loss of head, e.g., in an adjustable manner, to regulate the flow of the inhaled air through the inhalation device. Such a mechanism is embodied as either a sliding ring or the ability for the user to physically squeeze the body of the device between their thumb and forefinger to restrict airflow. Temporary closure means are provided on each side of the support such that when there is no inhalation, the substance impregnating the support cannot escape via evaporation. The device is embodied as being either a refillable inhaler or a disposable inhaler and provides a mechanism for inhaling volatile substances via either the users nose or mouth.

Austria patent AT522111 to Kornhausl ("'111") describes a passive inhaler for the delivery of volatile substances such as from natural essential oils from an exchangeable insert. The '111 device comprises an airflow channel in which the insert is positioned and held in place by an elastic seal, as well as a removable mouthpiece. The mouthpiece is made of vulcanite hard rubber or acryl and is held in place in an air-tight manner by means of an elastic seal. The main body of the device is made from solid wood or other wood-based material or from plastics.

Great Britain patent GB2412876 to Jones ("'876") describes a nicotine inhaler, suitable for use as a substitute for a cigarette for the inhalation of nicotine. The device is preferably disposable and constructed to visually mimic a cigarette, e.g., made of white, glossy cardboard. The '876 device comprises an elongated tube having an inlet and an outlet with a nicotine delivery element mounted inside the tube between the respective ends. The tube is provided with an adjustable regulating means, capable of adjusting the airflow through the device. The regulating means comprises two abutting members, e.g., discs, each with apertures therein. The two members are movable relative to one another to provide varying degrees of overlap of the apertures thus providing adjustable airflow.

U.S. Pat. No. 9,700,691 to Watanabe ("'691") describes a flavor inhalation pipe comprising a hollow, cylindrical pipe body, a mouthpiece, and a tobacco (flavor) cartridge maintained within the pipe body but attached to the mouthpiece, with a coupling device reversibly coupling the pipe body and the mouthpiece to one another. The flavor cartridge can be replaced by detaching the mouthpiece from the pipe body (e.g., uncoupling the coupling device) and pulling the mouthpiece with attached flavor cartridge away from and out of the pipe body by holding the mouthpiece. The mouthpiece can be covered with a cap to provide a hygienic way of removing and replacing the flavor generation cartridge.

United States patent publication number 2016012277 to Frobisher ("'277") describes a smoking "article" (e.g., an inhaler-type device in the form of a flow delivery article) having a flow control component. The device is configured to provide at least one flow during a draw on the flow delivery article and at least one flow comprising a respective plurality of flow peaks, e.g., the at least one flow comprising at least one of a smoke flow, an airflow, a flavoured flow, and a mixed smoke/air/flavoured flow. The flow control component is configured to cause a plurality of flow changes, providing a time-varying flow with each flow change comprising changing the relative amount of flow through the different flow pathways.

Other patent art describing passive, non-aerosolized, non-heated, cigarette-like inhalation devices include, e.g., EP2609822; U.S. Pat. Nos. 968,757, 4,175,556, 4,284,089, 4,429,703, and 4,800,903; US patent publication numbers 20060130857, 20180207370, 20210052832; and PCT publication number WO2016026094.

Despite the number of proposed devices, the number of passive inhaler devices that have been successfully developed remains limited. Exemplary devices presently marketed include those by Emitto Styx (see emittostyx.com), Lung Love (see etsy.com), Holy Smokes (see facebook.com), BreatheAura (see etsy.com), Kiff (see kickstarter.com), monq aromatherapy (see monq.com), Ripple+ (see therippleco.com), Oil & Bark (see oilandbark.com), and, e.g., breTH4life (see etsy.com). The Nicorette line of products from Johnson & Johnson, GlaxoSmithKline, is also present in this marketspace, providing a Nicorette inhaler (see medicines.org); however, notably, as is the approach for the plurality of nicotine replacement product lines sold under the Nicorette brand (e.g., Nicorette gum, lozenges, and nasal spray), this simple inhalation device delivers nicotine.

The Applicant also has developed and marketed an essential oil inhalation device marketed under the brand name FÜM™. This original FÜM device is a tobacco-free, vapor free, non-electronic inhaler made of 100% natural materials and marketed to aid in quitting smoking and vaping. The FÜM device is a single body device made of wood, having a first open end for placing within a user's mouth to facilitate the inhalation of one or more volatile compounds via the mouth, and a second open end, with an air passageway directly connecting the two ends. A flexible, fibrous insert is designed to be used within the device, the fibrous insert capable of holding (e.g., designed to hold) one or more volatile compounds (e.g., as provided by essential oils) prior to use, placed within the device by inserting the fibrous insert into the device via the second open end of the device. The inserts, or "cores", comprise medical-grade polyester designed to hold essential oil(s). To operate the device, a user is instructed to (a) obtain a core insert, (b) fray the end of the insert to activate it, (c) insert the non-frayed end of the core insert into the end of the device, and (c) inhale through the device using their mouth and to exhale out of their nose.

Despite all of the above-described efforts present in the art to set forth non-electronic, cigarette-mimicking devices for use in smoking cessation efforts, pleasure, or both, the electronic device/vaping market continues to grow. This is especially true among adolescents. As reported by Miech, et. al., in JAMA Pediatrics, 2021; 175 (2): 185-190, doi: 10.1001/jamapediatrics.2020.5667, published online Dec. 15, 2020, and corrected on Jan. 19, 2021, while increasing US adolescent nicotine vaping trends from 2017 to 2019 halted in 2020—due to decreases in perceived accessibility of some vaping products as well as increases in perceived risk of nicotine vaping between 2019 and 2020—adolescent nicotine vaping remains highly prevalent. 22% of $10^{th}$ and $12^{th}$ grade students in 2020 reported vaping within the previous 30-days of the time of the cited study and 41% reported vaping at least once in their lifetime. Worldwide, the global e-cigarette and vape market size was valued at 18.13 billion USD in 2021 and is estimated to balloon at a compound annual growth rate (CAGR) of 30.0% from 2022 to 2030 (See E-cigarette and Vape Market Size, Share & Trends Analysis Report by Product (Disposable, Rechargeable), By Distribution Channel (Online, Retail), By Region, And Segment Forecasts, 2022-2030) published March 2022). However, quite differently, the entire global aromatherapy market size was estimated to have a market size of less than $\frac{1}{10}^{th}$ that of e-cigarettes/vape products, with aromatherapy inhalant devices representing only a fraction of this total market. Thus, such products have demonstrated a very slow relative adoption of passive, non-nicotinic, vapor-free, non-electronic devices. In view of these facts, it is clear that more effective passive aromatherapy systems will require the application of inventive ingenuity.

CONSTRUCTION, TERMS, AND ACRONYMS

This section offers guidelines for reading this disclosure. The intended audience for this disclosure ("readers") are persons having ordinary skill in the practice of technologies discussed or used herein. Readers may also be called "skilled persons," and such technologies are called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," or "embodiments"). The invention encompasses all aspects as described individually and as can be arrived at by any combination of such individual aspects. The breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" & "herein" mean "in this disclosure." The term "i.a." means "inter alia" or "among other things." "Also known as" is abbreviated "aka" or "AKA." "Elsewhere" means "elsewhere herein."

For conciseness, symbols are used where appropriate. E.g., "&" is used for "and," & "~" for "about." Symbols such as < and > are given their ordinary meaning (e.g., "≤"

means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect of the invention.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means any or all possible/suitable combinations of such elements/steps.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all of an intended function, without causing or imparting significant negative/detrimental impact.

Uncontradicted, heading(s) (e.g., "Construction, Terms . . . ") and subheadings are included for convenience and do not limit the scope of any aspect(s). Uncontradicted, aspect(s), step(s), or element(s) described under one heading can apply to other aspect(s) or step(s)/element(s) here.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "~," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)."

Uncontradicted, any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both. Explicit listing of percentages of elements/steps in connection with aspects does not limit or contradict such implicit disclosure.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

The term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most," or "mostly," means detectably ≥50% (e.g., mostly comprises, predominately includes, etc., mean ≥50%) (e.g., a system that mostly includes element X is composed of >50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" an element mean comprising ≤25~% of an element and terms such as "substantially free" of an element mean comprising ≤~5% of an element.

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition can be assembled in any suitable manner by any suitable method. In general, any methods and materials similar or equivalent to those described here can be used in the practice of embodiments. Uncontradicted, the use of ordinal numbers such as "first," "second," "third," and so on is to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

Herein, the terms "component" and "element" may each be used to describe a particular part of a device. For example, disclosure herein may use language such as, e.g., "the X component of an inhalation device," "the X element of an inhalation device," "the X component," or "the X element." wherein "X" is the same named part. In a specific example, the following language may be used: "The compressible component of an inhalation device," "the compressible element of an inhalation device,", "the compressible component,", or "the compressible element." Uncontradicted, use of the terms "component" and "element" can be interpreted as interchangeable.

Further, in many places throughout this specification, a broad component identification term is accompanied by language identifying a name or names for such a component provided in a specific embodiment or specific embodiments. As one example, the broad component identifier, "selectively releasable engagement mechanism" (or "selectively releasable attachment mechanism") may be accompanied by additional language specifying specific embodiments, such as, e.g., "a rapidly releasable [or rapid release] force mechanism" or, e.g., "magnet." Where all such terms are not provided in a description of a particular component or mechanism, any singular reference should be interpreted as incorporating reference to any narrower or to any broader description of such a component or mechanism. That is, for example, use of only the term, e.g., "selectively releasable engagement mechanism" should be interpreted as encompassing, "rapidly releasable force [or rapid release force] mechanism" and "magnet." Uncontradicted, any use of only the term "rapidly releasable [or rapid release] force mechanism," should be interpreted as encompassing "selectively releasable engagement mechanism" and "magnet." Further, uncontradicted, any use of only the term "magnet" should be interpreted as encompassing, "selectively releasable engagement mechanism," and "rapidly releasable [or rapid release] force mechanism."

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

SUMMARY OF THE INVENTION

The inventions described and claimed herein have many attributes and aspects including, but not limited to, those set forth in, e.g., described or referenced in, this Summary. This Summary of the Invention ("Summary") is not intended to be all-inclusive, and the scope of the invention is not limited to or by the aspects, features, elements, or embodiments provided in this Summary, which is included for illustrative purposes only and not restriction. Any of the aspects described under this section can be combined with any other aspect described in this section or with any other aspect of this disclosure.

In a first aspect, the invention provides an inhalation device, e.g., a non-electronic inhalation device, a non-heating inhalation device, or both a non-electronic and non-heating inhalation device, for the inhalation of one or more volatile compounds.

In aspects, the inhalation device comprises a first component and a second component releasably held together by a selectively releasable attachment mechanism. In aspects, the first component and second component can be completely disengaged from one another or, alternatively, can be securely bound to one another. In aspects, the body of the inhalation device comprises at least a first component and a second component releasably bound together by a magnetic force.

In one aspect, the invention provides an inhalation device, e.g., a non-electronic inhalation device, a non-heating inhalation device, or both a non-electronic and non-heating inhalation device, for the inhalation of one or more volatile compounds, wherein the device comprises at least one visual indicator present on the exterior of the device. In aspects, the spatial orientation of the at least one visual indicator indicates the spatial orientation of at least one component of the device which is not externally visible. In one aspect, the inhalation device comprises at least two visual indicators present on the exterior of the device. In aspects, the spatial orientation of at least one visual indicator relative to at least one other visual indicator provides an indication of at least one operational status of the device. In one aspect, the inhalation device comprises at least two visual indicators present on the exterior of the device, and wherein (a) the spatial orientation of at least one visual indicator indicates the spatial orientation of at least one component of the device which is not externally visible and (b) the spatial orientation of at least one visual indicator relative to at least one other visual indicator provides an indication of at least one operational status of the inhalation device.

According to certain aspects, the invention provides an inhalation device, e.g., a non-electronic inhalation device, a non-heating inhalation device, or both a non-electronic and non-heating inhalation device, for the inhalation of one or more volatile compounds, wherein the inhalation device comprising an airflow control mechanism. In aspects, the inhalation device comprises an adjustable airflow control mechanism controlled by the rotation of a first device component and a second device component relative to one another. In certain aspects, the rotation of the first airflow control component relative to the second airflow control component can comprise a rotation of 360 degrees. In aspects, the airflow control mechanism is adjustable in pre-defined increments. In aspects, the inhalation device comprises an airflow path through the device and an adjustable airflow control mechanism wherein the adjustable airflow control mechanism comprises a closure mechanism for the airflow path. In aspects, the closure mechanism comprises at least three distinct airflow control settings, wherein moving from any first airflow control setting to any second airflow control setting provides a pre-determined increase or pre-determined decrease in airflow through the device. In aspects, the invention provides an inhalation device comprising an airflow control mechanism wherein the airflow control mechanism comprises a first component and a second component completely separable from one another during normal use of the inhalation device.

According to certain aspects, the invention provides an inhalation device, e.g., a non-electronic inhalation device, a non-heating inhalation device, or both a non-electronic and non-heating inhalation device, for the inhalation of one or more volatile compounds, wherein the device comprises an airflow control mechanism for establishing airflow control setting(s) comprising a first airflow control component and a second airflow control component, wherein the first airflow control component and the second airflow control component have an amount of interface at each airflow control setting. In aspects, the amount of interface between the first component and the second component decreases between any first airflow control setting and any second airflow control setting compared to the amount of interface between the components of the airflow control mechanism at any first or second airflow control setting. In aspects, the inhalation device comprises an adjustable airflow control mechanism wherein a change between any first airflow control setting and any second airflow control setting is accompanied by a tactile indicator. In aspects, the inhalation device comprises an adjustable airflow control mechanism having two distinct tactile indicators differentiating between a maximally closed airflow control setting and a partially open airflow control setting.

In one aspect, the invention provides an inhalation device, e.g., a non-electronic inhalation device, a non-heating inhalation device, or both a non-electronic and non-heating inhalation device, for the inhalation of one or more volatile compounds, wherein the device comprises an internal compartment designed to hold a solid material device capable of maintaining or releasing one or more volatile compounds. In aspects, the internal compartment has at least one dimension which is at least half as long as the longest dimension of the solid material device. In aspects, the internal compartment completely surrounds at least a first portion of the solid material device. In aspects, the internal compartment only partially surrounds at least a second portion of the solid material device.

According to aspects, the invention provides a removable insert for use within a device summarized here, wherein the removable insert is designed to maintain, release, or both maintain and release one or more volatile compounds. According to one aspect, the invention provides a porous, non-fibrous, solid material device (removable insert) capable of holding, delivering, or holding and delivering one or more volatile compounds to a user via inhalation when the device is inserted into an inhalation device described above. In aspects, the solid material device (removable insert) comprises a first end, a second end, and an outer diameter, and wherein the solid material device comprises at least one non-circuitous passageway within its outer diameter between its first and second ends allowing the passage of air through the solid material device via the passageway. In one aspect, the invention provides a fibrous solid material device (removable insert) capable of holding, delivering, or holding and delivering one or more volatile compounds, the fibrous device comprising a first end and a second end and a visible passageway through the device between the first and second ends.

According to certain aspects, the invention provides an inhalation device system for the delivery of one or more volatile compounds by inhalation, the device system comprising (a) a non-electronic, non-heating, or non-electronic and non-heating inhalation device and (b) a removable insert designed to be removably maintained therein. In aspects, the inhalation device of such a system comprises any one or more of the characteristics summarized here. In aspects, the removable insert comprises any one or more of the characteristics summarized here. In aspects, when in use, (a) at least one quarter of the removable insert's longest dimension is engaged with a first component of the inhalation device, and (b) the entirety of the removable insert is positioned within a second component of the inhalation device.

In aspects, the invention provides kits comprising one or more devices summarized here, kits providing one or more removable inserts summarized here, kits providing one or more systems summarized here, or any combination of any or all thereof.

In aspects, the invention provides a method of detectably or significantly reducing a smoking habit-related craving in an individual, the method comprising providing to an individual suffering from a smoking habit-related craving a passive inhalation device or system summarized here. In aspects, the method comprises instructing the individual to (i) inhale via their mouth at least one partial or full breath through the passive inhalation device such that a detectable amount of volatile compounds maintained by the removable insert is delivered to the individual and (ii) to repeat step (i) for as many times as is needed to detectably reduce the smoking habit-related craving as assessed by the individual.

According to certain aspects, the invention provides a method of detectably or significantly reducing a smoking habit-related craving in an individual, the method comprising providing to an individual suffering from a smoking habit-related craving an inhalation device or system summarized here. In aspects, the method comprises instructing the individual to (i) hold the device within their hand, between their fingers, between their lips, or any combination thereof, (ii) repeatedly rotate the first primary component in relation to the second primary component relative to one another in any direction or combination of directions, (iii) repeatedly separate and allow reattachment of the first primary component and the second primary component relative to one another, or any combination of (i)-(iii), until the individual experiences a detectable or significant decrease in the smoking habit related craving as assessed by the individual or as assessed by an appropriately conducted and powered trial or survey administered or conducted by suitably trained individual(s) recognized as capable of identifying reduction in addiction-related behavior.

BRIEF DESCRIPTION OF THE DRAWINGS/FIGURES

The drawings/figures provided here, and the associated following brief description of figures, are intended to exemplify certain aspects and principles of the invention without limiting its scope.

Figure 1B:
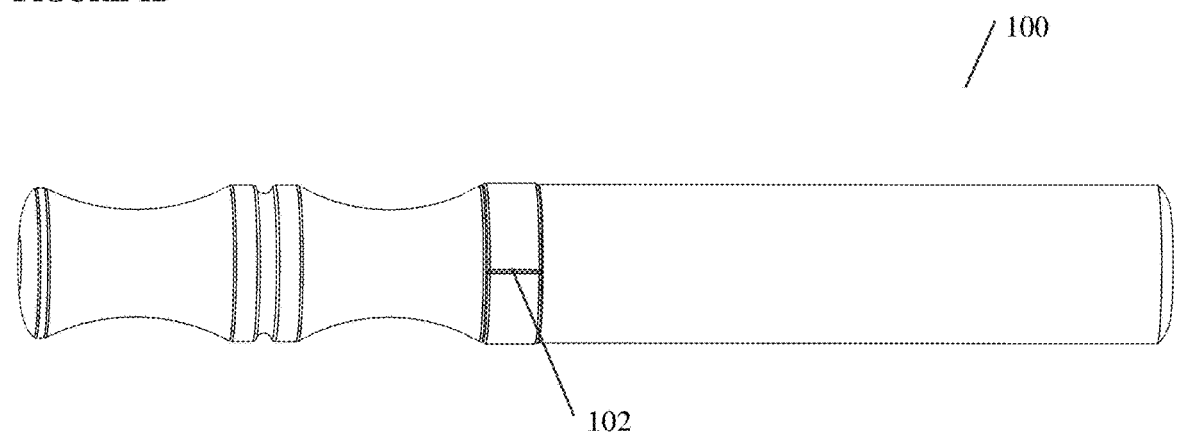
Figure 1C:
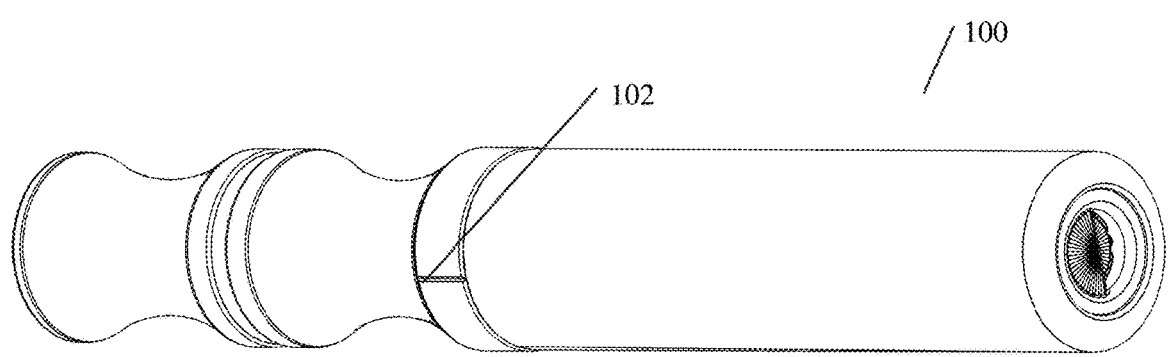

FIGS. 1A-1C (FIGS. 1A, 1B, 1C) provide an exemplary embodiment of a device provided by the invention in fully assembled form as viewed from three slightly different perspectives.

Figure 2A:
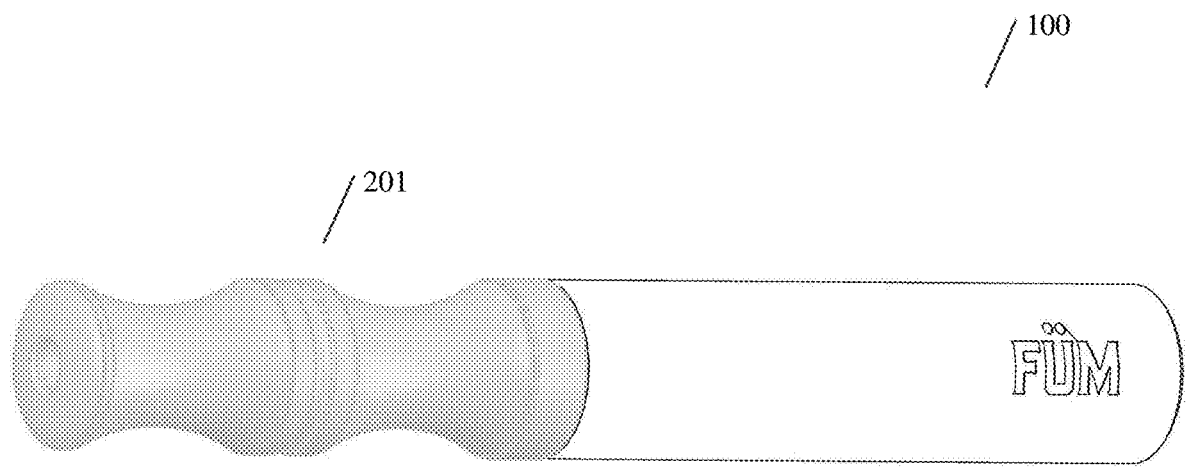

FIG. 2A provides an exemplary embodiment of a device provided by the invention in fully assembled form with the body assembly shaded for emphasis.

Figure 2B:
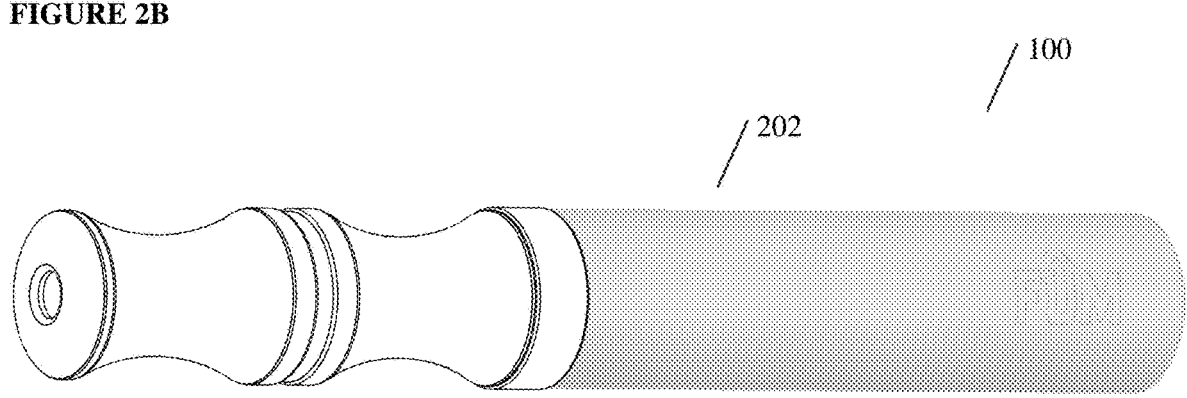

FIG. 2B provides an exemplary embodiment of a device provided by the invention in fully assembled form with the tip assembly shaded for emphasis.

Figure 2C:
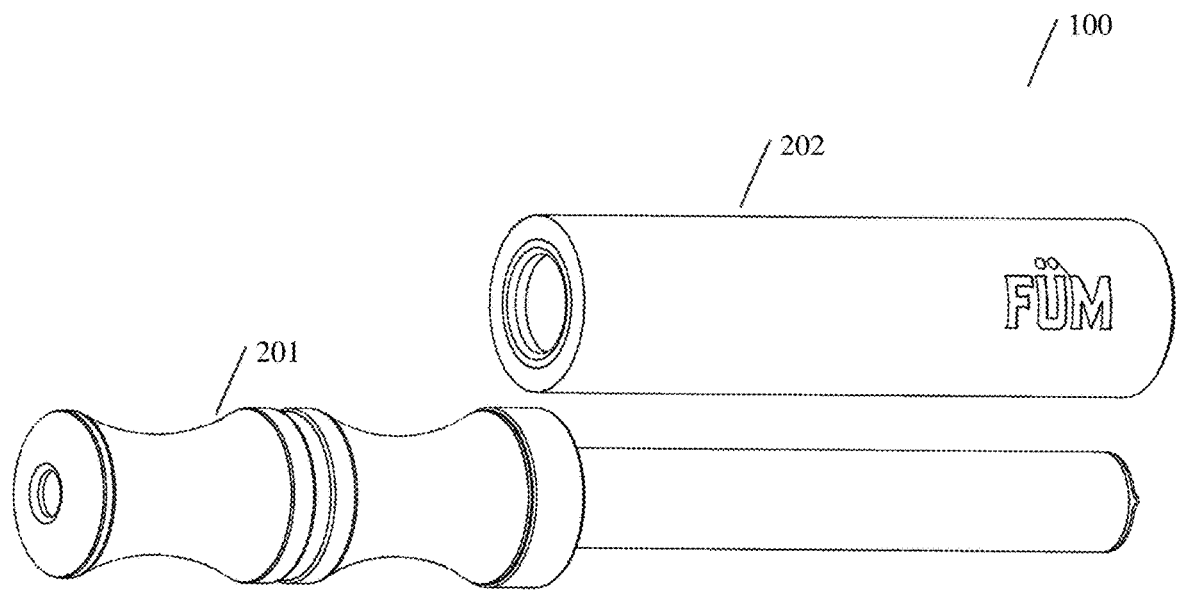

FIG. 2C provides an exemplary embodiment of a device provided by the invention with the tip assembly removed from the body assembly.

Figure 3A:
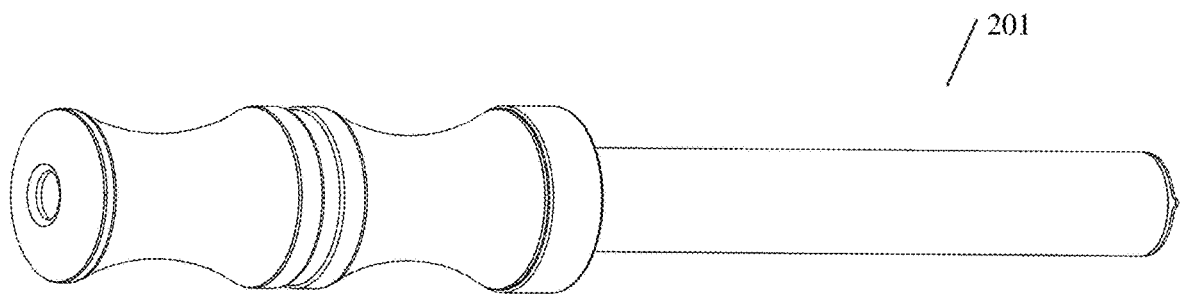

FIG. 3A provides an exemplary embodiment of a body assembly.

Figure 3B:
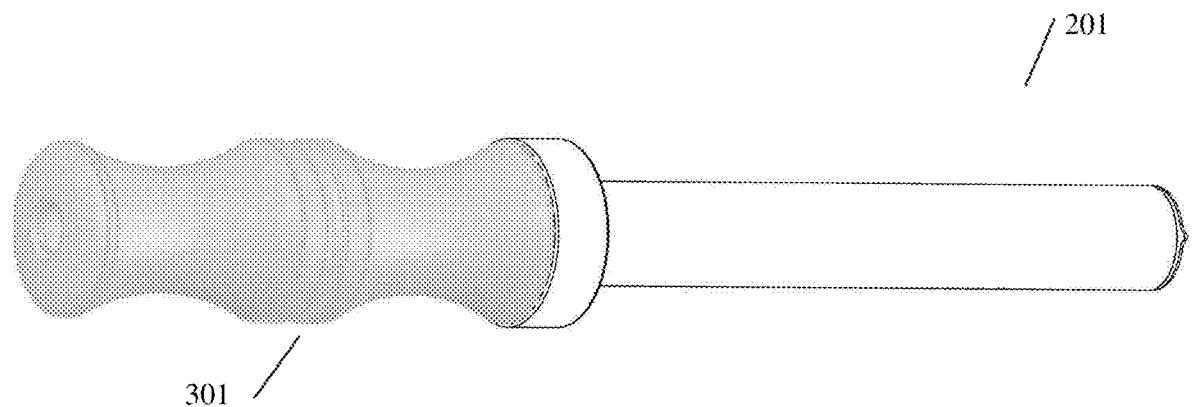

FIG. 3B provides an exemplary embodiment of a body assembly with the mouthpiece shaded for emphasis.

Figure 3C:
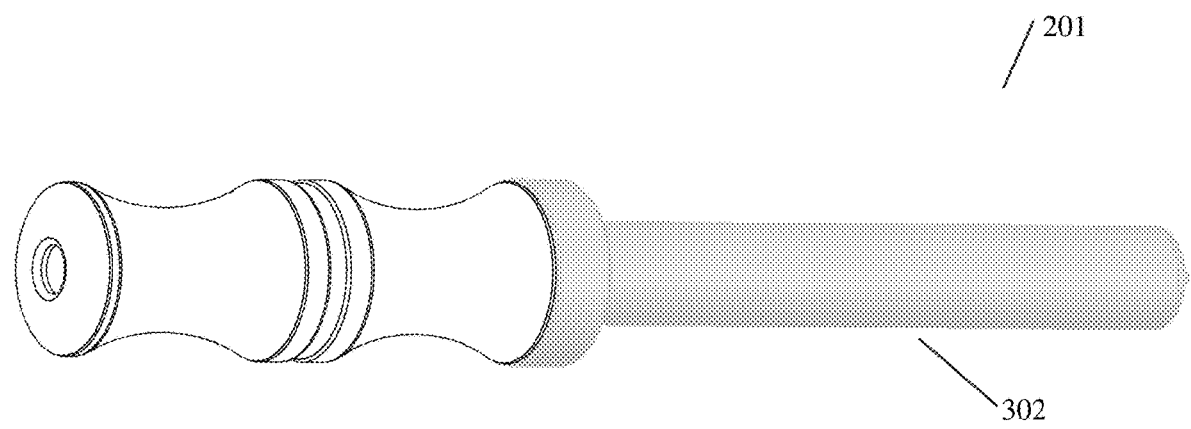

FIG. 3C provides an exemplary embodiment of a body assembly with the body sub-assembly shaded for emphasis.

Figure 3D:
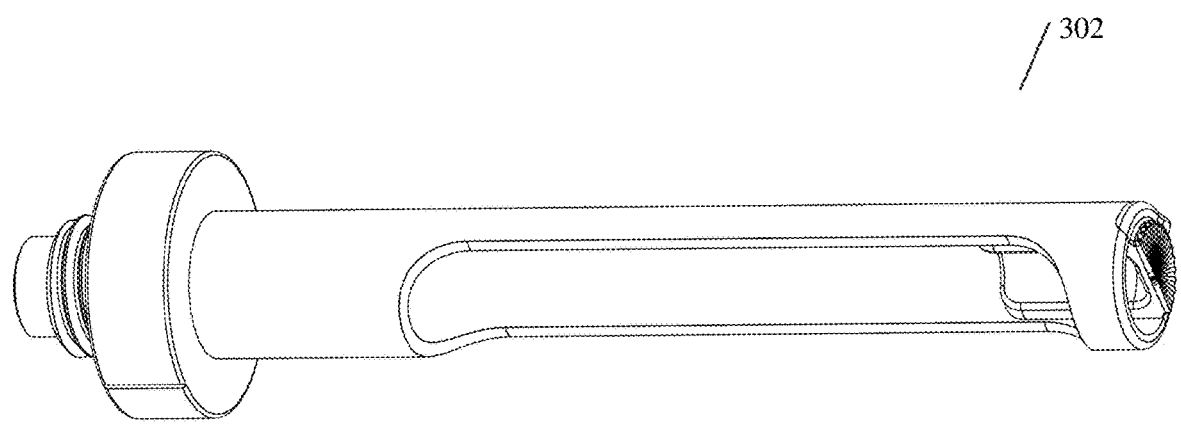

FIG. 3D provides an exemplary embodiment of a body sub-assembly.

Figure 4A:
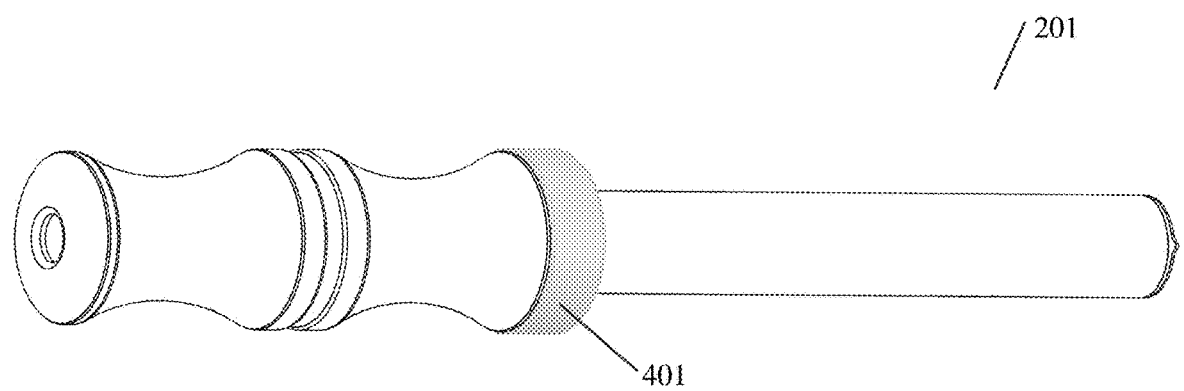

FIG. 4A provides an exemplary embodiment of a body assembly, with the magnet cover of the body sub-assembly shaded for emphasis.

Figure 4B:
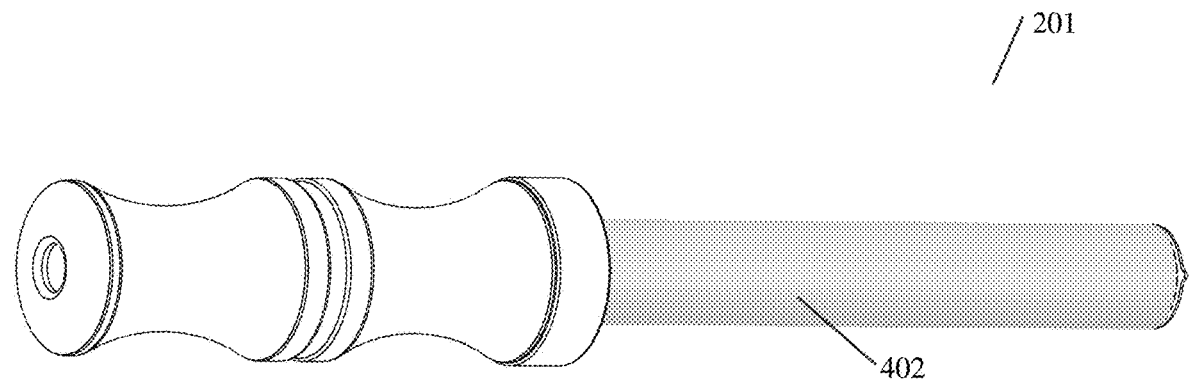

FIG. 4B provides an exemplary embodiment of a body assembly, with the body tube of the body sub-assembly shaded for emphasis.

Figure 4C:
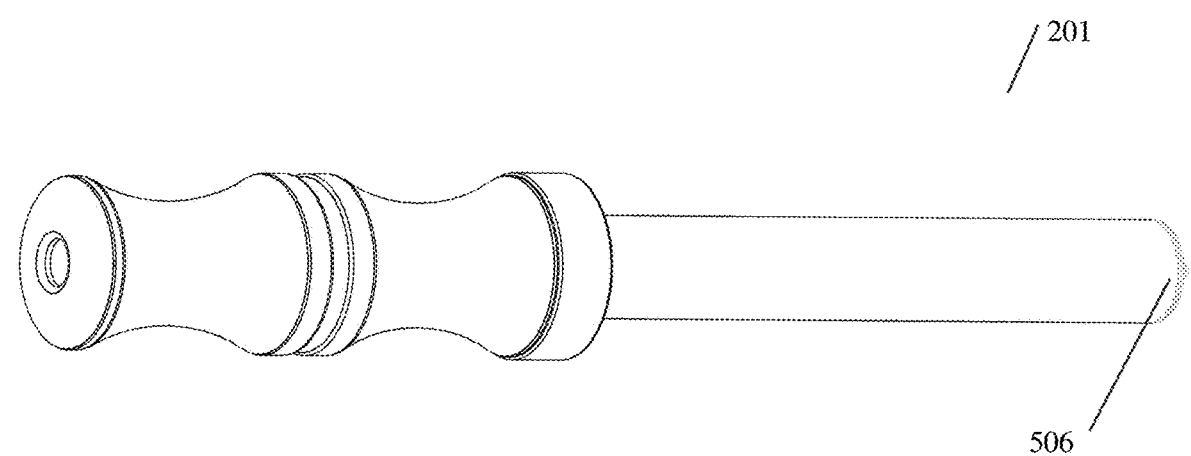

FIG. 4C provides an exemplary embodiment of a body assembly, with the body plug of the body sub-assembly shaded for emphasis.

Figure 5A:
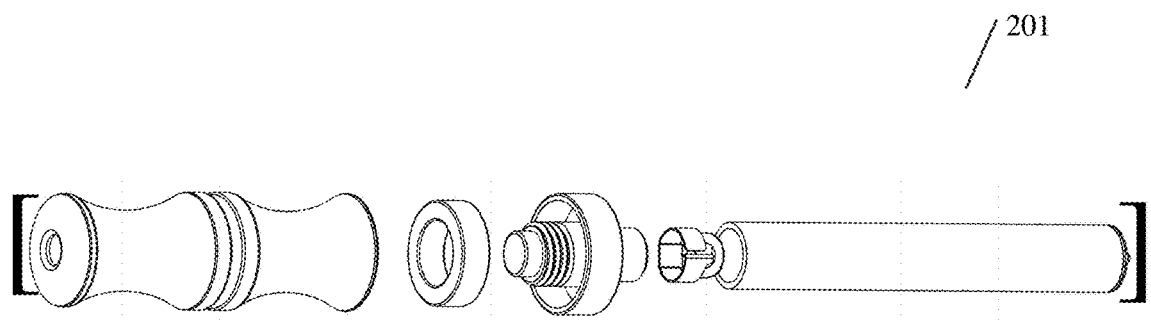
Figure 5A:
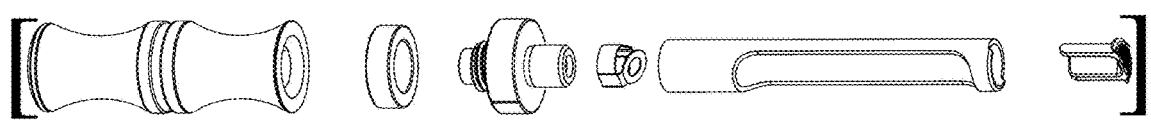

FIG. 5A provides an exploded-view perspective of an exemplary embodiment of a body assembly.

Figure 5B:
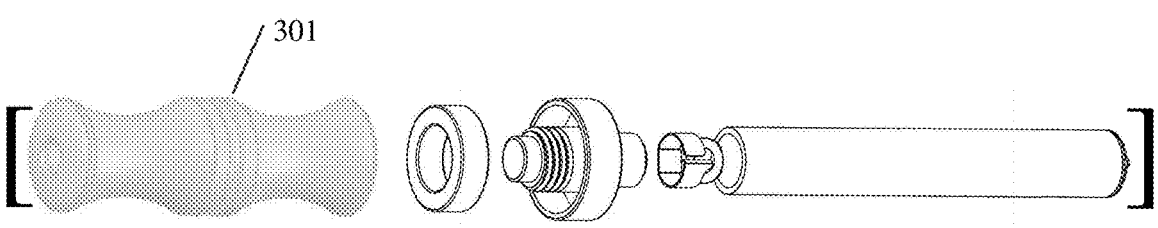
Figure 5B:
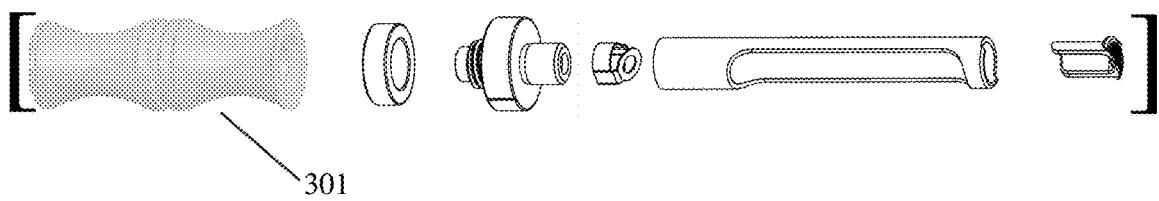
Figure 5C:
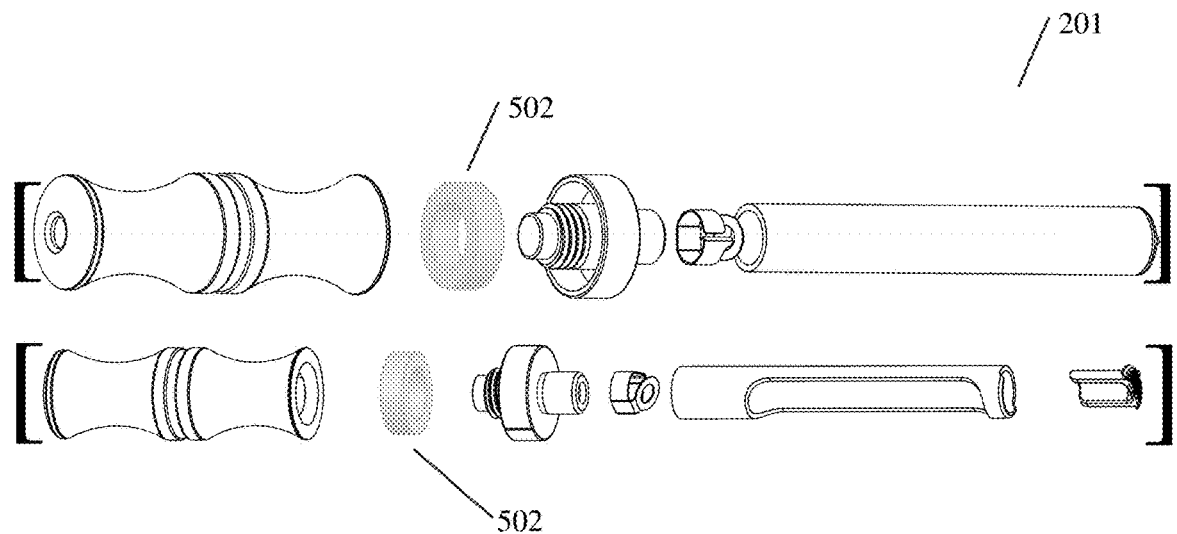
Figure 5D:
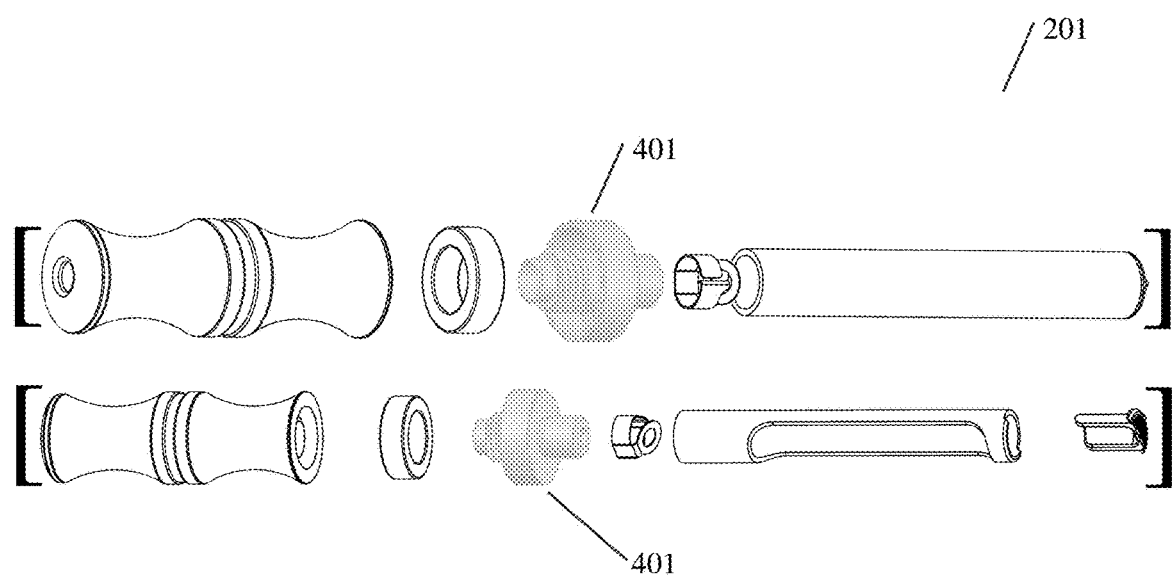
Figure 5E:
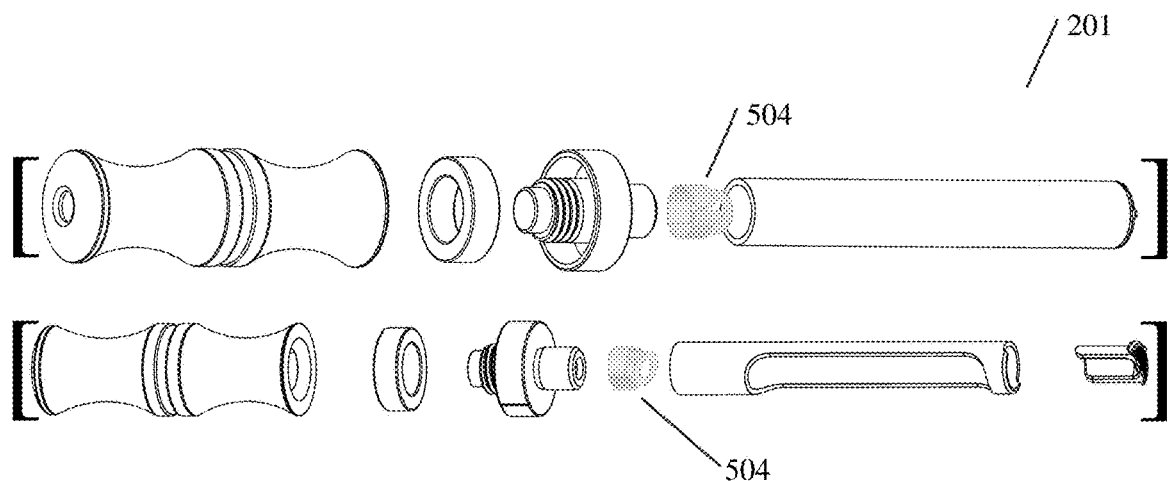
Figure 5F:
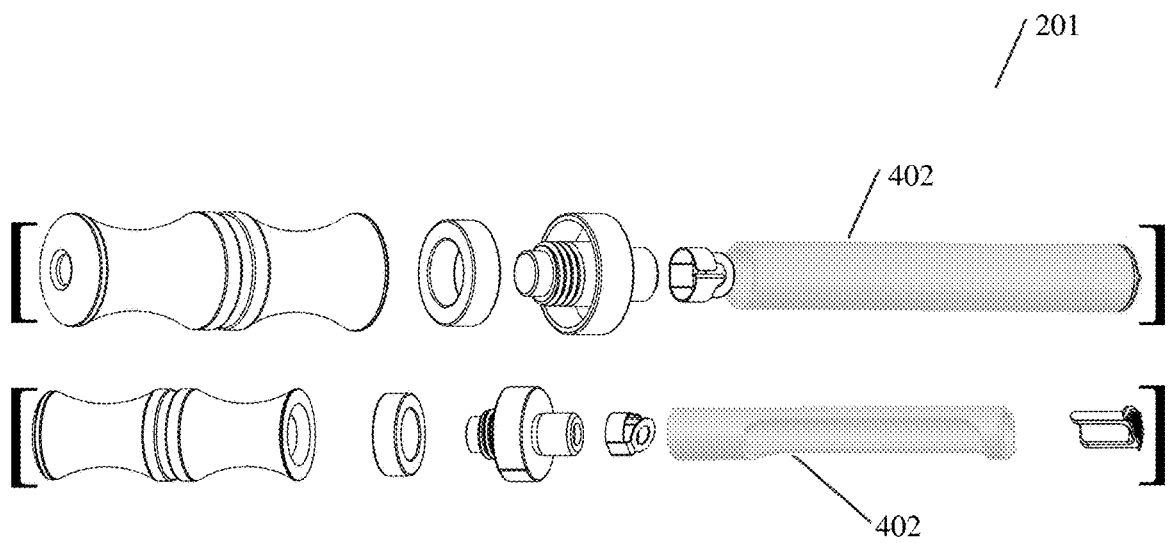
Figure 5G:
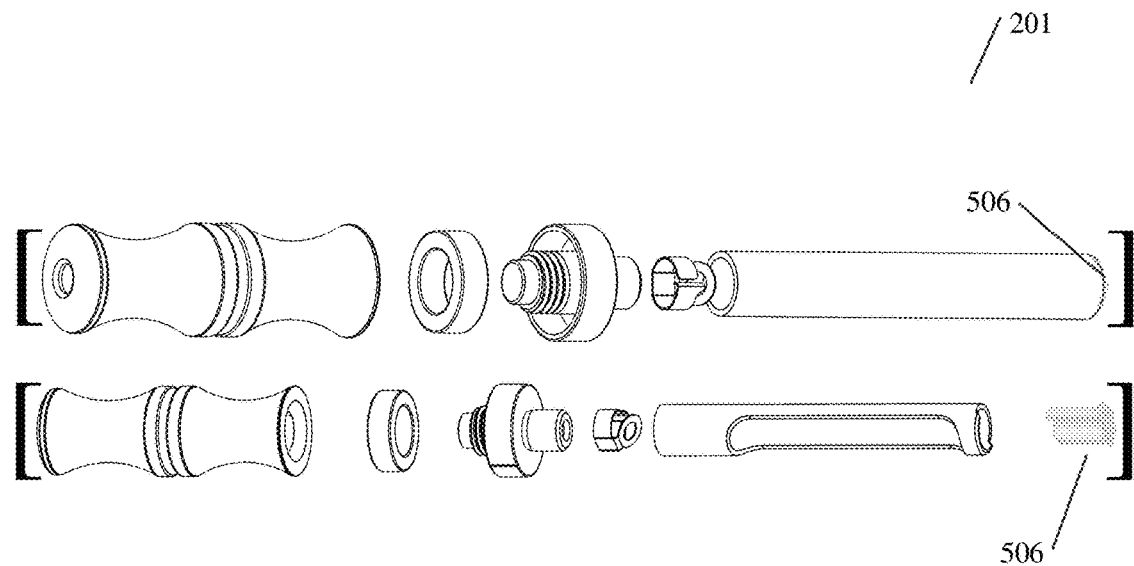

FIGS. 5B-5G, including FIGS. 5B, 5C, 5D, 5E, 5F, and 5G, provide the exploded-view perspective of the exemplary embodiment of a body assembly shown in FIG. 5A, with each component of the exemplary body assembly shaded for emphasis: mouthpiece (FIG. 5B), magnet (FIG. 5C), magnet cover (FIG. 5D), core spring (FIG. 5E), body tube (FIG. 5F), and body plug (FIG. 5G).

Figure 6A:
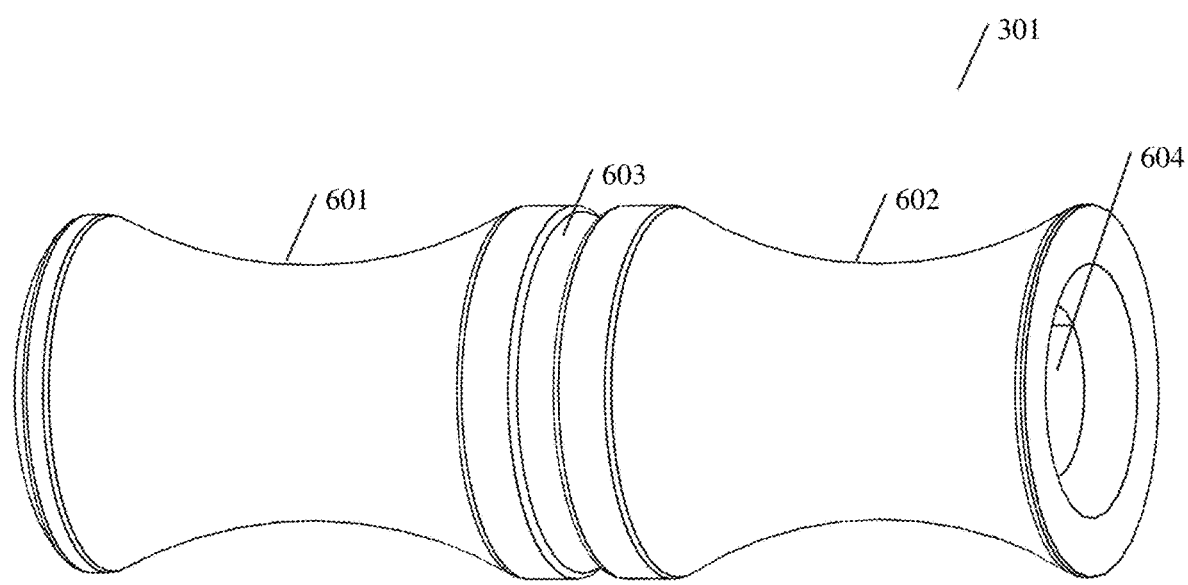
Figure 6B:
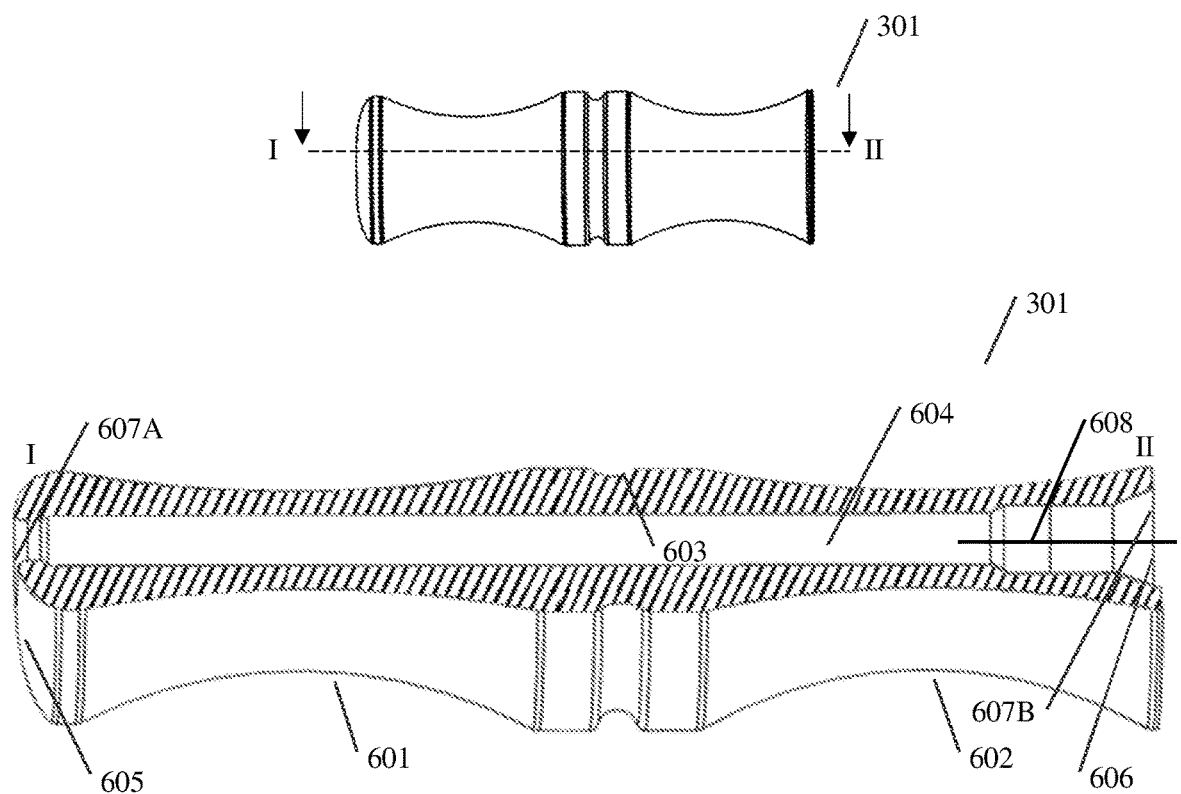

FIGS. 6A and 6B provide an exemplary embodiment of a mouthpiece, with FIG. 6B providing a plane-view of the mouthpiece of FIG. 6A.

Figure 6C:
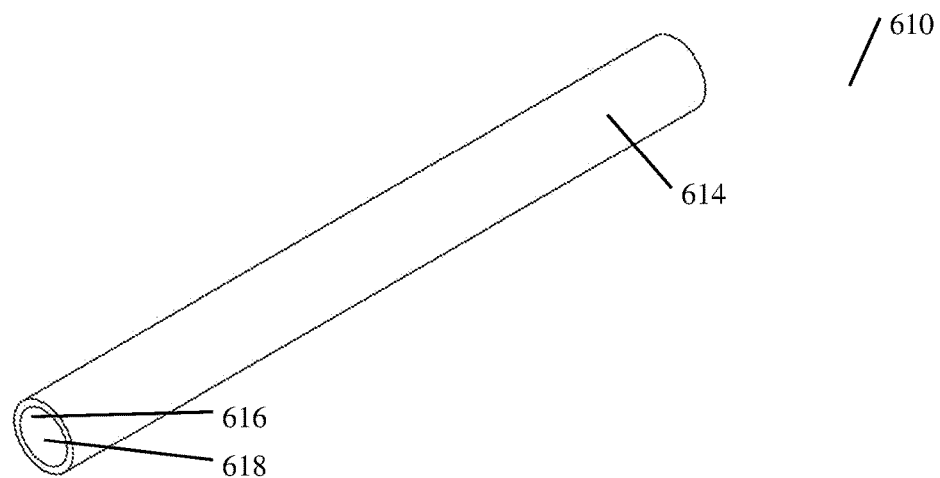

FIG. 6C provides an exemplary embodiment of an inhalation facilitation component supplement (mouthpiece tube) capable of being utilized with a mouthpiece such as the mouthpiece of FIGS. 6A and 6B.

Figure 7:
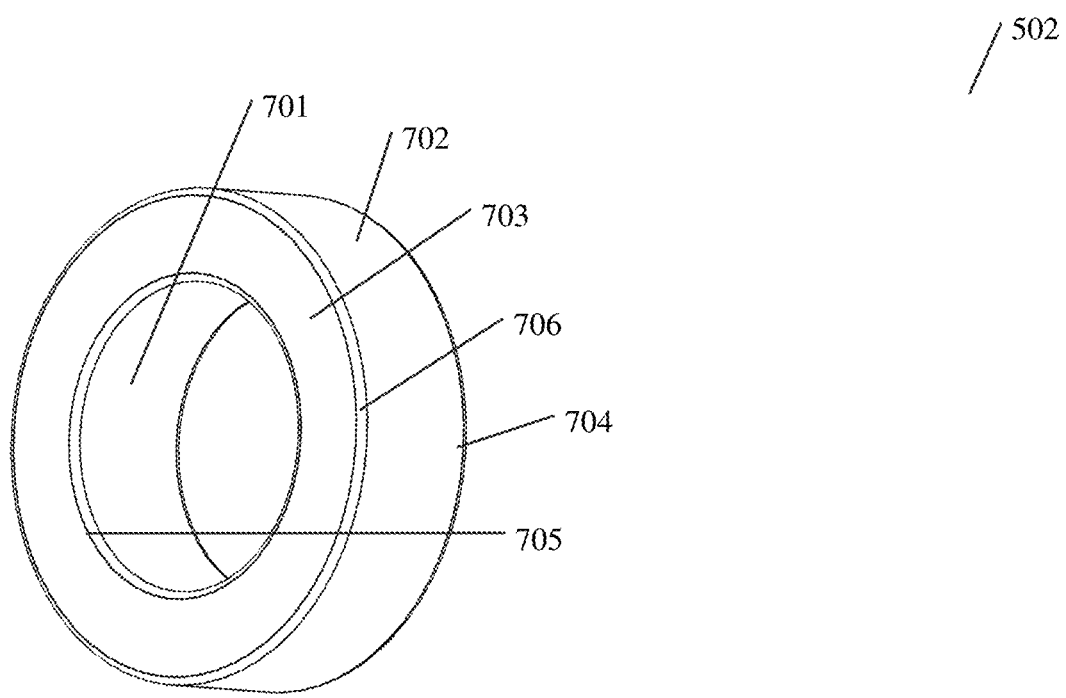

FIG. 7 provides an exemplary embodiment of a magnet.

Figure 8A:
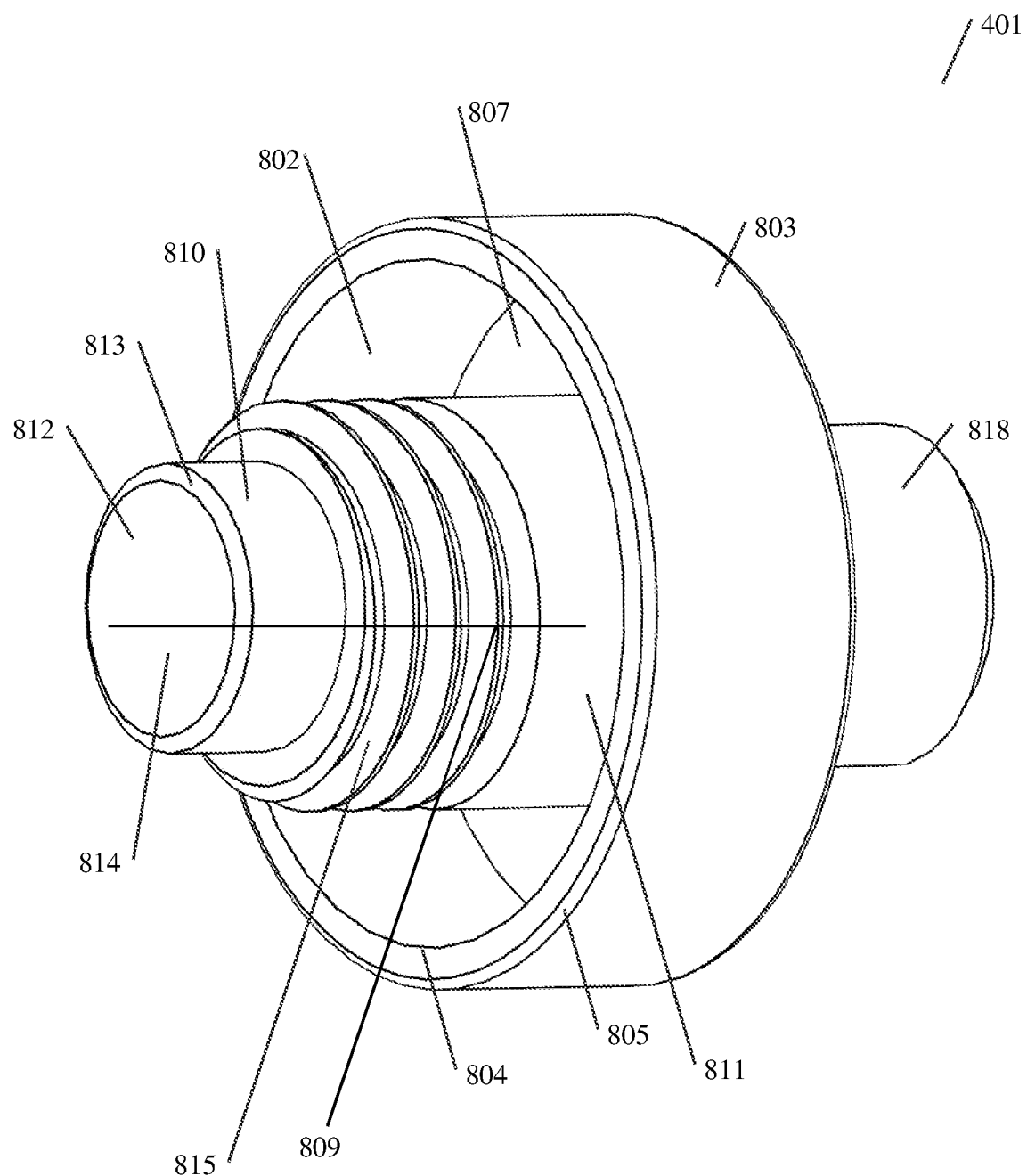
Figure 8B:
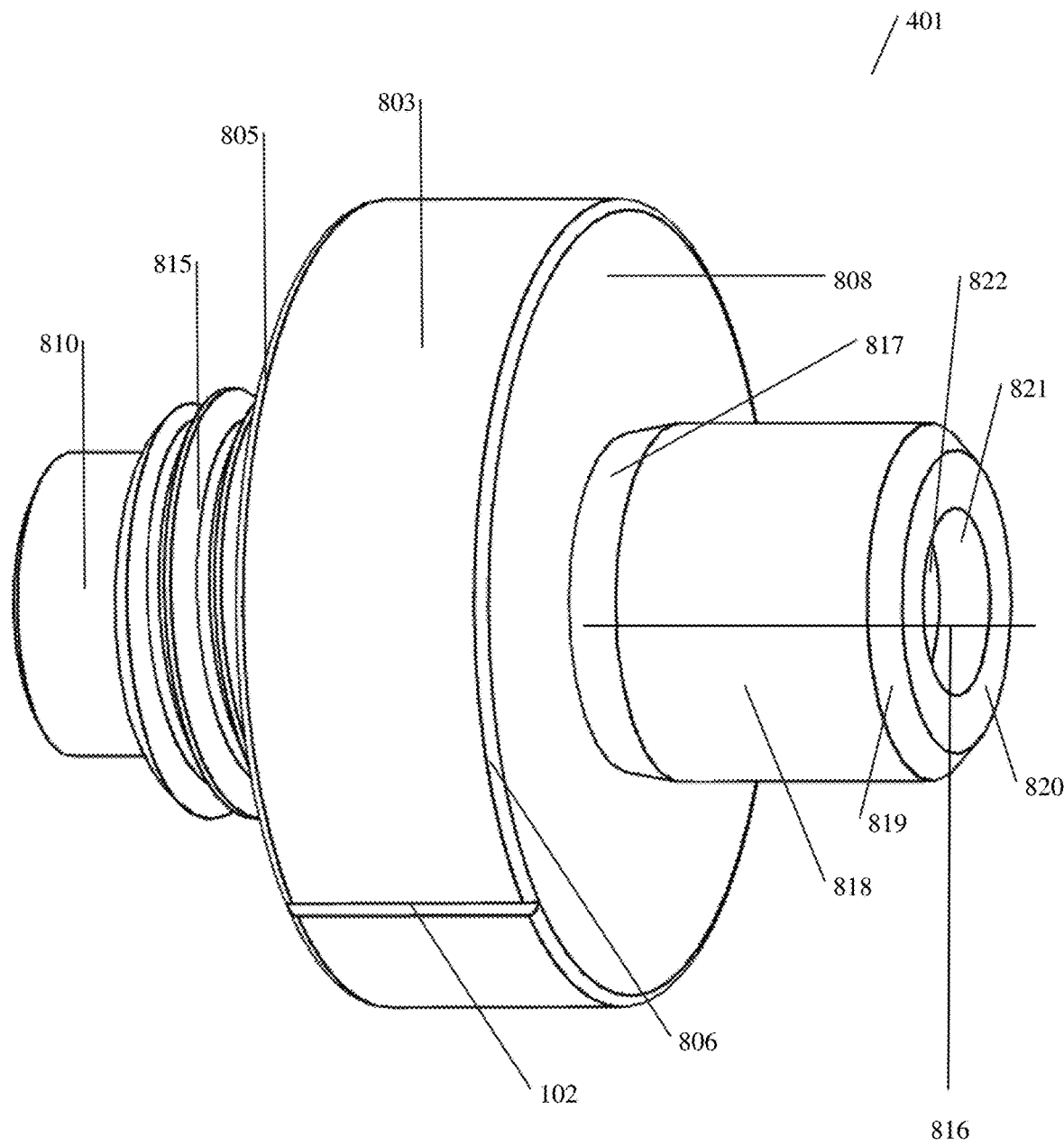

FIGS. 8A and 8B provide an exemplary embodiment of a magnet cover as viewed from two different perspectives.

Figure 9A:
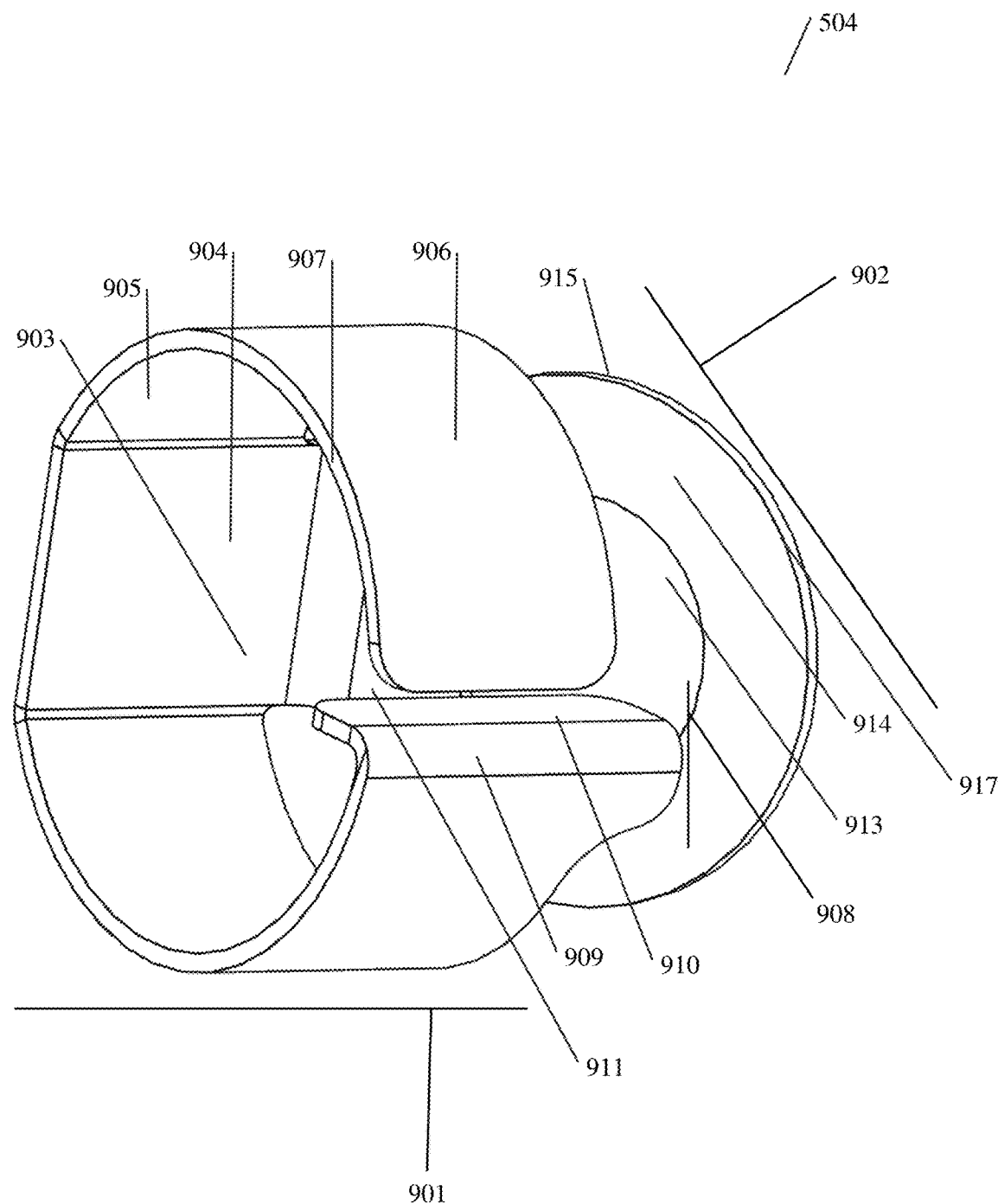
Figure 9B:
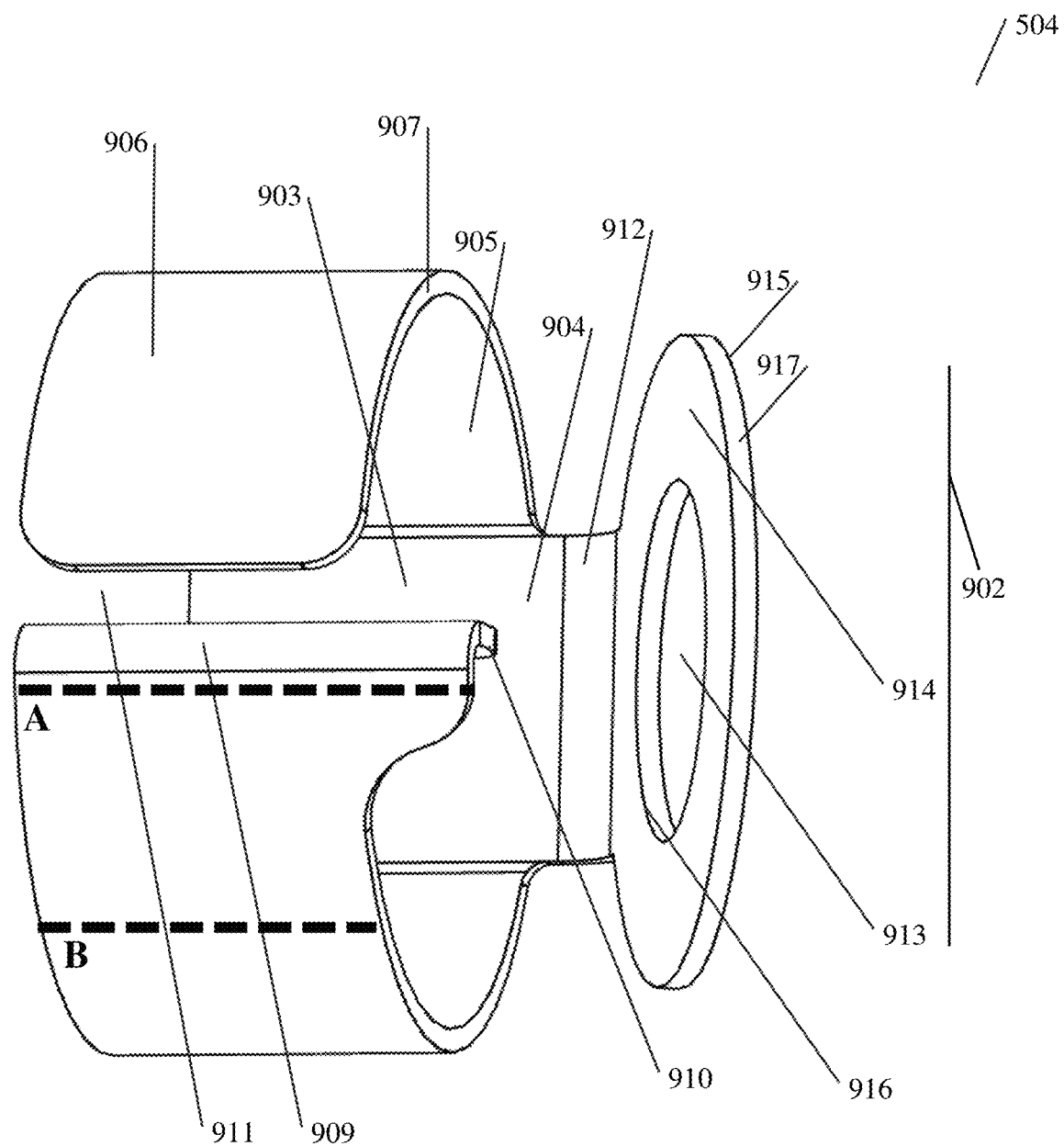

FIGS. 9A and 9B provide an exemplary embodiment of a core spring as viewed from two different perspectives.

Figure 10A:
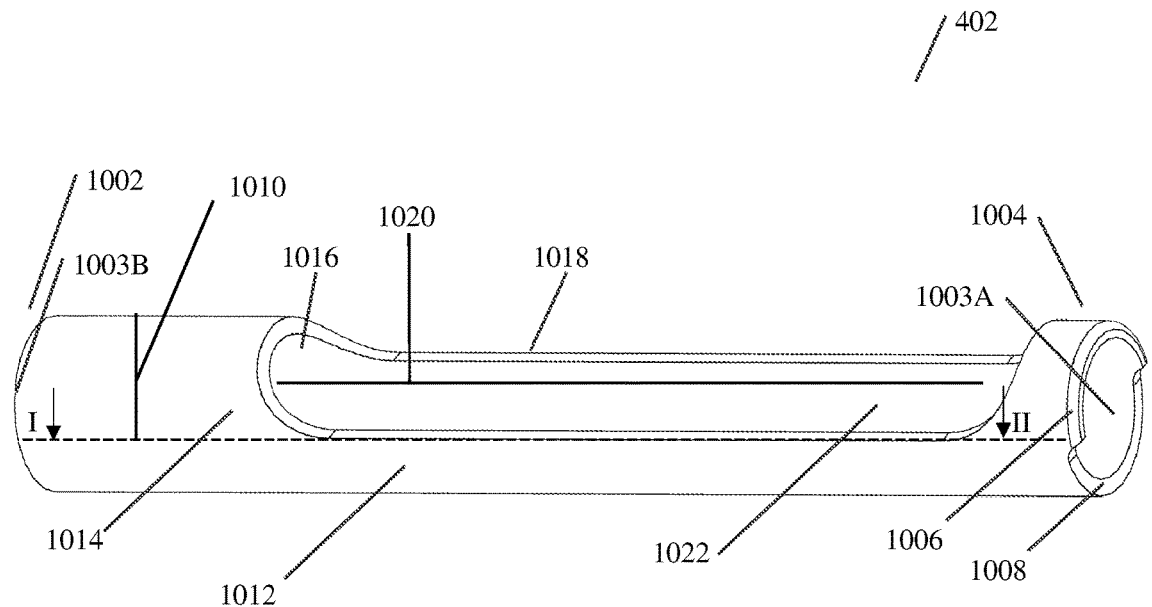
Figure 10B:
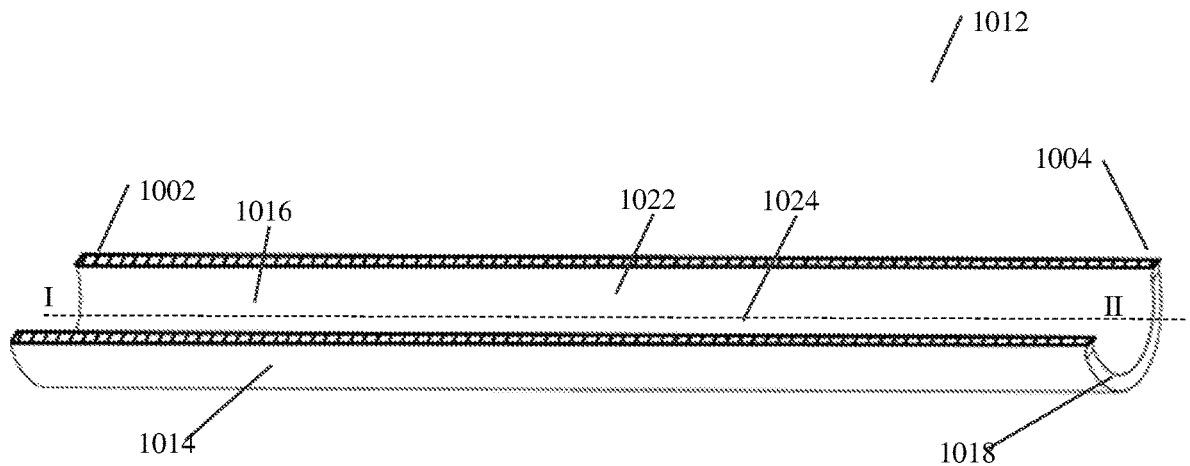

FIGS. 10A and 10B provide an exemplary embodiment of a body tube as viewed from two different perspectives, with FIG. 10B being a plane-view of the body tube of FIG. 10A.

Figure 11A:
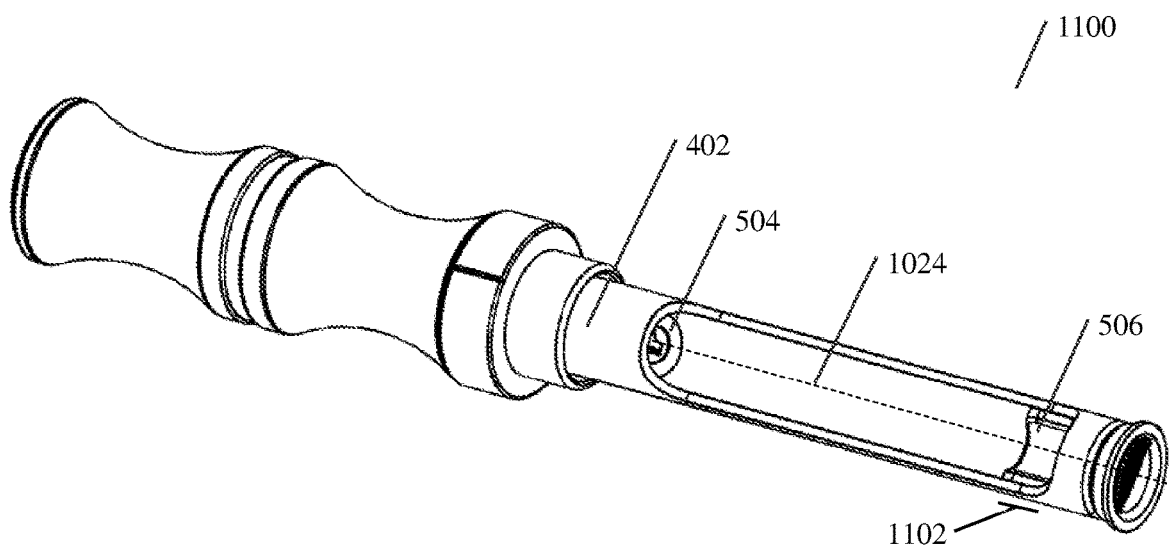
Figure 11B:
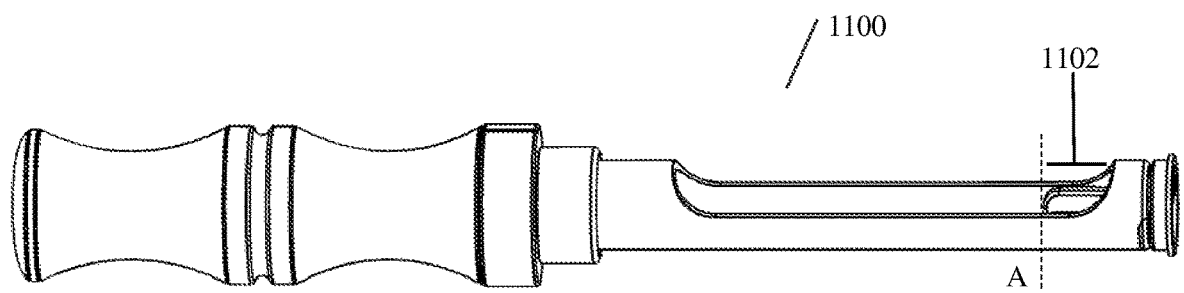

FIGS. 11A and 11B provide an exemplary embodiment of an access gap present to aid in the removal or insertion of a core insert.

Figure 12A:
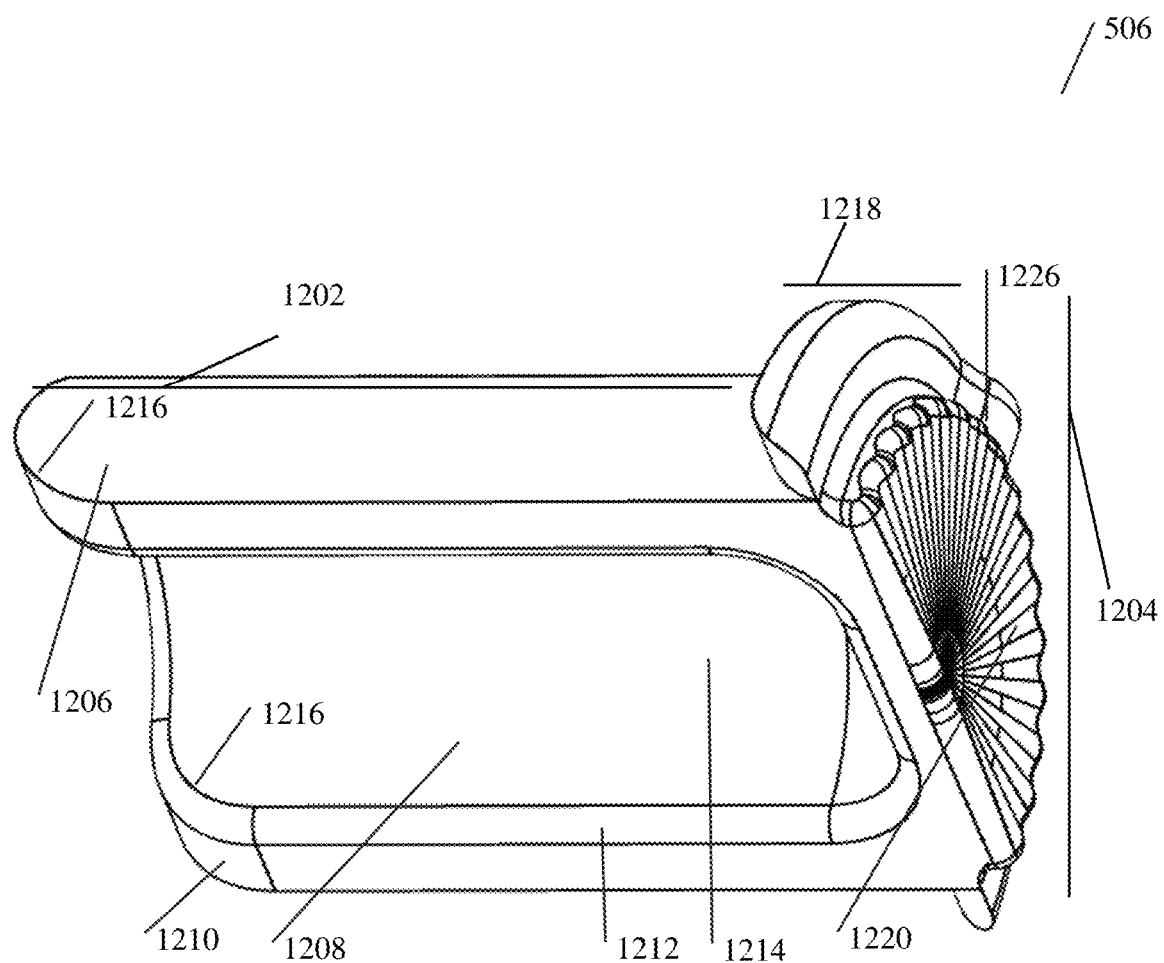
Figure 12B:
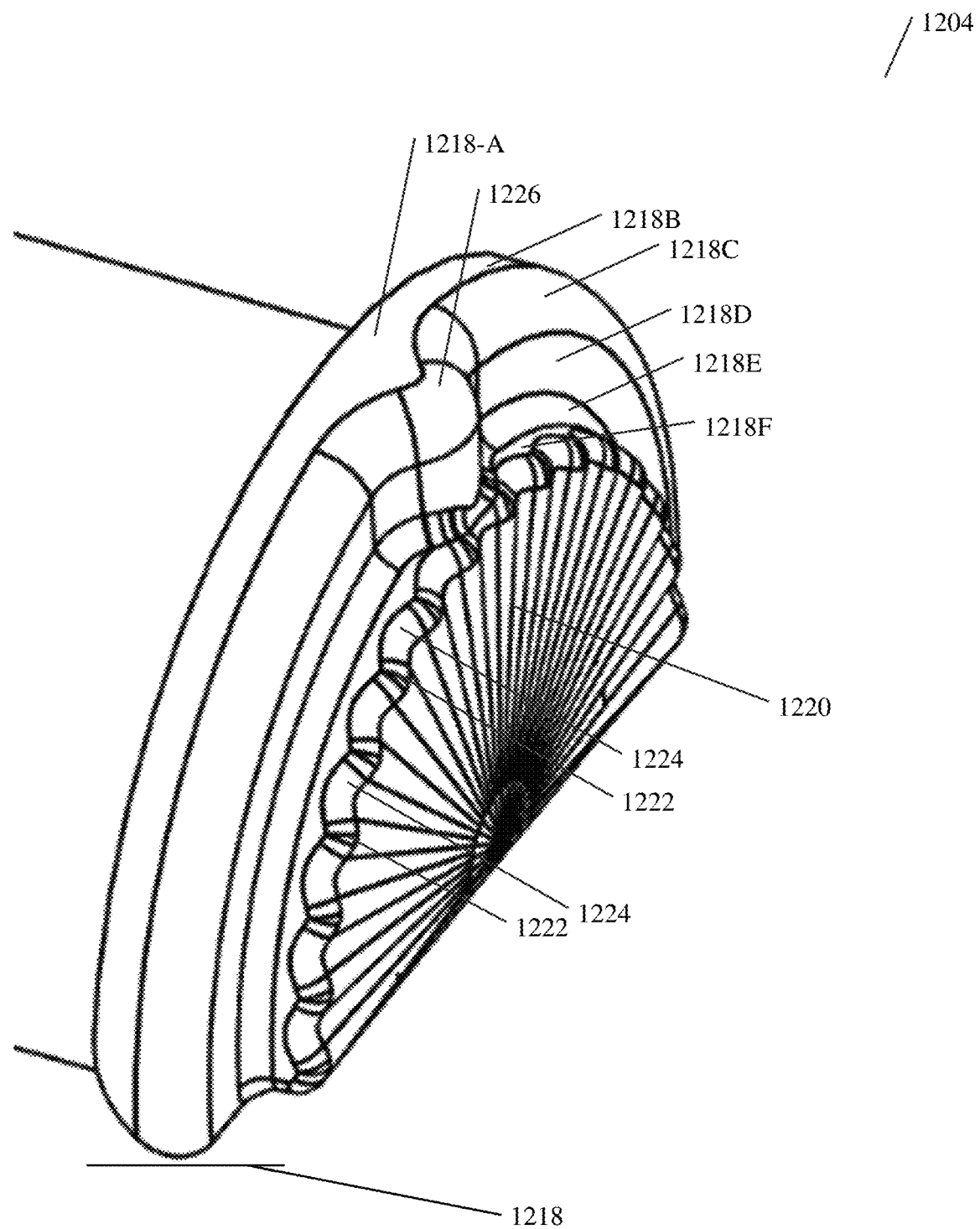

FIGS. 12A and 12B provide an exemplary embodiment of a body plug, with FIG. 12B emphasizing one particular portion of the body plug of FIG. 12A.

Figure 13A:
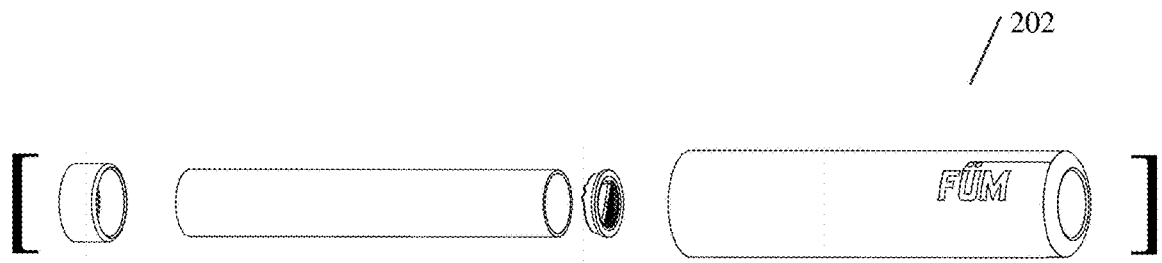

FIG. 13A provides an exploded view of an exemplary tip assembly.

Figure 13B:
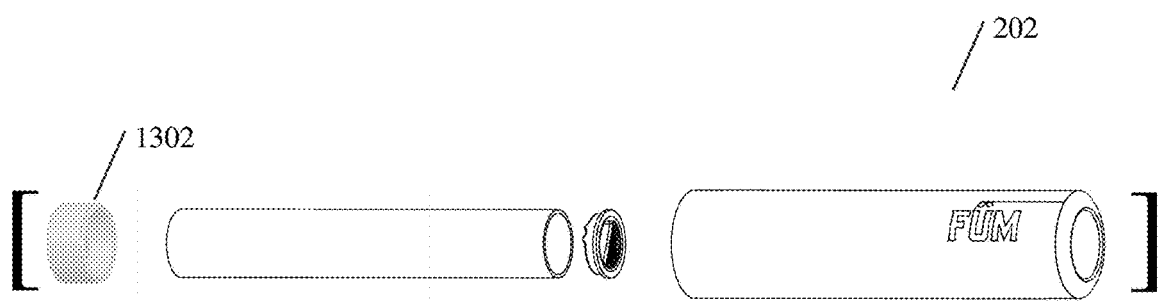
Figure 13C:
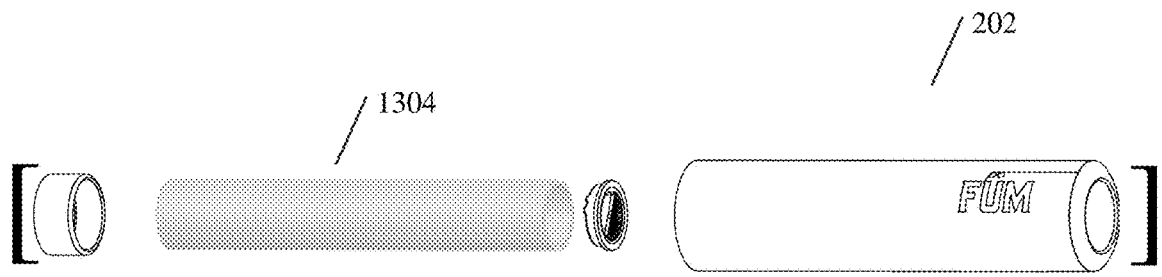
Figure 13D:
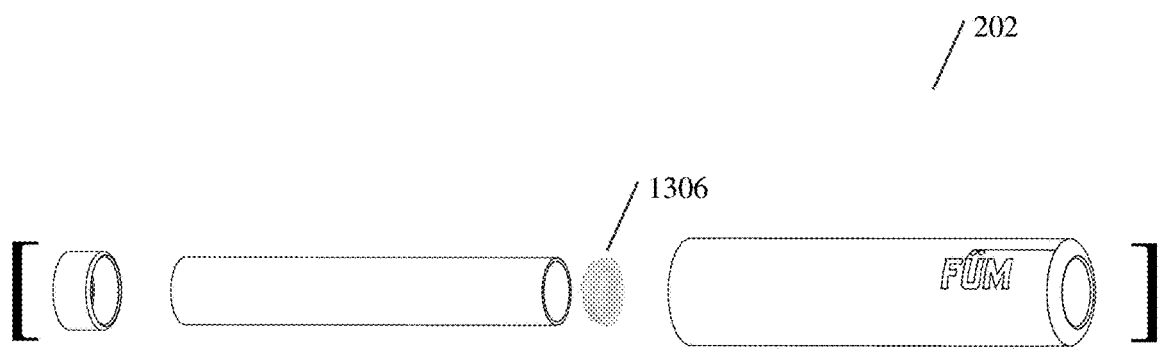
Figure 13E:
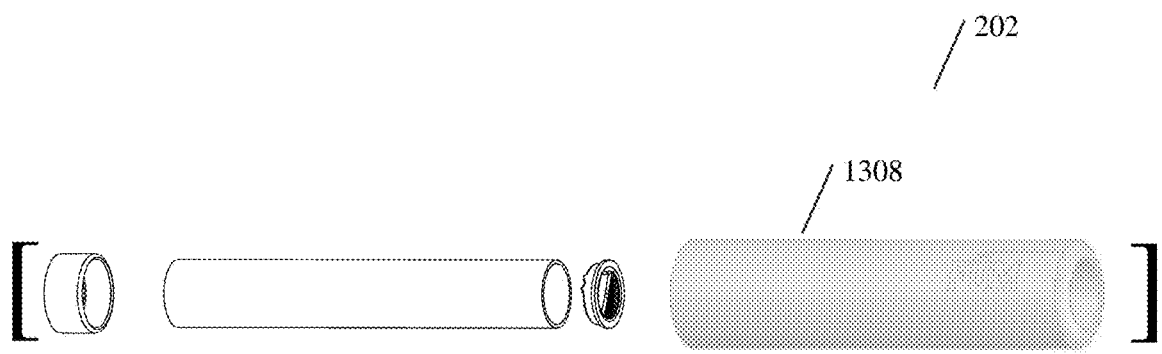

FIGS. 13B-13E provide the exploded view of the exemplary tip assembly shown in FIG. 13A, with each component shaded for emphasis: barrel collar (FIG. 13B), barrel tube (FIG. 13C), barrel plug (FIG. 13D), and barrel (FIG. 13E).

Figure 14:
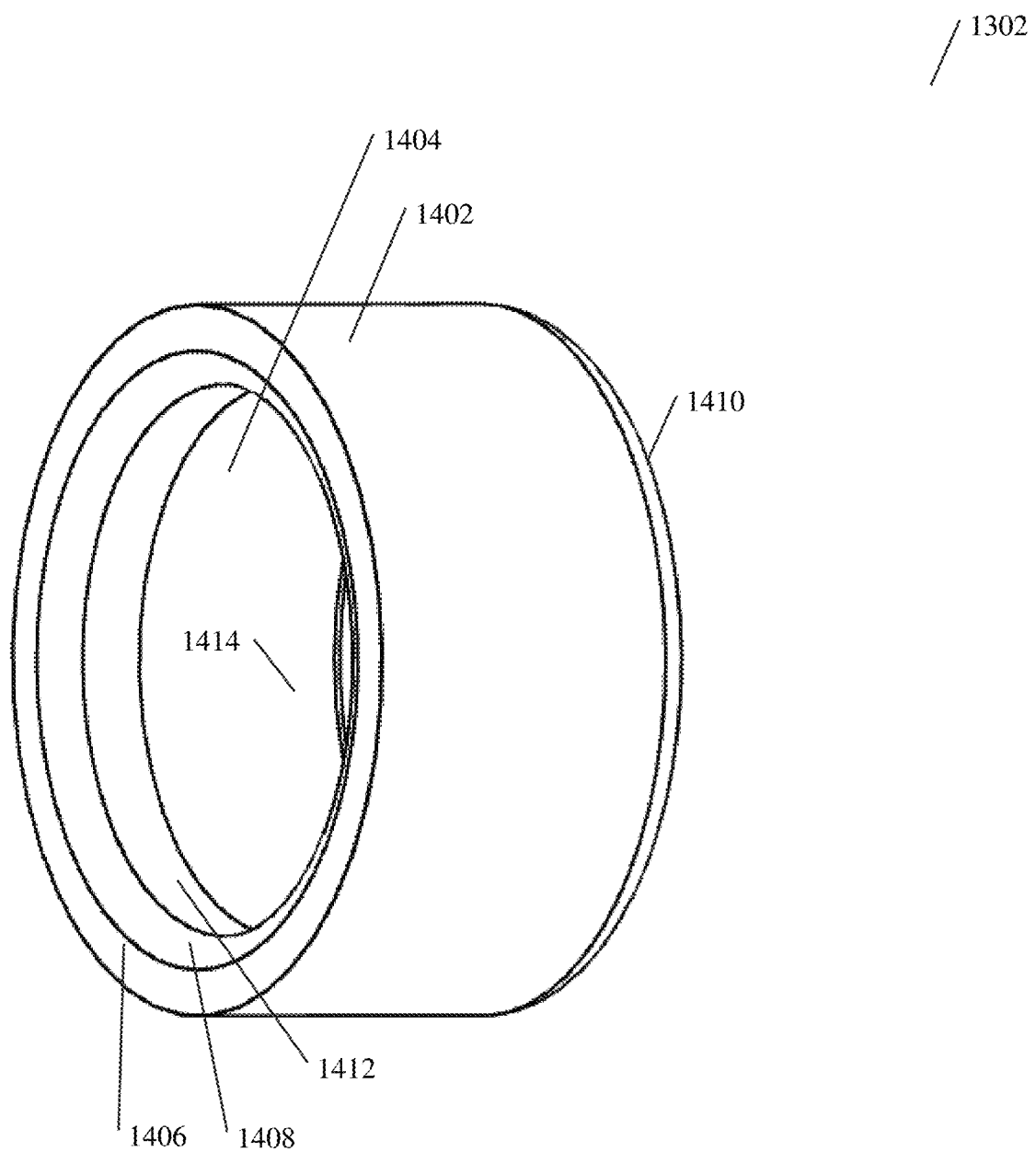

FIG. 14 provides an exemplary embodiment of a barrel collar.

Figure 15:
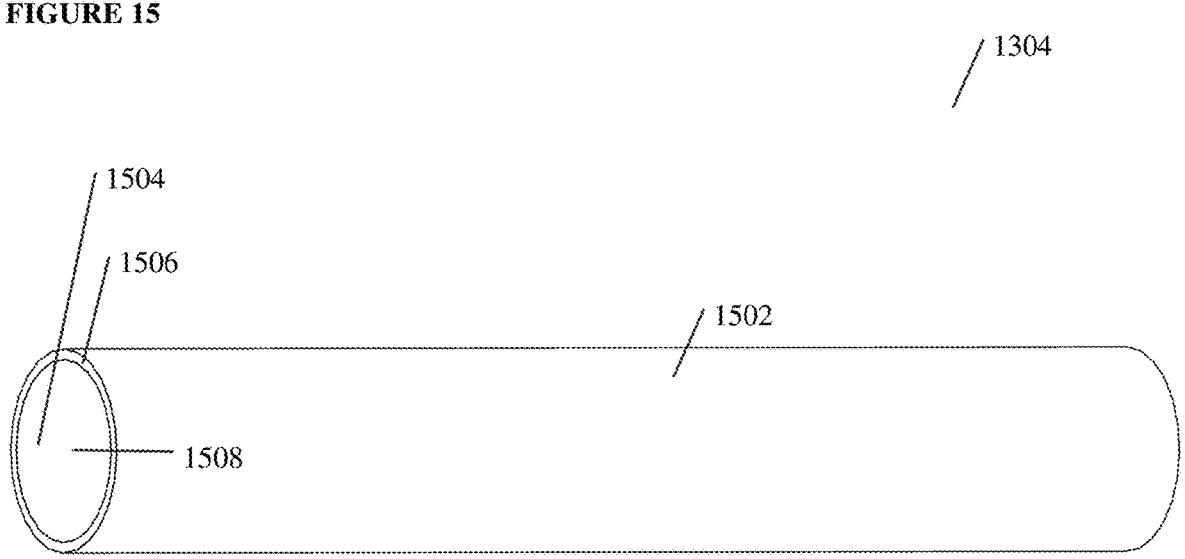

FIG. 15 provides an exemplary embodiment of a barrel tube.

Figure 16:
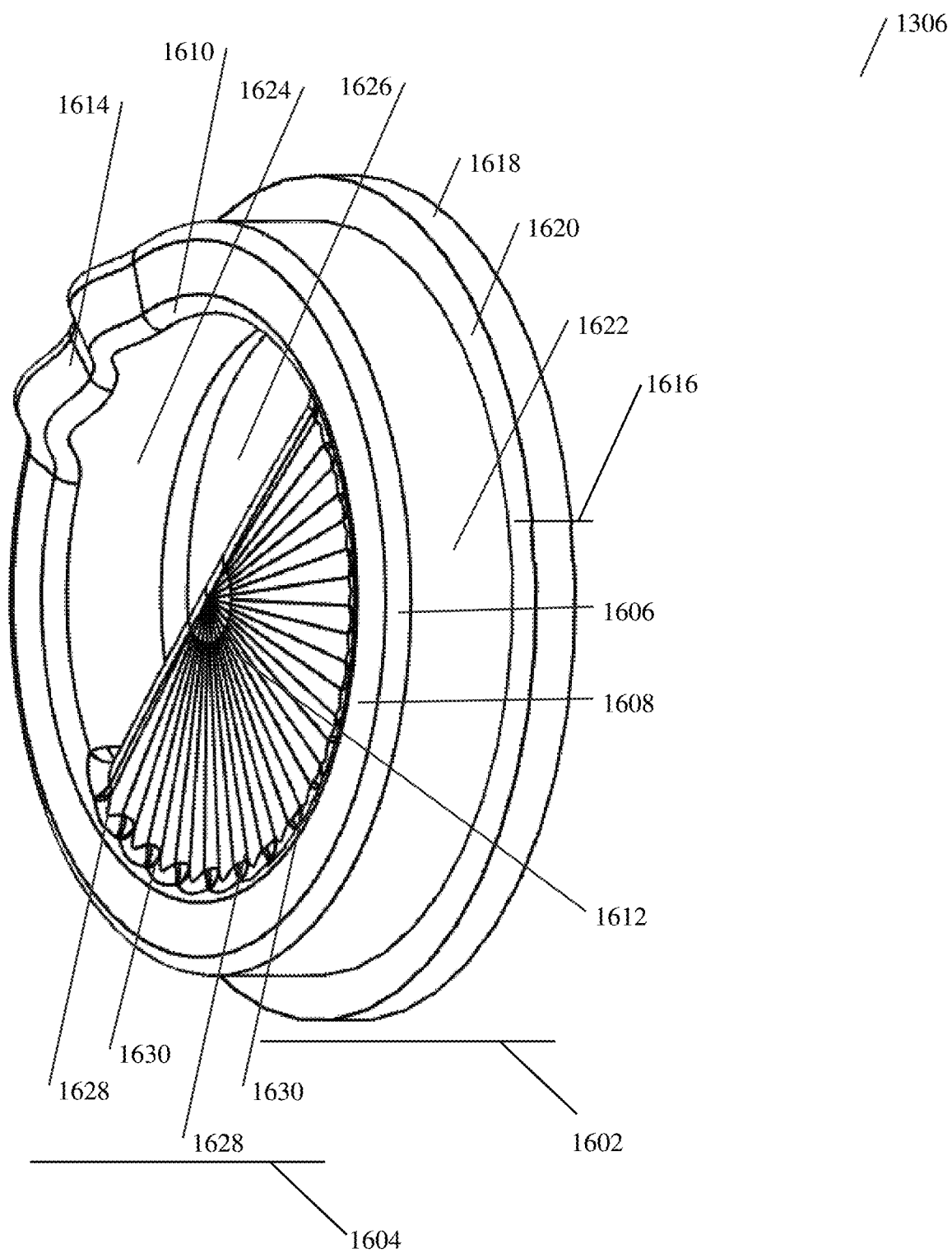

FIG. 16 provides an exemplary embodiment of a barrel plug.

Figure 17A:

FIG. 17A provides an exemplary embodiment of a barrel.

Figure 17B:
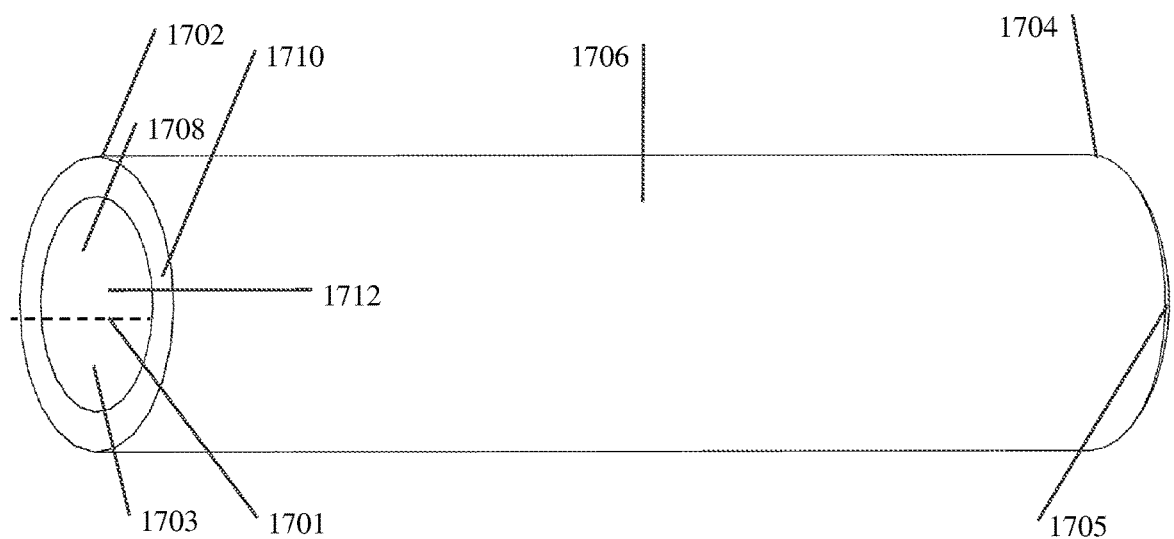

FIG. 17B provides an exemplary embodiment of a barrel, as an element of a tip assembly, in relation to an exemplary body assembly.

Figure 18A:
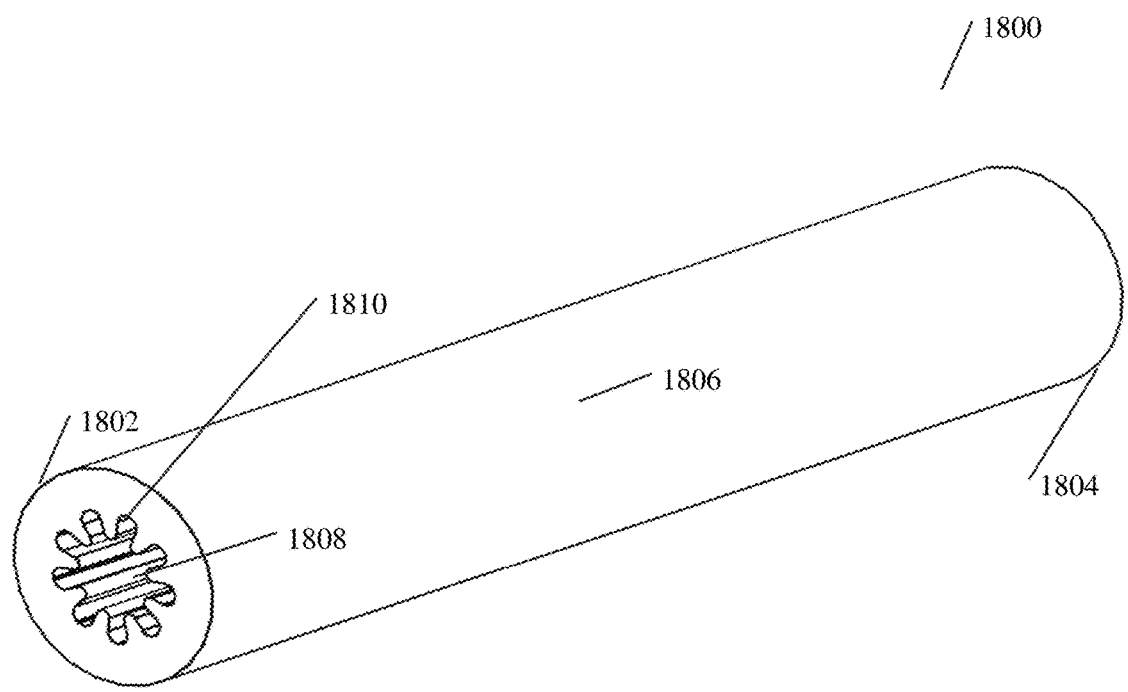
Figure 18B:
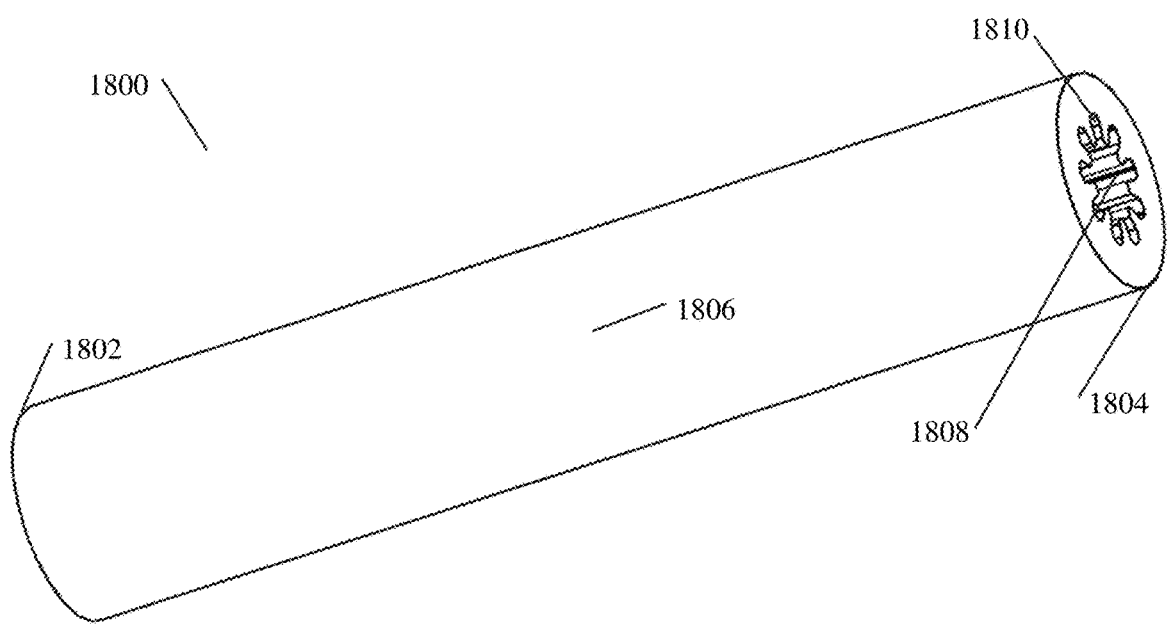
Figure 18C:
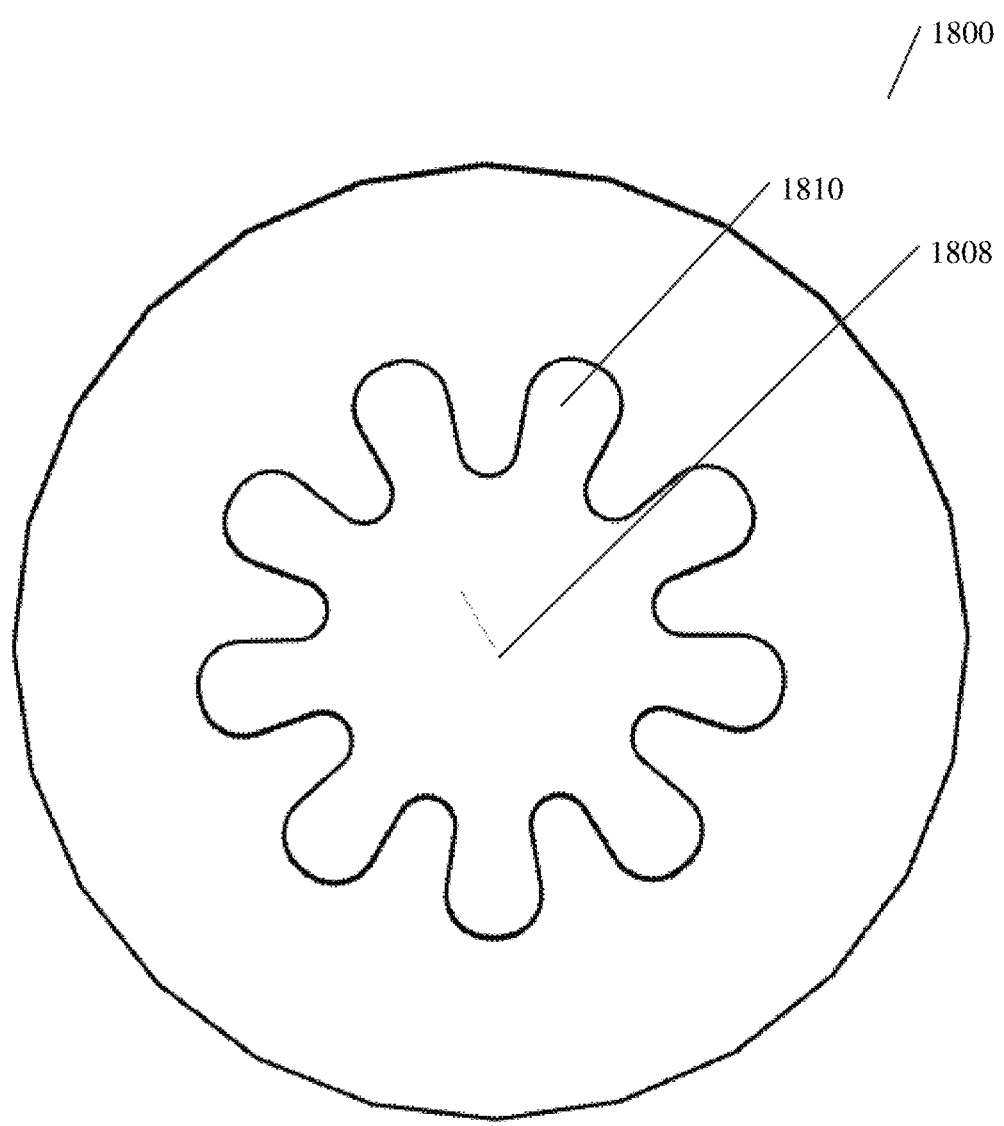

FIGS. 18A-18C, including FIGS. 18A, 18B, and 18C, provide an exemplary embodiment of a core insert viewed from different perspectives.

Figure 19:
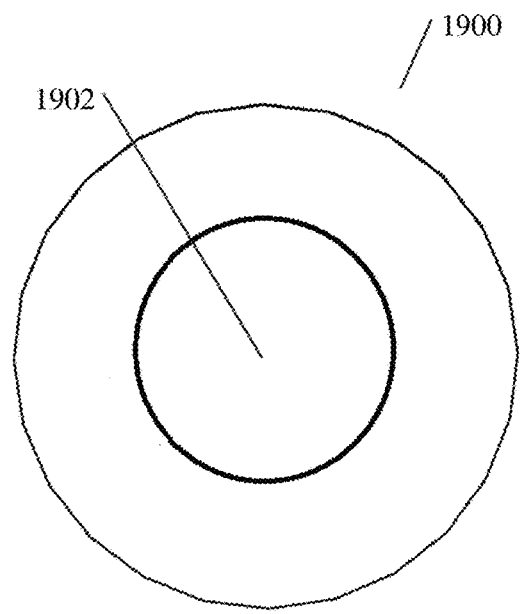

FIG. 19 provides an exemplary embodiment of a core insert as viewed from an end of the insert.

Figure 20:
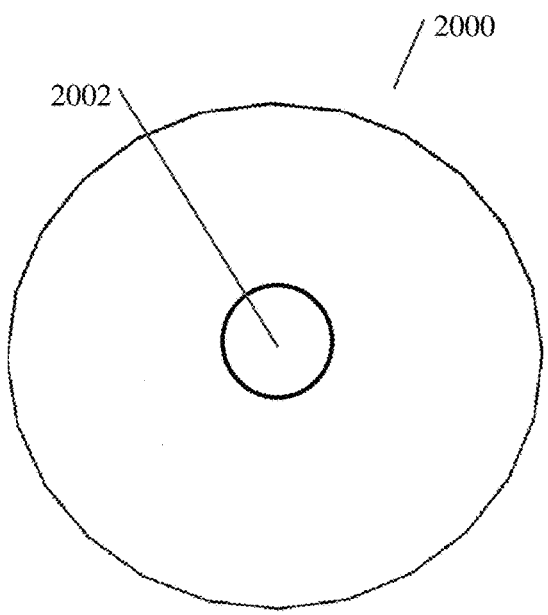

FIG. 20 provides an exemplary embodiment of a core insert as viewed from an end of the insert.

Figure 21:
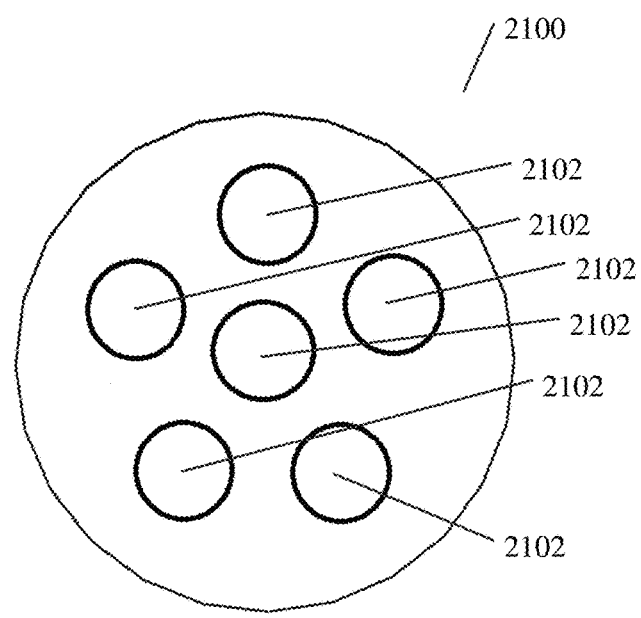

FIG. 21 provides an exemplary embodiment of a core insert as viewed from an end of the insert.

Figure 22A:
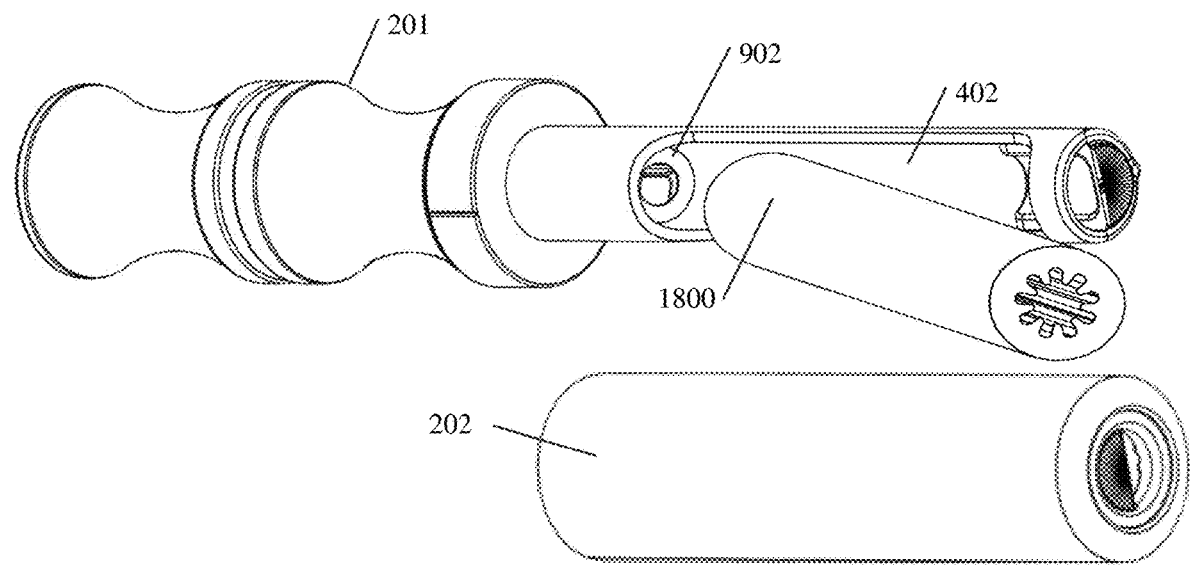
Figure 22B:
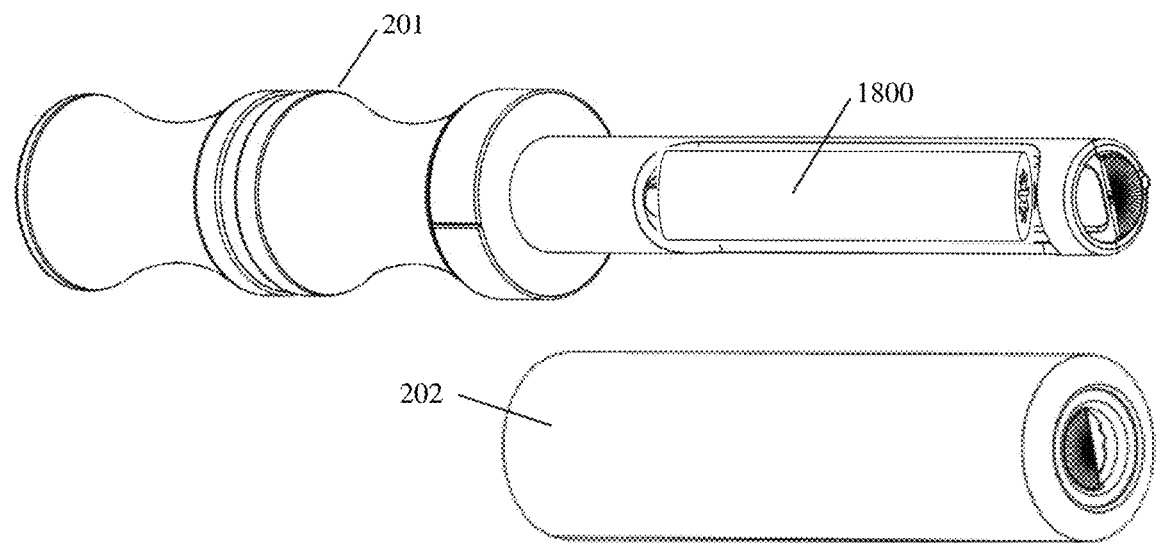

FIGS. 22A and 22B provide a simple visual description of the insertion of an exemplary core insert into an exemplary device.

Figure 23:
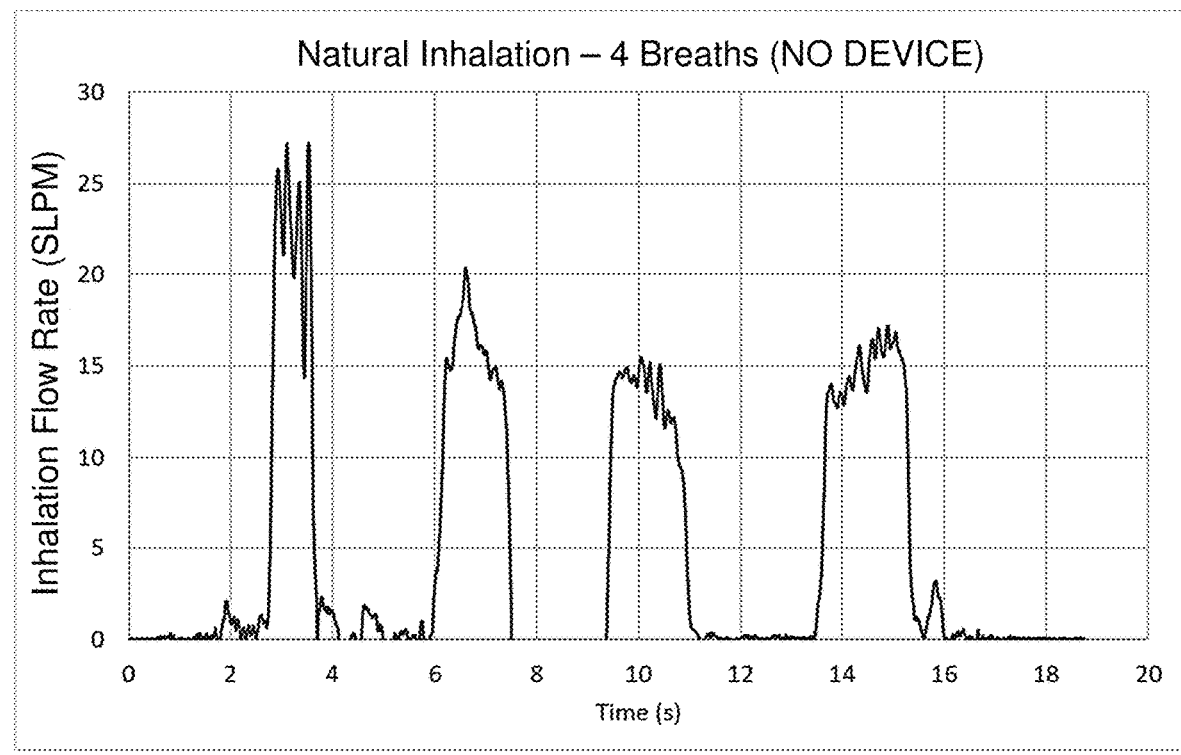

FIG. 23 provides a graph illustrating the results of an analysis of natural inhalation (no device) from an airflow control test.

Figure 24:
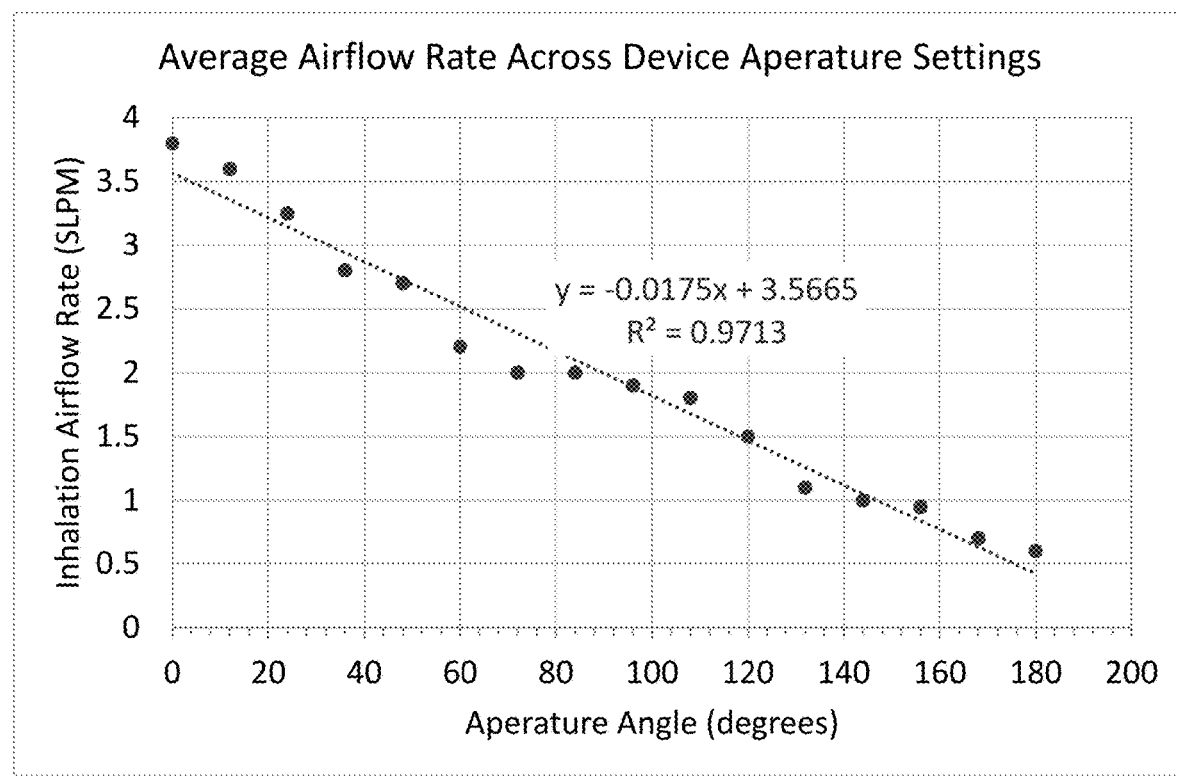

FIG. 24 provides a graph illustrating the results of an analysis of average flow rates through a device set across a spectrum of device airflow control settings.

EXEMPLARY ASPECTS OF THE INVENTION

The following is a non-limiting list of exemplary aspects of the invention, which illustrates embodiments of the invention in a summary form to aid readers in quickly understanding the overall scope of the invention. Similar to patent claims, listed aspects described in the paragraphs of this section may refer to (depend on/from) one or more other paragraphs. Readers will understand that such references mean that the features/characteristics or steps of such referenced aspects are incorporated into/combined with the referring aspect. E.g., if an aspect in a paragraph (e.g., a paragraph indicated by text at the end of the paragraph as aspect 2) refers to another aspect by one or more aspect numbers (e.g., aspect 1 or "any one of aspects 1-3"), it will be understood to include the elements, steps, or characteristics of such referenced aspects (e.g., aspect 1) in addition to those of the aspect in which the reference is made (e.g., if aspect 2 refers to aspect 1, it provides a description of a composition, method, system, device, etc., including the features of both aspect 1 and aspect 2).

Lists of aspects describing specific exemplary embodiments of the invention are sometimes employed for aiding the reader in understanding the invention. Such aspects can, within them, reference other exemplary aspects, either individually or as groups of aspects (e.g., via reference to a range within a list of numbered aspects when such aspects are provided as a numbered list). Reference to ranges of aspects should be interpreted as referencing all such aspects individually, each as unique embodiments of the invention, and in any combination with one another as unique embodiment(s) of the invention, according to the presentation provided of such aspects unless such an aspect within such a referenced range is either contradictory or non-sensical. If contradicted, reference to the contradictory aspect should be excluded. Uncontradicted, elements described in any one or more aspects of a list of aspects of the invention can be combined with one or more elements of any one or more other aspects of the invention described herein.

In a first aspect, the invention provides a non-electronic, non-heating inhalation device for the inhalation of one or more volatile compounds, the inhalation device comprising a first component and a second component releasably held together by a selectively releasable attachment mechanism, such that the first component and second component can be completely disengaged from one another or, alternatively, can be securely bound to one another, the inhalation device further comprising an adjustable airflow control mechanism controlled by the rotation of the first component and the second component relative to one another. ASPECT 1.

In one aspect, the invention provides a non-electronic, non-heating inhalation device for the inhalation of one or more volatile compounds, the body of the inhalation device comprising at least a first component and a second component releasably bound together by a magnetic force. ASPECT 2.

In one aspect, the invention provides a non-electronic, non-heating inhalation device for the inhalation of one or more volatile compounds, the inhalation device comprising at least one visual indicator present on the exterior of the device wherein the spatial orientation of the at least one visual indicator indicates the spatial orientation of at least one component of the device which is not externally visible. ASPECT 3.

In one aspect, the invention provides a non-electronic, non-heating inhalation device for the inhalation of one or more compounds, the inhalation device comprising at least two visual indicators present on the exterior of the device, wherein the spatial orientation of at least one visual indicator relative to at least one other visual indicator provides an indication of at least one operational status of the device. ASPECT 4.

In one aspect, the invention provides a non-electronic, non-heating inhalation device for the inhalation of one or more compounds, the inhalation device comprising at least two visual indicators present on the exterior of the device, wherein (a) the spatial orientation of at least one visual indicator indicates the spatial orientation of at least one component of the device which is not externally visible and (b) the spatial orientation of at least one visual indicator relative to at least one other visual indicator provides an indication of at least one operational status of the inhalation device. ASPECT 5.

In aspects, the invention provides a non-electronic, non-heating inhalation device for the delivery of one or more volatile compounds, the inhalation device comprising an airflow control mechanism wherein the airflow control mechanism is adjustable in pre-defined increments. ASPECT 6.

In aspects, the invention provides a non-electronic, non-heating inhalation device for the delivery of one or more volatile compounds, the inhalation device comprising an airflow path through the device and an adjustable airflow control mechanism, wherein the adjustable airflow control mechanism comprises a closure mechanism for the airflow path, the closure mechanism comprising at least three distinct airflow control settings, wherein moving from any first airflow control setting to any second airflow control setting provides a pre-determined increase or pre-determined decrease in airflow through the device. ASPECT 7.

In aspects, the invention provides a non-electronic, non-heating inhalation device for the delivery of one or more volatile compounds, the inhalation device comprising an airflow control mechanism wherein the airflow control mechanism comprises a first component and a second component completely separable from one another during normal use of the inhalation device. ASPECT 8.

In aspects, the invention provides a non-electronic, non-heating inhalation device for the delivery of one or more volatile compounds, the inhalation device comprising an airflow control mechanism adjustable by the movement of a first airflow control component relative to a second airflow control component, wherein (a) the movement of the first airflow control component relative to the second airflow control component is a relational movement, (b) the movement of the first airflow control component relative to the second airflow control component is a concurrent or associated relational movement, (c) the movement of the first airflow control component relative to the second airflow control component is a rotational movement and, optionally, the rotation of the first airflow control component relative to a second airflow control component can comprise a rotation of 360 degrees, or (d) any one, combination of two or more, or all of (a)-(c) are true. ASPECT 9.

In aspects, the invention provides a non-electronic, non-heating inhalation device for the delivery of one or more volatile compounds, the device comprising an airflow control mechanism for establishing airflow control setting(s), the airflow control mechanism comprising a first airflow control component and a second airflow control component, each of the first airflow control component and the second airflow control component having an amount of interface with the other at each airflow control setting, and wherein the amount of interface between the first component and the second component decreases between any first airflow control setting and any second airflow control setting compared to the amount of interface between the first and second components of the airflow control mechanism at any first or second airflow control setting. ASPECT 10.

In one aspect, the invention provides a non-electronic, non-heating inhalation device for the inhalation of one or more volatile compounds, the inhalation device comprising an adjustable airflow control mechanism wherein a change between any first airflow control setting and any second airflow control setting is accompanied by a tactile indicator. ASPECT 11.

In one aspect, the invention provides a non-electronic, non-heating inhalation device for the inhalation of one or more volatile compounds, the inhalation device comprising an adjustable airflow control mechanism having two distinct tactile indicators differentiating between a maximally closed airflow control setting and a partially open airflow control setting. ASPECT 12.

In one aspect, the invention provides a non-electronic, non-heating inhalation device for the inhalation of one or more volatile compounds comprising an internal compartment designed to hold a solid, infusible, or solid and infusible material device comprising one or more volatile compounds, wherein the internal compartment has at least one dimension which is at least half as long as the longest dimension of the solid material device. ASPECT 13.

In one aspect, the invention provides a non-electronic, non-heating inhalation device for the inhalation of one or more volatile compounds comprising an internal compartment designed to hold a solid material device capable of maintaining, releasing, or maintaining and releasing one or more of the volatile compounds, wherein the internal compartment completely surrounds (or encircles) at least a first portion of the solid material device and wherein the internal compartment only partially surrounds at least a second portion of the solid material device. ASPECT 14.

In one aspect, the invention provides the device of any one or more of aspects 1-14, wherein the device is designed for the inhalation of one or more volatile compounds via the mouth of the inhalation device user. ASPECT 15.

In one aspect, the invention provides the inhalation device of any one or more of aspects 1-15, wherein the device comprises at least a first component and a second component bound together by a selectively releasable attachment mechanism. ASPECT 16.

In one aspect, the invention provides the inhalation device of aspect 16, wherein the selectively releasable attachment mechanism is a rapidly releasable attachment mechanism. ASPECT 17.

In one aspect, the invention provides the inhalation device of aspect 17, wherein the rapidly releasable attachment mechanism is a rapidly releasable force mechanism. ASPECT 18.

In one aspect, the invention provides the inhalation device of any one or both of aspect 17 or aspect 18, wherein the rapidly releasable force mechanism is a snap fit or magnetic attraction. ASPECT 19.

In one aspect, the invention provides the inhalation device of aspect 16, wherein the selectively releasable attachment mechanism is not a screw-fit mechanism. ASPECT 20.

In one aspect, the invention provides the inhalation device of any one or more of aspects 18-20, wherein the rapidly releasable force mechanism is a magnetic force. ASPECT 21.

In one aspect, the invention provides the inhalation device of aspect 21, wherein the strength of the magnetic force is between about 1 gauss (0.0001 tesla) and about 2000 gauss (0.2 tesla). ASPECT 22.

In one aspect, the invention provides the inhalation device of aspect 22, wherein the strength of the magnetic force is between about 1 gauss (0.0001 tesla) and about 1000 gauss (0.1 tesla). ASPECT 23.

In one aspect, the invention provides the inhalation device of aspect 23, wherein the strength of the magnetic force is about 500 gauss (0.05 tesla). ASPECT 24.

In one aspect, the invention provides the inhalation device of aspect 21, wherein the strength of the magnetic force is sufficient to lift a weight of between 1 g and about 500 g. ASPECT 25.

In one aspect, the invention provides the inhalation device of aspect 25, wherein the strength of the magnetic force is sufficient to lift a weight of between about 10 g and about 400 g. ASPECT 26.

In one aspect, the invention provides the inhalation device of aspect 26, wherein the strength of the magnetic force is sufficient to lift a weight of about 300 g. ASPECT 27.

In one aspect, the invention provides the inhalation device of any one or more of aspects 16-27, wherein the selectively releasable attachment mechanism is a rapidly releasable force mechanism operable with a single hand of a user, such that the first and second components of the inhaler can be separated and re-attached repeatedly by the single hand (single hand movement(s)) of the user. ASPECT 28.

In one aspect, the invention provides the inhalation device of any one or more of aspects 16-28, wherein the selectively releasable attachment mechanism is a rapidly releasable force mechanism capable of providing an entertainment experience for the user separate from any volatile compound(s) inhalation experience provided by the device. ASPECT 29.

In one aspect, the invention provides the inhalation device of any one or more of aspects 1-29, wherein the device provides an experience, e.g., a manually-focused experience characterizable as a "fidget" experience capable of detectably or significantly reducing one or more non-inhalation smoking habit-related craving(s) as measured or reported by the user or as measured by an appropriately conducted and powered trial or survey administered or conducted by suitably trained individual(s) recognized as capable of identifying reduction in addiction-related behavior. ASPECT 30.

In one aspect, the invention provides the inhalation device of aspect 30, wherein the manually-focused "fidget" experience is derived from (a) the rotation of the first component of the device relative to the second component of the device, (b) the repeated disengagement and re-engagement of the first component of the device relative to the second component of the device, or (c) any combination of (a) and (b). ASPECT 31.

In one aspect, the invention provides the inhalation device of any one or more of aspects 1-31, wherein the device comprises a first primary component and a second primary component and wherein the first component and the second component are movable relative to one another. ASPECT 32.

In one aspect, the invention provides the inhalation device of aspect 32, wherein the first component of the device comprises at least one visual indicator. ASPECT 33.

In one aspect, the invention provides the inhalation device of any one or both of aspect 32 or aspect 33, wherein the second component of the device comprises at least one visual indicator. ASPECT 34.

In one aspect, the invention provides the inhalation device of any one or more of aspects 32-34, wherein each of the first device component and the second device component comprise one or more visual indicator(s). ASPECT 35.

In one aspect, the invention provides the inhalation device of any one or more of aspects 32-35, wherein a visual indicator comprises a tick mark, intentional scratch, carving, engraved element, painted marking, stamped marking, or any other type of visually observable marking such as, e.g., a line or other shape, number, letter, symbol, or collection of letters, numbers, or symbols (e.g., a word, name, or other product identifier), or image. ASPECT 36.

In one aspect, the invention provides the inhalation device of any one or more of aspects 32-36, wherein at least one visual indicator is different from at least one other visual indicator. ASPECT 37.

In one aspect, the invention provides the inhalation device of aspect 37, wherein at least one visual indicator is a tick mark and at least one visual indicator is a product logo. ASPECT 38.

In one aspect, the invention provides the inhalation device of any one or more of aspects 32-38, wherein the spatial orientation of one or more visual indicators on the first component of the device, when interpreted alone or in relation to the positioning of one or more indicators on the second component, indicate(s) one or more operational characteristics of the device. ASPECT 39.

In one aspect, the invention provides the inhalation device of aspect 39, wherein the positioning of one or more indicators on the first component of the device indicate(s) the spatial orientation of one or more components of the device which are not externally visible. ASPECT 40.

In one aspect, the invention provides the inhalation device of any one or both of aspect 39 or aspect 40, wherein the positioning of one or more visual indicator(s) on the first component of the device, when interpreted in relationship to the positioning of one or more visual indicator(s) on the second component of the device, indicate the operational status of an airflow control mechanism present within the device, e.g., the degree to which the device is open to airflow therethrough. ASPECT 41.

In one aspect, the invention provides the inhalation device of any one or more of aspects 32-41, wherein the device comprises at least two externally visible visual indicators that, when the device is in a ready to use state, provide an indication of at least two operational characteristics of the device. ASPECT 42.

In one aspect, the invention provides the device of aspect 42, wherein at least one of the operational characteristics is the spatial orientation of a component of the device which is not externally visible. ASPECT 43.

In one aspect, the invention provides the inhalation device of aspect 43, wherein the component of the device which is not externally visible is a component that participates in maintaining a removable insert capable of maintaining, releasing, or maintaining and releasing one or more volatile compounds during use of the device. ASPECT 44.

In one aspect, the invention provides the inhalation device of any one or more of aspects 42-44, wherein at least one of the operational characteristics is an indication of the status of an airflow control mechanism of the inhalation device. ASPECT 45.

In one aspect, the invention provides the inhalation device of any one or more of aspects 1-45, wherein the device comprises a component which stably maintains a removable insert therein, the removable insert being an insert capable of holding, releasing, or holding and releasing one or more volatile compounds for inhalation. ASPECT 46.

In one aspect, the invention provides the inhalation device of aspect 46, wherein the device comprises a first component (e.g., "first primary" component) and a second component (e.g., a "second primary" component) releasably engaged to one another by a selectively releasable attachment (engagement) mechanism and wherein the component stably maintaining the removable insert is an internal component attached to, directly or indirectly, the first component of the device but resides at least predominantly (e.g., at least ≥50%), at least generally (e.g., at least ≥75%, or at least substantially (e.g., at least ≥95%) within the second component of the device when the first device component and the second device component are releasably engaged to one another by the selectively releasable engagement (attachment) mechanism. ASPECT 47.

In one aspect, the invention provides the inhalation device of aspect 47, wherein at least about 60% of the internal component stably maintaining the removable insert resides within the second device component when the first device component and the second device component are releasably bound to one another by the selectively releasable attachment mechanism. ASPECT 48.

In one aspect, the invention provides the inhalation device of aspect 48, wherein at least about 70% of the internal component stably maintaining the removable insert resides within the second device component when the first device component and the second device component are releasably bound to one another by the selectively releasable attachment mechanism. ASPECT 49.

In one aspect, the invention provides the inhalation device of aspect 49, wherein at least about 80% of the internal component stably maintaining the removable insert resides within the second device component when the first device component and the second device component are releasably bound to one another by the selectively releasable attachment mechanism. ASPECT 50.

In one aspect, the invention provides the inhalation device of aspect 50, wherein at least about 90% of the internal component stably maintaining the removable insert resides within the second device component when the first device component and the second device component are releasably bound to one another by the selectively releasable attachment mechanism. ASPECT 51.

In one aspect, the invention provides the inhalation device of aspect 51, wherein about 100% of the internal component stably maintaining the removable insert resides within the second device component when the first device component and the second device component are releasably bound to one another by the selectively releasable attachment mechanism. ASPECT 52.

In one aspect, the invention provides the inhalation device of any one or more of aspects 46-52, wherein the component maintaining the removable insert is an internal component comprising at least one dimension which is at least half as long as the longest dimension of the removable insert. ASPECT 53.

In one aspect, the invention provides the inhalation device of aspect 53, wherein the internal component comprises at least one dimension which is at least as long as the longest dimension of the removable insert. ASPECT 54.

In one aspect, the invention provides the inhalation device of aspect 54, wherein the internal component comprises at least one dimension which is longer than the longest dimension of the removable insert. ASPECT 55.

In one aspect, the invention provides the inhalation device of any one or more of aspects 46-55, wherein the component stably maintaining the removable insert comprises a compressible element capable of being both compressed by a force and applying an opposing force to such compression. ASPECT 56.

In one aspect, the invention provides the inhalation device of aspect 56, wherein the component is an internal compartment and the compressible element aids in the stable maintenance of a removable insert within the internal compartment. ASPECT 57.

In one aspect, the invention provides the inhalation device of any one or more of aspects 46-57, wherein the component stably maintaining a removable insert is an internal component, and wherein the internal component maintains a removable insert having a first end and a second end within it by the application of opposing first and second forces to first and second ends of the removable insert. ASPECT 58.

In one aspect, the invention provides the inhalation device of aspect 58, wherein at least one of the opposing first and second forces is applied as a restoring force. ASPECT 59.

In one aspect, the invention provides the inhalation device of aspect 59, wherein at least one of the opposing first and second forces is induced only upon the application of a first opposing force. ASPECT 60.

In one aspect, the invention provides the inhalation device of any one of aspects 58-60, wherein the first force applied to the first end of the removable insert is a restoring force and the second force is applied to the second end of the removable insert by a fixed element preventing movement of the removable insert in the direction of the applied restoring force. ASPECT 61.

In one aspect, the invention provides the inhalation device of aspect 61, wherein the fixed element comprises a thickness (e.g., depth) which is less than 100% of the depth of the internal component, the removable insert, or both. ASPECT 62.

In one aspect, the invention provides the inhalation device of aspect 62, wherein the fixed element comprises a thickness (e.g., depth) which is less than 75% of the depth of the internal component, the removable insert, or both. ASPECT 63.

In one aspect, the invention provides the inhalation device of aspect 63, wherein the fixed element comprises a thickness (e.g., depth) which is less than 50% of the depth of the internal component, the removable insert, or both. ASPECT 64.

In one aspect, the invention provides the inhalation device of aspect 64, wherein the fixed element comprises a thickness (e.g., depth) which is less than 25% of the depth of the internal component, the removable insert, or both. ASPECT 65.

In one aspect, the invention provides the inhalation device of any one or more of aspects 61-65, wherein the fixed element extends into an interior portion of the internal component which is not enclosed by a circumferentially disposed wall of the internal component. ASPECT 66.

In one aspect, the invention provides the inhalation device of any one or more of aspects 61-66, wherein the fixed element has at least two dimensions which join together in an orientation which is not 90 degrees. ASPECT 67.

In one aspect, the invention provides the inhalation device of aspect 67, wherein the non-90-degree orientation of the two dimensions facilitates the ease of entry, the smoothness of entry, or both the ease and smoothness of entry of a removable insert into the internal component. ASPECT 68.

In one aspect, the invention provides the inhalation device of any one or more of aspects 47-68, wherein the internal component is a component of the first component of the device and wherein, when the first component of the device and second component of the device are sufficiently separated from one another, a removable insert capable of holding, releasing, or holding and releasing one or more volatile compounds can be laterally inserted into and stably held by the exposed internal component. ASPECT 69.

In one aspect, the invention provides the inhalation device of any one or more of aspects 47-69, wherein the internal component stably maintains a removable insert therein when both the first device component and the second device component are separated from one another and when the first device component and the second device component are bound to one another by a releasable force mechanism. ASPECT 70.

In one aspect, the invention provides the inhalation device of any one or more of aspects 1-70, wherein the device receives the insertion of a removable insert capable of maintaining, releasing, or maintaining and releasing one or more volatile compounds for inhalation from a direction which does not correspond to, is not parallel to, or does not correspond to the long axis of the inhalation device. ASPECT 71.

In one aspect, the invention provides the inhalation device of any one or more of aspects 1-71, wherein the device receives the insertion of a removable insert capable of maintaining, releasing, or maintaining and releasing one or more volatile compounds for inhalation from a direction which is lateral to the long axis of the inhalation device. ASPECT 72.

In one aspect, the invention provides the inhalation device of any one or more of aspects 46-72, wherein the component stably maintaining the removable insert is an internal compartment having a width, a depth, and a length, the length being the longest dimension of the internal compartment, and wherein the internal compartment receives a removable insert from a position lateral to its length via an opening in a wall defining the length of the internal compartment which does not completely circumferentially surround the internal compartment. ASPECT 73.

In one aspect, the invention provides the inhalation device of any one or more of aspects 46-73, wherein the component stably maintaining the removable insert is an internal compartment comprising an interior defined by a circumferentially disposed wall between a first end and a second end of the internal compartment, wherein the wall is at least partially opened along at least one portion of the length between the first and second ends of the compartment and fully enclosed along at least one portion of the length between the first and second ends of the compartment. ASPECT 74.

In one aspect, the invention provides the inhalation device of any one or more of aspects 46-74, wherein the component stably maintaining the removable insert is a partially enclosed internal compartment such that when a removable insert is present in the compartment, at least a portion of the removable insert is completely surrounded by a circumferentially disposed wall of the compartment and at least a portion of the removable insert is only partially surrounded by the wall of the compartment. ASPECT 75.

In one aspect, the invention provides the inhalation device of any one or more of aspects 46-75, wherein the internal component is an internal compartment comprising a circumferentially disposed wall defining a compartment interior, wherein the circumferentially disposed wall at least partially surrounds the removable insert when the removable insert is present within the compartment. ASPECT 76.

In one aspect, the invention provides the inhalation device of aspect 76, wherein the circumferentially disposed wall defining the internal compartment interior at least partially surrounds the removable insert along at least one portion of the removable insert but does not surround the entirety of the length of the removable insert. ASPECT 77.

In one aspect, the invention provides the inhalation device of aspect 77, wherein the positioning of a fixed element within the internal compartment provides for the positioning of a removable insert having a first end and a second end, when present within the internal compartment, to be positioned such that at least one of the first and second ends of the removable insert is accessible via a portion of the internal compartment which is not fully enclosed by a circumferentially disposed wall defining the interior of the internal compartment. ASPECT 78.

In one aspect, the invention provides the inhalation device of aspect 77, wherein a fixed element within the internal compartment has a dimension, e.g., thickness or depth, which is sufficiently less than the depth of the internal compartment and the thickness of a removable insert such that when the removable insert is present in the internal compartment and is stably maintained in the internal compartment by a compressible element and the fixed element making contact with first end and second ends of the insert respectively, a user of the device can access at least a portion of the second end of the insert. ASPECT 79.

In one aspect, the invention provides the inhalation device of aspect 77, wherein a fixed element within the internal compartment is positioned such that a detectable or significant space exists between an end of a removable insert, when present in the internal compartment, and an edge of a partial opening in the internal compartment formed by the only partial surrounding of the removable insert by a circumferential wall defining the interior of the internal compartment, such that at least a portion of the end of the removable insert contacting the fixed element can be accessed. ASPECT 80.

In one aspect, the invention provides the inhalation device of any one or more of aspects 46-80, wherein the device comprises an internal compartment having a width, a depth, and a length, the internal compartment further comprising (a) a compressible element capable of being both compressed by a force and applying an opposing force to such compression, and (b) a fixed element positioned opposite the compressible element of (a) within the internal compartment, wherein (a) and (b) stably maintain a removable insert comprising one or more volatile compounds and having a width, a depth (or, e.g., a thickness), a first end, and a second end when such an insert is inserted therebetween, wherein the fixed element of (b) has a dimension, e.g., thickness, which is sufficiently less than the depth of the internal compartment and the depth or thickness of the removable insert such that when an insert is present in the compartment and is stably maintained in the compartment by the compressible element (a) and the fixed element (b) making contact with the first end and second end of the insert respectively, a user of the device can access at least a portion of the second end of the insert with their finger to facilitate removal of the removable insert. ASPECT 81.

In one aspect, the invention provides the inhalation device of any one or more of aspects 46-81, wherein the component stably maintaining the removable insert is an internal component not visible from the exterior of the device when the device is in a configuration ready for use, and wherein the spatial orientation of the internal compartment, is discernable by the spatial orientation of at least one visual indicator present on an external surface of the device. ASPECT 82.

In one aspect, the invention provides the inhalation device of any one or more of aspects 1-82, wherein the device comprises an adjustable airflow control mechanism comprising a first airflow control component and a second airflow control component and wherein the first and second airflow control components are in releasable contact with one another during normal operation of the device. ASPECT 83.

In one aspect, the invention provides the inhalation device of aspect 83, wherein the degree of interface between the first and second airflow control components is modifiable in three or more discrete (non-gradual) increments. ASPECT 84.

In one aspect, the invention provides the inhalation device of any one or both of aspect 83 or aspect 84, wherein the amount of contact between the first airflow control component and the second airflow control component is reduced between any first and second airflow control setting compared to the amount of contact between the two airflow control components when in any first and second airflow control settings. ASPECT 85.

In one aspect, the invention provides the inhalation device of any one or more of aspects 83-85, wherein the first and second airflow control components of the device can be completely separated from one another during operation of one or more features of the device. ASPECT 86.

In one aspect, the invention provides the inhalation device of any one or more of aspects 83-86, wherein the device comprises a first component and a second component movable in relation to one another, and the adjustable airflow control mechanism is controlled by the rotation of the first component and the second component relative to one another. ASPECT 87.

In one aspect, the invention provides the inhalation device of any one or more of aspects 83-87, wherein the first airflow control component and second airflow control component of the airflow control mechanism are rotatable in relation to on another, and further wherein the first component of the airflow control mechanism comprises at least one element which alternatingly nests within at least one element of the second component of the airflow control mechanism and similarly the second component of the airflow control mechanism comprises at least one element which alternatingly nests within at least one element of the first component of the airflow control mechanism as the first airflow control component and the second airflow control component of the airflow control mechanism are rotated in relation to one another. ASPECT 88.

In one aspect, the invention provides the inhalation device of any one or more of aspects 83-88, wherein the adjustable airflow control mechanism comprises a first part and a second part capable of rotating at least a full 360 degrees (e.g., at least one full rotation) in relation to one another. ASPECT 89.

In one aspect, the invention provides the inhalation device of aspect 89, wherein the at least 360-degree rotation includes within it three or more pre-determined, selectable, and distinct airflow control settings wherein moving from any first distinct airflow control setting to any second distinct airflow control setting provides a predetermined increase or decrease in airflow. ASPECT 90.

In one aspect, the invention provides the inhalation device of aspect 90, wherein the at least 360-degree rotation includes within it five or more pre-determined, selectable, and distinct airflow control settings wherein moving from any first distinct airflow control setting to any second distinct airflow control setting provides a predetermined increase or decrease in airflow. ASPECT 91.

In one aspect, the invention provides the inhalation device of aspect 91, wherein the at least 360 degree rotation includes within it ten (10) or more pre-determined, selectable, and distinct airflow control settings wherein moving from any first distinct airflow control setting to any second distinct airflow control setting provides a predetermined increase or decrease in airflow. ASPECT 92.

In one aspect, the invention provides the inhalation device of aspect 92, wherein the at least 360 degree rotation includes within it fifteen (15) or more pre-determined, selectable, and distinct airflow control settings wherein moving from any first distinct airflow control setting to any second distinct airflow control setting provides a predetermined increase or decrease in airflow. ASPECT 93.

In one aspect, the invention provides the inhalation device of any one or more of aspects 89-93, wherein the at least 360-degree rotation includes within it a single distinct airflow control setting indicating full closure of the airflow control mechanism. ASPECT 94.

In one aspect, the invention provides the inhalation device of any one or more of aspects 89-94, wherein the at least 360 degree rotation comprises within it (a) three or more distinct airflow control settings wherein moving from any first distinct airflow control setting to any second distinct airflow control setting provides a predetermined increase or decrease in airflow and (b) a single airflow control setting indicating full closure of the airflow control mechanism. ASPECT 95.

In one aspect, the invention provides the inhalation device of any one or more of aspects 84-95, wherein the airflow rate is decreased by between about 0.01-1 standard liters per minute (SLPM) on average with each single airflow control setting adjustment increment. ASPECT 96.

In one aspect, the invention provides the inhalation device of aspect 96, wherein the airflow rate is decreased by between about 0.01-0.8 standard liters per minute (SLPM) on average with each single airflow control setting adjustment increment. ASPECT 97.

In one aspect, the invention provides the inhalation device of aspect 97, wherein the airflow rate is decreased by between about 0.05-0.6 standard liters per minute (SLPM) on average with each single airflow control setting adjustment increment. ASPECT 98.

In one aspect, the invention provides the inhalation device of aspect 98, wherein the airflow rate is decreased by between about 0.1-0.4 standard liters per minute (SLPM) on average with each single airflow control setting adjustment increment. ASPECT 99.

In one aspect, the invention provides the inhalation device of aspect 99, wherein the airflow rate is decreased by about 0.2 standard liters per minute (SLPM) on average with each single airflow control setting adjustment increment. ASPECT 100.

In one aspect, the invention provides the inhalation device of any one or more of aspects 84-100, wherein the airflow rate is modified, e.g., either increased or decreased, by an amount of between about 1% and about 20% on average with each single airflow control setting adjustment increment. ASPECT 101.

In one aspect, the invention provides the inhalation device of aspect 101, wherein the airflow rate is modified, e.g., either increased or decreased, by an amount of between about 2% and about 18% on average with each single airflow control setting adjustment increment. ASPECT 102.

In one aspect, the invention provides the inhalation device of aspect 102, wherein the airflow rate is modified. e.g., either increased or decreased, by an amount of between about 5% and about 15% on average with each single airflow control setting adjustment increment. ASPECT 103.

In one aspect, the invention provides the inhalation device of aspect 103, wherein the airflow rate is modified, e.g., either increased or decreased, by an amount of between about 8% and about 13% on average with each single airflow control setting adjustment increment. ASPECT 104.

In one aspect, the invention provides the inhalation device of aspect 104, wherein the airflow rate is modified, e.g., either increased or decreased, by an amount of between about 10% and about 12% on average with each single airflow control setting adjustment increment. ASPECT 105.

In one aspect, the invention provides the inhalation device of aspect 105, wherein the airflow rate is modified, e.g., either increased or decreased, by an amount of about 11% on average with each single airflow control setting adjustment increment. ASPECT 106.

In one aspect, the invention provides the inhalation device of any one or more of aspects 84-106, wherein with each single airflow control setting adjustment increment, the airflow rate is modified, e.g., either increased or decreased, by an amount of representing between about 1% and about 10% on average of the average maximum airflow through the device present when the airflow control mechanism is in a maximally open configuration. ASPECT 107.

In one aspect, the invention provides the inhalation device of any one or more of aspects 84-107, wherein with each single airflow control setting adjustment increment, the airflow rate is modified, e.g., either increased or decreased, by an amount of representing between about 2% and about 8% on average of the average maximum airflow through the device present when the airflow control mechanism is in a maximally open configuration. ASPECT 108.

In one aspect, the invention provides the inhalation device of any one or more of aspects 84-108, wherein with each single airflow control setting adjustment increment, the airflow rate is modified, e.g., either increased or decreased, by an amount of representing between about 3% and about 7% on average of the average maximum airflow through the device present when the airflow control mechanism is in a maximally open configuration. ASPECT 109.

In one aspect, the invention provides the inhalation device of any one or more of aspects 84-109, wherein with each single airflow control setting adjustment increment, the airflow rate is modified, e.g., either increased or decreased, by an amount of representing between about 4% and about 6% on average of the average maximum airflow through the device present when the airflow control mechanism is in a maximally open configuration. ASPECT 110.

In one aspect, the invention provides the inhalation device of any one or more of aspects 84-110, wherein with each single airflow control setting adjustment increment, the airflow rate is modified, e.g., either increased or decreased, by an amount of representing about 5% on average of the average maximum airflow through the device present when the airflow control mechanism is in a maximally open configuration. ASPECT 111.

In one aspect, the invention provides the inhalation device of any one or more of aspects 83-111, wherein the airflow control mechanism is capable of decreasing the airflow through the device by between about 20% and about 100% on average when modified from its maximum airflow configuration (maximally open position) to its minimum airflow configuration (maximally closed position). ASPECT 112.

In one aspect, the invention provides the inhalation device of any one or more of aspects 83-112, wherein the airflow control mechanism is capable of decreasing the airflow through the device by between about 40% and about 95% on average when modified from its maximum airflow configuration (maximally open position) to its minimum airflow configuration (maximally closed position). ASPECT 113.

In one aspect, the invention provides the inhalation device of any one or more of aspects 83-113, wherein the airflow control mechanism is capable of decreasing the airflow through the device by between about 60% and about 90% on average when modified from its maximum airflow configuration (maximally open position) to its minimum airflow configuration (maximally closed position). ASPECT 114.

In one aspect, the invention provides the inhalation device of any one or more of aspects 83-114, wherein the airflow control mechanism is capable of decreasing the airflow through the device by between about 70% and about 85% on average when modified from its maximum airflow configuration (maximally open position) to its minimum airflow configuration (maximally closed position). ASPECT 115.

In one aspect, the invention provides the inhalation device of any one or more of aspects 83-115, wherein the airflow control mechanism is capable of decreasing the airflow through the device by between about 80% and about 85% on average when modified from its maximum airflow configuration (maximally open position) to its minimum airflow configuration (maximally closed position). ASPECT 116.

In one aspect, the invention provides the inhalation device of any one or more of aspects 83-116, wherein the airflow control mechanism is capable of decreasing the airflow through the device by about 84% on average when modified from its maximum airflow configuration (maximally open position) to its minimum airflow configuration (maximally closed position). ASPECT 117.

In one aspect, the invention provides the inhalation device of any one or more of aspects 83-117, wherein modification of the airflow control mechanism from any first airflow setting to any second airflow setting is accompanied by a tactile indicator of such a modification. ASPECT 118.

In one aspect, the invention provides the inhalation device of aspect 118, wherein the modification of the airflow control mechanism from any first airflow setting to any second airflow setting is accompanied by one of two differentiable tactile indicators of such a modification. ASPECT 119.

In one aspect, the invention provides the inhalation device of aspect 119, wherein the device comprises a first airflow control component and a second airflow control component capable of rotating at least 360 degrees (e.g., at least one full rotation) in relation to one another, and further wherein one of the two differentiable tactile indicators accompanying the modification of the airflow control mechanism from a first airflow setting to a second airflow setting is only experienced once in any 360 degree rotation of the first airflow control component relative to the second airflow control component. ASPECT 120.

In one aspect, the invention provides the inhalation device of aspect 120, wherein the tactile indication occurring only once in any 360-degree rotation of the first airflow control component relative to the second airflow control component occurs when the airflow control mechanism is in a maximally closed position (e.g., allowing for minimum airflow through the device. ASPECT 121.

In one aspect, the invention provides the inhalation device of any one or more of aspects 119-121, wherein the two differentiable tactile indicators are clicks, snaps, or other similar indicator of varying magnitude (e.g., a "large click" and a "small click" having a difference in decibels of between about 1 decibel and about 60 decibels). ASPECT 122.

In one aspect, the invention provides the inhalation device of any one or more of aspects 83-122, wherein the device comprises a first component and a second component rotatable in relation to one another and each of the first and second components comprise at least a portion visible on the exterior of the device, wherein the status of the airflow control mechanism is indicated by (a) the positioning of one or more visual indicators on the first component of the device when interpreted in relationship to the positioning of one or more visual indicators on the second component of the device, (b) a tactile indicator when the first component of the device and the second component of the device are rotated relative to one another, or (c) both (a) and (b). ASPECT 123.

In one aspect, the invention provides the inhalation device of any one or more of aspects 83-123, wherein when the airflow control mechanism is in a configuration representing its most open position, the airflow control mechanism provides an airflow channel through at least one portion of the device having a cross sectional area which is about 40% to about 60% of the cross-sectional area of the airflow channel otherwise present in the device. ASPECT 124.

In one aspect, the invention provides the inhalation device of aspect 124, wherein when the airflow control mechanism is in a configuration representing its most open position, the airflow control mechanism provides an airflow channel through the device having a cross sectional area which is about 50% of the cross-sectional area of the airflow channel otherwise present in the device. ASPECT 125.

In one aspect, the invention provides the inhalation device of any one or both of aspect 124 or aspect 125, wherein when the airflow control mechanism is in a configuration representing its most open position, the airflow control mechanism provides an airflow channel through the device providing for the flow of a volume of air which is about one half of the volume of air which would otherwise be able to flow through the device if the airflow control mechanism were not present in the device. ASPECT 126.

In one aspect, the invention provides the inhalation device of any one or more of aspects 1-126, wherein the device comprises a first device component and a second device component releasably bound to one another by a releasable attachment mechanism, and wherein the total length of the device when the first and second device components are bound to one another is no more than about 80% of the total length of each of the first component and the second component independently added together. ASPECT 127.

In one aspect, the invention provides the inhalation device of aspect 127, wherein the device comprises a first device component and a second device component releasably bound to one another, and wherein the total length of the device when the first and second device components are bound to one another is no more than about 70% of the total length of each of the first component and the second component independently added together. ASPECT 128.

In one aspect, the invention provides the inhalation device of aspect 128, wherein the device comprises a first device component and a second device component releasably bound to one another, and wherein the total length of the device when the first and second device components are bound to one another is no more than about 60% of the total length of each of the first component and the second component independently added together. ASPECT 129.

In one aspect, the invention provides the inhalation device of aspect 129, wherein the device comprises a first device component and a second device component releasably bound to one another, and wherein the total length of the device when the first and second device components are bound to one another is no more than about 60% of the total length of each of the first component and the second component independently added together. ASPECT 130.

In one aspect, the invention provides the inhalation device of aspect 130, wherein the device comprises a first device component and a second device component releasably bound to one another, and wherein the total length of the device when the first and second device components are bound to one another is no more than about 50% of the total length of each of the first component and the second component independently added together. ASPECT 131.

In one aspect, the invention provides the inhalation device of any one or more of aspects 127-131, wherein at least about 25% of the length of the first device component resides within the second device component when the first device component and second device component are bound together by the releasable attachment mechanism. ASPECT 132.

In one aspect, the invention provides the inhalation device of aspect 132, wherein at least about 30% of the length of the first device component resides within the second device component when the first device component and second device component are bound together by the releasable attachment mechanism. ASPECT 133.

In one aspect, the invention provides the inhalation device of aspect 133, wherein at least about 35% of the length of the first device component resides within the second device component when the first device component and second device component are bound together by the releasable attachment mechanism. ASPECT 134.

In one aspect, the invention provides the inhalation device of aspect 134, wherein at least about 40% of the length of the first device component resides within the second device component when the first device component and second device component are bound together by the releasable attachment mechanism. ASPECT 135.

In one aspect, the invention provides the inhalation device of aspect 135, wherein at least about 45% of the length of the first device component resides within the second device component when the first device component and second device component are bound together by the releasable attachment mechanism. ASPECT 136.

In one aspect, the invention provides the inhalation device of aspect 136, wherein at least about 30% of the length of the first device component resides within the second device component when the first device component and second device component are bound together by the releasable attachment mechanism. ASPECT 137.

In one aspect, the invention provides the inhalation device of any one or more of aspects 127-137, wherein the device has at least a widest diameter and a narrowest diameter, and further wherein the narrowest diameter of the device represents a diameter which is between about 50% and about 95% of that of the widest diameter of the device. ASPECT 138.

In one aspect, the invention provides the inhalation device of aspect 138, wherein the narrowest diameter of the device represents a diameter which is between about 55% and about 90% of that of the widest diameter of the device. ASPECT 139.

In one aspect, the invention provides the inhalation device of aspect 139, wherein the narrowest diameter of the device represents a diameter which is between about 60% and about 85% of that of the widest diameter of the device. ASPECT 140.

In one aspect, the invention provides the inhalation device of aspect 140, wherein the narrowest diameter of the device represents a diameter which is between about 65% and about 80% of that of the widest diameter of the device. ASPECT 141.

In one aspect, the invention provides the inhalation device of aspect 141, wherein the narrowest diameter of the device represents a diameter which is between about 70% and about 75% of that of the widest diameter of the device. ASPECT 142.

In one aspect, the invention provides the inhalation device of any one or more of aspects 127-142, wherein the device has a length, and the device comprises at least two separate portions along its length comprising a diameter which is less than the widest diameter of the device. ASPECT 143.

In one aspect, the invention provides the inhalation device of any one or more of aspects 138-143, wherein the device has a length, and wherein the device comprises two separate portions of its length comprising a diameter which is between about 50% and about 95% of the widest diameter of the device. ASPECT 144.

In one aspect, the invention provides the inhalation device of aspect 144, wherein the device comprises two separate portions of its length comprising a diameter which is between about 55% and about 90% of the widest diameter of the device. ASPECT 145.

In one aspect, the invention provides the inhalation device of aspect 145, wherein the device comprises two separate portions of its length having a diameter which is between about 60% and about 85% of the widest diameter of the device. ASPECT 146.

In one aspect, the invention provides the inhalation device of aspect 146, wherein the device comprises two separate portions of its length having a diameter which is between about 65% and about 80% of the widest diameter of the device. ASPECT 147.

In one aspect, the invention provides the inhalation device of aspect 147, wherein the device comprises two separate portions of its length having a diameter which is between about 70% and about 75% of the widest diameter of the device. ASPECT 148.

In one aspect, the invention provides the inhalation device of any one or more of aspects 138-148, wherein the device has a length and wherein at least one portion of the device along its length has a diameter which is less than the widest diameter of the device, and further wherein the center of gravity of the device is positioned at a location along the length of the device corresponding to a portion of the device having a diameter which is less than the widest diameter of the device. ASPECT 149.

In one aspect, the invention provides the inhalation device of any one or more of aspects 143-149, wherein the device comprises at least two separate portions along its length having a diameter which is less than the widest diameter of the device, and wherein one portion having a diameter less than the widest diameter of the device is positioned to facilitate placement of the users lips and at least a second portion is positioned to facilitate placement of a user's finger(s). ASPECT 150.

In one aspect, the invention provides the inhalation device of aspect 150, wherein at least one portion positioned to facilitate placement of a user's fingers is positioned along the length of the device in a location corresponding to the center of gravity of the device such that when holding the device at such location, the device is essentially weight balanced. ASPECT 151.

In one aspect, the invention provides the inhalation device of any one or more of aspects 1-14, wherein the device comprises any combination of aspects described in aspects 15-151 that is not contradictory or non-sensical, such as, e.g., a non-electronic, non-heating inhalation device, e.g., for use in the inhalation of one or more volatile compounds via the mouth, comprising, e.g., any combination of any one or more characteristics described in aspects 16-31, any combination of any one or more characteristics described in aspects 32-45, any combination of any one or more characteristics described in aspects 46-82, any combination of any one or more characteristics described in aspects 83-126, any combination of any one or more characteristics described in aspects 127-151, or any combination of any or all thereof. ASPECT 152.

In one aspect, the invention provides a porous, non-fibrous, solid material device capable of holding, delivering, or holding and delivering one or more volatile compounds to a user via inhalation when the device is inserted into a non-electronic, non-heating inhalation device. ASPECT 153.

In one aspect, the invention provides a solid material device for use within a non-electronic, non-heating inhalation device, the solid material device capable of holding, delivering, or holding and delivering one or more volatile compounds, the solid material device comprising a first end, a second end, and an outer diameter, and wherein the solid material device comprises at least one non-circuitous passageway within its outer diameter between its first and second ends allowing the passage of air through the solid material device via the passageway. ASPECT 154.

In one aspect, the invention provides a fibrous solid material device capable of holding, delivering, or holding and delivering one or more volatile compounds, the fibrous device comprising a first end and a second end and a visible passageway through the device between the first and second ends. ASPECT 155.

In one aspect, the invention provides the solid material device of any one or more of aspects 153-155, wherein the solid material device is a removable device (also referred to herein as a removable insert), insert capable of being inserted into and removed from an inhalation device. ASPECT 156.

In one aspect, the invention provides the removable insert of aspect 156, wherein the removable insert is a fibrous, flexible or semi-flexible material for holding, delivering, or holding and delivering one or more volatile compounds. ASPECT 157.

In one aspect, the invention provides the removable insert of aspect 157, wherein the removable insert at least generally, at least substantially, at least essentially, essentially, or is composed of a polyester fiber. ASPECT 158.

In one aspect, the invention provides the removable insert of aspect 156, wherein the removable insert is a porous, non-fibrous, at least essentially inflexible, solid material device for holding, delivering, or holding and delivering one or more volatile compounds. ASPECT 159.

In one aspect, the invention provides the removable insert of aspect 157, wherein the removable insert at least generally, at least substantially, at least essentially, essentially, or is composed of ceramic. ASPECT 160.

In one aspect, the invention provides the solid material device of any one or more of aspects 153-160, wherein the solid material device is a removable insert designed for use within a non-electronic, non-heating inhalation device. ASPECT 161.

In one aspect, the invention provides the solid material device of any one or more of aspects 153-161, wherein the solid material device is a removable insert having a length defined by a distance between a first end of the removable insert and a second end of the removable insert, wherein the removable insert is capable of resisting a detectable or significant bending across its length when a force of between about 10 g to about 500 g is applied to one or both ends of the removable insert. ASPECT 162.

In one aspect, the invention provides the removable insert of aspect 162, wherein the removable insert is capable of resisting a detectable or significant bending across its length when a force of between about 100 g to about 450 g is applied to one or both ends of the removable insert. ASPECT 163.

In one aspect, the invention provides the removable insert of aspect 163, wherein the removable insert is capable of resisting a detectable or significant bending across its length when a force of between about 200 g to about 400 g is applied to one or both ends of the removable insert. ASPECT 164.

In one aspect, the invention provides the removable insert of any one or more of aspects 153-164, wherein when a force of about 350 g is applied to one or both ends of the removable insert, the removable insert defines a minor arc subtending an angle of no less than 170 degrees or the removable insert does not exhibit any detectable or significant bend across its length. ASPECT 165.

In one aspect, the invention provides the solid material device of any one or more of aspects 153-165, wherein the solid material device is a removable insert, and wherein the removable insert maintains a stable position within a compartment of a device described in any one or more of aspects 46-83. ASPECT 166.

In one aspect, the invention provides the solid material device of aspect 166, wherein the removable insert is stably maintained within the compartment of the device when the device is dropped from a distance of between about 1" to about 10". ASPECT 167.

In one aspect, the invention provides the solid material device of aspect 167, wherein the removable insert is stably maintained within the compartment of the device when the device is dropped from a distance of between about 1" to about 20". ASPECT 168.

In one aspect, the invention provides the solid material device of aspect 168, wherein the removable insert is stably maintained within the compartment of the device when the device is dropped from a distance of between about 1" to about 30". ASPECT 169.

In one aspect, the invention provides the solid material device of aspect 169, wherein the removable insert is stably maintained within the compartment of the device when the device is dropped from a distance of between about 1" to about 40". ASPECT 170.

In one aspect, the invention provides the solid material device of aspect 170, wherein the removable insert is stably maintained within the compartment of the device when the device is dropped from a distance of between about 1" to about 50". ASPECT 171.

In one aspect, the invention provides the solid material device of aspect 171, wherein the removable insert is stably maintained within the compartment of the device when the device is dropped from a distance of between about 1" to about 60". ASPECT 172.

In one aspect, the invention provides the solid material device of aspect 166, wherein the removable insert is stably maintained within the compartment of the device when the device is dropped from a distance of 60" or more. ASPECT 173.

In one aspect, the invention provides the solid material device of any one or more of aspects 166-173, wherein the removable insert requires a pull force of between about −0.02 N-about −2 N to manually remove the removable element from the compartment. ASPECT 174.

In one aspect, the invention provides the solid material device of aspect 174, wherein the removable insert requires a pull force of between about −0.02 N-about −1 N to manually remove the removable element from the compartment. ASPECT 175.

In one aspect, the invention provides the solid material device of aspect 175, wherein the removable insert requires a pull force of between about −0.02 N-about −0.5 N to manually remove the removable element from the compartment. ASPECT 176.

In one aspect, the invention provides the solid material device of any one or more of aspects 166-176, wherein the removable insert is stably maintained within the compartment within the device such that when the compartment maintaining the removable insert is exposed to the outside environment, the insert is stably maintained within the container when the container is rotated 360 degrees in any direction. ASPECT 177.

In one aspect, the invention provides the solid material device of any one or more of aspects 153-177, wherein the solid material insert comprises at least one non-circuitous passageway, e.g., a direct path, through at least one dimension of the solid material device. ASPECT 178.

In one aspect, the invention provides the solid material device of aspect 178, wherein the solid material device comprises a first end and a second end, the distance between the first and second ends of the solid material device defining the longest dimension of the solid material device, wherein at least one of the at least one non-circuitous passageways pass(es) from the first end of the solid material device to the second end of the solid material device. ASPECT 179.

In one aspect, the invention provides the solid material device of any one or both of aspect 178 or aspect 179, wherein the at least one non-circuitous passageway increases the surface area of the device compared to the same device lacking the at least one non-circuitous passageway. ASPECT 180.

In one aspect, the invention provides the solid material device of any one or more of aspects 178-180, wherein at least one of the at last one non-circuitous passageways, e.g., direct paths, through the solid material device has a shape characterizable as a circular shape, a squircle, a quadrilateral or other polygon, or a multilobed (multi-petaled) flower shape, e.g., zygomorphic flower shape, or actinomorphic flower shape. ASPECT 181.

In one aspect, the invention provides the solid material device of aspect 181, wherein the solid material device comprises a plurality of non-circuitous passageways through the solid material device. ASPECT 182.

In one aspect, the invention provides the solid material device of aspect 182, wherein each of the plurality of non-circuitous passageways through the solid material device are at least generally, at least substantially, at least essentially, essentially, or are the same shape. ASPECT 183.

In one aspect, the invention provides the solid material device of aspect 182, wherein at least one of the non-circuitous passageways through the solid material device has a shape which is different from one or more other non-circuitous passageways through the solid material device. ASPECT 184.

In one aspect, the invention provides the solid material device of any one or more of aspects 166-184, wherein the removable insert has a shape having a first end and a second end, the shape characterizable as a cylinder, triangular prism, rectangular prism (cuboid), pentagonal prism, hexagonal prism, octagonal prism, or other multi-sided prism. ASPECT 185.

In one aspect, the invention provides the solid material device of any one or more of aspects 166-185, wherein the removable insert has a depth (e.g., thickness/diameter) which is detectably or significantly less than the depth of the compartment of the device in which it resides during operation of the device with the removable insert present. ASPECT 186.

In one aspect, the invention provides the solid material device of any one or more of aspects 153-186, wherein the solid material device is a solid material device capable of maintaining, releasing, or maintaining or releasing one or more volatile compounds, wherein the one or more volatile compounds are safe for mammalian inhalation. ASPECT 187.

In one aspect, the invention provides the solid material device of aspect 187, wherein the one or more volatile compounds is/are volatile compound(s) maintained within an oil, is provided to the solid material device in an oil, or both. ASPECT 188.

In one aspect, the invention provides the solid material device of any one or both of aspect 187 or aspect 188, wherein at least one of the volatile compounds is a non-nicotinic compound. ASPECT 189.

In one aspect, the invention provides the solid material device of any one or more of aspects 187-189, wherein none of the one or more volatile compounds is a tobacco-related compound, nicotine-related compound, or any combination thereof. ASPECT 190.

In one aspect, the invention provides the solid material device of any one or more of aspects 187-190, wherein the one or more volatile compounds are derived from, provided in, or both derived from and provided in one or more botanicals or extracted oils of such botanicals including botanicals from, e.g., the botanical family Lamiaceae, e.g., *Mentha piperita* (peppermint), *Mentha spicata* (spearmint), *Lavandula* (lavender), *Salvia rosmarinus* (rosemary), *Origanum vulgare* (oregano). *Thymus vulgaris* (thyme), etc.; the botanical family Piperaceas, e.g., *Piper nigrum* (black pepper); the botanical family Myrtaceae, e.g., *Eucalyptus radiata* (eucalyptus), *Eucalyptus globulus* (eucalyptus), *Syzygium aromaticum* (clove), *Melaleuca alternifolia* (tea tree); the botanical family Rutaceae, e.g., *Citrus limon* (lemon), Citrus x sinensis (orange), *Aurantifolia* (lime) (or, e.g., *Citrus aurantifolia, Citrus latifolia, Citrus glauca*, and *Citrus hystrix*), *Citrus paradisi* (grapefruit), *Citrus bergamia* (bergamot orange); the botanical family Annonacea, e.g., *Cananga adorate* (ylang-ylang); the botanical family Lauraceae, e.g., *Cinnamomum verum* (cinnamon), *Ocotea quixos* (Ocotea or Ishpingo); the botanical family Myristicaceae, e.g., *Myristica fragrans* (nutmeg); the botanical family Pine, e.g., *Cedrus* (cedarwood), *Picea mariana* (black spruce); the botanical family Fabaceae, e.g., Genus *Copaifera* (copaiba); the botanical family Orchidaceae, e.g., *Vanilla planifolia* (vanilla); the botanical family Poaceae, e.g., *Cymbopogon* species (including, e.g., lemongrass); the botanical family Malvaceae, e.g., *Theobroma cacao* (cocoa); the botanical family Ericaceae, e.g., *Vaccinium macrocarpon* (cranberry); the botanical family Asteraceae, e.g., *Artemisia pallens* (davana), the botanical family Cupressaceae, e.g., *Juniperus communis* (juniper), *Cupressus* (cypress), the botanical family Burseraceae, e.g., *Boswellia sacra* (frankincense); and, e.g., the botanical family Geraniaceae, e.g., *Pelargonium graveolens* (geranium), etc. and any combination of any or all thereof. ASPECT 191.

In one aspect, the invention provides the inhalation device having any one or more of the characteristics described in any one or more of aspects 1-152, wherein the device is capable of receiving a solid material device therein, wherein the solid material device is capable of maintaining, releasing, or maintaining and releasing one or more volatile compounds, and wherein the solid material device has any one or more of the characteristics described in any one or more of aspects 153-186. ASPECT 192.

In one aspect, the invention provides the inhalation device of aspect 192, wherein the one or more volatile compounds has/have any one or more of the characteristics described in any one or more of aspects 187-191. ASPECT 193.

In one aspect, the invention provides the solid material device of any one or more of aspects 153-186, wherein the solid material device is a removable insert capable of being inserted into, used in coordination with, or both, a device having any one more of the characteristics described in any one or more of aspects 1-152. ASPECT 194.

In one aspect, the invention provides the device of aspect 194, wherein the solid material device is capable of maintaining, releasing, or maintaining and releasing one or more volatile compounds having any one or more of the characteristics described in any one or more of aspects 187-190. ASPECT 195.

In aspects, the invention can comprise devices, components, or any combination thereof having any combination of characteristics described in any one or more of aspects 1-195, which are not contradictory or non-sensical; e.g., the invention can provide a non-electronic, non-heating device designed for the inhalation of one or more volatile compounds described in, having any one or more characteristics of, or capable of being used with any additional device described in, any one or more of aspects 1-152, or, e.g., the invention can provide a solid material device capable of maintaining, releasing, or maintaining or releasing one or more volatile compounds, the solid material device being described in, having any one or more of the characteristics of, or capable of being used with any additional device described in, any one or more of aspects 153-186, and wherein any such disclosed inhalation device, solid material device, or both, can deliver to a user one or more volatile compounds described in any one or more of aspects 187-191. ASPECT 196.

In one aspect, the invention provides a non-electronic, non-heating inhalation device system for the delivery of one or more volatile compounds by inhalation, the device system comprising (a) a non-electronic, non-heating inhalation device and (b) a removable insert designed to be removably maintained therein, wherein the non-electronic, non-heating inhalation device comprises a first component and a second component releasably bound to one another by a rapidly releasable force mechanism such that the first component and second component can be completely disengaged from one another or, alternatively, can be securely bound to one another, the inhalation device further comprising an adjustable airflow control mechanism controlled by the rotation of the first component and the second component relative to one another, and the removable insert is designed to maintain, release, or maintain and release the one or more volatile compounds for inhalation. ASPECT 197.

In one aspect, the invention provides a non-electronic, non-heating inhalation device system for the delivery of one or more volatile compounds by inhalation, the device system comprising a non-electronic, non-heating inhalation device and a solid material device capable of being inserted therein, the solid material device capable of maintaining, releasing, or maintaining and releasing the one or more volatile compounds for inhalation, wherein, in use, (a) at least one quarter of the solid material device's longest dimension is engaged with a first component of the non-electronic, non-heating inhalation device, and (b) the entirety of the solid material device is positioned within a second component of the non-electronic, non-heating inhalation device, and wherein the first and second components of the non-electronic, non-heating inhalation device are selectively disengageable from one another. ASPECT 198.

In one aspect, the invention provides a non-electronic, non-heating inhalation device system for the delivery of one or more volatile compounds by inhalation, the device system comprising a non-electronic, non-heating inhalation device and a solid material device capable of maintaining, releasing, or maintaining and releasing one or more volatile compounds, wherein the solid material device comprises a first end, a second end, and at least one non-circuitous passageway passing through the solid material device from its first end to its second end. ASPECT 199.

In one aspect, the invention provides a non-electronic, non-heating inhalation device system for the delivery of one or more volatile compounds by inhalation, the device system comprising a non-electronic, non-heating inhalation device comprising a first component and a second component capable of rotating relative to one another and a removable solid material device capable of maintaining, releasing, or maintaining and releasing the one or more volatile compounds for inhalation, wherein the non-electronic, non-heating inhalation device comprises an airflow control mechanism adjustable in discrete increments by the rotation of the first component and the second component of the non-electronic, non-heating inhalation device in relation to one another. ASPECT 200.

In one aspect, the invention provides a non-electronic, non-heating inhalation device system for the delivery of one or more volatile compounds by inhalation, the device system comprising a non-electronic, non-heating inhalation device described in any one or more of aspects 1-152, 192, and 193, and a removable insert described in any one or more of aspects 153-190, 194, and 195. ASPECT 201.

In aspects, the invention provides a kit comprising (a) one or more of the inhalation devices described in any one or more of aspects 1-152, 192, and 193, and (b) one or more of the solid material devices capable of maintaining, releasing, or maintaining and releasing one or more volatile compounds described in any one or more of aspects 153-190, 194, and 195. ASPECT 202.

In aspects, the invention provides a kit providing two or solid material devices capable of maintaining, releasing, or maintaining and releasing one or more volatile compounds described in any one or more of aspects 153-190, 194, and 195. ASPECT 203.

In aspects, the invention provides the kit of aspect 203, wherein all solid material devices of the kit comprise at least generally the same, at least substantially the same, at least essentially the same, essentially the same, or the same one or more volatile compounds. ASPECT 204.

In aspects, the invention provides the kit of aspect 203, wherein at least one of the solid material devices of the kit comprises at least generally different, at least substantially different, or different one or more volatile compounds than at least one other solid material device in the kit. ASPECT 205.

In aspects, the invention provides a method of providing volatile compound(s) for inhalation to an individual, the method comprising providing to an individual an inhalation device of any one or more of aspects 1-152 with or containing a removable insert of any one or more of aspects 153-191, or a system of any one or more of aspects 197-201, wherein the individual inhales via their mouth at least one partial or full breath through the inhalation device such that a detectable amount of volatile compound(s) maintained by the removable insert is delivered to the individual. ASPECT 206.

In aspects, the invention provides a method of providing volatile compound(s) for inhalation to an individual, the method comprising (a) providing to an individual an inhalation device of any one or more of aspects 1-152 with or containing a removable insert of any one or more of aspects 153-191, or a system of any one or more of aspects 197-201, (b) instructing the individual to (i) inhale via their mouth at least one partial or full breath through the inhalation device such that a detectable amount of volatile compound(s) maintained by the removable insert is delivered to the individual and (ii) to repeat step (i) for as many times as is desired by the individual to obtain a satisfactory olfactory experience as judged by the individual. ASPECT 207.

In aspects, the invention provides a method of providing an olfactory experience comprising the inhalation of volatile compound(s) to an individual, the method comprising providing to an individual an inhalation device of any one or more of aspects 1-152 with or containing a removable insert of any one or more of aspects 153-191, or a system of any one or more of aspects 197-201, wherein the individual inhales via their mouth at least one partial or full breath through the inhalation device such that a detectable amount of volatile compound(s) maintained by the removable insert is delivered to the individual. ASPECT 208.

In aspects, the invention provides a method of providing an olfactory experience comprising the inhalation of volatile compound(s) to an individual, the method comprising (a) providing to an individual an inhalation device of any one or more of aspects 1-152 with or containing a removable insert of any one or more of aspects 153-191, or a system of any one or more of aspects 197-201, (b) instructing the individual to (i) inhale via their mouth at least one partial or full breath through the inhalation device such that a detectable amount of volatile compound(s) maintained by the removable insert is delivered to the individual and (ii) to repeat step (i) for as many times as is desired by the individual to obtain a satisfactory olfactory experience as judged by the individual. ASPECT 209.

In aspects, the invention provides a method of reducing one or more smoking habit-related cravings(s) in an individual, the method comprising providing to an individual suffering from a smoking habit-related craving a inhalation device of any one or more of aspects 1-152 with or containing a removable insert of any one or more of aspects 153-191, or a system of any one or more of aspects 197-201, wherein the individual inhales via their mouth at least one partial or full breath through the inhalation device such that a detectable amount of volatile compounds maintained by the removable insert is delivered to the individual. ASPECT 210.

In aspects, the invention provides a method of reducing one or more smoking habit-related craving(s) in a significant number of individuals in an adequately powered population of individuals, the method comprising providing to each individual in the population of individuals an inhalation device of any one or more of aspects 1-152 with or containing a removable insert of any one or more of aspects 153-191, or a system of any one or more of aspects 197-201, wherein the individual(s) inhale(s) via their mouth(s) at least one partial or full breath through the inhalation device such that a detectable amount of volatile compounds maintained by the removable insert is delivered to the individual(s). ASPECT 211.

In aspects, the invention provides a method of reducing one or more smoking habit-related cravings in an individual, the method comprising (a) providing to the individual suffering from one or more smoking habit-related craving(s) an inhalation device of any one or more of aspects 1-152 with or containing a removable insert of any one or more of aspects 153-191, or a system of any one or more of aspects 197-201, (b) instructing the individual to (i) inhale via their mouth at least one partial or full breath through the inhalation device such that a detectable amount of volatile compound(s) maintained by the removable insert is delivered to the individual and (ii) to repeat step (i) at least one additional time. ASPECT 212.

In aspects, the invention provides a method of detectably or significantly reducing one or more smoking habit-related craving(s) in a significant number of individuals in an adequately powered population of individuals, the method comprising (a) providing to each of the individual(s) suffering from one or more smoking habit-related craving(s) an inhalation device of any one or more of aspects 1-152 with or containing a removable insert of any one or more of aspects 153-191, or a system of any one or more of aspects 197-201, (b) instructing the individual(s) to (i) inhale via their mouth(s) at least one partial or full breath through the inhalation device such that a detectable amount of volatile compounds maintained by the removable insert is delivered to the individual(s) and (ii) to repeat step (i) at least one additional time. ASPECT 213.

In aspects, the invention provides a method of detectably or significantly reducing one or more smoking habit-related craving(s) in an individual, the method comprising providing to an individual suffering from a smoking habit-related craving an inhalation device of any one or more of aspects 1-152 with or containing a removable insert of any one or more of aspects 153-191, or a system of any one or more of aspects 197-201, wherein the individual (i) holds the device within their hand, between their fingers, between their lips, or any combination thereof, (ii) repeatedly, e.g., at least two or more times, rotates the first primary component in relation to the second primary component relative to one another in any direction or combination of directions, (iii) repeatedly, e.g., at least two or more times, separates and allows reattachment of the first primary component and the second primary component relative to one another, or (iv) any combination of (i)-(iii). ASPECT 214.

In aspects, the invention provides a method of detectably or significantly reducing one or more smoking habit-related craving(s) in a significant number of individuals in an adequately powered population of individuals, the method comprising providing to each of the individual(s) suffering from one or more smoking habit-related craving(s) an inhalation device of any one or more of aspects 1-152, or a system of any one or more of aspects 197-201, wherein the individual(s) (i) hold(s) the device within their hand(s), between their fingers, between their lips, or any combination thereof, (ii) repeatedly, e.g., at least two or more times, rotate(s) the first primary component in relation to the second primary component relative to one another in any direction or combination of directions, (iii) repeatedly, e.g., at least two or more times, separate(s) and allow(s) reattachment of the first primary component and the second primary component relative to one another, or (iv) any combination of (i)-(iii). ASPECT 215.

In aspects, the invention provides a method of detectably or significantly reducing one or more smoking habit-related craving(s) in an individual, the method comprising (a) providing to an individual suffering from a smoking habit-related craving an inhalation device of any one or more of aspects 1-152, or a system of any one or more of aspects 197-201, and (b) instructing the individual to (i) hold the device within their hand, between their fingers, between their lips, or any combination thereof, (ii) repeatedly, e.g., at least two or more times, rotate the first primary component in relation to the second primary component relative to one another in any direction or combination of directions, (iii) repeatedly, e.g., at least two or more times, separate and allow reattachment of the first primary component and the second primary component relative to one another, or (iv) any combination of (i)-(iii). ASPECT 216.

In aspects, the invention provides a method of detectably or significantly reducing one or more smoking habit-related craving(s) in a significant number of individuals in an adequately powered population of individuals, the method comprising (a) providing to each individual(s) suffering from a smoking habit-related craving an inhalation device of any one or more of aspects 1-152, or a system of any one or more of aspects 197-201, and (b) instructing the individual(s) to (i) hold the device(s) within their hand(s), between their fingers, between their lips, or any combination thereof, (ii) repeatedly, e.g., two or more times, rotate the first primary component in relation to the second primary component relative to one another in any direction or combination of directions, (iii) repeatedly, e.g., two or more times, separate and allow reattachment of the first primary component and the second primary component relative to one another, or (iv) any combination of (i)-(iii). ASPECT 217.

In aspects, the invention provides a method of controlling airflow in an inhalation device designed to deliver volatile compound(s) to a user of the inhalation device, the method comprising moving at least two airflow control components of the inhalation device in relation to one another such that the movement of the two airflow control components occurs only in pre-defined increments and with each movement of the two airflow control components in a pre-defined increment provides a pre-determined increase or pre-determined decrease in airflow through the device. ASPECT 218.

In aspects, the invention provides a method of controlling airflow in an inhalation device designed to deliver volatile compound(s) to a user of the inhalation device, the method comprising moving at least two airflow control components of the inhalation device in relation to one another and wherein, during normal operation of the device, at least two of the at least two airflow control components of the inhalation device are, selectively, completely separable from one another. ASPECT 219.

In aspects, the invention provides a method of controlling airflow in an inhalation device designed to deliver volatile compound(s) to a user of the inhalation device, the method comprising moving at least two airflow control components of the inhalation device in relation to one another, wherein movement of a first airflow control component relative to a second airflow control component comprises a rotational movement, and the rotational movement comprises movement capable of an at least 360 degree rotation. ASPECT 220.

In aspects, the invention provides a method of visually identifying an airflow control setting of an inhalation device designed to deliver volatile compound(s) to a user of the inhalation device, the method comprising evaluating the positioning of at least one first visual indicator present on an external surface of the inhalation device relative to at least one second visual indicator present on an external surface of the inhalation device, wherein the relative positioning of one visual indicator to another indicates the status of the airflow control mechanism. ASPECT 221.

In aspects, the invention provides a method of determining the spatial positioning of an internal component, not externally visible, of an inhalation device designed to deliver volatile compound(s) to a user of the inhalation device, the method comprising evaluating the positioning of at least one first visual indicator present on an external surface of the inhalation device, wherein the spatial positioning of at least one visual indicator indicates the spatial positioning of an otherwise externally invisible internal component. ASPECT 222.

In aspects, the invention provides a method of audibly, tactily, or both audibly and tactily, determining the status of an airflow control setting of an inhalation device designed to deliver volatile compound(s) to a user of the inhalation device, the method comprising moving at least two airflow control components of the inhalation device in relation to one another, wherein movement of a first airflow control component relative to a second airflow control component is accompanied by an audible sound, a tactile indicator, or both, such audible sound, tactile indicator, or both, providing an indication to the user of the status of the airflow control setting. ASPECT 223.

In aspects, the invention provides an inhalation device for delivering one or more volatile compounds for inhalation to a user of the device, wherein the inhalation device comprises (1) a means for selective engagement; (2) a means for inhalation facilitation; (3) a means for protecting an inhalation facilitation means; (4) a means for housing a removable insert; (5) a means for stabilizing a removable insert; (6); a means for airflow control; (7) a means for protecting an outer shell; (8) a means for visual indicator(s); (9) a means for providing a tactile indication of movement, control setting, or both; (10) a means for providing an audible indication of a movement, control setting, or both; (11) a means for delivering volatile compound(s); or (12) any one, more, or all of (1)-(11). ASPECT 224.

In aspects, the invention provides the device of aspect 224, wherein the device is used in any one or more of the methods described in any one or more of aspects 206-223. ASPECT 225.

In aspects, the invention provides the method of aspect 210, wherein the method is applied for or over a sufficient period of time or repeated a sufficient number of times such that the individual experiences a detectable or significant decrease in the smoking habit-related craving as assessed by the individual, a suitably trained individual recognized as capable of identifying reduction in addiction-related behavior, or both. ASPECT 226.

In aspects, the invention provides the method of aspect 211, wherein a detectable or significant reduction in smoking habit-related craving(s) is reduced in the population of individuals receiving, applying, or otherwise using the method within a period of at least about 1 year, such as, e.g., within at least about 11 months (mos), ~10 mos, ~9 mos, ~8 mos, ~7 mos, ~6 mos, ~5 mos, ~4 mos, ~3 mos, ~2 mos, or, e.g., within about 1 month. ASPECT 227.

In aspects, the invention provides the method of aspect 212, wherein step (b) (i) is repeated a sufficient number of times, or, e.g., the method is applied for or over a sufficient period of time, such that the individual experiences a detectable or significant decrease in the smoking habit-related craving as assessed by the individual, a suitably trained individual recognized as capable of identifying reduction in addiction-related behavior, or both. ASPECT 227.

In aspects, the invention provides the method of aspect 213, wherein a detectable or significant reduction in smoking habit-related craving(s) is reduced in the population of individuals receiving, applying, or otherwise using the method within a period of at least about 1 year, such as, e.g., within at least about 11 months (mos), ~10 mos, ~9 mos, ~8 mos, ~7 mos, ~6 mos, ~5 mos, ~4 mos, ~3 mos, ~2 mos, or, e.g., within about 1 month. ASPECT 229.

In aspects, the invention provides the method of aspect 214, wherein the method is applied for or over a sufficient period of time or repeated a sufficient number of times such that the individual experiences a detectable or significant decrease in the smoking habit related craving as assessed by the individual, a suitably trained individual recognized as capable of identifying reduction in addiction-related behavior, or both. ASPECT 230.

In aspects, the invention provides the method of aspect 215, wherein a detectable or significant reduction in smoking habit-related craving(s) is reduced in the population of individuals receiving, applying, or otherwise using the method within a period of at least about 1 year, such as, e.g., within at least about 11 months (mos), ~10 mos, ~9 mos, ~8 mos, ~7 mos, ~6 mos, ~5 mos, ~4 mos, ~3 mos, ~2 mos, or, e.g., within about 1 month. ASPECT 231.

In aspects, the invention provides the method of aspect 216, wherein step (b) (i), step (b) (ii), step (b) (iii), or step (b) (iv) is repeated a sufficient number of times, or, e.g., the method is applied for or over a sufficient period of time, such that the individual experiences a detectable or significant decrease in the smoking habit-related craving as assessed by the individual, a suitably trained individual recognized as capable of identifying reduction in addiction-related behavior, or both. ASPECT 232.

In aspects, the invention provides the method of aspect 217, wherein a detectable or significant reduction in smoking habit-related craving(s) is reduced in the population of individuals receiving, applying, or otherwise using the method within a period of at least about 1 year, such as, e.g., within at least about 11 months (mos), ~10 mos, ~9 mos, ~8 mos, ~7 mos, ~6 mos, ~5 mos, ~4 mos, ~3 mos, ~2 mos, or, e.g., within about 1 month. ASPECT 233.

DETAILED DESCRIPTION OF THE INVENTION

For convenience, both combinations of elements/steps and individual elements/steps may be described in this section of this disclosure. Despite the inclusion of passages focused on specific elements/steps, any aspect, facet, embodiment, or other description of particular step(s) or element(s) can be applied to any general description of the devices/compositions/methods of the invention, or any other recited element(s)/step(s) thereof, which are provided in any part of this disclosure.

As used herein, the word "exemplary" means "serving as an example, instance, or illustration." The following detailed description is merely exemplary in nature and is not intended to limit application and uses. Any specific embodiment or aspect described herein explicitly described as "exemplary" is not necessarily to be construed as preferred or advantageous over other embodiments or aspect of the inventive devices/compositions/methods described herein.

Overview

Disclosed herein are devices and systems for the delivery of one or more volatile compounds by inhalation and related methods of their use. Herein, use of the term "volatile" in relation to compound(s) should be interpreted to mean a compound which is volatizable. In aspects, a volatile compound herein is a compound which detectably or significantly evaporates at normal temperatures. In aspects, a volatile compound herein is a compound which can become volatized under certain conditions. In aspects, such a condition is the application of a detectable or significant amount of heat. In aspects, such a condition is a normal condition of use. In aspects, a normal condition of use is an inhalation of a breath by a device user causing air to pass over a device maintaining the compound(s). In aspects, a normal condition of use is any condition by which no electronic source of heat is used to release the compound(s) from a device in which they are maintained. In aspects, such a condition is a condition which does not require a device maintaining the compound(s) at a first average temperature to change in average temperature by an amount of more than about, e.g., 2%, ~4%, ~5%, ~10%, ~15%, ~20%, ~25%, ~50%, ~75%, ~100%, ~150%, ~200%, ~250%, ~300%, ~350%, ~400%, ~450%, or, e.g., by an amount of more than about 500% or more of its first average temperature. In aspects, such a condition is a condition which does not require a device maintaining the compound(s) at a first average temperature to change in temperature by an amount of more than about 5° Celsius (° C.), such as, e.g., by an amount of more than ~10° C., ~15° C., ~20° C., ~25° C., ~30° C., ~40° C., ~50°

C., ~60° C., ~70° C., ~80° C., ~90° C., ~100° C., ~120° C., ~140° C., ~160° C., ~180° C., or, e.g., by more than ~200° C. or more.

In aspects, devices and systems disclosed herein can be used for pleasure. Devices and systems herein can be used simply for entertainment and enjoyment, e.g., as a hobby or simple pleasurable activity. In aspects, entertainment (enjoyment or pleasure) is obtained from inhaling one or more volatile compounds delivered by a device or system described herein. Entertainment (enjoyment or pleasure) can also be provided by manual manipulation of the device, such as, e.g., by a user playing with a device with their hand(s) or finger(s), e.g., such as play characterizable as fondling or fidgeting. Devices can also or additionally be used for assuaging one or more smoking habit-related cravings, such as one or more smoking habit-related cravings experienced by a subject attempting to quit or having quit a smoking habit. In aspects such a craving may be an oral craving, e.g., having something in their mouth, inhaling one or more compounds, e.g., inhaling a flavored inhalant or, e.g., a drug such as, e.g., nicotine, holding an object, e.g., a device to their lips, feeling the device on or between their lips, or similar such oral-fixation-related craving. In certain aspects, the invention provides a customizable inhalation experience, by, e.g., in embodiments providing a device for the inhalation of one or more volatile compounds wherein the device comprises an adjustable airflow control mechanism. In aspects a smoking-habit related craving may be a manual manipulation-related craving, such as, e.g., holding an object, e.g. device, in their hand, e.g., between two or more fingers, playing with a device with their hand(s) or fingers(s), e.g., such play characterizable as fondling, or, e.g., fidgeting, keeping their hands and or fingers occupied with such an object or device, or similar such oral-fixation-related craving. In aspects, devices and systems herein can provide both entertainment value and assistance in reducing or eliminating one or more smoking habit-related cravings.

In certain aspects, devices provided by the invention can comprise one or more electronic components. In aspects, devices provided by the invention can comprise one or more heating elements. In certain aspects, devices provided by the invention can comprise an electronic heating component. In aspects, uncontradicted, any one or more characteristics of the device described herein, e.g., any one or more aspects of the invention provided herein, can be applied to a device which comprises one or more electronic components. In aspects, uncontradicted, any one or more of the characteristics of the device described herein, e.g., any one or more aspects of the invention provided herein, can be applied to a device which comprises one or more heating components. In aspects, uncontradicted, any one or more characteristics of the device described herein, e.g., any one or more aspects of the invention provided herein, can be applied to a device which comprises an electronic heating component.

In certain aspects an inhalation device of the invention does not comprise an electronic component (e.g., the device is characterizable as non-electronic). In aspects, an inhalation device of the invention does not comprise a heating component (e.g., the device is characterizable as non-heating). In aspects, an inhalation device of the invention does not comprise electronic or heating component(s) (e.g., the device is characterizable as non-electronic and non-heating.) In aspects, uncontradicted, any one or more of the characteristics of the device described herein, e.g., any one or more aspects of the invention provided herein, can be applied to a device which lacks a component characterizable as an electronic component, any component characterizable as a heating component, or both.

In aspects, in operation, e.g., in a ready to use state, devices provided by the invention can comprise a first non-electronic, non-heating device for the delivery of one or more volatile compounds and further a solid material device capable of maintaining, releasing, or maintaining and releasing the one or more volatile compounds. In aspects, such a combination, e.g., a non-electronic, non-heading device for the delivery of one or more volatile compounds in combination with a solid material device capable of providing such one or more volatile compounds is characterizable as a system, e.g., a system for delivering one or more volatile compounds by inhalation. In aspects, such a system can further provide one or more mechanisms which provide entertainment, or detectable or significant smoking habit-related craving reduction separate from inhalation or oral interaction, such as, e.g., by providing a manually manipulatable mechanical mechanism.

Detailed characteristics of various embodiments of the invention are provided herein. Throughout the detailed description, certain terms, e.g., names of components, are capitalized. Such capitalization can indicate that such a component is described as a specific embodiment in the figures and detailed description of figures provided herewith. In aspects, the component described in the specification, with which the specific component name is provided as one possible embodiment, should be interpreted as, in aspects, comprising or at a minimum optionally comprising one or more of the characteristics of the specifically embodied component provided in the figures or described in the detailed description of figures provided herewith.

Inhalation Device

In one aspect, the invention provides a device designed for the inhalation of one or more volatile compounds. Herein, the term "inhalation device" is used to describe this aspect of the invention. In aspects, the inhalation device facilitates the inhalation of one or more volatile compounds via the nose, the mouth, or both the nose and the mouth. In certain aspects, the inhalation device facilitates the inhalation of one or more volatile compounds at least generally, at least substantially, at least essentially, essentially, or completely by mouth.

Herein, an inhalation device in a "ready to use state" is an inhalation device which is fully assembled, e.g., all components are present, and e.g., and wherein the inhalation device is in a configuration suitable for the inhalation of one or more volatile compounds. In aspects, such a configuration is a configuration wherein a device first primary component and a device second primary component are engaged to one another via a selectively releasable attachment mechanism (also referred to herein as a selectively releasable engagement mechanism), e.g., rapidly releasable attachment mechanism.

In certain aspects, the inhalation device is a device capable of delivering, e.g., designed to deliver or which delivers, one or more volatile compounds without the intentional application of heat, such as heat provided by a heating element of the device. In aspects, the device is a non-electronic, non-heating device, comprising no electronic component and, e.g., no heating element. In aspects, the inhalation device is characterizable as a "passive" device, wherein "passive" is used to describe the ability to release or provide one or more volatile compounds without the application of heat. In aspects, one or more volatile compounds are released by a component of a device, a complementary device designed for use with the inhalation device, or both. In aspects, the release of the one or more volatile compounds occurs simply due to their volatile nature and not due to the application of any external force(s). In certain aspects, an inhalation device provided by the invention provides non-electronic volatilization/vaporization of one or more volatile compounds. In aspects, an inhalation device provided by the invention provides non-heat-directed volatilization/vaporization of one or more volatile compounds. In aspects, an inhalation device can comprise one or more electronic components which are not directly related to the release of volatile compound(s). As an example, in aspects, an inhalation device provided by the invention can comprise, e.g., an electronic component capable of generating a location signal such that such a feature can be used by a user to locate the inhalation device. However, such an electronic component or feature is not directly related to, e.g., is not present to cause, the release of one or more volatile compound(s).

Inhalation Device-Primary Components

In aspects, an inhalation device provided by the invention comprises at least two components which are selectively disengaged from one another. In aspects, the inhalation device is characterizable as having at least two "primary" components. Herein, a primary component is a component which is not a subcomponent of a larger component. While a primary component itself can comprise one or more subcomponents, it itself is not a subcomponent of another device component. In certain aspects, a primary component can comprise one or more other subcomponents or even assemblies of subcomponents. In certain aspects, one or more subcomponents of a primary component cannot be selectively disassembled or disengaged from one another during normal operation of the device. In certain aspects, one or more subcomponents of a primary component do not require disassembly, disengagement, or movability relative to any other component in order to facilitate the full range of uses of the device. In aspects, a primary component is selectively dis-engageable from another primary component. In aspects, the inhalation device comprises only two components which can be selectively disengaged from one another, each being a primary component. In other aspects, the inhalation device comprises a first primary component and a second primary component movable in relation to one another. In aspects, a first primary component and a second primary component are selectively dis-engageable from one another. In some aspects, one or more other components of the inhalation device are also selectively dis-engageable from one or more other components of the device, however because such a component is a subcomponent of a larger component, such a component is not characterizable herein as a "primary component."

Herein, and as exemplified in the figures, a first primary component can be, e.g., a "body assembly." Herein, as exemplified in the figures, a second primary component can be, e.g., a "tip assembly." To further clarify use of the term "primary component," a body assembly and a tip assembly in embodiments herein can rotate in relation to one another. Further, a body assembly and a tip assembly are capable, in aspects, of being selectively disengaged from one another. In certain aspects, the body assembly and the tip assembly are the only two selectively dis-engageable components of the inhalation device. In aspects, each is referred to as a primary component because at the highest level, they represent the two components of the system which are not subcomponents of larger components. In some aspects, for example, a primary component, such as, e.g., a body assembly, can have one or more further dis-engageable components. For example, a body assembly can comprise a mouthpiece as a subcomponent and in embodiments the mouthpiece can be disengaged from the remainder of the body assembly to facilitate exchange with a different mouthpiece, e.g., a mouthpiece comprising a different material, a different aesthetic design (e.g., shape, color, etc.), etc. However, because the mouthpiece is a subcomponent of the body assembly, it would not be referred to herein as a primary component.

To be clear, use of the term "primary component" is not intended to convey a particular hierarchy of value for such a component. Use of the term "primary component" should not be interpreted as disclosing a particular requirement for such a component. However, use of such a term to distinguish components of the inhalation device described herein having particular characteristic(s), such as described above, facilitates the ability to describe the device clearly to the reader.

According to aspects, an inhalation device provided by the invention comprises a first primary component and a second primary component which are movable in relation to one another. In aspects, movement of a first primary component relative to a second primary component (or vice versa) is characterizable as a relational movement. In aspects, a relational movement is a movement wherein one component remains static while the second component moves in relation to the first component (or vice versa). In other aspects, a relational movement is a movement where two components move simultaneously in relation to one another. In aspects, such a simultaneous movement of a first primary component relative to a second primary component (or vice versa) is characterizable as a concurrent or associated relational movement. For example, a first primary component can, e.g., move in a first direction while a second primary component moves in a second direction. In certain aspects, the movement of a first primary component relative to a second primary component (or vice versa) is characterizable as a rotational movement. According to certain further aspects, as is described in detail elsewhere herein, a first primary component can comprise a first airflow control component and a second primary component can comprise a second airflow control component. In aspects, when a first primary component comprises a first airflow control component and a second primary component comprises a second airflow control component, movement of the two airflow control components relative to one another can be similarly described (e.g., can have any one or more of the movement characteristics described in this paragraph.)

Inhalation Device—Applications

In aspects, the inhalation device described herein is a device intended for use by a mammalian user, e.g., a human. In aspects, the device can be used by a human of any age, so long as the human user is capable of (a) sufficient manual dexterity to hold and/or manipulate the device, (b) independently inhale a volume of air through the device, or both (a) and (b). Therefore, in general, the inhalation device is intended for use by adult human subjects or, e.g., at least human subjects having an age of at least 2 years. In specific aspects, the device is used by, e.g., teen-aged human or adult human subjects.

In aspects, the inhalation device described herein is intended for use in delivering one or more volatile compounds to a user. In aspects, such a delivery of one or more volatile compounds can be for pure entertainment (pleasure) purpose(s). In aspects, a user does not use the device in association with any defined need or craving, but simply for enjoyment purposes. In other aspects, use of the device is in response to a need or craving, such as a craving associated with a smoking habit. In aspects, the device herein can be used by human subjects attempting to quit a smoking habit or to maintain a non-smoking status. In aspects, use of the device herein can be in response to one or more smoking habit-related craving(s), and use of the device is designed to detectably or significantly assuage one or more such smoking habit-related cravings. Thus, in one specific aspect, one application of the inhalation device described herein is the provision of entertainment, e.g., pleasure. In another specific aspect, one application of the inhalation device described herein is to aid a user having a current smoking habit, e.g., tobacco-product smoking habit, nicotine drug-related smoking habit, or both in reducing or eliminating such a habit. In another specific aspect, one application of the inhalation device described herein is to aid a former smoker maintain a smoke-free (e.g., tobacco-, nicotine-, or tobacco- and nicotine-free) status. In certain aspects, the inhalation device herein mimics many of the characteristics of a smoking device, e.g., a cigarette, a cigar, an e-cigarette, a vaping device, etc. Thus, in aspects, one application of the inhalation device is to serve as a replacement for, e.g., an alternative to, any one or more such devices.

Inhalation
Device—Size/Shape/Dimensions/Aesthetics

According to certain aspects, inhalation device(s) provided by the invention are characterizable has having two primary dimensions: a length and a width. Herein, length of an inhalation device generally describes the distance between the proximal end of the device (portion of the device through which the user receives volatile compound(s)) and a distal end of the device (opposing portion of the device through which air initially enters the device upon inhalation by a user.) Herein, width of an inhalation device generally describes the diameter of the device, e.g., a dimension perpendicular to the length. In certain aspects, the length of a device when fully assembled is less than the length of the device when not fully assembled. In certain aspects, the width of an inhalation device can vary across the length of a device, such as, e.g., an inhalation device can have a maximum width and a minimum width. In aspects, at least one, e.g., at least a first, portion of the device has a width which is different from at least one other, e.g., at least a second, portion of the device. In aspects, the device has at least one portion along its length, closer to its proximal end than its distal end, having a width which is detectably or significantly less than the width of at least one portion of the inhalation device located closer to its distal end. According to certain aspects, the inhalation device provided by the invention is between about 2 inches and about 10 inches (between about 50 mm and about 254 mm) in length, such as, e.g., ~2"-~9" (~50 mm-~229 mm), ~2"-~8" (~50 mm-~203 mm), ~2"-~7" (~50 mm-~178 mm), ~2"-~6" (~50 mm-~152 mm), or ~2"-~5" (~50 mm-~127 mm), such as, e.g., ~3"-~10" (~76 mm-~254 mm), ~4"-~10" (~102 mm-~254 mm), ~5"-~10" (~127 mm-~254 mm), or, e.g., ~6"-~10" (~152 mm-~254 mm), such as, for example, ~3"-~9" (~76 mm-~229 mm), ~4"-~8" (~102 mm-~203 mm), or, e.g., ~5"-~7" (~127 mm-178 mm).

In certain aspects, the inhalation device can be about 100" in length when fully assembled, e.g., in a ready-to-use state.

According to certain aspects, the inhalation device provided by the invention is between about 0.25 inches (about 6.3 mm) and about 1.5 inches (about 38 mm) wide, or, stated alternatively, the inhalation device in aspects comprises a widest diameter which is between about 0.25" and about 1.5" (about 6.3 mm and about 38 mm). In aspects, the inhalation device can take on any shape, such as, e.g., cylinder, triangular prism, rectangular prism (cuboid), pentagonal prism, hexagonal prism, octagonal prism, or other multi-sided prism. In common aspects, the inhalation device is presented with a general cylindrical shape, however wherein one or more portions of its cylindrical shape have a diameter which is less than one or more other portions of its cylindrical shape. This is illustrated in exemplary figures provided herein.

In aspects, the inhalation device comprises a widest diameter of between about 0.25" and about 1.5" (about 6.3 mm and about 38 mm), e.g., ~0.25"-~1.25" (~6.3 mm-~31.8 mm), ~0.25"-~1" (~6.3 mm-~25.4 mm), ~0.25"-~0.75" (~6.3 mm-~19.1 mm), or, e.g., ~0.25"-~0.5" (~6.3 mm-~12.7 mm), such as ~0.5"-~1.5" (~12.7 mm-~38.1 mm), ~0.75"-~1.5" (~19.1 mm-~38.1 mm), ~1"-~1.5" (~25.4 mm-~38.1 mm), or ~1.25"-~1.5" (31.8 mm-~38.1 mm), as in, for example, ~0.5"-~1.25" (~12.7 mm-~31.8 mm), or, e.g., ~0.75"-~1" (~19.1 mm-~25.4 mm). In certain aspects, the inhalation device can have a maximum diameter of about 22 mm when fully assembled, e.g., in a ready-to-use state.

In aspects wherein the inhalation device comprises one or more portions, e.g. one or more portions along its length, having a diameter which is less than the widest diameter described above, the inhalation device can comprise a narrowest diameter of between about 0.25" and about 1.25" (~6.3 mm-~31.8 mm), e.g., ~0.25"-~1" (~6.3 mm-~25.4 mm), ~0.25"-~0.75" (~6.3 mm-~19.1 mm), or ~0.25"-~0.5" (~6.3 mm-~12.7 mm), such as ~0.5"-~1.25" (~12.7 mm-~31.8 mm), ~0.75"-~1.25" (~19.1 mm-~31.8 mm), or ~1"-~1.25" (~25.4 mm-~31.8 mm), as in, for example, ~0.5"-~1" (~12.7 mm-~25.4 mm), or, e.g., ~0.75" (~19.1 mm), or, e.g., ~0.4" (~10.2 mm) or, e.g., ~0.6" (~15.2 mm). In aspects, the inhalation device can have a narrowest diameter of about 0.6" (~15 mm) when fully assembled, e.g., in a ready-to-use state.

In embodiments wherein the cross-sectional shape of the inhalation device is not circular, e.g., the inhalation device is presented in a shape not characterizable generally as a cylindrical (even if having one or more narrower dimensions skewing the shape from a true cylinder), the inhalation device can have a first non-length dimension, e.g., width, and a second non-length dimension, e.g., height, which do not vary by more than about 50% from one another, such as, e.g., they do not vary by more than ~45%, ~40%, ~35%, ~30%, ~25%, ~20%, ~15%, ~10%, or, e.g., which do not vary by more than ~5% relative to one another. In aspects, a maximum width or a maximum height is about 1.5," e.g., ~1.25" or, e.g., ~1".

According to some aspects, the inhalation device can comprise a length and a diameter, diameter referring to the thickness or width of the device. In certain aspects, the diameter is uniform across the length of the inhalation device. In aspects, as provided above, the diameter is non-uniform across the length of the inhalation device. In aspects, the device has at least a widest diameter and a narrowest diameter, and further the narrowest diameter of the device represents a diameter which is between about 20% and about 95% of that of the widest diameter of the device, such as, e.g., a narrowest diameter which is ~20%-~90%, ~20%-~85%, ~20%-~80%, ~20%-~75%, ~20%-~70%, ~20%-~65%, ~20%-~60%, ~20%-~55%, ~20%-~50%, ~20%-~45%, ~20%-~40%, ~20%-~35%, ~20%-~30%, or ~20%-~25% of that of the widest diameter of the device. In aspects, the narrowest diameter of the device represents a diameter which is between about ~25%-~95% of the widest diameter of the device, such as, e.g., ~30%-~95%, ~35%-~95%, ~40%-~95%, ~45%-~95%, ~50%-~95%, ~55%-~95%, ~60%-~95%, ~65%-~95%, ~70%-~95%, ~75%-~95%, ~80%-~95%, or ~85%-~95%, as in, for example, ~25%-~90%, ~30%-~85%, ~35%-~80%, ~40%-~75%, ~45%-~70%, ~50%-~65%, or, e.g., ~55%-~60% of that of the widest diameter of the device.

In one aspect, the inhalation device has a length, and the inhalation device comprises at least two separate portions, e.g., sections, along its length having a diameter (e.g., thickness) which is less than the widest diameter of the device. In such embodiments, either, both, or all such diameter-reduce portions can comprise, e.g., any of the dimensions described for a single diameter-reduced portion of an inhalation device above. For example, in aspects, the inhalation device comprises at least two separate portions of its length having a diameter which is less than its widest diameter, for example, either, both, or all such portions comprising a narrowest device diameter which is between about 20% and about 95% of that of the widest diameter of the device, such as, e.g., a narrowest diameter which is ~20%-~90%, ~20%-~85%, ~20%-~80%, ~20%-~75%, ~20%-~70%, ~20%-~65%, ~20%-~60%, ~20%-~55%, ~20%-~50%, ~20%-~45%, ~20%-~40%, ~20%-~35%, ~20%-~30%, or ~20%-~25%. In aspects, either, both, or all such portions comprise a narrowest device diameter which is between about, e.g., ~25%-~95%, ~30%-~95%, ~35%-~95%, ~40%-~95%, ~45%-~95%, ~50%-~95%, ~55%-~95%, ~60%-~95%, ~65%-~95%, ~70%-~95%, ~75%-~95%, ~80%-~95%, or ~85%-~95% of that of the widest diameter of the device. In aspects, either, both, or all such portions comprise a narrowest device diameter which is between about, for example, ~25%-~90%, ~30%-~85%, ~35%-~80%, ~40%-~75%, ~45%-~70%, ~50%-~65%, or, e.g., ~55%-~60% of that of the widest diameter of the device.

According to certain aspects, the inhalation device comprises at portion along its length having a diameter which is less than the widest diameter of the device, wherein the portion is positioned to facilitate placement of the user's lips about the device. In such aspects, such a diameter-reduced portion, e.g., a "lip groove", of the inhalation device is positioned near a first end of the inhalation device, e.g., within the first 50% of the length of the device from a first end, or, e.g., within the first about 45%, ~40%, ~35%, ~30%, ~25%, or, e.g., within the first about 20% of the length of the device from a first end.

According to some aspects, the inhalation device comprises at portion along its length having a diameter which is less than the widest diameter of the device, wherein the portion is positioned to facilitate placement of the user's fingers, e.g., for placement of the device between two fingers, such as positioning the device between two fingers as a typical cigarette smoker may hold a cigarette (e.g., between a forefinger and a middle finger). In such aspects, such a diameter-reduced portion, e.g., a "finger groove," of the inhalation device is positioned within, e.g., the central 80% of the length of the inhalation device. That is, such a finger groove can be positioned outside of the first 10% of the length of the device from either end. In certain aspects, a finger groove can be positioned within the central ~80%, ~75%, ~70%, ~65%, ~60%, ~55%, or, e.g., within about the central ~50% of the length of the inhalation device. Again, e.g., the central 50% of the length of the device being a portion of the device beginning at a point located at 25% of the inhalation device's length from a first end of the device and ending at a point which is located at 75% of the inhalation device's length from that same first end of the device, or, e.g., ending at a position which is located at 25% of the length of the device from the second end of the device. In aspects, a finger groove is positioned along the length of an inhalation device in a position outside of the first 10% of the inhalation device's length from a first end but within the first 60% of the device's length from the same first end, such as at a position located at about 15%, ~20%, ~25%, ~30%, ~35%, ~40%, ~45%, or about 50% of the inhalation device's length from a first end. In aspects, a first end of the device can be the end comprising the portion of the device intended to be placed onto the lips or into the mouth of the user, and the second end of the device can be the end distal to the user's lips.

In one aspect, the inhalation device comprises at least two separate portions along its length having a diameter which is less than the widest diameter of the device, and wherein one portion having a diameter less than the widest diameter of the device is positioned to facilitate placement of the user's lips and at least a second portion is positioned to facilitate placement of a user's finger(s).

In aspects, portion(s) of the device having a reduced diameter provide(s) functionality, e.g., facilitating comfortably holding the device within the mouth of the user (e.g., using a "lip groove"), holding the device with or between fingers (e.g., using a "finger groove") or both. In aspects, portion(s) of the device having a reduced diameter provide(s) an aesthetically pleasing nature to the design of the inhalation device, making it pleasurable to hold, manipulate, utilize, etc.

According to certain aspects, as described above, the inhalation device can comprise a first primary component and a second primary component (also simply referred to herein, as first and second device components). In some aspects, the two components are releasably bound to one another, such as by, e.g., a rapidly releasable force mechanism described elsewhere herein. In aspects, the total length of the device when the first primary component and second primary component are bound to one another is less than total length of each of the first component and the second component independently added together. That is, in aspects, the first primary component has a length A, the second primary component has a length B, and the inhalation device, when the first primary component and second primary component are bound together, has a length C, length C being a length which is less than the sum of lengths A and B. To facilitate this, the first primary component can have a feature or subcomponent(s) which reside(s) at least partially within the second primary component when the two components are bound together. Also, or alternatively, the second primary component can have a feature or subcomponent(s) which reside(s) at least partially within the first primary component when the two components are bound together.

In certain embodiments, the inhalation device comprises a first device component (e.g., a first primary component) and a second device component (e.g., a second primary component) releasably bound to one another, wherein the total length of the device when the first and second device components are bound to one another is no more than about 90%, such as no more than ~70%, ~60%, ~50%, ~40% or, e.g., no more than ~30% of the total length of each of the first component and the second component independently added together. In aspects, the total length of the inhalation device when the first and second device components (e.g., first and second primary components of the device) are bound to one another is between about 30% and about 90%, such as, e.g., ~30%-~80%, ~30%-~70%, ~30%-~60%, ~30%-~50%, ~30%-~40%, or, e.g., ~40%-~90%, ~50%-~90%, ~60%-~90%, ~70%-~90%, or ~80%-~90%, such as, for example, about 40%-~80%, or, e.g., ~50%-~70% of the total length of the first and second device components (first and second primary components) individually added together.

According to certain aspects, at least a portion of a first primary component resides within the second primary component (at least a portion of a first device component resides within the second device component) when the first and second components are bound together, e.g., bound together by a selectively releasable attachment mechanism. In certain aspects, at least about 25% the length of the first primary component of the inhalation device resides within the second primary component of the inhalation device when the first and second primary components of the inhalation device are bound together, e.g., bound together by a selectively releasable attachment mechanism.

In aspects, between about 25% and about 75% of the full length of the first primary component of the inhalation device resides within the second primary component of the inhalation device, e.g., ~30%-~75%, ~35%-~75%, ~40%-~75%, ~45%-~75%, ~50%-~75%, ~55%-~75%, ~60%-~75%, ~65%-~75%, or ~70%-~75%, such as, e.g., ~25%-~70%, ~25%-~65%, ~25%-~60%, ~25%-~55%, ~25%-~50%, ~25%-~45%, ~25%-~40%, ~25%-~35%, or ~25%-~30%, such as for example ~30%-~70%, ~35%-~65%, ~40%-~60%, or, e.g., ~45%-~55% of the first primary component of the inhalation device resides within the second primary component of the inhalation device when the first and second primary components of the inhalation device are bound together, e.g., bound together by a selectively releasable attachment mechanism. In certain aspects, more than 75% of the full length of the first primary component of the inhalation device resides within the second primary component of the inhalation device when the first and second primary components of the inhalation device are bound to one another, e.g., are releasably bound to one another by a selectively releasable attachment mechanism.

The inhalation device can weigh, e.g., between about 10 g and about 100 g when not comprising a removable insert for the delivery of one or more volatile compounds, e.g., a solid material device or core. Such as, for example, an "empty" inhalation device (lacking a removable insert) can weigh between about, e.g., 10 g-about 90 g, ~10 g-~80 g, ~10 g-~70 g, ~10 g-~60 g, or ~10 g-~50 g, as in ~20 g-~90 g, ~30 g-~90 g, ~40 g-~90 g, or ~50 g-~90 g, such as for example between ~20 g-~80 g, ~30 g-~70 g, ~40 g-~60 g, ~50 g-~60 g, or, e.g., in aspects ~55 g.

In aspects, the inhalation device does not comprise a means for refilling or recharging an existing removable insert present in the device with additional volatile compound(s). That is, for example, in aspects, the inhalation device does not comprise an opening or component designed to facilitate the entry of a liquid composition, such as, e.g., an essential oil, which re-fill or otherwise recharge a solid material device present within the inhalation device capable of maintaining, releasing, or maintaining or releasing one or more volatile compounds, e.g., a removable insert/core. This is discussed further elsewhere herein.

Inhalation Device—Materials & Manufacturing

In aspects, one or more components of an inhalation device can be at least substantially composed of or composed of any material safe for placement in the mouth of a human device user. In aspects, one or more components of an inhalation device can be at least substantially composed of or composed of any material having a sufficient hardness, density, moisture resistance, scratch resistance, or any combination thereof appropriate for its long-term function in an inhalation device (e.g., is suitable to perform the function of the component comprising the material for a period of at least about 1 month, ~2 months, ~4 months, ~6 months, ~12 months, ~18 months, ~24 months, ~30 months, ~36 months, ~42 months, ~48 months, ~54 months, or ~60 months or longer, such as, e.g., ~1-~60 months, ~2-~60 months, ~4-~60 months, ~6-~60 months, ~12-~60 months, ~18-~60 months, ~24-~60 months, ~30-~60 months, ~36-~60 months, ~42-~60 months, ~48-~60 months, or ~54-~60 months, or, e.g., for a period of at least about 60 months.) In aspects, one or more components of an inhalation device can be composed of a metal, such as, e.g., a metal alloy (e.g., comprising a combination of, e.g., two or more of iron, chromium, nickel, etc.) such as, e.g., stainless steel, or, e.g., a precious metal or precious metal alloy, e.g., gold (including, e.g., find gold, gold alloy, yellow gold, rose gold, or white gold), silver, platinum, palladium, titanium, etc. In aspects wherein one or more components of an inhalation device is made of stainless steel, in aspects any grade stainless steel can be used. In certain aspects, the stainless steel used for one or more components of an inhalation device can be, e.g., 434 or 416 grade stainless steel. In some aspects, the stainless steel can be ferritic. In some aspects, a high magnetism stainless steel is used for one or more components of an inhalation device. In some aspects, the stainless steel used for one or more components can be, e.g., 316 or 304 grade stainless steel. In certain aspects, a non-magnetic stainless steel is used for one or more components of an inhalation device. In aspects, one or more components of an inhalation device can be composed of a polymeric material such as a plastic. In aspects, a plastic can be a polyethylene terephthalate (PET or PETE), high-density polyethylene (HDPE), polyvinyl chloride (PVC or vinyl), low-density polyethylene (LDPE), polypropylene (PP), polystyrene (PS or Styrofoam, as long as such plastics are sufficiently hard, e.g., durable, for use in the application. In aspects, one or more components of an inhalation device can be composed of an organic material, such as bamboo, cellulose, clay, diamond, nacre, or, wood, e.g., such as maple, rosewood, or olive wood, or, e.g., a ceramic material, e.g., an alumina or zirconia ceramic. In aspects one or more components of an inhalation device can be composed of a stone or shell. In certain aspects, two or more components can be composed of at least substantially the same material and have at least substantially the same appearance, such as, e.g., two components made of, e.g., stainless steel having at least substantially the same coloration, reflectivity, and the like. In certain aspects, two or more components can be composed of at least substantially the same type of material and have at least substantially the same appearance or have detectably or significantly different appearances. As one example, two components can each be made of a metal, however one may be made of titanium and one may be made of platinum and thus each may have a detectably or significantly different color, reflectivity, or the like. Another example is two components made of a plastic, wherein one plastic has a first color, and the second plastic has a second color. A further example is two components both made of wood however a first component is made of a first wood, e.g., maple, and a second component is made of a second wood, e.g., rosewood, and thus each component has a distinguishably different visual appearance.

According to certain aspects, all components of an inhalation device can be made of the at least generally the same, at least substantially the same, at least essentially the same, essentially the same, or the same material. In some aspects, one or more components of an inhalation device can be made of a different material from one or more other components of a device. For example, in aspects, one or more components of a device can be made of stainless steel and one or more components of a device can be made of wood. In certain aspects, three or more materials may be present in an inhalation device, such as, e.g., one or more components made of ceramic, one or more components made of stainless steel or precious metal, and one or more components made of wood.

In certain aspects, it can be desirable, beneficial, or otherwise advantageous for one or more components to be made of a particular material or particular type of a material. As the device is designed for the inhalation of one or more compounds, moisture from, e.g., a user's mouth or breath may affect the performance, longevity, or both of one or more components. In aspects, it may be desirable, beneficial, or otherwise advantageous for a component which comes into contact with such moisture to be made of a more durable material, e.g., a metal as opposed to a wood. In aspects, it may be desirable, beneficial, or otherwise advantageous for a component which could come into contact with such moisture to be protected from such moisture by the placement of one or more other components in a position to offer protection. As one example, in aspects, a barrel of a device can be made of an organic material, e.g., a wood, providing an aesthetically pleasing, visually appealing appearance. In aspects, such a wood can be a hard wood, such as, e.g., maple, rosewood, or, e.g., olive wood, as opposed to a softwood, such as pine, balsam, or other wood which can be more prone to denting, scratching, or other malformation(s). However, regardless of the wood, because such a barrel could come into contact with moisture within the device, the barrel may be positioned over a tube, e.g., a barrel tube, made of an even more durable material, such as, e.g., stainless steel, or a metal such as titanium or platinum, the barrel tube protecting the barrel from an amount of moisture which may be detrimental to the longevity or performance of the barrel. In certain other aspects, one or more components can be designed for selective disengagement from one or more other components of the inhalation device. In such aspects, the ability of the interfacing components to be repeatedly engaged and disengaged from one another is critical, and a component made of a non-durable material may present challenges to functionality, durability, or both. As an example, an inhalation device can be designed to have a dis-engageable, e.g., replaceable, mouthpiece. In aspects, a mouthpiece made of, e.g., ceramic or, e.g., an organic material such as wood, may not comprise sufficient durability to be repeatedly engaged and disengaged from one or more other components of the inhalation device by a mechanism such as, e.g., screwing the mouthpiece onto and off of one or more other components. Therefore, e.g., a component of a second, more durable material may be necessary to provide durable repeated engageability/disengageability of an e.g., organic material-based or otherwise non-durable mouthpiece. In such an aspect, a mouthpiece attachment mechanism or, e.g., a mouthpiece tube, can be placed at least partially inside of the mouthpiece to facilitate its repeated engagement/disengagement. Such an attachment mechanism can be made of, e.g., a durable material such as stainless steel, and can comprise, e.g., threading compatible with threading with a second component of the device to which the mouthpiece can releasably attach.

In certain aspects, all externally visible components are made of at least generally the same, at least substantially the same, at least essentially the same, essentially the same, or the same material and have at least generally the same, at least substantially the same, at least essentially the same, essentially the same, or the same visual appearance. In certain aspects, at least one externally visible component is made of a material which is different from at least one other externally visible component. In certain aspects, at least three externally visible components are each comprised of a different material.

According to certain aspects, one or more components of an inhalation device are customized parts, e.g., a part or component which is custom made for use in the device and is not otherwise available as used in the device on the mass market. In aspects, the customization can be a custom molding or machining of the part. In aspects, a part or component can be custom machined, carved, or die cast. In aspects, the inhalation device comprises less than 5, such as less than ~4, ~3, ~2, or only 1 or no part which is not custom made for specific use within the device.

In aspects, two or more components can be fixedly attached to one another by welding. In aspects two or more components can be fixedly attached to one another by brazing. In aspects, brazing is accompanied by the removal of any resulting debris so as to leave a substantially clean joint between the two components such that no material remains which detectably or significantly interferes with the operation of the inhalation device. In other aspects two or more components can be fixedly attached to one another by gluing the two components to one another, such as by using a glue such as an epoxy glue. In aspects, no adhesive residue is visible during normal operation of the inhalation device or when viewing a completely assembled device upon the completion of manufacturing.

Weight Balancing

In certain aspects, the inhalation device has a length and a center of gravity. In aspects, at least one portion of the inhalation device along its length has a diameter which is less than the widest diameter of the device. In certain facets, the center of gravity of the device is positioned at a location along the length of the device corresponding to a portion of the device having a diameter which is less than the widest diameter of the device. A portion of the inhalation device along its length having a reduced diameter relative to the widest diameter of the device can be positioned at a location corresponding to the center of gravity of the device. In facets, such a reduced diameter portion of the length of the device can be a portion facilitating placement of a user's fingers to hold the device, and such a reduced diameter portion (e.g., finger groove) is in a location corresponding to the center of gravity of the device such that when holding the inhalation device between two fingers at such location, the inhalation is essentially weight balanced.

According to certain aspects, the center of gravity of the device is located at a position corresponding to locations marking between about 10% to about 90% of the total length of the inhalation device as measured from a first end, such as between a location marking ~10%-~85%, ~10%-~80%, ~10%-~75%, ~10%-~70%, ~10%-~65%, ~10%-~60%, ~10%-~55%, or ~10%-~50%, such as, e.g., ~15%-~90%, ~20%-~90%, ~25%-~90%, ~30%-~90%, ~35%-~90%, ~40%-~90%, ~45%-~90%, or, e.g., ~50%-~90% of the total length of the inhalation device as measured from the first end. In aspects, the center of gravity of the device is located within the first ½ of the total length of the device as measured from the inhalation device's first end (e.g., the end intended for placement onto the lips of or into the mouth of the user). In aspects, the center of gravity of the device is located within the first $\tfrac{2}{5}^{ths}$ of the total length of the device or within the first $\tfrac{1}{3}^{rd}$ of the total length of the device as measured from the inhalation device's first end. In aspects, the device is designed with its center of gravity in mind, such that the positioning of the center of gravity, positioned to provide the device in a balanced position when held via an, e.g., finger groove, adds to a user's enjoyment, comfort, or both in using the device, enhancing the user experience of the device.

2 Primary Components

As described above, in aspects, the inhalation device provided by the invention comprises two components which are not subcomponents of at least one other component. Accordingly, herein these two components can be referred to as primary components. In one aspect, one primary component is referred to herein as a Body Assembly. In one aspect, one primary component is referred to herein as a Tip Assembly. Each is further described elsewhere herein.

Selective Releasable Engagement

In aspects, the two primary components of the system are selectively attached to one another by a selectively releasable attachment mechanism. That is, the first and second components can be connected to one another or, alternatively, not connected to one another over a course of operating the device. The status of the attachment is determined by the user, in that the user can engage or disengage the two components. Further, the first and second primary components of the device are movable in relation to one another. In aspects, the two primary components can maintain some degree of contact between one another when the two primary components are rotated in relation to one another.

In certain aspects, the inhalation device can, for example, begin in a state wherein the first primary component and second primary component are in a first configuration and are selectively connected to one another. The user can, e.g., rotate the first and second primary device components in relation to one another in a way that maintains some degree of contact between the two primary components during such rotation, wherein at the end of the rotation the first and second primary components are in a second configuration and are still selectively connected to one another. During such an example, the degree of contact between the two primary components can change. For example, the degree of interface between the two primary components can drop, e.g., be reduced, before increasing again once reaching the second configuration. In certain aspects, the degree of interface between the two primary components drops between any two configurations established by the positioning of the first primary component relative to the second primary component. In certain aspects, the degree of interface between the two primary components does not increase between any two configurations established by the positioning of the first primary component relative to the second primary component.

From the first configuration, the user alternatively, e.g., can disengage the first and second primary device components, rotate them in relation to one another while the two components are disengaged from one another, and reengage the two primary components such that they result in having a second configuration and then are again selectively connected to one another.

In certain aspects, the selective attachment mechanism can be any reversible attachment mechanism, such as a snap fit mechanism, including an annular snap-fit, a cantilever snap-fit (e.g., a multiple-use cantilever snap-fit), or, e.g., a torsional snap-fit, or, e.g., a screw fit (e.g., using threading), a push-and-turn release mechanism (similar to or the same as the type of mechanism used commonly for child-proofing a medicinal container), a push-and-release attachment mechanism (sometimes referred to as a push-latch (or push latch) mechanism), an attachment via a clip, pin, lock, latch, attractive force mechanism such as a magnetic force, or any other type of reversible, non-permanent connection mechanism known in the art. In aspects, a first selectively engageable connection mechanism component can reside in a first primary device component, while a second selectively engageable connection mechanism component can reside in a second primary device component, the two selectively engageable connection mechanism components each being a component of a reversible attachment mechanism described in this paragraph. In aspects, such components cooperate to provide a selectively releasable connection mechanism for the inhalation device.

According to certain specific aspects, the selectively releasable connection mechanism is not a snap fit mechanism (including, e.g., an annular snap-fit, a cantilever snap-fit (e.g., a multiple-use cantilever snap-fit), or, e.g., a torsional snap-fit). In aspects, the selectively releasable connection mechanism is not a screw fit (e.g., using threading). In aspects, the selectively releasable connection mechanism is not a push-and-turn release mechanism (similar to or the same as the type of mechanism used commonly for child-proofing a medicinal container). In aspects, the selectively releasable connection mechanism is not a push-and-release attachment mechanism. In aspects, the selectively releasable connection mechanism is not an attachment mechanism utilizing a component recognizable as a clip, pin, lock, or latch.

In certain aspects, the selective attachment mechanism is a rapidly releasable connection mechanism, also referred to as a rapidly releasable force mechanism. Herein, a rapidly releasable connection mechanism and rapidly releasable force mechanism should be considered interchangeable. Herein, "rapidly releasable" should be interpreted as meaning essentially immediate, direct, or capable of unidirectional (the two components can be rapidly released from one another by moving in a single direction, e.g., away from each other) disengagement. As an example, a screw fit utilizing threading would not be considered a rapidly releasable connection mechanism, as at least some rotation in a direction of, e.g., a first primary component and a second primary component of a device would need to occur before the two primary components disengage, such rotation further accompanied by, upon completion of the disengagement of the threading, pulling the first and second components apart. As another example, a mechanism comprising a latch, pin, or lock which require the user to manipulate them prior to separating the two components from one another would not be considered a rapidly releasable connection mechanism, as the disengagement is not immediate—a step of manipulating the mechanism is required before separating the components—nor is it direct for the same reason. Alternatively, examples of rapidly releasable connection mechanisms can include, e.g., a snap fit or, e.g., a connection by an attractive force mechanism such as magnetic force. In such examples, the two components can be pulled directly away from one another effectively immediately without additional manipulation. In aspects, the rapidly releasable connection mechanism or rapidly releasable force mechanism is an attractive force mechanism. In certain aspects, the rapidly releasable connection mechanism or rapidly releasable force mechanism is a magnetic attraction. In aspects, the magnetic attraction is accomplished by the positioning of a magnet in a first primary component and positioning at least one component attractive to the magnet in the second primary component. In such aspects, two separate components, e.g., the first primary component and the second primary component of the inhalation device can be selectively and releasable bound to one another by the magnetic attraction, the magnetic attraction allowing the two primary components to be completely pulled apart rapidly as desired by the user, however the two primary components can also move or rotate in relation to one another while still maintaining at least a degree or some detectable or significant amount of interface, e.g., a connection, to one another as the magnet does not force a fixed positional relationship between the two primary components. In certain aspects, the first primary component and the second primary component are connected to one another by a selectively releasable attachment mechanism, wherein the selectively releasable attachment mechanism provides for complete disengagement of the two primary components and also allows for the two components to continue to interface with one another while being rotatable a full 360 degrees relative to one another. In certain aspects, the selectively releasable attachment mechanism is a rapidly releasable attachment. In aspects, the rapidly releasable attachment mechanism is a magnetic force.

According to certain aspects, a selective attachment mechanism is a rapidly releasable connection mechanism (or, as stated above, a rapidly releasable force mechanism) which is operable with a single hand of a user, e.g., a single hand of the average (e.g., typical) adult. In such aspect, two components of an inhalation device, e.g., the first primary component and the second primary component can be separated and re-attached repeatedly from one another quickly and easily by a user, such as by, e.g., single hand movement(s) of the user. In aspects, such rapid release and reconnection provides one aspect of an entertainment embodiment of the inhalation device, such as, e.g., by providing a fidget experience through manual manipulation of the device. In certain respects, a rapid disengageability and reattachability of the first primary component and second primary component by a rapid release force mechanism provided by a magnet is one aspect of the invention. In certain respects, such an embodiment provides entertainment pleasure to a user, provides a mechanism for assuaging a smoking habit-related craving such as a craving to hold, fondle, or otherwise play with or manually manipulate a smoking device, or any combination thereof. In certain aspects, an ability to provide an entertainment experience or assuage a smoking habit-related craving which is separate from any volatile compound(s) inhalation experience is an inventive element of the inhalation device provided herein. In aspects, the device(s) herein provide an experience, e.g., a manually-focused experience characterizable as a "fidget" experience, capable of detectably or significantly reducing one or more non-inhalation smoking habit-related craving(s) as measured or reported by the user, as measured by an appropriately conducted and powered trial or survey administered or conducted by suitably trained individual(s) recognized as capable of identifying reduction in addiction-related behavior, or both. In certain aspects, a suitably trained individual recognized as capable of identifying reduction in addiction-related behavior can be, e.g., an addiction counselor, therapist, psychologist, medical physician, or other medical or non-medical personnel trained in identifying or suitably familiar with addiction related habit(s).

In this and other component, function, or operational aspect(s) of the invention, the invention also can be characterized as comprising a "means" for selectively and releasable attaching one component of an inhalation device, e.g., a first primary component, to another component of an inhalation device, e.g., a second primary component. In such a respect, any known equivalents of such named releasable, non-permanent attachment mechanisms can also be, e.g., are, incorporated into devices or methods of the invention. As with other sections similarly described herein, any of the components of the invention can be, where suitable, described as means (e.g., the above-described releasable connection mechanisms can be described as selectively releasable attachment means or means for providing releasable engagement, e.g., rapidly releasable engagement, of a first primary component and a second primary component).

Characteristics of first and second primary components are described in further detail here.

First Primary Component

In aspects, a first primary component can comprise of a single device component. In aspects, a first primary component can be comprised of a plurality of device components. In aspects, a first primary component can comprise a sub-component characterizable as a single device component or a sub-assembly of multiple components. Herein, the term subassembly may be used to describe a group of components of a device which begin as individual components however during the manufacturing process are assembled together into a collection of components which are not intentionally dis-engageable from one another during normal (e.g., standard or routine) operation of the device. However, such a description should not be interpreted as limiting, and, thus components described as being a part of a subassembly should be considered in alternative embodiments to be able to be provided as an individual component.

Body Assembly

In aspects, a first primary component can be referred to as a Body Assembly. In aspects, a Body Assembly comprises at least one component of the device which is an externally visible component(s). In aspects, a function of the first primary component, e.g., a Body Assembly, can be to contribute to the visual aesthetics of the device. In aspects, a function of the first primary component, e.g., a Body Assembly, can be to provide an inhalation facilitation component, e.g., a Mouthpiece (described below). In aspects, therefore, at least one component of the first primary component, e.g., Body Assembly, can establish a first portion of the full length of the device starting at a device first end, the first end being the end of the device being that which is designed for placement onto a user's lips or into a user's mouth.

In aspects, a function of a first primary component, e.g., a Body Assembly, can be to maintain a volatile compound maintenance and delivery element (such a volatile compound maintenance and delivery element referred to herein as a solid material device capable of maintaining, releasing, or maintaining and releasing one or more volatile compounds, or, e.g., a "removable insert" or a "core".) In aspects, a function of a first primary component, e.g., a Body Assembly, can be to maintain a removable insert stably within the inhalation device during operation of the device and during device movement or storage. In aspects, a function of a primary component, e.g., a Body Assembly, can be to facilitate the case of insertion, removal, or insertion and removal of a removable insert (core).

Inhalation Facilitation Component (Mouthpiece)

According to embodiments, inhalation devices provided by the invention comprise one or more component(s) facilitating the inhalation of one or more volatile compounds. In aspects, such one or more component(s) can facilitate the inhalation of one or more volatile compounds via the nose of a user. In alternative aspects, such one or more component(s) is/are not designed to specifically facilitate the inhalation of one or more volatile compounds via the nose of a user. In common embodiments, the one or more components facilitating inhalation of one or more volatile compounds is designed to facilitate the delivery of the one or more volatile compounds via the mouth.

In certain aspects, a component facilitating the inhalation of one or more volatile compounds ("inhalation facilitation component") can be, e.g., one or more openings, e.g., holes or apertures in a device. In aspects such one or more openings can be selectively openable and closable hole(s) or opening(s). In aspects, such an inhalation facilitation component can be, e.g., a short tube, cannula, or other component designed with the shape of the nose in mind, e.g., with one or more elements for placement into one or more nostrils of a user. In aspects, such a component facilitating inhalation of one or more volatile compounds is designed to facilitate the placement of the inhalation device upon the user's lips, between the user's lips, into the mouth of the user, or a combination thereof.

In aspects, an inhalation facilitation component facilitating the inhalation of one or more volatile compounds can be, e.g., embodied as a Mouthpiece. In aspects, an inhalation facilitation component can comprise one or more of the characteristics of a Mouthpiece described in the figures or detailed description of figures provided herein. In aspects, the inhalation facilitation component, e.g., Mouthpiece, can facilitate the inhalation of one or more volatile compounds via the device, can facilitate holding the inhalation device within the mouth of the individual, or both. In aspects, the inhalation facilitation component, e.g., Mouthpiece, can comprise one or more design features which detectably or significantly increase the case by which a user can hold or stably maintain the device during use. For example, in aspects, an inhalation facilitation component embodied as a mouthpiece can comprise one or more portions along its length comprising a diameter, or, e.g., width or height in a device not having a circular cross-sectional shape, which is less than the maximum diameter, or, e.g., maximum width or height, of the mouthpiece, of the inhalation device itself, or both. Such a portion of narrowed diameter can be characterizable as a "lip groove" as described above, wherein the narrowed section aids the user in maintaining the inhalation device between their lips or, e.g., within their mouth.

An inhalation facilitation component, e.g., Mouthpiece can, in embodiments, comprise two or more portions along its length having a diameter, or, e.g., width or height in a device not having a circular cross-sectional shape, which is less than the maximum diameter, or, e.g., maximum width or height, of the mouthpiece, of the inhalation device itself, or both. In such aspects, one such narrowed portion can aid, facilitate, or otherwise improve upon the ability of the user in maintaining the inhalation device between their lips or, e.g., within their mouth. Such a narrowed portion providing such functionality can also or alternatively improve upon the comfort experienced by the user in maintaining the device between their lips or within their mouth. Further, a second such narrowed portion can facilitate holding the device, such as a narrowed portion characterizable as a "finger groove" as described above. In certain aspects, an inhalation facilitation component, e.g., Mouthpiece, can comprise a reduced diameter (e.g., reduced thickness or width) portion in a location which corresponds with the center of gravity for the device when the device is fully assembled and in a ready-to-use state.

In aspects, an inhalation facilitation component, e.g., Mouthpiece can be made of any material safe for use in the mouth of a user. In aspects, such a material can be an organic material, such as, e.g., a wood, such as, e.g., maple, rosewood, or olive wood. In aspects, such a material can be a metal or metal alloy material, such as, e.g., those described elsewhere herein, e.g., stainless steel, gold, titanium, platinum, etc. In aspects, such a material can be a plastic such as those described elsewhere herein.

In certain aspects, an inhalation facilitation component, e.g., Mouthpiece, can be releasably attached to one or more components of an inhalation device, e.g., one or more components of a first primary component (e.g., Body Assembly) such as, for example to a component of a selectively releasable attachment mechanism (comprising, e.g., in embodiments, a Magnet, a Magnet Cover, and a Barrel Collar). In aspects for example, an inhalation facilitation component, e.g., Mouthpiece, can be releasably attached to a Magnet Cover. In certain embodiments, wherein the exemplary Magnet and Magnet cover components of a selectively releasable attachment mechanism reside in a first primary component of an inhalation device (e.g., Body Assembly), along with an inhalation facilitation component (e.g., Mouthpiece), and an exemplary Barrel Collar component of a selectively releasable attachment mechanism resides in a second primary component of an inhalation device (e.g., Tip Assembly), the, e.g., Mouthpiece is not releasably attached to an, e.g., Barrel Collar. In aspects, an inhalation facilitation component, e.g., Mouthpiece, can be releasably attached to the inhalation device and therefore can be replaced or is characterizable as interchangeable. One embodiment of the inhalation device provided herein therefore is an inhalation device comprising an interchangeable, e.g., replaceable mouthpiece, such that a user can customize the mouthpiece according to user preferences directed to visual appearance (e.g., color), material, weight, shape, etc.

In aspects, an inhalation facilitation component is a custom machined component, designed specifically for use in an inhalation device described herein.

In this and other component, function, or operational aspect(s) of the invention, the invention also can be characterized as comprising a "means" for facilitating the inhalation of one or more volatile compounds. In such a respect, any known equivalents of such named inhalation facilitation mechanisms can also be, e.g., are, incorporated into devices or methods of the invention. As with other sections similarly described herein, any of the components of the invention can be, where suitable, described as means (e.g., the above-described inhalation facilitation component can be described as inhalation facilitation means or means for providing or facilitating the inhalation of one or more volatile compounds).

Inhalation Facilitation Component Supplement (Mouthpiece Tube)

According to aspects, an inhalation device may comprise an inhalation facilitation component (e.g., Mouthpiece), made at least substantially of a material which is (a) at risk of being compromised due to exposure to excessive moisture, (b) not sufficiently durable to facilitate attachment to at least one additional component of the inhalation device, (c) not sufficiently durable to facilitate repeated engagement and disengagement from at least one additional component of the inhalation device, or (d) any combination of (a)-(c). In aspects, an inhalation facilitation component or, e.g., an inhalation device, can comprise as an additional component an inhalation facilitation component supplement. In certain aspects, such an inhalation facilitation component supplement can be, e.g., a Mouthpiece Tube. In aspects, an inhalation facilitation component supplement can comprise one or more of the characteristics of the Mouthpiece Tube described in the figures or detailed description of figures provided herein.

In aspects, an inhalation facilitation component supplement can be, e.g., any component which operates to protect an inhalation facilitation component (e.g., Mouthpiece) from damage, such as by, e.g., exposure to excessive moisture or, e.g., wear and tear associated with repeated engagement/disengagement from another inhalation device component. In aspects, such an inhalation facilitation component supplement can be any component accomplishing this purpose, such as, e.g., a liner, a coating, an inserted component, such as, an insert made of, e.g., a plastic, metal, or, e.g., metal alloy, etc. In aspects, such an inhalation facilitation component supplement can be made of, e.g., stainless steel. In aspects, the inhalation facilitation component supplement is a stainless-steel tube, e.g., a Mouthpiece Tube.

In certain aspects, an inhalation facilitation component supplement, e.g., Mouthpiece Tube, can be positioned within an interior of an inhalation facilitation component, e.g., Mouthpiece. In such aspects, the inhalation facilitation component supplement is not obviously externally visible under normal inhalation device operating conditions. In aspects, the inhalation facilitation component supplement detectably or significantly reduces the exposure of the inhalation facilitation component to moisture. In aspects, the inhalation facilitation component supplement is at least generally, at least substantially, at least essentially is, essentially is, or is the same length as the inhalation facilitation component. In aspects, the inhalation facilitation component supplement has a length which is shorter than that of the inhalation facilitation component, such that, e.g., it does not encompass the full length of an airflow path through the inhalation facilitation component. In aspects, its length is, e.g., at least about 10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, or, e.g., is at least about 97.5%, ~98%, ~99%, or, e.g., is about 100% of the length of the inhalation facilitation component. In aspects, the inhalation facilitation component supplement is designed with an attachment mechanism facilitating the durable, repeatable, selective engagement/disengagement of the inhalation facilitation component with at least one other component of the device. In aspects, the inhalation facilitation component supplement detectably or significantly extends the usable lifespan of an inhalation facilitation component, such as by at least ~2×, ~5×, ~10×, ~20×, ~50×, ~100×, ~1000×, or ~2000× or more over an inhalation facilitation component lacking such a component.

In aspects, such an attachment mechanism can be, e.g., any selectively releasable attachment mechanism described elsewhere herein, such as, e.g., a threading connection mechanism to allow for a volatile compound inhalation facilitation component to be selectively screwed onto or off of one or more other components of an inhalation device. In certain specific aspects, a Mouthpiece can comprise a Mouthpiece Tube, the Mouthpiece Tube comprising threading to facilitate the attachment of the Mouthpiece to another component of a first primary device component, e.g., a Magnet Holder. In certain aspects, an inhalation facilitation component supplement (e.g., Mouthpiece Tube) can be press-fit into/onto a removable insert housing component (Body Tube).

In aspects, an inhalation facilitation component supplement, e.g., Mouthpiece Tube, can be custom made, e.g., custom cast, machined, or otherwise custom manufactured for use with the inhalation device(s) herein. In aspects, an inhalation facilitation component supplement, e.g., Mouthpiece Tube, can be purchased as a typical on-market machine part.

In this and other component, function, or operational aspect(s) of the invention, the invention also can be characterized as comprising a "means" for protecting the inhalation facilitation component. In such a respect, any known equivalents of such named inhalation facilitation protection component supplement elements can also be, e.g., are, incorporated into devices or methods of the invention. As with other sections similarly described herein, any of the components of the invention can be, where suitable, described as means (e.g., the above-described inhalation facilitation component supplements can be described as inhalation facilitation component supplement means or means for providing or facilitating protection of an inhalation facilitation component).

Inhalation Facilitation Component Attachment Insert (Mouthpiece Attachment Insert)

According to certain aspects, similar to the inhalation facilitation component supplement component, a modified version of such a component can be provided to facilitate the attachment of the inhalation facilitation component to another component of the inhalation device without, e.g., providing full protection of the inhalation facilitation component (e.g., Mouthpiece) from excessive moisture, etc. This could be helpful, for example, in embodiments wherein the inhalation facilitation component, e.g., Mouthpiece, is made of, e.g., a material not detectably or significantly impacted by contact with excessive moisture, e.g., a ceramic material, but which may not be sufficiently durable to withstand repeated engagement/disengagement from another component of an inhalation device, such as may be accomplished by, e.g., screwing the mouthpiece onto or off of another component. In such embodiments, an inhalation facilitation component attachment insert, e.g., a Mouthpiece Attachment Insert, can be beneficial.

In aspects, an inhalation facilitation component attachment insert can be, e.g., any component which operates to protect an inhalation facilitation component (e.g., Mouthpiece) from damage, e.g., wear and tear, associated with repeated engagement/disengagement from another inhalation device component. In aspects, such an inhalation facilitation component attachment insert can be any component accomplishing this purpose, such as, e.g., a liner, a coating, an inserted component, such as, an insert made of, e.g., a plastic, metal, or, e.g., metal alloy, etc. In aspects, such an inhalation facilitation component attachment insert can be made of, e.g., stainless steel. In aspects, the inhalation facilitation component attachment insert is a stainless-steel component, e.g., a Mouthpiece Attachment Insert.

In certain aspects, an inhalation facilitation component attachment insert, e.g., Mouthpiece Attachment Insert, can be positioned within an interior of an inhalation facilitation component, e.g., Mouthpiece. In such aspects, the inhalation facilitation component attachment insert is not obviously externally visible under normal inhalation device operating conditions. In aspects, the inhalation facilitation component attachment insert detectably or significantly reduces damage to the inhalation facilitation component over time, such that the number of times an inhalation facilitation component can be attached to and removed from another device component increases by at least 2 times ("2×"), or, e.g., increases by at least ~5×, ~10×, ~20×, ~50×, ~100×, ~1000×, or ~2000× or more over an inhalation facilitation component lacking such a component.

In aspects, the inhalation facilitation component attachment insert is designed with an attachment mechanism facilitating the durable, repeatable, selective engagement/disengagement of the inhalation facilitation component with at least one other component of the device. In aspects, such an attachment mechanism can be, e.g., any selectively releasable attachment mechanism described elsewhere herein, such as, e.g., a threading connection mechanism to allow for a volatile compound inhalation facilitation component to be selectively screwed onto or off of one or more other components of an inhalation device. In certain specific aspects, a Mouthpiece can comprise a Mouthpiece Attachment Insert, the Mouthpiece Attachment Insert comprising threading to facilitate the attachment of the Mouthpiece to another component of a first primary device component, e.g., a Magnet Holder.

In aspects, an inhalation facilitation component attachment insert, e.g., Mouthpiece Attachment Insert, can be custom made, e.g., custom cast, machined, or otherwise custom manufactured for use with the inhalation device(s) herein. In aspects, an inhalation facilitation component attachment insert, e.g., Mouthpiece Attachment Insert, can be purchased as a typical on-market machine part. In certain aspects, an inhalation facilitation component attachment insert, e.g., Mouthpiece Attachment Insert, is designed to conform with a shape defined by the inhalation facilitation component, e.g., a contour within the interior of the inhalation facilitation component (e.g., Mouthpiece).

In this and other component, function, or operational aspect(s) of the invention, the invention also can be characterized as comprising a "means" for protecting the inhalation facilitation component. In such a respect, any known equivalents of such named inhalation facilitation protection component attachment insert elements can also be, e.g., are, incorporated into devices or methods of the invention. As with other sections similarly described herein, any of the components of the invention can be, where suitable, described as means (e.g., the above-described inhalation facilitation component attachment insert can be described as inhalation facilitation component attachment means or means for providing or facilitating protection of an inhalation facilitation component).

Body Subassembly

In aspects, a first primary component, e.g., a Body Assembly, can comprise, e.g., an inhalation facilitation component, e.g., Mouthpiece, an inhalation facilitation component supplement or attachment insert, e.g., a Mouthpiece Tube or Mouthpiece Attachment Insert, and at least one other inhalation device component. In aspects, the at least one other inhalation device component can be a plurality of components. In certain aspects, the plurality of additional components can be provided during manufacturing as a subassembly, e.g., Body Subassembly. In aspects, a Body Subassembly can comprise, e.g., a selectively releasable engagement mechanism or a component thereof, e.g., a Magnet, an engagement mechanism positioning component, e.g., Magnet Cover, a removable insert housing component, e.g., Body Tube, a compressible element, e.g., Core Spring, and one or more components of an airflow control mechanism, e.g., a first airflow control component, e.g., a Body Plug. Such components are described in detail herein.

Selectively Releasable Engagement Mechanism (Magnet)

According to aspects, an inhalation device provided by the invention can comprise a selectively releasable engagement mechanism (as described elsewhere herein). In aspects, the selectively releasable engagement mechanism, also referred to as a selectively releasable attachment mechanism, is a rapidly releasable force mechanism. In some aspects, the rapidly releasable force mechanism is a magnetic force. In such aspects, an inhalation device can comprise, e.g., a selectively releasable engagement mechanism comprising a magnet. In aspects, a selectively releasable engagement mechanism component can comprise one or more of the characteristics of the Magnet described in the figures or detailed description of figures provided herein. In aspects, a Magnet is, e.g., one component of the selectively releasable engagement mechanism, or, one component of a rapidly releasable force mechanism, or both.

In some aspects, an inhalation device can comprise a magnet in a first primary component of the device, e.g., Body Assembly, while one or more components attractive to or attracted by the magnet is positioned in a second primary component of the device, e.g., a second primary component of the device, e.g., Tip Assembly. In such an embodiment, the first primary and second primary components of the device are releasably bound to one another by the magnetic attraction. In aspects, the purpose of a magnet present in the inhalation device is to provide a selectively releasable engagement mechanism between at least two components of the device.

In aspects, a magnet of an inhalation device is positioned, designed, or both such that it does not interfere with the flow of air through the device and thus does not detectably or significantly interfere with the delivery of one or more volatile compounds. In certain aspects, the magnet is annular in shape. In aspects, the center of the annular shape provides a passageway for airflow through the device and, e.g., through the magnet.

According to certain aspects, the strength of the magnetic force is between about 1 gauss (0.0001 tesla) and about 2000 gauss (0.2 tesla), such as, e.g., ~10 gauss-~2000 gauss, ~10 gauss-~1500 gauss, ~10 gauss-~1000 gauss, ~10 gauss-~750 gauss, or ~10 gauss-~500 gauss, or, e.g., ~50 gauss-~2000 gauss, ~100 gauss-~2000 gauss, ~200 gauss-~2000 gauss, ~300 gauss-~2000 gauss, ~400 gauss-~2000 gauss, or, e.g., ~500 gauss-~2000 gauss, as in, for example, ~50 gauss-~1500 gauss, ~100 gauss-~1000 gauss, ~200 gauss-~800 gauss, ~300 gauss-~700 gauss, or, e.g., ~400 gauss (0.04 tesla)-~600 gauss (0.06 tesla).

According to certain aspects, the magnet has a size and attractive force (strength) sufficient to lift a weight of up to about 5 g, ~10 g, ~20 g, ~40 g, ~60 g, ~80 g, ~100 g, ~120 g, ~140 g, ~160 g, ~180 g, or, e.g., up to about 200 g or more.

According to certain aspects, the magnet has a size and attractive force (strength) sufficient to lift a weight of up to about 200 g, 250 g, 300 g, 350 g, 400 g, or more. According to certain aspects, the magnet is a 10 g-force (gf) to about 1000 g-force (gf) magnet, such as, e.g., ~10 gf-~900 gf, ~10 gf-~800 gf, ~10 gf-~700 gf, ~10 gf-~600 gf, ~10 gf-~500 gf, or ~10 gf-~400 gf magnet, e.g., ~50 gf-~1000 gf, ~100 gf-~1000 gf, ~150 gf-~1000 gf, ~200 gf-~1000 gf, ~250 gf-~1000 gf, ~300 gf-~1000 gf, or ~350 gf-~1000 gf magnet, such as, e.g., ~100 gf-~900 gf, ~200 gf-~700 gf, ~300 gf-~500 gf, or, e.g., ~300 gf-~400 gf magnet. In certain aspects, the magnet is characterizable as a 350 gram-force (0.8 lbf) magnet.

In aspects, the magnet described herein can be custom made for use within the device. In certain aspects, a standard stock magnet having the appropriate strength and shape can be utilized.

In this and other component, function, or operational aspect(s) of the invention, the invention also can be characterized as comprising a "means" for selectively releasable engagement of two or more components. In such a respect, any known equivalents of such named selectively releasable engagement components or mechanisms can also be, e.g., are, incorporated into devices or methods of the invention. As with other sections similarly described herein, any of the components of the invention can be, where suitable, described as means (e.g., the above-described selectively releasable engagement mechanism component can be described as selectively releasable engagement means or means for providing or facilitating the selectively releasable engagement of two or more inhalation device components).

Engagement Mechanism Positioning Component (Magnet Cover)

According to certain aspects, an inhalation device provided by the invention can comprise, e.g., a component for maintaining the proper positioning of a selectively releasable engagement mechanism component, e.g., a Magnet, within the inhalation device. In some facets, such an engagement mechanism positioning component further provides the ability to connect the magnet to at least a first other component of the first primary component (e.g., Body Assembly). In other facets, such an engagement mechanism positioning component further provides the ability to connect the magnet to at least a second other component of the first primary component (e.g., Body Assembly).

In aspects, an engagement mechanism positioning component can be any component suitable for the stable positioning of a selectively releasable engagement mechanism component, e.g., a Magnet, suitable for connecting the magnet (that is, indirectly connecting the magnet by holding the magnet therein and further connecting) to one or more other components of an inhalation device, connecting to one or more further components of the device such as, e.g., a removable insert housing component (e.g., Body Tube), or both. Such a component can be, e.g., a single component or a plurality of components acting together. In aspects, such a component can be, e.g., a series of two or more ridges within the interior wall(s) of one or more components of a device to maintain an, e.g., Magnet, in a single position; snap-fit, threaded bar, or other connection mechanism(s) provided separately from such other securing mechanisms such as, e.g., ridges, or any other suitable mechanism for attaining such aims.

In aspects, such an engagement mechanism positioning component connects to two or more first primary component (e.g., Body Assembly) components while, e.g., maintaining the stable positioning of a selectively releasable engagement mechanism (e.g., Magnet). In aspects, an engagement mechanism positioning component provides or at a minimum participates in (a) the stable positioning of a selectively releasable engagement mechanism component, e.g., a Magnet, (b) a mechanism for attaching the engagement mechanism positioning component (and, e.g., a selectively releasable engagement mechanism, e.g., Magnet stably held therein) to a first component of a first primary component, e.g., an inhalation facilitation component (e.g., Mouthpiece), and (c) a mechanism for attaching the engagement mechanism positioning component (and, e.g., a selectively releasable engagement mechanism, e.g., Magnet stably held therein) to a second component of a second primary component, such as, e.g., a component embodied herein as a body tube. In certain aspects, an engagement mechanism positioning component connects to both an inhalation facilitation component, e.g., Mouthpiece (either directly or indirectly via an inhalation facilitation component supplement or attachment insert (Mouthpiece Tube or Mouthpiece Attachment Insert)) and an internal compartment, e.g., internal compartment which stably maintains a removable insert/core (Body Tube).

In certain aspects, an engagement mechanism positioning component is, e.g., a Magnet Cover. In aspects, an engagement mechanism positioning component can comprise one or more of the characteristics of the Magnet Cover described in the figures or detailed description provided herein. In aspects, an engagement mechanism positioning component provides a holder for a Magnet. In aspects, a selectively releasable engagement mechanism, e.g., a Magnet, is stably maintained by, and in aspects at least partially within, an engagement mechanism positioning component. In aspects, an engagement mechanism positioning component, e.g., Magnet Cover, protects the selectively releasable engagement mechanism, e.g., Magnet, from the exterior environment, e.g., protecting the, e.g., Magnet, from scratching or other damage. In aspects, a Magnet is attached to the Magnet Cover by, e.g., the application of a glue or epoxy, or, e.g., is held in place by an, e.g., separate element, such as, for example an O-ring to maintain the position of the magnet without undesirable movement or shifting during manufacturing, use, or both.

In certain aspects, an engagement mechanism positioning component, e.g., Magnet Cover, comprises one or more specific features facilitating the connection of the component to one or more other components of a device. For example, an engagement mechanism positioning component can comprise, e.g., an extension comprising, e.g., threading to mate with an attachment mechanism of an inhalation facilitation component (Mouthpiece). An engagement mechanism positioning component can further comprise, e.g., an extension for suitably mating with, e.g., a component forming an internal compartment which stably maintains a removable insert/core (e.g., Body Tube). In aspects, an engagement mechanism positioning component, e.g., Magnet Cover, comprises both an area for holding or otherwise stably maintaining a selectively releasable engagement mechanism (e.g., Magnet), as well as two or more features facilitating the attachment to two or more other components of the inhalation device, e.g., two or more other components of a primary device component (e.g., Body Assembly).

According to certain aspects, an engagement mechanism positioning component, e.g., Magnet Cover, comprises a passageway therethrough to allow for a continuous air passage to flow from a second end to a first end of the device passage upon inhalation through the device by the inhalation device user. Therefore, in aspects, a feature of the engagement mechanism positioning component can in aspects be a generally open space or internal area located at least substantially in the middle of the component. In aspects, such an opening operates as a portion of the full airflow passageway through the inhalation device when the inhalation device is in a fully assembled state.

In aspects, an engagement mechanism positioning component, e.g., Magnet Cover, can be made of any one or more of the materials described elsewhere herein. In certain aspects, the engagement mechanism positioning component, e.g., Magnet Cover, is not magnetically attractive. In certain aspects, the engagement mechanism positioning component, e.g., Magnet Cover, is made of a metal or metal alloy, such as, e.g., titanium, platinum, gold, or stainless steel. In certain specific aspects, the engagement mechanism positioning component, e.g., Magnet Cover, is made of stainless steel.

In aspects, the engagement mechanism positioning component, e.g., Magnet Cover, described herein can be custom made for use within the device. In certain aspects, a standard stock component having a non-magnetic make-up and having the appropriate shape and functionality requirements can be utilized.

In this and other component, function, or operational aspect(s) of the invention, the invention also can be characterized as comprising a "means" for stably positioning the selectively releasable engagement mechanism. In such a respect, any known equivalents of such named engagement mechanism positioning component(s) can also be, e.g., are, incorporated into devices or methods of the invention. As with other sections similarly described herein, any of the components of the invention can be, where suitable, described as means (e.g., the above-described engagement mechanism positioning component can be described as engagement mechanism positioning means or means for providing or facilitating the stable positioning of a selectively releasable engagement mechanism).

Removable Insert Housing Component (Body Tube)

In aspects, an inhalation device provided by the invention comprises a component for holding, housing or otherwise stably maintaining a means for maintaining, releasing, or maintaining and releasing one or more volatile compounds, such as, e.g., a solid material device capable of maintaining, releasing, or maintaining and releasing one or more volatile compounds, e.g., a component for housing a removable insert/core. In certain facets, the removable insert housing component is a component of the primary device component.

According to embodiments, a removable insert housing component is a component capable of stably maintaining, e.g., designed to stably or maintain or which stably maintains a removable insert/core within the inhalation device, such a removable insert housing component can be any component capable of stably maintaining a removable insert/core within the inhalation device such that the removable insert/core remains in a suitable position for inhalation device operation when the first and second primary device components are separated from one another, when the first and second primary device components are selectively bound together by a selectively releasable attachment mechanism, when the device is jostled, manipulated, or otherwise moved, during normal use or operation, such as, e.g., a clamp capable of releasably attaching to at least a portion of a removable insert/core, a hollowed compartment capable of suitably securing a portion of a removable insert/core within it (e.g., by positioning an end of a removable insert/core within it), ridges, spikes, partial walls, or other such elements capable of preventing movement of a removable core upon insertion of a removable core into an area of a device, or any other mechanism capable of maintaining positioning of a removable insert/core such that it can suitably release one or more volatile compounds to a user of the inhalation device when provided therein, without interfering with, e.g., blocking or otherwise disturbing or causing a redirection of, an air passageway through the inhalation device. In certain aspects, the removable insert housing component is an internal compartment.

In certain aspects, the removable insert housing component is an internal compartment embodied as a Body Tube. In aspects, a removable insert housing component can comprise one or more of the characteristics of the Body Tube described in the detailed description provided herein.

In certain aspects, the internal compartment comprises at least one dimension which is at least half as long as the longest dimension of the removable insert, such as, e.g., a dimension which is at least about 50%, ~55%, ~60%, ~65%, ~70%, ~75%, ~80%, ~85%, ~90%, ~95%, or, e.g., is at least as long as, the longest dimension of the removable insert. For example, an internal compartment can comprise at least one dimension having a length which is between about 50% and 200%, ~60%-~200%, ~70%-~200%, ~80%-~200%, or ~90%-~200% as long as the longest dimension of the removable insert, such as, e.g., ~50% as long as, ~60%, ~70%, ~80%, ~90%, ~100%, ~110%, ~120%, ~130%, ~140%, ~150%, ~160%, ~170%, ~180%, ~190%, or, e.g., ~200% as long as the longest dimension of the removable insert. In aspects, the removable insert housing component, e.g., internal compartment, e.g., Body Tube, is longer than the longest dimension of the removable insert/core. In aspects, the removable insert housing component, e.g., internal compartment, e.g., Body Tube, is at least as long as or longer than the longest dimension of the removable insert/core.

According to certain embodiments, the removable insert housing component, e.g., internal compartment, e.g., Body Tube, is a component of a device first primary component. According to certain embodiments, the removable insert housing component, e.g., internal compartment, e.g., Body Tube, is a component of a device first primary component such that when the first primary component is separated from the second primary component of the inhalation device, the removable insert housing component, e.g., internal compartment, e.g., Body Tube, is completely separated from the second primary component.

In aspects, the removable insert housing component, e.g., internal compartment, e.g., Body Tube, is attached to, directly or indirectly, the first primary component of the device but resides at least substantially within the second primary component of the device when the first device component and the second device component are bound to one another by the releasable attachment mechanism. In one aspect, at least about 60%, such as, e.g., at least ~70%, ~80%, ~90%, or ~100%, such as, e.g., ~60%-~100%, ~70%-~100%, ~80%-~90%, or, e.g., ~90%-~100% or 100% of the removable insert housing component, e.g., internal compartment, e.g., Body Tube, resides within the second primary device component when the first primary device component and the second primary device component are bound to one another by a releasable attachment mechanism.

In aspects, the removable insert housing component, e.g., internal compartment, e.g., Body Tube, has a width, a depth, a length, a first end, and a second end. In aspects, the length is the longest dimension of the internal compartment. In facets, the removable insert housing component, e.g., internal compartment, e.g., Body Tube, comprises an interior defined by an at least partially circumferentially disposed wall between the first end and a second end of the removable insert housing component, e.g., internal compartment, e.g., Body Tube. In aspects, the at least partially circumferentially disposed wall is at least partially opened along at least one portion of the length between the first and second ends of the removable insert housing component, e.g., internal compartment, e.g., Body Tube, and fully circumferentially encloses the removable insert housing component, e.g., internal compartment, e.g., Body Tube along at least one portion of the length between the first and second ends of the removable insert housing component, e.g., internal compartment, e.g., Body Tube. According to certain aspects, the circumferentially disposed wall defining removable insert housing component, e.g., internal compartment, e.g., Body Tube, interior at least partially surrounds (e.g., encircles) a removable insert when present therein along at least one portion of the removable insert but does not surround the entirety of the removable insert. In aspects, the portion of the removable insert housing component, e.g., internal compartment, e.g., Body Tube, which only partially circumferentially encloses a removable insert when positioned therein encloses, greater than about 10%, >~15%, >~20%, >~25%, >~30%, >~35%, >~40%, or >~45% of the circumference of the removable insert. In certain aspects, the portion of the removable insert housing component, e.g., internal compartment, e.g., Body Tube, which only partially circumferentially encloses a removable insert when positioned therein encloses, less than about 50%, <~45%, <~40%, <~35%, <~30%, <~25%, <~20%, or >~15% of the circumference of the removable insert. In aspects where such a compartment is not cylindrical, or, e.g., in aspects where such a removable insert is not cylindrical, such enclosure may be more appropriately simply referred to as enclosure (vs. "circumferentially" enclosed) as would be understood by the reader. In aspects where the internal compartment, the removable insert, or both, are not cylindrical, the portion of the removable insert housing component, e.g., internal compartment, e.g., Body Tube, which only partially encloses a removable insert when positioned therein can enclose between, e.g., about 10%-about 75% of the perimeter of the removable device, such as, e.g., ~10%-~70%, ~10%-~65%, ~10%-~60%, ~10%-~55%, or, e.g., ~10%-~50%, such as, e.g., ~20%-~75%, ~25%-~75%, ~30%-~75%, ~35%-~75%, ~40%-~75%, ~45%-~75%, or, e.g., ~50%-~75% of the perimeter of the removable device. In aspects, the portion of the removable insert housing component, e.g., internal compartment, e.g., Body Tube, which does not fully enclose or circumferentially surround the interior of the same has a gap (or opening) in its perimeter or circumference which is at least detectably wider than that of the removable device such that the removable device can be suitably inserted therethrough.

Stated differently, when a removable insert is present in the partially enclosed internal compartment, at least a portion of the removable insert is completely surrounded by (or, e.g., encircled by) a circumferentially disposed wall of the compartment and at least a portion of the removable insert is only partially surrounded by the wall of the compartment.

According to certain aspects, when a removable insert (e.g., Core) is present within the removable insert housing component, a fully circumferentially disposed wall surrounds at least about 0.5% of the length of the removable insert, such as at least about 1%, ≥~1.5%, ≥~2%, ≥~2.5%, ≥~3%, ≥~3.5%, ≥~4%, ≥~4.5%, or, e.g., ≥~5%, of the length of the removable insert. In aspects, when a removable insert (e.g., Core) is present within the removable insert housing component, a fully circumferentially disposed wall surrounds no more than about 10% of the length of the removable insert, such as, e.g., ≤~9%, ≤~8%, ≤~7%, ≤~6%, ≤~5%, ≤~4%, ≤~3%, ≤~2%, or ≤~1% of the length of the removable insert. In certain embodiments, when a removable insert (e.g., Core) is present within the removable insert housing component, a fully circumferentially disposed wall surrounds between about 0.5% and about 5% of the length of the removable insert, such as, e.g., ~1%-~5%, ~1.5%-5%, ~2%-~5, ~2.5%-~5, or ~3%-~5%, e.g., ~0.5%-~4.5%, ~0.5%-~4%, ~0.5%-~3.5%, or ~0.5%-~3%, as in, for example, between about 1% and about 5% or ~1.5%-~4.5%, ~2%-~4%, ~2.5%-~3.5%, or, e.g., ~3% of the length of the removable insert.

In certain embodiments, when a removable insert (e.g., Core) is present within the removable insert housing component, a fully circumferentially disposed wall surrounds between about 0.5 mm and about 3 mm of the length of the removable insert, such as, e.g., ~0.5 mm-~2.5 mm, ~0.5 mm-~2 mm, ~0.5 mm-~1.5 mm, or, e.g., ~0.5 mm-~1 mm, or ~1 mm-~3 mm, such as, e.g., about 1 mm of the length of the removable insert.

In aspects, features of the removable insert housing component, e.g., the removable insert housing component having the characteristic of comprising at least one opening in a wall allowing for access to the interior of the insert housing component (such that, e.g., when a solid material device capable of maintaining, releasing, or maintaining and releasing one or more of volatile compound(s) is housed within the removable insert housing component, at least one part of the device is not completely surrounded or encircled by the removable insert housing component), increases ease of insertion of a volatile compound-comprising device (e.g., Core). In aspects, such feature(s) increase ease of removal of a volatile compound-comprising device (e.g., Core). In aspects, such feature(s) improve upon or facilitate airflow through the device such that a suitable amount of volatile compound(s) are provided to the user upon inhalation. In aspects, such feature(s) improve upon the user experience of the device. For example, in aspects, a user may be able to insert or remove a volatile compound-comprising device (e.g., Core) while minimizing contact with the carrier(s) of the volatile compound(s), e.g., oil(s) present in the volatile compound-comprising device.

In aspects, the removable insert housing component, e.g., internal compartment, e.g., Body Tube, is designed to receive a removable insert from a position lateral to its length via an opening in the circumferentially disposed wall defining the length of the removable insert housing component, e.g., internal compartment, e.g., Body Tube. Such insertion can be, e.g., through the partial opening in the circumferentially disposed wall of the, e.g., removable insert housing component. The inhalation device, or, e.g., the first primary component of an inhalation device, or, e.g., a removable insert housing component (e.g., internal compartment, e.g., Body Tube) can in aspects be capable of, e.g., designed to, or which receives the insertion of a removable insert from a direction which is lateral to the long axis of the device, e.g., from a direction which does not correspond to, is not parallel to, or does not correspond to the long axis of the device. In aspects, a removable insert can be inserted into an inhalation device from a position lateral to the device as opposed to from a position axial to the device.

In aspects, a removable insert can be laterally inserted into a removable insert housing component such that at least a portion of the removable insert is circumferentially encompassed by a completely circumferentially disposed wall of the removable insert housing component. In aspects the removable insert is inserted at an angle which is between about 5 degrees and about 20 degrees, such as, e.g., ~6 degrees--~20 degrees, ~7 degrees--~20 degrees, ~8 degrees--~20 degrees, ~9 degrees--~20 degrees, or, e.g., ~10 degrees--~20 degrees, e.g., ~5 degrees--~19 degrees, ~5 degrees--~18 degrees, ~5 degrees--~17 degrees, ~5 degrees--~16 degrees, ~5 degrees--~15 degrees, ~5 degrees--~14 degrees, ~5 degrees--~13 degrees, ~5 degrees--~12 degrees, or ~5 degrees--~11 degrees, as in, for example, ~6 degrees--~18 degrees, ~7 degrees--~16 degrees, ~8 degrees--~14 degrees, ~8 degrees--~12 degrees, or, e.g., about 10 degrees to about 11 degrees relative to the long axis of the inhalation device. In aspects, once fully inserted, a removable insert is positioned such that its long axis is at least generally, at least substantially, at least essentially, essentially, or is aligned with, parallel to, or coaxial with the long axis of the inhalation device.

In one specific aspect, the removable insert housing component, e.g., internal compartment, e.g., Body Tube, is a component of the first primary component of the device and wherein, when the first primary component of the device and second primary component of the device are sufficiently separated from one another, a removable insert capable of holding, releasing, or holding and releasing one or more volatile compounds can be laterally inserted into and stably held by the exposed internal compartment (herein "internal compartment" may also be referred to as an "internal component").

According to certain aspects, the removable insert housing component is not visible from the exterior of the device when the device is in a configuration ready for use. In certain aspects, the orientation of the removable insert housing component may be advantageous to know, such that, e.g., a user can selectively orient the device such that the opening in the circumferentially disposed wall of the removable insert housing component faces upward prior to exposing the removable insert housing component by, e.g., selectively disengaging the first primary component from the second primary component. This can, in aspects, further ensure that, for example, a removable insert within the removable insert housing component does not inadvertently fall out upon the selective disengagement of the first and second primary device components. In aspects, the spatial orientation of the internal compartment is discernable by the spatial orientation of at least one visual indicator present on an external surface of the device. In aspects, the visual indicator can be any visible indicator described herein. In aspects, the at least one visual indicator is present on, e.g., a component of the device fixedly attached to (e.g., not intentionally disengageable from), either directly or indirectly, the removable insert housing component (e.g., internal compartment, e.g., Body Tube). In certain aspects, such an externally visible component can be, e.g., an engagement mechanism positioning component (e.g., Magnet Cover). In aspects, such a visual indicator can be, e.g., a line, such as, e.g., is described elsewhere herein. Therefore, in one aspect, the inhalation device can comprise a removable insert housing component (e.g., internal compartment, e.g., Body Tube) which is not externally visible but the orientation of which, e.g., the orientation of an opening therein, is discernable by the orientation of the at least one visual indicator located on an outside (external) surface of the inhalation device.

According to certain embodiments, the interior of the removable insert housing component, e.g., internal compartment, e.g., Body Tube, comprises at least 2 components, e.g., a compressible element (Core Spring), and, e.g., a fixed element positioned opposite the compressible element (Core Spring) within the removable insert housing component. In aspects, such two components cooperate to stably maintain the removable insert within the removable insert housing component, e.g., internal compartment, e.g., Body Tube. In aspects, the removable insert housing component, e.g., internal compartment, e.g., Body Tube, is designed to maintain a removable insert between the compressible element and the fixed element, wherein the fixed element is capable of resisting, e.g., is designed to resist, or which resists the movement of a removable element when the compressible element applies a force to the end of the removable element opposite the fixed element.

With regard to the characteristics of the interior of the removable insert housing component, e.g., internal compartment, e.g., Body Tube, the positioning of the fixed element aids in defining the characteristics of the interior of the removable insert housing component when a removable insert is present therein. In aspects, the positioning of a fixed element within the internal compartment provides for the positioning of a removable insert having a first end and a second end, when present within the internal compartment, to be positioned such that at least one of the first and second ends of the removable insert is accessible via a portion of the internal compartment which is not fully enclosed by the circumferentially disposed wall defining the interior of the internal compartment. This creates a gap or space which allows for a user to insert their finger at least partially into the interior of the removable insert housing component at the end of a removable insert present therein to then remove the removable insert therefrom.

In aspects, a removable insert housing component can be made of any material described herein. In aspects, a suitable material is a material which does not detectably or significantly absorb any one or more compounds released by a removable insert positioned therein. In aspects, a suitable material is a metal or metal alloy, such as, e.g., titanium, platinum, gold, or, e.g., stainless steel. In aspects, a removable insert housing component can be made of stainless steel.

According to aspects, removable insert housing component can be a custom fabricated component, e.g., made by machining, casting, or other suitable manufacturing process.

In this and other component, function, or operational aspect(s) of the invention, the invention also can be characterized as comprising a "means" for stably maintaining, holding, or otherwise housing a removable insert (Core) present to maintain, release, or maintain and release one or more volatile compounds. In such a respect, any known equivalents of such named housing mechanisms can also be, e.g., are, incorporated into devices or methods of the invention. As with other sections similarly described herein, any of the components of the invention can be, where suitable, described as means (e.g., the above-described removable insert housing component can be described as housing means or means for housing a removable insert/Core).

Compressible Element (Core Spring)

According to one aspect of the invention, the inhalation device can comprise one or more components which participates in the stable maintenance of a means of maintaining, delivering, or maintaining and delivering one or more volatile compounds, e.g., a removable insert or Core, within the inhalation device. In specific aspects, the inhalation device can comprise one or more components which participates in the stable maintenance of a removable insert within a removable insert housing component (e.g., Body Tube). In aspects, two or more such components cooperate to achieve the stable maintenance of a removable insert. In aspects, one such component participating in the stable maintenance of a removable insert is, e.g., a compressible element. In aspects, the compressible element cooperates with one or more other elements, e.g., a fixed element, to stably maintain a removable insert in a suitable position within the inhalation device.

In certain aspects, a compressible element can be any element capable of comprising and applying a restoring force when the compression element is compressed. In aspects, a compressible element is capable of being both compressed by a force and applying an opposing force to such compression. In aspects, such a compressible element can be any element capable of applying such a restoring force upon being compressed, such as, e.g., a spring, a flexed element such as a tab, or an element made of a compressive material such as, e.g., a rubber, a foam, etc. In certain aspects, the compressible element is a spring-like element, e.g., a spring or, e.g., a component comprising a compressible tab. In aspects, the compressible element is a Core Spring. In aspects, the compressible element can comprise one or more of the characteristics of a Core Spring described in the figures or the detailed description of figures provided herein.

In aspects, a fixed element positioned in a location opposite that of the compressible element such that the fixed element is capable of resisting or resists the movement of any object to which the restoring force of the compressible element is applied, e.g., resisting the movement of a removable insert (e.g., Core) when the compressible element applies a force to an end of the removable insert (e.g., Core) opposite the fixed element.

According to a specific embodiment, a compressible element participates in the stable maintenance of a means for maintaining, delivering, or maintaining and delivering one or more volatile compounds, e.g., a removable insert (e.g., Core) by the application of a first force, e.g., a restoring force, to a first end of the removable insert. In aspects, the removable insert has previously compressed the compressible element. In aspects, stable maintenance of the volatile compound delivery means, e.g., removable insert (e.g., Core) is achieved by the further application of a second force to a second end of the volatile compound delivery means, e.g., removable insert (e.g., Core) by a fixed element preventing movement of the removable insert in the direction of the applied restoring force applied by the compressible element.

In certain aspects, a compressible element applies a force which is between an about 0.1 pound force (lbf) and an about 1.5 pound force (lbf), such as, e.g., a force which is ~0.2 lbf-~1.5 lbf, ~0.3 lbf-~1.5 lbf, ~0.4 lbf-~1.5 lbf, ~0.5 lbf-~1.5 lbf, ~0.6 lbf-~1.5 lbf, ~0.7 lbf-~1.5 lbf, or ~0.8 lbf-~1.5 lbf, such as, e.g., ~0.1 lbf-~1.4 lbf, ~0.1 lbf-~1.3 lbf, ~0.1 lbf-~1.2 lbf, ~0.1 lbf-~1.1 lbf, ~0.1 lbf-~1 lbf, ~0.1 lbf-~0.9 lbf, or, e.g., ~0.1 lbf-~0.8 lbf, as in, for example, ~0.2 lbf-~1.4 lbf, ~0.3 lbf-~1.3 lbf, ~0.4 lbf-~1.2 lbf, ~0.5 lbf-~1.1 lbf, ~0.6 lbf-~0.9 lbf, or ~0.7 lbf-~0.9 lbf, such as, e.g., a force which is an about 0.8 lbf.

In certain aspects, a compressible element applies a force which is a force of between about a 50 gram-force (gf) to about 500 gram-force (gf), such as, e.g., ~50 gf-~450 gf, ~50 gf-~400 gf, or ~50 gf-~350 gf, as in, e.g., ~100 gf-~500 gf, ~150 gf-~500 gf, ~200 gf-~500 gf, ~250 gf-~500 gf, ~300 gf-~500 gf, or, e.g., ~350 gf-~500 gf, as in, for example, ~100 gf-~450 gf, ~150 gf-~400 gf, ~200 gf-~400 gf, ~300 gf-~400 gf, or, e.g., an about 350 gf.

According to aspects, the compressible element, e.g., Core Spring, working in cooperation with one or more additional components of an inhalation device, e.g., a removable insert housing component (e.g., internal component, e.g., Body Tube), a fixed element (e.g., which may be functionally accomplished by, e.g., a Body Plug), or both, stably maintains a removable insert in a suitable position for device operation when the inhalation device, or, e.g., in specific aspects when the removable insert housing component (e.g., internal compartment, e.g., Body Tue) is oriented in any spatial orientation.

According to certain embodiments, a compressible element is positioned within a first primary component of a device. In aspects, a compressible element is positioned within a removable insert housing (e.g., internal compartment, e.g., Body Tube). In aspects, a compressible element maintains its positioning within an inhalation device via its own restoring force, e.g., spring-like force, e.g., spring tension, whereby in its relaxed state (e.g., manufactured "open" state), the compressible element has a diameter which is greater than the diameter of a component into which it is positioned, e.g., a removable insert housing component, e.g., Body Tube. In aspects, when the compressible element is compressed and fed or placed into the interior of such a component, e.g., a removable insert housing component, e.g., Body Tube, the natural desire of the compressible component is to expand to its relaxed state, creating a spring tension which maintains the compressible component in place within the inhalation device, e.g., within the primary component of the inhalation device, e.g., within a removable insert housing component, e.g., with a Body Tube.

A compressible element can be made of any suitable material, such as, e.g., any compressible material capable of providing the characteristics and operational capabilities described relative to this component here, such as, e.g., a suitable rubber, a suitable foam, or the like, or, e.g., can be made of a material such as a metal, e.g., a metal or metal alloy described herein. In aspects, a compressible element is provided in the form of a metallic or metal alloy component comprising sufficient durability to withstand repeated compression and expansion over the lifespan of the device. In aspects, a suitable material is a material which can withstand, e.g., more than about 25, ≥~50, ≥~100, ≥~200, ≥~400, ≥~600, ≥~800, ≥~1000, ≥~1200, ≥~1400, ≥~1600, ≥~1800, or ≥~2000 or more compression/expansion cycles without breaking or without at least substantially impacting the ability of the compressible component to maintain a volatile compound releasing means, e.g., removable insert (e.g., Core) stably in place during operation of the inhalation device.

According to aspects, the compressible element can be a component provided as a standard stock component. In aspects, the compressible element is an element which is custom made. In aspects, the compressible element is an element customized for use in inhalation device(s) described herein. In aspects, such a compressible element can be machined, cast, or otherwise manufactured specifically for used in an inhalation device described herein.

In this and other component, function, or operational aspect(s) of the invention, the invention also can be characterized as comprising a "means" for stabilizing a removable insert (Core) present to maintain, release, or maintain and release one or more volatile compounds. In such a respect, any known equivalents of such insert stabilization components can also be, e.g., are, incorporated into devices or methods of the invention. As with other sections similarly described herein, any of the components of the invention can be, where suitable, described as means (e.g., the above-described compressible element can be described as insert stabilization means or means for stably maintaining a removable insert/Core).

Airflow Control First Component (Body Plug)

In aspects, an inhalation device comprises at least two components, movable in relation to one another, which cooperate to provide airflow control functionality to the inhalation device. In aspects, at least one of the at least two components, e.g., an airflow control first component, reside(s) in a first primary component of the inhalation device. In aspects, the function of an airflow control first component is to participate in the airflow control of an inhalation device. Such airflow control can also be referred to as drag control (herein, "drag" being the drawing of air by inhalation of user through an inhalation device, wherein the airflow control or drag control impacts the amount of air passing through the device upon inhalation by a user). In aspects, an airflow control first component provides a means of customizing the airflow through an inhalation device, providing selectable airflow control setting(s).

According to aspects, an airflow control first component (also referred to herein as a first airflow control component) is designed to cooperatively engage with an airflow control second component (also referred to herein as a second airflow control component) to selectively control the amount of air which is drawn through the inhalation device upon inhalation by the inhalation device user. In aspects, a first airflow control component repeatedly engages with, at least partially disengages from, and reengages with, a second airflow control component during normal operation of the device.

According to certain aspects, a first airflow control component can be any component suitable for interfacing with a second airflow control component to control airflow, such as, e.g., a shutter, a disc-shaped device comprising, e.g., one or more apertures, a device comprising a mechanism for modifying an opening by selectively expanding outward to form a larger opening or converging inward to form a smaller opening, a solid device capable of blocking at least a portion of but not all of an airflow passageway through a device, or any other such mechanism or component capable of cooperatively participating in airflow control through an inhalation device.

In certain aspects, a first airflow control component is a component which alone is capable of blocking, is designed to block, or which blocks at least about, e.g., 25% of an airflow passageway through an inhalation device (e.g., an airflow passageway in at least a portion of the device), such as, e.g., ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, or more, but not 100% of, an airflow passageway through an inhalation device. In aspects, the amount of an airflow passageway through a device which is blocked by a first airflow control component of an inhalation device described herein is no more than about 75%, such as no more than ~75%, ~70%, ~65%, ~60%, ~55%, or no more than ~50% of the airflow passageway through an inhalation device. According to certain aspects, the first airflow control component is a semi-circular-shaped component. In aspects, the semi-circular shaped component is capable of blocking, designed to block, or which blocks about 50% of the airflow passageway through an inhalation device (or, e.g., at least a portion of the device), such that due to its presence, a maximally open airflow passageway through a device has at least one dimension which is no more than about half of the diameter (or, e.g., width or height) of an interior passageway passing from a first end of an inhalation device to a second end of an inhalation device. In aspects, such an interior passageway would have, absent the presence of at least the first airflow control component, a cross sectional area across its length or at a minimum in a single location along its length which is about twice that of the cross-sectional area across its length or at a minimum in a single location along its length which is present when the at least first airflow control component is present.

In aspects, the first airflow control component is movable in relation to a second airflow control component. In aspects, the degree of interface between the first and second airflow control components is established by the rotation of the first primary device component and the second primary device component relative to one another.

In aspects, a first airflow control component is provided as a Body Plug. In aspects, a first airflow control component can comprise any one or more of the characteristics of the Body Plug described in the detailed description of figures provided herein.

In aspects, a first airflow control component, e.g., Body Plug, can comprise a body feature facilitating its fixed attachment to one or more additional components of an inhalation device. In aspects, one or more elements of such a body feature can provide one or more additional functional or operational characteristics of an inhalation device, such as, e.g., serving as a fixed element aiding in the maintenance of a removable insert stably in position within an inhalation device, e.g., a first primary component of an inhalation device, e.g., within a removable insert housing component, e.g., Body Tube. This is described further below.

In aspects, in a fully assembled device, and with first and second primary components of such a device fully engaged with one another, a second airflow control component, e.g., Barrel Plug, is in contact with a first airflow control component, e.g., Body Plug. In aspects, a first airflow control component, e.g., Body Plug, can comprise a plurality of features which, in aspects, can be describable as belonging to a fan feature, of the first airflow control component, e.g., Body Plug. Such features can, in aspects, repeatedly engage with and at least partially disengage from compatible features present on a second airflow control component, e.g., Barrel Plug. A second airflow control component can, in aspects, comprise any one or more characteristics of a Barrel Plug described in the detailed description of figures provided herein. In aspects, such repeated engagement and disengagement of such fan features can occur upon the movement, e.g., rotation, of the first airflow control component (e.g., Body Plug) relative to the second airflow control component (e.g., Barrel Plug).

In aspects, a first airflow control component can comprise a fan-like feature comprising a series of ridges and recessions such as, e.g., a series of alternating ridges and recessions. In aspects, the alternating ridges and recessions of a first airflow control component repeatedly alternatingly engage with and disengage from a coordinating series of ridges and recessions present on a second airflow control component (e.g., Barrel Plug) which in aspects comprises a complementary fan-like feature comprising the complementary set of ridges and recessions. In aspects, the degree of interface between the first and second airflow control components, e.g., the degree of overlap between the two components, provides the airflow control mechanism of the device. In aspects, the more the first airflow control component, e.g., the Body Plug, overlaps with the second airflow control component, e.g., the Barrel Plug, the more airflow through the device is blocked. In aspects, the less the first airflow control component, e.g., the Body Plug, overlaps with the second airflow control component, the more airflow through the device is allowed (the less the airflow through the device is blocked.)

The interaction between the first and second airflow control components and their ability to cooperatively control the airflow through an inhalation device is further described elsewhere herein.

In aspects, a first airflow control component can comprise a component or feature which participates in a tactile indication of an operational status of the inhalation device. In aspects, such a feature intermittently interfaces with one or more features of a second airflow control component, e.g., Barrel Plug. In aspects, a first airflow control component can comprise one or more protrusions which intermittently interface(s) with one or more protrusion component(s) on a second airflow control component. In aspects, the interface between the two distinct protrusions on the first and second airflow control components, respectively, provide a distinguishably different tactile sensation compared to the interaction between the ridge(s)/recession(s) of each of the first and second airflow control components. This is further described or exemplified elsewhere herein. In aspects, such intermittently interfacing components providing a distinctly different tactile indication can be any feature providing such an indication. Herein, this/these intermittently interfacing feature(s) is/are described as protrusion(s).

In aspects, the distinguishably different tactile sensation indicates a specific airflow control setting of the device. In aspects, the distinguishably different tactile sensation indicates that the airflow control mechanism is in a maximally closed position. In aspects, any other tactile sensation provided by alternating interface of ridges/recessions on the first and second airflow control components indicate some degree of opening of the airflow control mechanism.

According to certain embodiments, a first airflow control component, e.g., Body Plug, can comprise, e.g., between about 2 and about 30 ridges (or, e.g., peaks) and recessions. In aspects, a first airflow control component can comprise the same number of ridges as recessions. In alternative aspects, a first airflow control component can comprise a different number of ridges and recessions. In some aspects, a first airflow control component can comprise, e.g., one or two more ridges than recessions. In some aspects, a first airflow control component can comprise, e.g., one or two more recessions than ridges. In certain aspects, a first airflow control component can comprise, e.g., ~4-~30, ~6-~30, ~8-~30, ~10-~30, ~12-~30, ~14-~30, ~16-~30, ~18-~30, ~20-~30, ~22-~30, ~24-~30, ~26-~30, or ~28-~30 ridges, recessions, or both ridges and recessions (e.g., such values representing the number of each of ridges and recessions), such as, e.g., ~2-~28, ~2-~26, ~2-~24, ~2-~22, ~2-~20, ~2-~18, ~2-~16, ~2-~14, ~2-~12, ~2-~10, ~2-~8, ~2-~6, or ~2-~4 ridges, recessions or both ridges and recessions (e.g., such values representing the number of each of ridges and recessions), as in, for example, ~4-~28, ~6-~26, ~8-~24, ~10-~22, ~12-~20, ~14-~18, or, e.g., about 16 ridges, recessions, or both ridges and recessions (e.g., such values representing the number of each of ridges and recessions).

According to certain embodiments, an angle of between about 6 and about 60 degrees, such as, e.g., an angle of ~7-~60, ~8-~60, ~9-~60, ~10-~60, ~11-~60, ~12-~60, or ~13-~60 degrees, such as, e.g., ~6-~50, ~6-~40, ~6-~30, ~6-~20, or, e.g., ~6-~10 degrees, as in, for example, ~8-~50, ~6-~20, or, e.g., ~6-~10 degrees, as in, for example, ~8-~50, ~8-~40, ~8-~30, ~8-~20, or ~8-~25 degrees, such as, e.g., between about 11 and about 13 degrees, e.g., an angle of about 12 degrees separates each recession, separates each ridge, or separate each recession and each ridge from the next (e.g., adjacent) respective recession or ridge.

In aspects, the number of recessions and peaks (ridges) present in a first airflow control component (e.g., Body Plug) contributes to the specificity with which airflow through the device can be controlled. For example, an increased number of such features recessions and peaks/ridges of a first airflow control component can increase the level of fine tuning a user can accomplish to control airflow (e.g., drag control) when using the inhalation device, while a decreased number of such features can decrease the level of fine tuning a user can accomplish to control airflow during device use.

As previously stated, a first airflow control component, e.g., Body Plug, can comprise a body feature facilitating its attachment to one or more additional components of an inhalation device. In aspects, an element (feature) of such a body feature can provide an additional functional or operational characteristic of an inhalation device, different or separate from, e.g., airflow control. In aspects, a feature of a first airflow control component can operate as a fixed element aiding in the maintenance of a removable insert stably in position within an inhalation device, e.g., a first primary component of an inhalation device, e.g., within a removable insert housing component, e.g., Body Tube. In aspects, at least a portion of the first airflow control component is positioned within a removable insert housing component (e.g., Body Tube). In aspects, a first airflow control component can be brazed onto a removable insert housing component (e.g., Body Tube). In aspects, the portion of the first airflow control component positioned within the removable insert housing component can be the fixed element described above which participates in the stable maintenance of a removable insert within the device, or, e.g., within the removable insert housing component. In aspects, the first airflow control component therefore works cooperatively with the, e.g., compressible element, to stably maintain the removable insert within the removable insert housing component as is described above, as the first airflow control component serves as the fixed element of the above-described stability maintenance mechanism. Accordingly, the first airflow control component can withstand the application of restoring forces applied by the compressible element to the removable insert, and therefore, applied by the removable insert to the fixed element, e.g., the first airflow control component. Such restoring forces are described elsewhere herein.

Further, an element (feature) of such a body feature can be designed to facilitate the entry, removal, or entry and removal of a removable insert, e.g., Core, into the inhalation device. In aspects, one or more surfaces of a first airflow control component can form a non-right angle. In aspects, such a shape feature allows for the case of positioning or placement of the first airflow control component into or within one or more other components of the device during assembly. For example, in aspects, a first airflow control component rounded (non-90 degree) shape feature facilitates the fitting of the first airflow control component into the removable insert housing component, e.g., Body Tube. In aspects, the rounded shape of one or more first airflow control component shape features allows for the first airflow control component to be "slid" or easily guided into place within a removable insert hosing component, e.g., Body Tube, such that it can, in aspects, slide, fall, or follow contour(s) of body tube (402) into place with limited guidance required. In further aspects, one or more of the first airflow control shape features, e.g., rounded interface between two surfaces, provide for limiting detectable or significant damage to a removable insert, e.g., Core, when placed into a removable insert housing component, e.g., Body Tube. In aspects, one or more of shape features of a first airflow control component limits detectable or significant damage to a removable insert (e.g., Core) when such a removable insert is made of a fragile material, e.g., a material capable of being caught on, or, e.g., scratched by, or, e.g., potentially at risk of experiencing flaking when, contacted by a suitably shaped or sharp surface, such as a fibrous core or a core comprising a ceramic material.

According to aspects, at least a portion of a first airflow control component positioned within the removable insert housing component (e.g., Body Tube) extends to an area of the removable insert housing component (e.g., Body Tube) which is not completely circumferentially enclosed by a circumferentially disposed wall, such that at least a portion of the first airflow control component extends into the portion of the removable insert housing component which is at least partially open on one side. In aspects, such a portion of the first airflow control component comprises a thickness, e.g., depth, which is less than 100%, such as, e.g., ≤~90%, ≤80%, ≤70%, ≤60%, ≤50%, ≤40%, ≤30%, ≤20%, or, e.g., ≤10% of the diameter, e.g., depth, of the removable insert housing component, e.g., the internal compartment as described herein.

In aspects, the first airflow control component, (a) extending at least partially into area of the removable insert housing component which is at least partially open (not fully circumferentially disclosed), and (b) operating as a fixed element participating in the stable maintenance of a removable insert, establishes a gap between the end of an insertable insert which can abut the first airflow control component (e.g., as it operates as a fixed element described herein) and the complete circumferential enclosure of the internal compartment (established by/as the removable insert housing component). This gap can be referred to as an access space or finger recess, allowing a user to insert their finger at least partially into the gap to facilitate the removal of a removable insert (e.g., Core).

In aspects, the first airflow control component can be made of any material described herein. In certain aspects, the first airflow control component is made of a metal or metal alloy, such as, e.g., gold, titanium, platinum, or, e.g., stainless steel. In particular aspects, the first airflow control component is made of stainless steel.

In aspects, the first airflow control component is a custom-made component. In aspects, the first airflow control component is machined, cast, or otherwise custom manufactured for use in inhalation devices described herein.

In this and other component, function, or operational aspect(s) of the invention, the invention also can be characterized as comprising a "means" for controlling airflow. In such a respect, any known equivalents of such airflow control components or mechanisms can also be, e.g., are, incorporated into devices or methods of the invention. As with other sections similarly described herein, any of the components of the invention can be, where suitable, described as means (e.g., the above-described first airflow control component can be described as airflow control means or means for controlling airflow).

Finger Recess

The access space or finger recess which in aspects is present in an inhalation device, e.g., a first primary component, e.g., a removable insert housing component (e.g., Body Tube) is described elsewhere herein. See, e.g., the sections entitled, "Removable Insert Housing Component (Body Tube)," "Airflow Control First Component (Body Plug)," and, e.g., the figures and detailed description thereof.

The finger recess is established, in aspects, by the presence of a fixed element within the internal compartment, the internal compartment being, e.g., the removable insert housing component, e.g., Body Tube or, e.g., the interior defined therein, having a dimension, e.g., thickness or depth, which is (a) detectably or significantly less than the depth of the internal compartment and (b) detectably or significantly less than the thickness of a removable insert. In aspects, when the removable insert is present in the internal compartment and is stably maintained in the internal compartment by a compressible element and the fixed element contacting first end and second ends of the insert respectively, a dimension of the fixed element and a dimension of a removable insert housing component, e.g., Body Tube (or, e.g., interior defined therein) are sufficiently different such that the user of the device can access at least a portion of the second end of the insert. In a specific aspect, a fixed element within the internal compartment has a dimension. e.g., thickness or depth, which is sufficiently less than the depth of the internal compartment and the thickness of a removable insert such that when the removable insert is present in the internal compartment and is stably maintained in the internal compartment by a compressible element and the fixed element making contact with first end and second ends of the insert respectively, a user of the device can access at least a portion of the second end of the insert. In aspects, a sufficient difference can be, e.g., a difference in thickness or depth between the two elements can be an difference of at least about 1%, >~2%, >~4%, >~6%, >~8%, >~10%, >~15%, >~20%, >>25%, >~30%, >~40%, >~45%, >~50%, >~55%, >~60%, >~70%, >~75%, >~80%, >~85%, >~90%, or, e.g., >~95% or more. In aspects, a difference between the depth of the interior compartment and the thickness of the fixed element is sufficient to expose at least a portion of a removable insert which the user can access to selectively remove the insert when desired.

Therefore, in one specific aspect, the invention provides an inhalation device, wherein the device comprises an internal compartment having a width, a depth, and a length, the internal compartment further comprising (a) a compressible element capable of being, designed to be, or which is both compressed by a force and applying/applies an opposing force to such compression, and (b) a fixed element positioned opposite the compressible element of (a) within the internal compartment. In aspects, the compressible element and the fixed element stably maintain a removable insert comprising one or more volatile compounds and having a width, a depth (or, e.g., a thickness), a first end, and a second end when such an insert is inserted therebetween. In aspects, the fixed element has a dimension, e.g., thickness, which is detectably or significantly less than the depth of the internal compartment and the depth or thickness of the removable insert. Accordingly, in aspects, when an insert is present in the internal compartment and is stably maintained in the compartment by the compressible element and the fixed element contacting the first end and second end of the insert respectively, a user of the device can access at least a portion of the second end of the removable insert with their finger to facilitate removal of the removable insert.

In certain aspects, the fixed element described above comprises at least two dimensions which join together in an orientation which is not a "sharp" 90-degree angle, such that the two dimensions meet at a curve. In aspects, the presence of the curved edge where the two dimensions meet facilitate the ease of insertion of the removable insert as is described elsewhere herein.

Second Primary Component

Tip Assembly

According to aspects, an inhalation device provided by the invention comprises a second primary component. In aspects, the second primary component comprises, e.g., a selectively releasable engagement mechanism component, e.g., a rapidly releasable force mechanism component, e.g., a component attractive to a magnet/magnetic force, such as, e.g., a Barrel Collar, a Barrel Tube, one or more components of an airflow control mechanism, e.g., a second airflow control component, e.g., a Barrel Plug, and, e.g., a Barrel. In certain aspects, such a collection of components can be referred to herein as the second primary component or the Tip Assembly.

According to certain aspects, the second primary component, e.g., Tip Assembly, is positioned over at least a portion of the first primary component, e.g., Body Assembly, when the inhalation device is fully assembled. In aspects, at least a portion of the first primary component, e.g., Body Assembly, is positioned inside of at least a portion of the Tip Assembly when the inhalation device is fully assembled. In certain aspects, the second primary component, e.g., Tip Assembly, has a smooth, sliding fit with, e.g., over, the first primary component, e.g., Body Assembly. In aspects, upon such fit, a selectively releasable engagement mechanism, e.g., rapidly releasable force mechanism, e.g., magnetic attraction maintains the connection of the first primary component, e.g., Body Assembly, to the second primary component, e.g., Tip Assembly, unless or until otherwise intentionally disengaged. In certain aspects, when the first primary component, e.g., Body Assembly, and second primary component, e.g., Tip Assembly, are engaged or sufficiently partially engaged, two or more elements of an airflow control mechanism, e.g., a Body Plug of a first primary component, e.g., Body Assembly, contacts a Barrel Plug of a second primary component, e.g., Tip Assembly, providing operability and selective control capability of the airflow control mechanism.

Selectively Releasable Engagement Mechanism (Barrel Collar)

According to certain aspects, a second primary component, e.g., a Tip Assembly, can comprise, e.g., a component of a selectively releasable engagement mechanism, e.g., a rapidly releasable force mechanism. In aspects, the component of the selectively releasable engagement mechanism, e.g., a rapidly releasable force mechanism present in, e.g., a second primary component, e.g., Tip Assembly, is a component complementary to a first selectively releasable engagement mechanism component. In aspects, the component of the selectively releasable engagement mechanism, e.g., a rapidly releasable force mechanism present in, e.g., a second primary component, e.g., Tip Assembly, is a component complementary to a first selectively releasable engagement mechanism component present in the first primary component, e.g., Body Assembly, of the device such that the two selectively releasable engagement mechanism components cooperate to provide the selectively releasable, e.g., rapidly releasable, engagement mechanism of the inhalation device. In aspects, the second selectively releasable engagement mechanism component can be any component capable of cooperating with a first selectively releasable engagement mechanism component to provide a reversible engagement of two device components, e.g., a first primary component and a second primary component. In aspects, a second selectively releasable engagement mechanism component can be, e.g., a component of an annular snap-fit mechanism, a cantilever snap-fit mechanism (e.g., a multiple-use cantilever snap-fit), or, e.g., a torsional snap-fit mechanism, or, e.g., a screw fit mechanism (e.g., using threading), a push-and-turn release mechanism (similar to or the same as the type of mechanism used commonly for child-proofing a medicinal container), a push-and-release attachment mechanism, an attachment mechanism comprising a clip, pin, lock, or latch, or, e.g., an attractive force mechanism such as a magnetic force mechanism.

In aspects, the second selectively releasable engagement mechanism component is a component of a magnetic force connection mechanism. In aspects, the second selectively releasable engagement mechanism component is a component which is magnetic. In aspects, the second primary component, e.g., Tip Assembly, can comprise more than one component which is magnetic. In aspects, the second primary component, e.g., Tip Assembly, can comprise a single component which is magnetic. In aspects, such a magnetic component is embodied as Barrel Collar. In aspects, a component of a selectively releasable engagement mechanism can comprise one or more characteristics of a Barrel Collar described in the figures or detailed description of figures provided herein.

According to certain aspects, a second selectively releasable engagement mechanism component, e.g., Barrel Collar, is configured so as to allow for an airflow passageway therethrough. In aspects, the second selectively releasable engagement mechanism component, e.g., the second rapidly releasable force mechanism component, e.g., Barrel Collar, is an annularly shaped, e.g., ring-shaped, component. In aspects, the, second selectively releasable engagement mechanism component, e.g., Barrel Collar, is positioned around one or more other components of a second primary device component; e.g., one or more other components of a second primary device component, e.g., Tip Assembly, is positioned at least partially inside of the second selectively releasable engagement mechanism component, e.g., Barrel Collar. In aspects, a barrel protection mechanism, e.g., Barrel Tube, is positioned at least partially within the interior of the second selectively releasable engagement mechanism component, e.g., Barrel Collar.

According to certain aspects, a second selectively releasable engagement mechanism component, e.g., Barrel Collar, is made of a magnetic material. That is, in aspects, the second selectively releasable engagement mechanism component, e.g., Barrel Collar, is made of a material which is capable of being magnetized. In aspects, a first component of a first primary component, e.g., a Body Assembly, comprising a first component of a selectively releasable engagement mechanism, e.g., a Magnet, is magnetically attracted to the second selectively releasable engagement mechanism component, e.g., Barrel Collar positioned within the second primary component, e.g., Tip Assembly. In certain aspects, the second selectively releasable engagement mechanism, e.g., Barrel Collar, is the only component of the inhalation device capable of being detectably or significantly attracted by, connected by force to, or connected by a rapidly releasable connection mechanism to, a first selectively releasable engagement mechanism component. In aspects, it is, e.g., a magnetic attraction between a first primary component, e.g., a Body Assembly component, e.g., Magnet and a second primary component, e.g., Tip Assembly component, e.g., Barrel Collar, which facilitates the selective engagement, of the first device primary component, e.g., Body assembly and second device primary component, e.g., Tip Assembly. In aspects, it is the selective and, e.g., rapid engagement and disengagement of these two device components which facilitates the ability to rotate a first primary component and a second primary component in relation to one another, such rotation controlling the status or modification of the airflow control mechanism.

According to certain aspects, the selectively releasable engagement mechanism, e.g., Barrel Collar can be a standardly available stock component. In aspects, the second selectively releasable engagement mechanism component, e.g., Barrel Collar, is a custom-made component. In aspects, the second selectively releasable engagement mechanism component, e.g., Barrel Collar, is custom machined, cast, or otherwise manufactured specifically for use within the inhalation device described herein.

In this and other component, function, or operational aspect(s) of the invention, the invention also can be characterized as comprising a "means" for selectively releasable engagement of two or more components. In such a respect, any known equivalents of such named selectively releasable engagement components or mechanisms can also be, e.g., are, incorporated into devices or methods of the invention. As with other sections similarly described herein, any of the components of the invention can be, where suitable, described as means (e.g., the above-described selectively releasable engagement mechanism component can be described as selectively releasable engagement means or means for providing or facilitating the selectively releasable engagement of two or more inhalation device components).

Outer Shell (Barrel)

In some aspects, a second primary component of an inhalation device can comprise, e.g., a component which is externally visible. In aspects, such a component can be, e.g., characterizable as an outer cover or shell of the second primary component, e.g., Tip Assembly. In aspects, an outer shell, e.g., Barrel (or "barrel component"), is an exterior device component which an inhalation device user contacts to remove the second primary device component, e.g., Tip Assembly, from the first primary device component, e.g., Body Assembly, when the inhalation device user wishes to access the interior of the first primary component, e.g., Body Assembly to insert or remove a component comprising (or having comprised) compounds for inhalation, such as, e.g., a removable insert (e.g., Core).

In aspects, such an outer cover or shell can be any type of outer cover or shell taking on any type of size, shape, or appearance, which is suitable, e.g., compatible, with any one or more other device components which it must mate, engage with, or otherwise interact with during operation of the inhalation device. For example, such an outer cover or shell can comprise any shape, such as, e.g., cylinder, triangular prism, rectangular prism (cuboid), pentagonal prism, hexagonal prism, octagonal prism, or other multi-sided prism. In aspects, an outer cover or shell can be made of any material described herein, such as, e.g., a metal, metal alloy, wood, plastic, ceramic, stone, shell, etc. In aspects, an outer cover or shell can be interchangeable, so as to, e.g., provide a customizable inhalation device to a device user. In aspects, an outer cover or shell is not interchangeable. According to certain aspects, the outer cover or shell is cylindrical in shape. In aspects, the outer cover of shell is made of a wood. In aspects, the outer cover or shell is a cylindrical body made of wood, such as, e.g., is embodied by a Barrel. In aspects, an outer shell component can comprise one or more characteristics of a Barrel described in the figures or the detailed description of figures provided herein.

According to aspects, the outer shell of a second primary component, e.g., Barrel, is capable of housing, is designed to house, or houses within it one or more other components of an inhalation device. In aspects, the outer shell of a second primary component can be a cylinder within which at least a portion of one or more of a second selectively releasable engagement mechanism, e.g., Barrel Collar, an outer shell protection mechanism (Barrel Tube), and, e.g., a component of an airflow control mechanism, e.g., an airflow control second component (also referred to herein as a second airflow control component), e.g., a Barrel Plug, is/are housed therein.

In certain aspects, in a fully assembled inhalation device, a second selectively releasable engagement mechanism, e.g., Barrel Collar can be positioned around an outer shell protection mechanism (e.g., Barrel Tube), In aspects, both the second selectively releasable engagement mechanism, e.g., Barrel Collar and outer shell protection mechanism (e.g., Barrel Tube) are positioned within the outer shell (e.g., Barrel). In aspects, an outer shell protection mechanism, e.g., Barrel Tube, can detectably or significantly limit the exposure of the outer shell, e.g., Barrel, to a condition which may detectably or significantly impact the performance of or detectably or significantly limit the longevity of, the outer shell, e.g., Barrel. In aspects, such a condition can be, e.g., exposure to excess amount of moisture, sufficient exposure to one or more volatile compounds to cause the detectable or significant absorption of one or more volatile compounds, or both.

In aspects, an outer shell, e.g., Barrel, is provided as a cylinder which is open on both its first and second ends. In aspects, one or more components of an airflow control mechanism is/are visible to an inhalation device user when an inhalation device user peers into an end of the outer shell (e.g., Barrel) (e.g., the end of the outer shell distal from an inhalation facilitation component, e.g., Mouthpiece). In aspects, by viewing an inhalation device from an end distal to the inhalation facilitation component, e.g., Mouthpiece, a user can see one or more, e.g., all relevant airflow control mechanism components to discern the airflow control status of the inhalation device (e.g., a user can discern the degree of openness or closure of the airflow control mechanism.)

In aspects, an outer shell (e.g., Barrel) exterior surface can comprise one or more visual indicators. In aspects, such a one or more visible indicator(s) is/are visible to the user when using the device. In aspects, an outer shell, e.g., Barrel, can comprise a first indicator which can, in aspects, participate in establishing the spatial orientation of the device, one or more operational status(es) of the device, or both. In aspects, such a first visual indicator can be any visual indicator described herein. In certain specific aspects, the visual indicator is, e.g., a product logo.

According to certain aspects, the outer shell, e.g., Barrel, can be a standardly available stock component. In aspects, the outer shell, e.g., Barrel, is a custom-made component. In aspects, outer shell, e.g., Barrel, is custom machined, cast, carved, molded, or otherwise manufactured specifically for use within the inhalation device described herein.

In this and other component, function, or operational aspect(s) of the invention, the invention also can be characterized as comprising a "means" for providing an aesthetically pleasing inhalation device while housing one or more device components required for expected use or operation of the device. In such a respect, any known equivalents of such selectively named outer shell components or mechanisms can also be, e.g., are, incorporated into devices or methods of the invention. As with other sections similarly described herein, any of the components of the invention can be, where suitable, described as means (e.g., the above-described outer shell component can be described as outer shell means or means for providing an outer shell or facilitating the housing of one or more device components required for suitable device use or operation while providing an aesthetically pleasing device).

Outer Shell Protection Mechanism (Barrel Tube)

According to aspects, an inhalation device may comprise an outer shell component (e.g., Barrel), made at least substantially of a material which is (a) at risk of being compromised due to exposure to excessive moisture, or (b) made at least substantially of a material at risk of absorbing or, e.g., allowing entry of, one or more volatile compounds released from a means of maintaining, releasing, or maintaining and releasing one or more volatile compounds, such as, e.g., a removable insert (e.g., Core). Therefore, in aspects, an inhalation device, e.g., an outer shell (e.g., Barrel) of an inhalation device, can comprise as an additional component an outer shell protection mechanism. In certain aspects, such an outer shell protection mechanism can be, e.g., a Barrel Tube. In aspects, an outer shell protection mechanism can comprise one or more of the characteristics of a Barrel Tube described in the figures or detailed description of figures provided herein.

In aspects, an outer shell protection mechanism can be, e.g., any component which operates to protect an outer shell component (e.g., Barrel) from (a) damage or degradation, such as by, e.g., exposure to excessive moisture, or from (b) contamination with a detectable or significant amount of one or more volatile compounds. A detectable or significant amount of one or more compounds can be an amount which is detectable by a user of the inhalation device to an extent that the user can taste the one or more volatile compounds during a time period in which the inhalation device no longer contains an, e.g., releasable insert (e.g., Core) comprising such one or more volatile compounds. In aspects, such an outer shell protection component can be any component accomplishing this purpose, such as, e.g., a liner, a coating, an inserted component, such as, an insert made of, e.g., a plastic, metal, or, e.g., metal alloy, etc. In aspects, such an outer shell protection component can be made of, e.g., stainless steel. In aspects, the outer shell protection component is a stainless-steel tube, e.g., a Barrel Tube.

In certain aspects, an outer shell protection component, e.g., Barrel Tube, can be positioned within an interior of an outer shell component, e.g., Barrel. In aspects, an epoxy glue is used on an outer surface of an outer shell protection component. e.g., Barrel Tube, to bond the outer shell protection component, e.g., Barrel Tube, to the interior of an outer shell, e.g., Barrel. In such aspects, the outer shell protection component is not obviously externally visible under normal inhalation device operating conditions. In aspects, the outer shell protection component detectably or significantly reduces the exposure of the outer shell component, e.g., Barrel, to moisture. In aspects, the outer shell protection component, e.g., Barrel Tube, detectably or significantly extends the usable lifespan of an inhalation facilitation component, such as by at least ~2×, ~5×, ~10×, ~20×, ~50×, ~100×, ~1000×, or ~2000× or more over an inhalation facilitation component lacking such a component.

In aspects, an outer shell, e.g., Barrel, is positioned around at least a portion of a first primary component, e.g., Body Assembly. In aspects, an outer shell, e.g., Barrel, is positioned around at least a portion of a removable insert housing component (e.g., internal compartment, e.g., Body Tube or internal compartment formed by a Body Tube.) In aspects, one or more volatile compounds provided by a means of providing such compounds, e.g., a removable insert (e.g., Core), can seep into and therefore become present in an outer shell if such an outer shell comprises a sufficiently soft or porous material allowing entry of one or more such volatile compounds. In such scenarios, the outer shell can later release such one or more volatile compounds, impacting, e.g., in aspect negatively impacting, the experience of the inhalation device user (such as by, for example, releasing a volatile compound having a first flavor obtained from a first removable insert which has since been removed and, e.g., replaced by a second removable insert comprising different volatile compound(s)). Therefore, in aspects, an outer shell protection mechanism, e.g., Barrel Tube, can detectably or significantly reduce the volume of volatile compound(s) released by a removable insert (e.g., Core) which make their way into the outer shell, e.g., Barrel. In aspects, an outer shell protection mechanism, e.g., Barrel Tube, prevents a detectable or significant volume of one or more volatile compounds from entering a material of which outer shell, e.g., Barrel, is composed. In aspects, an outer shell protection mechanism, e.g., a Barrel Tube, reduces or prevents a sufficient volume of one or more volatile compounds, released from a first removable insert, from entering the Barrel to be detectable by the user when the user replaces the first removable insert with a second removable insert delivering different one or more volatile compounds.

In this and other component, function, or operational aspect(s) of the invention, the invention also can be characterized as comprising a "means" for protecting the inhalation facilitation component. In such a respect, any known equivalents of such named inhalation facilitation protection component supplement elements can also be, e.g., are, incorporated into devices or methods of the invention. As with other sections similarly described herein, any of the components of the invention can be, where suitable, described as means (e.g., the above-described outer shell protection mechanism can be described as outer shell protection means or means for providing or facilitating protection of an inhalation device outer shell).

In aspects, an outer shell protection component, e.g., Barrel Tube, can be custom made, e.g., custom cast, machined, or otherwise custom manufactured for use with the inhalation device(s) herein. In aspects, an outer shell protection component, e.g., Barrel Tube, can be purchased as a typical on-market (stock) machine part.

In this and other component, function, or operational aspect(s) of the invention, the invention also can be characterized as comprising a "means" for protecting an outer shell component. In such a respect, any known equivalents of such named outer shell protection component elements can also be, e.g., are, incorporated into devices or methods of the invention. As with other sections similarly described herein, any of the components of the invention can be, where suitable, described as means (e.g., the above-described outer shell protection component can be described as outer shell protection component means or means for protecting an outer shell of an inhalation device).

Airflow Control Second Component (Barrel Plug)

As stated previously, in aspects, an inhalation device comprises at least two components, movable in relation to one another, which cooperate to provide airflow control functionality to the inhalation device. In aspects, at least one of the at least two components, e.g., an airflow control second component, reside(s) in a second primary component of the inhalation device.

In aspects, an inhalation device comprises at least two components, movable in relation to one another, which cooperate to provide airflow control functionality to the inhalation device. In aspects, at least one of the at least two components, e.g., an airflow control second component, reside(s) in a second primary component of the inhalation device. In aspects, the function of an airflow control second component is to participate in the airflow control of an inhalation device. Such airflow control can also be referred to as drag control. In aspects, an airflow control second component provides a means of customizing the airflow through an inhalation device, providing selectable airflow control setting(s).

According to aspects, an airflow control second component (also referred to herein as a second airflow control component) is designed to cooperatively engage with an airflow control first component (also referred to herein as a first airflow control component) to selectively control the amount of air which is drawn through the inhalation device upon inhalation by the inhalation device user. In aspects, a second airflow control component repeatedly engages with, at least partially disengages from, and reengages with, a first airflow control component during normal operation of the device.

According to certain aspects, a second airflow control component can be any component suitable for interfacing with a first airflow control component to control airflow, such as, e.g., a shutter, a disc-shaped device comprising, e.g., one or more apertures, a device comprising a mechanism for modifying an opening by selectively expanding outward to form a larger opening or converging inward to form a smaller opening, a solid device capable of blocking at least a portion of but not all of an airflow passageway through a device, or any other such mechanism or component capable of cooperatively participating in airflow control through an inhalation device.

In certain aspects, a second airflow control component is a component which alone is capable of blocking at least about, e.g., 25% of an airflow passageway through an inhalation device, such as, e.g., ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, or more, but not 100% of, an airflow passageway through an inhalation device. In aspects, the amount of an airflow passageway through a device which is blocked by a second airflow control component of an inhalation device described herein is no more than about 75%, such as no more than ~75%, ~70%, ~65%, ~60%, ~55%, or no more than ~50% of the airflow passageway through an inhalation device. According to certain aspects, the second airflow control component is a semi-circular-shaped component. In aspects, the semi-circular shaped component is capable of blocking, is designed to block or blocks about 50% of the airflow passageway through an inhalation device, such that due to its presence, a maximally open airflow passageway through a device has at least one dimension which is no more than about half of the diameter (or, e.g., width or height) of an interior passageway passing from a first end of an inhalation device to a second end of an inhalation device. In aspects, such an interior passageway would have, absent the presence of at least the second airflow control component, a cross sectional area across its length or at a minimum in a single location along its length which is about twice that of the cross-sectional area across its length or at a minimum in a single location along its length which is present when the at least second airflow control component is present.

As previously stated, in aspects, the second airflow control component is movable in relation to a first airflow control component. In aspects, the degree of interface between the first and second airflow control components is established by the rotation of the first primary device component and the second primary device component relative to one another.

In aspects, a second airflow control component is provided as a Barrel Plug. In aspects, a second airflow control component can comprise any one or more of the characteristics of the Barrel Plug described in figures or the detailed description of figures provided herein.

In aspects, a second airflow control component, e.g., Barrel Plug, can comprise a body feature facilitating its fixed attachment to one or more additional components of an inhalation device. In aspects, at least a portion of a second airflow control component, e.g., Barrel Plug, is positioned within an outer shell protection mechanism, e.g., Barrel Tube.

In aspects, a second airflow control component, e.g., Body Plug, can comprise a plurality of features which, in aspects, can be describable as belonging to a fan feature of the second airflow control component, e.g., Barrel Plug. Such features can, in aspects, repeatedly engage with and at least partially disengage from compatible features present on a first airflow control component, e.g., Body Plug. A first airflow control component can, in aspects, comprise any one or more characteristics of a Body Plug described in the detailed description of figures provided herein. In aspects, such repeated engagement and disengagement of such fan features can occur upon the movement, e.g., rotation, of the second airflow control component (e.g., Barrel Plug) relative to the first airflow control component (e.g., Body Plug). In aspects, in a fully assembled device, and with first and second primary components of such a device maximally engaged with one another, a first airflow control component, e.g., Body Plug, is in contact with the second airflow control component, e.g., Barrel Plug.

In aspects, a second airflow control component can comprise a fan-like feature comprising a series of ridges (or peaks) and recessions such as, e.g., a series of alternating ridges and recessions. In aspects, the alternating ridges and recessions of a second airflow control component repeatedly alternatingly engage with and disengage from a coordinating series of ridges and recessions present on a first airflow control component (e.g., Body Plug) which in aspects comprises a complementary fan-like feature comprising the complementary set of ridges and recessions. In aspects, the degree of interface between the second and first airflow control components, e.g., the degree of overlap between the two components, provides the airflow control mechanism of the device. In aspects, the more the second airflow control component, e.g., the Barrel Plug, overlaps with the first airflow control component, e.g., the Body Plug, the more airflow through the device is blocked. In aspects, the less the second airflow control component, e.g., the Barrel Plug, overlaps with the first airflow control component, e.g., the Body Plug, the more airflow through the device is allowed (the less the airflow through the device is blocked.)

The interaction between the first and second airflow control components and their ability to cooperatively control the airflow through an inhalation device is further described elsewhere herein.

In aspects, a second airflow control component can comprise a component or feature which participates in a tactile indication of an operational status of the inhalation device. In aspects, such a feature intermittently interfaces with one or more features of a first airflow control component, e.g., Body Plug. In aspects, a second airflow control component can comprise one or more protrusions which intermittently interface(s) with one or more protrusion component(s) on a second airflow control component. As previously described in relation to the first airflow control component (e.g., Body Plug), in aspects, the interface between the two distinct protrusions on the first and second airflow control components, respectively, provide a distinguishably different tactile sensation compared to the interaction between the ridge(s)/recession(s) of each of the first and second airflow control components. This is further described or exemplified elsewhere herein. In aspects, such intermittently interfacing components providing a distinctly different tactile indication can be any feature providing such an indication. Herein, this/these intermittently interfacing feature(s) is/are described as protrusion(s). In aspects, the distinguishably different tactile sensation indicates a specific airflow control setting of the device. In aspects, the distinguishably different tactile sensation indicates that the airflow control mechanism is in a maximally closed position. In aspects, any other tactile sensation provided by alternating interface of ridges/recessions on the first and second airflow control components indicate some degree of opening of the airflow control mechanism.

According to certain embodiments, a second airflow control component, e.g., Barrel Plug, can comprise, e.g., between about 2 and about 30 ridges (or, e.g., peaks) and recessions. In aspects, a second airflow control component can comprise the same number of ridges as recessions. In alternative aspects, a second airflow control component can comprise a different number of ridges and recessions. In some aspects, a second airflow control component can comprise, e.g., one or two more ridges than recessions. In some aspects, a second airflow control component can comprise, e.g., one or two more recessions than ridges. In certain aspects, a second airflow control component can comprise, e.g., ~4-~30, ~6-~30, ~8-~30, ~10-~30, ~12-~30, ~14-~30, ~16-~30, ~18-~30, ~20-~30, ~22-~30, ~24-~30, ~26-~30, or ~28-~30 ridges, recessions, or both ridges and recessions (e.g., such values representing the number of each of ridges and recessions), such as, e.g., ~2-~28, ~2-~26, ~2-~24, ~2-~22, ~2-~20, ~2-~18, ~2-~16, ~2-~14, ~2-~12, ~2-~10, ~2-~8, ~2-~6, or ~2-~4 ridges, recessions or both ridges and recessions (e.g., such values representing the number of each of ridges and recessions), as in, for example, ~4-~28, ~6-~26, ~8-~24, ~10-~22, ~12-~20, ~14-~18, or, e.g., about 16 ridges, recessions, or both ridges and recessions (e.g., such values representing the number of each of ridges and recessions).

According to certain embodiments, an angle of between about 6 and about 60 degrees, such as, e.g., an angle of ~7-~60, ~8-~60, ~9-~60, ~10-~60, ~11-~60, ~12-~60, or ~13-~60 degrees, such as, e.g., ~6-~50, ~6-~40, ~6-~30, ~6-~20, or, e.g., ~6-~10 degrees, as in, for example, ~8-~50, ~8-~40, ~8-~30, ~8-~20, or ~8-~25 degrees, such as, e.g., between about 11 and about 13 degrees, e.g., an angle of about 12 degrees separates each recession, separates each ridge, or separate each recession and each ridge from the next (e.g., adjacent) respective recession or ridge.

In aspects, the number of airflow control second component (e.g., Barrel Plug) fan ridge recessions and peaks (ridges) present in a second airflow control component contributes to the specificity with which airflow through the device can be controlled. For example, an increased number of such features recessions and peaks/ridges of a second airflow control component can increase the level of fine tuning a user can accomplish to control airflow (e.g., drag control) when using the inhalation device, while a decreased number of such features can decrease the level of fine tuning a user can accomplish to control airflow during device use.

In aspects, the second airflow control component can be made of any material described herein. In certain aspects, the second airflow control component is made of a metal or metal alloy, such as, e.g., gold, titanium, platinum, or, e.g., stainless steel. In particular aspects, the first airflow control component is made of stainless steel.

In aspects, the second airflow control component is a custom-made component. In aspects, the second airflow control component is machined, cast, or otherwise custom manufactured for use in inhalation devices described herein.

In this and other component, function, or operational aspect(s) of the invention, the invention also can be characterized as comprising a "means" for controlling airflow. In such a respect, any known equivalents of such airflow control components or mechanisms can also be, e.g., are, incorporated into devices or methods of the invention. As with other sections similarly described herein, any of the components of the invention can be, where suitable, described as means (e.g., the above-described second airflow control component can be described as airflow control means or means for controlling airflow).

Visual Indicators

According to certain aspects, an inhalation device provided by the invention can comprise at least one, such as, e.g., ≥2, ≥3, ≥4, or ≥5 visual indicators, e.g., indicators which are detectable by a user of the device (e.g., exist on an exterior surface of the device or are otherwise able to be detected by a user by sight or touch when the device is in a ready to use state. Notably, while the term "visual indicator" is used, such an indicator can, in aspects, be detectable by touch. In some aspects, such a feature may be useful for a user with impaired vision. In aspects, a visual indicator, when viewed independently, in conjunction with one or more other visual indicators, or both, can provide an indication of one or more characteristics of the device, such as, e.g., the spatial orientation of a non-visible (e.g., internal) inhalation device component, the operational status of one or more inhalation device mechanisms, e.g., an airflow control setting, or both. In aspects, one or more visual indicators can be present on one or more external surfaces of a first primary component, second primary component, or both.

In aspects, a visual indicator can be any distinguishable, e.g., externally distinguishable, mark, shape, feature, or otherwise distinguishable element. In aspects, a visual indicator comprises a raised element (e.g., an elevated element which is detectable by touch), or a recessed element (e.g., a carving or indentation which is detectable by touch), a tick mark, intentional scratch, carving, engraved element, painted marking, stamped marking, or any other type of observable marking such as, e.g., a line or other shape, number, letter, symbol, or collection of letters, numbers, or symbols (e.g., a word, name, or other product identifier), or image.

In one aspect, an inhalation device can comprise at least two visual indicators, wherein at least one visual indicator is different from at least one other visual indicator in one or more ways, such as, e.g., by size, shape, color, feel (e.g., feel to the touch, such as, e.g., one being raised and one being recessed), position (e.g., placement on the device), or any other visually differentiable characteristic. In other aspects, an inhalation device can comprise at least two visual indicators, wherein at least two of the visual indicators are at least generally the same, at least substantially the same, at least essentially the same, essentially the same, or are the same as one another.

In an aspect, an inhalation device comprises at least two visual indicators wherein at least one visual indicator is a tick mark and at least one visual indicator is a product logo.

In one aspect, the invention provides a device comprising a first primary component and a second primary component movable relative to one another. In one aspect, the first primary component of the device comprises at least one visual indicator. In aspects, the inhalation device comprises at least one visual indicator present on the exterior of the device positioned on a device component which is fixedly attached to, either directly or indirectly, a removable insert housing component, e.g., Body Tube. For example, the visual indicator is present on an engagement mechanism positioning component. In aspects, the spatial orientation of the at least one visual indicator indicates the spatial orientation of at least one component of the device which is not externally visible. In aspects, the internal component is the removable insert housing component. Thus, in aspects, the spatial orientation of the visual indicator can indicate the spatial orientation of the removable insert housing component, indicating, for example, the orientation of the portion of the removable insert housing component which is not completely circumferentially enclosed by a circumferentially disposed wall (e.g., the orientation of the at least partially open portion of the removable insert housing component, e.g., Body Tube.)

In aspects, at least one visual indicator present on the first primary component is positioned such that it is on the opposite side of the inhalation device from the position of an airflow control first component (e.g., Body Plug). In aspects, the fan-like feature of a first airflow control component (e.g., Body Plug), is positioned on the opposite side of the device from a visual indicator on a first primary component. In aspects, the spatial orientation of the at least one visual indicator positioned on the first primary component can indicate the position of the first airflow control component (Body Plug).

In a specific example, in aspects, when a visual indicator on the first primary component is spatially oriented upward, the opening within the removable insert housing component (e.g., internal compartment, e.g., Body Tube) is oriented upward, and the fan-like feature of the first airflow control component is positioned on the lower half of the inhalation device.

In a further aspect, the second primary component of the device comprises at least one visual indicator. In aspects, the at least one visual indicator present on the second primary component is positioned such that it corresponds to the positioning of an airflow control second component (e.g., Barrel Plug). In aspects, the positioning of the visual indicator on the second primary component, e.g., the outer shell (e.g., Barrel) of the second primary component corresponds with the fan-feature of the second airflow control component such that both are positioned on the same side of the device. In aspects, the spatial orientation of the second visual indicator can indicate the position of the second airflow control second component (Barrel Plug).

In a specific example, in aspects, when a visual indicator on the second primary component is spatially oriented upward, the fan-like feature of the second airflow control component (e.g., Barrel Plug), is positioned on the upper half of the inhalation device.

In aspects, an inhalation device comprises at least two visual indicators present on the exterior (e.g., externally visible) of the inhalation device. In aspects, at least one of the at least two visual indicators is present on a first primary component. In aspects, at least one of the at least two visual indicators is present on a second primary component. In aspects, wherein the first and second primary components are movable relative to one another, the spatial orientation of at least one visual indicator relative to at least one other visual indicator provides an indication of at least one operational status of the device.

In certain aspects, the inhalation device comprises at least one visual indicator on a first primary component and at least one visual indicator on a second primary component wherein the orientation of the two visual indicators relative to one another indicates the status of the airflow control mechanism. In aspects, the orientation of the two visual indicators relative to one another indicates the airflow control, (or, e.g., drag control) setting of the inhalation device.

In aspects, when a first visual indicator, e.g., a visual indicator present on, e.g., a second primary component, is aligned with a second visual indicator, e.g., a visual indicator present on a first primary component, the alignment indicates that the airflow control mechanism is completely closed. For example, in such an orientation, there is minimal overlap between the fan features of the airflow control first and second components.

In aspects, when a first visual indicator, e.g., a visual indicator present on, e.g., a second primary component, is positioned opposite that of a second visual indicator, e.g., a visual indicator present on a first primary component, the opposite positioning indicates that the airflow control mechanism is completely open. For example, in such an orientation, there is maximum overlap between the fan features of the airflow control first and second components.

According to certain aspects, at least one particular alignment between at least one visual indicator and at least one other visual indicator is accompanied by a distinctly different, e.g., distinguishable, tactile indicator. In aspects, when a first primary component and a second primary component are rotated 360 degrees relative to one another, the particular alignment between the at least one visual indicator and the at least one other visual indicator only occurs one time, and such a distinguishable tactile indication is sensed only once when such alignment is attained.

In one specific exemplary embodiment, the invention described herein provides a passive inhalation device comprising at least a first primary component and a second primary component movable in relation to one another, the passive inhalation device having an internal compartment designed to hold a removable insert comprising one or more volatile compounds and the first primary component comprising one or more visual indicators, wherein the orientation of one or more visual indicators on the first primary component indicates the spatial orientation of the internal compartment designed to hold the removable insert.

In this and other component, function, or operational aspect(s) of the invention, the invention also can be characterized as comprising a "means" for indicating the spatial orientation of one or more internal components, an operational status of the inhalation device, or both. In such a respect, any known equivalents of such indicators can also be, e.g., are, incorporated into devices or methods of the invention. As with other sections similarly described herein, any of the components of the invention can be, where suitable, described as means (e.g., the above-described visual indicators can be described as spatial orientation or operational status indicator means or means for indicating spatial orientation or operational status).

Movement of First Primary Component Relative to Second Primary Component

According to certain embodiments, an inhalation device comprises at least two components movable in relation to one another. In aspects, an inhalation device comprises a first primary component, e.g., a Body Assembly, and a second primary component, e.g., a Tip Assembly, capable of rotating, designed to rotate, or which rotate 360 degrees in relation to one another. In aspects, an inhalation device comprises a first primary component and a second primary component capable of rotating, designed to rotate, or which rotate 360 degrees in relation to one another in either direction. In aspects, an inhalation device comprises a first primary component and a second primary component capable of continuous rotation, e.g., multiple 360-degree rotations, in relation to one another in either direction.

In aspects, movement of a first primary component, e.g., a Body Assembly, and, e.g., a second primary component, e.g., a Tip Assembly, is accompanied by a tactile indication of such movement. In aspects, the tactile indication of movement is provided by the interface of components of the airflow control mechanism (e.g., the first and second airflow control component, e.g., the Body Plug and the Barrel Plug) rotating about one another according to the rotation of the first and second primary components. In aspects, the tactile indicator is caused by the changing interface between first and second components of the airflow control mechanism. In aspects, the tactile indicator is caused by, e.g., the changing interface between fan-like features of the first and second airflow control components (such fan-like features described herein). In aspects, the tactile indicator is caused by, e.g., the alternating separation and reattachment of the first and second primary components as they rotate relative to one another.

In aspects, movement, e.g., rotation, of the first primary component relative to the second primary component (e.g., movement of the Body Assembly relative to the Tip Assembly) yields an alternating at least partial separation and reuniting of the two components. In aspects, the selectively releasable engagement mechanism, e.g., the rapidly releasable force mechanism, e.g., the magnetic attraction, which selectively engages the two components maintains at least a detectable amount of contact between the two components as they rotate in relation to one another. However, in aspects the amount of contact between the two components alternatingly increases and decreases as the two components are rotated in relation to one another. In aspects, the amount of interface between the first airflow control component and the second airflow control component decreases between any first airflow control setting and any second airflow control setting compared to the amount of interface between the first and second components of the airflow control mechanism at any first or second airflow control setting as rotation occurs and as, e.g., the first primary component, e.g., Body Assembly, comprising a first airflow control component, e.g., Body Plug, and the second primary component, e.g., Tip Assembly, comprising a second airflow control component, e.g., Barrel Plug, alternatingly at least partially separate and reunite. In aspects, the amount of surface area of a first airflow control component making contact with a second airflow control component decreases between any first airflow control setting and any second airflow control setting compared to the amount of surface area of a first airflow control component making contact with a second airflow control component at any first or second airflow control setting as rotation occurs. In aspects, the amount of surface area of a second airflow control component making contact with a first airflow control component decreases between any first airflow control setting and any second airflow control setting compared to the amount of surface area of a second airflow control component making contact with a first airflow control component at any first or second airflow control setting as rotation occurs. This is also discussed elsewhere herein.

Airflow Control Mechanism

According to certain embodiments, an inhalation device comprises a means for airflow control (or drag control). Such possible means have been described elsewhere herein.

In aspects, an inhalation device comprises a passageway allowing for air to pass from a distal end of an inhalation device to a proximal end of an inhalation device (e.g., a proximal end being an end comprising an inhalation facilitation component, e.g., Mouthpiece, and a distal end being an end opposite or distanced from the proximal end. For example, an inhalation device can comprise an air passage which passes through, e.g., the airflow control mechanism (e.g., first and second components of the airflow control mechanism (e.g., Body Plug and Barrel Plug); through an outer shell (e.g., Barrel) or, e.g., more specifically through an outer shell protection mechanism (e.g., Barrel Tube); through a removable insert housing component (e.g., Body Tube); through a means for maintaining, delivering, or maintaining and delivering one or more volatile compounds (e.g., a removable insert, e.g., a Core); through a compressible element (e.g., Core Spring); through an engagement mechanism positioning component (e.g., Magnet Cover); through one or more components of a selectively releasable engagement mechanism (e.g., a Magnet, a Barrel Collar, or both); and through an inhalation facilitation component (e.g., a Mouthpiece) including, e.g., in aspects an inhalation facilitation component supplement (e.g., a Mouthpiece Tube) or an Inhalation Facilitation Component Attachment Insert (Mouthpiece Attachment Insert). In aspects, an airflow control mechanism positioned within this pathway can selectively modulate how open or how closed this passageway is.

Characteristics of components of an airflow control mechanism provided by the invention are described elsewhere herein. However, for sake of aiding the reader in understanding the airflow control mechanism, the following specific examples of an exemplary mechanism are provided.

According to aspects, the inhalation device comprises an airflow control mechanism adjustable by the movement of a first airflow control component relative to a second airflow control component. In aspects, the movement of the first airflow control component relative to the second airflow control component is a relational movement (as described elsewhere herein). In aspects, the movement of the first airflow control component relative to the second airflow control component is a concurrent or associated relational movement (as described elsewhere herein). In aspects, the movement of the first airflow control component relative to the second airflow control component is a rotational movement and, optionally, the rotation of the first airflow control component relative to a second airflow control component can comprise a rotation of between about 1 degree and about 360 degrees, such as, e.g., ~1 degree-~330 degrees, ~1 degree-~300 degrees, ~1 degree-~270 degrees, ~1 degree-~240 degrees, ~1 degree-~210 degrees, or, e.g., ~1 degree-~180 degrees, such as, e.g., ~30 degrees-~360 degrees, ~60 degrees-~360 degrees, ~90 degrees-~360 degrees, ~120 degrees-~360 degrees, ~150 degrees-~360 degrees, or, e.g., ~180 degrees-~360 degrees. In aspects, the movement of the first airflow control component relative to the second airflow control component can have any one or more of the movement characteristics described in this paragraph.

In one aspect, the airflow control mechanism is an adjustable airflow control mechanism comprising a first airflow control component and a second airflow control component wherein the first and second airflow control components are in releasable contact with one another during normal operation of the device. In aspects, the first and second airflow control components are capable of rotating, are designed to rotate or can rotate at least 360 degrees relative to one another. In aspects, the first and second airflow control components are capable of rotating at least 360 degrees in either direction relative to one another. In aspects, the first and second airflow control components are capable of rotating, are designed to rotate, or can rotate more than 360 degrees in either direction relative to one another, such as, e.g., capable of multiple full rotations relative to one another in either direction. In aspects, first and second airflow control components can be completely disengaged and reengaged from one another during normal operation of an inhalation device. For example, such a complete disengagement can in aspects occur when, e.g., a first means of maintaining, delivering, or maintaining and delivering one or more volatile compounds, e.g., a removable insert, e.g., Core, is inserted or removed from the inhalation device.

In aspects, complete overlap, e.g., complete or, e.g., maximum interface, of a first airflow control component and second airflow control component establishes the device in a "maximally open" position, such that the device is in a configuration providing the lowest amount of drag and the highest level of possible airflow. Further, the smallest possible overlap, or e.g., a lack of any overlap, e.g., a lack of significant interface, of the first and second airflow control components establishes the device in a "maximally closed" position, such that the device is in a configuration providing the highest amount of drag and the lowest level of possible airflow. Any overlap of the two components between these two extreme positions modulates the airflow (and, e.g., drag), accordingly. In certain aspects, a sufficient amount of air can still be drawn through the device upon inhalation by a user to render the device operable when the device is in a maximally closed position.

In one aspect, when the airflow control mechanism is in a configuration representing its most open position, the airflow control mechanism provides an airflow channel through the device having a cross sectional area which is about 40% to about 60%, such as, e.g., ~42%-~60%, ~44%-~60%, ~46%-~60%, ~48%-~60%, or, e.g., ~50%-~60%, or, e.g., ~40%-~58%, ~40%-~56%, ~40%-~54%, ~40%-~52%, or ~40%-~50%, as in, for example, ~42%-~58%, ~44%-~56%, ~46%-~54%, ~48%-~52%, or, e.g., ~50% of a cross-sectional area of at least one portion of an airflow channel otherwise present in, e.g., at least a portion of, the device.

In aspects, when the airflow control mechanism is in a configuration representing its most open position, the airflow control mechanism provides an airflow channel through the device providing for the flow of a volume of air which is about 40% to about 60%, such as, e.g., ~42%-~60%, ~44%-~60%, ~46%-~60%, ~48%-~60%, or, e.g., ~50%-~60%, or, e.g., ~40%-~58%, ~40%-~56%, ~40%-~54%, ~40%-~52%, or ~40%-~50%, as in, for example, ~42%-~58%, ~44%-~56%, ~46%-~54%, ~48%-~52%, or, e.g., ~50% of the volume of air which would otherwise be able to flow through the device if the airflow control mechanism were not present in the device.

In aspects, adjustment of the airflow control mechanism, e.g., by moving, e.g., rotating two airflow control components in relation to one another (which, e.g., in aspects is accomplished by the rotation of a first primary device component and a second primary device component relative to one another) is accompanied by a tactile indication of such movement. In aspects, the tactile indication is further accompanied by an audible indication of such movement. In aspects, modification of the airflow control mechanism from any first airflow setting to any second airflow setting is accompanied by one of two differentiable tactile indicators of such a modification. In aspects, one of the two differentiable tactile indicators accompanying the modification of the airflow control mechanism from a first airflow setting to a second airflow setting is only experienced once in a 360-degree rotation of a first airflow control component relative to a second airflow control component. In aspects, the tactile indication of the status of the airflow control mechanism being completely closed is differentiable from the tactile indication received upon movement between any first airflow setting and any other second airflow setting where the second airflow setting does not place the status of the airflow control mechanism in a completely closed position. In aspects, this differentiable tactile indication, audible indication, or both, is experienced only once in a 360-degree rotation of a first airflow control component relative to a second airflow control component. In aspects, the tactile indicator, audible indicator, or both, are clicking indicators.

In aspects, a detectably different, e.g., distinguishable audible indication, tactile indication, or both can indicate that the device is in a maximally closed state. In certain aspects, two distinguishable audible indications, e.g., a "large click" and a "small click", can differ from one another by at least about 1 decibel, such as, e.g., at least about 2 decibels, ~3, ~4, ~5, ~6, ~7, ~8, ~9, or, e.g., at least about 10 decibels. In certain aspects, two distinguishable audible indications can differ from one another by between about 1 decibel and about 80 decibels, such as, e.g., between ~1 decibel-~70 decibels, ~1 decibel-~60 decibels, ~1 decibel-~50 decibels, ~1 decibel-~40 decibels, ~1 decibel-~30 decibels, ~1 decibel-~20 decibels, or, e.g., ~1 decibel-~100 decibels, such as, e.g., ~5 decibels-~80 decibels, ~10 decibels-~80 decibels, ~20 decibels-~80 decibels, ~30 decibels-~80 decibels, ~40 decibels-~80 decibels, ~50 decibels-~80 decibels, ~60 decibels-~80 decibels, or, e.g., ~70 decibels-~80 decibels, as in, e.g., between about 5 decibels-about 70 decibels, or, e.g., about 10-about 60 decibels. In aspects, a maximally closed configuration of the inhalation device is indicated by a larger indicator (e.g., an indicator having a greater magnitude, such as an audible indicator having a distinguishably higher decibel value) than that of any other airflow control setting. In aspects, such distinguishable indication(s) is only received once in a 360-degree rotation of a first airflow control component relative to a second airflow control component (e.g., Body Plug relative to a Barrel Plug), or, e.g., once in a 360-degree rotation of a first primary component relative to a second primary component. As stated elsewhere, this operational status can also be accompanied by, e.g., a visual indication of such status (e.g., as indicated by the spatial orientation between two visual indicators).

In aspects, the tactile indication, the audible indication, or both, of the modification of the airflow control mechanism is derived from the changing degree of contact between the first airflow control component and the second airflow control component as the first and second airflow control components are rotated in relation to one another. In aspects, the degree of contact between the first and second airflow control components is reduced between any first and second airflow control setting compared to the amount of contact between the first airflow control component and the second airflow control component in any first airflow control setting or second airflow control setting. This can occur, e.g., as the two components detectably separate from one another as they are rotated in relation to one another. In aspects, separation occurs by the alternating interface of components on each of the first and second airflow control components which do not mate, nest, or otherwise interface to the same degree as other component son each of the first and second airflow control components. For example, in embodiments wherein each of a first and second airflow control component comprise alternating peaks/ridges and recessions, when peak(s) of each of the first and second airflow control component interface, the two components are pushed apart and their degree of interface decreases. When peaks(s) of one airflow control component interface with recession(s) of the other airflow control component, the two components are brought closer together and their degree of interface increases. This alternating separation and reunification can yield a tactile indication, an audible indication, or both. In aspects, a distinguishably different tactile indicator, audible indicator, or both is received when a single, unique (relative to other) elements of each of the first and second airflow control components meet during a rotation, causing, e.g., a larger separation of the two components.

In aspects, the tactile indications, audible indications, or both, provided by the inhalation device, e.g., provided by the airflow control mechanism of the inhalation device, or, e.g., provided by, e.g., the changing interface between the Body Plug and the Barrel Plug, might be described as snaps or clicks. The exact sound and exact tactile sensation can change, e.g., according to the materials making up the components participating in the sound (e.g., the material(s) of which the first airflow component, e.g., Body Plug, and second airflow component, e.g., Barrel Plug, are at least substantially composed).

According to aspects, the airflow control mechanism is adjustable via a gradual mechanism, such that, e.g., airflow control can be adjusted over a continuous gradient. In alternative aspects, the airflow control mechanism is not adjustable via a gradual mechanism, e.g., cannot be adjusted over a continuous gradient.

In aspects, the airflow control mechanism is adjustable in pre-defined increments. In aspects, each pre-defined incremental adjustment of the airflow control mechanism provides a pre-determined increase or pre-determined decrease in airflow through the device or, e.g., increased or decreases the amount, volume, rate, or any combination thereof, of airflow passing through the device upon inhalation by a pre-determined amount.

In aspects, the airflow control mechanism provided herein is adjustable in pre-defined increments, such as, e.g., at least about 3, ≥4, ≥5, ≥6, ≥7, ≥8, ≥9, ≥10, ≥11, ≥12, ≥13, ≥14, ≥15, ≥16, ≥17, ≥18, ≥19, ≥20, ≥21, ≥22, ≥23, ≥24, ≥25, ≥26, ≥27, ≥28, ≥29, or, e.g., ≥30 or more, such as, e.g., ~3-~30, ~3-~25, ~3-~20, or ~3-~15, e.g., ~5-~30, ~10-~30, or ~15-~30, such as, e.g., ~4-~28, ~6-~24, ~8-~20, or, e.g., ~10-~18 pre-defined increments.

In certain aspects, the airflow control mechanism decreases or increases the average airflow rate through the device by between about 0.01-about 1 standard liter(s) per minute (SLPM), on average, per each single airflow control setting defined adjustment increment, such as, e.g., ~0.02 SLPM-~1 SLPM, ~0.04 SLPM-~1 SLPM, ~0.06 SLPM-~1 SLPM, ~0.08 SLPM-~1 SLPM, ~0.1 SLPM-~1 SLPM, ~0.12 SLPM-~1 SLPM, ~0.14 SLPM-~1 SLPM, ~0.16 SLPM-~1 SLPM, ~0.18 SLPM-~1 SLPM, or ~0.2 SLPM-~1 SLPM, e.g., ~0.01 SLPM-~0.9 SLPM, ~0.01 SLPM-~0.8 SLPM, ~0.01 SLPM-~0.7 SLPM, ~0.01 SLPM-~0.6 SLPM, ~0.01 SLPM-~0.5 SLPM, ~0.01 SLPM-~0.4 SLPM, ~0.01 SLPM-~0.3 SLPM, or ~0.01 SLPM-~0.2 SLPM, as in, for example, ~0.02 SLPM-~0.9 SLPM, ~0.04 SLPM-~0.8 SLPM, ~0.06 SLPM-~0.7 SLPM, ~0.08 SLPM-~0.6 SLPM, ~0.08 SLPM-~0.5 SLPM, ~0.1 SLPM-~0.4 SLPM, ~0.12 SLPM-~0.4 SLPM, ~0.14 SLPM-~0.4 SLPM, ~0.16 SLPM-~0.4 SLPM, ~0.18 SLPM-~0.3 SLPM, or, e.g., ~0.2 SLPM, on average, per each single airflow control setting adjustment increment. In aspects, such values represent an exemplary device user, e.g., an average device user. In aspects, such rates can vary based upon inhalation characteristics of a user (e.g., speed and depth of inhalation). In aspects, the flow rate through the device is at least generally, at least substantially, at least essentially, is essentially, or is linear across a series of sequential airflow control settings. In aspects, such airflow control settings can be characterized by their aperture angle (e.g., angle of one or more airflow device control components or elements thereof). In aspects, the flow rate through the device is decreased in an at least generally, at least substantially, at least essentially, essentially, or completely linear manner as a user incrementally adjusts the airflow control mechanism from a first, completely open, state to a second, completely closed state. In aspects, the flow rate through the device is increased in an at least generally, at least substantially, at least essentially, essentially, or completely linear manner as a user incrementally adjusts the airflow control mechanism from a first, completely closed, state to a second, completely open state. In aspects, such a pattern is present for an average user or, e.g., any user of the device. In aspects, while the specific average flow rate through the device may vary from user to user across specific airflow control settings, the average pattern of average airflow flow rate through the device, e.g., increasing or decreasing in an at least generally, at least substantially, at least essentially, essentially, or completely linear pattern, is observed across at least generally all, at least substantially all, at least essentially all, essentially all, or all inhalation device users. In aspects, plotting airflow device control mechanism aperture angle vs. inhalation airflow rate in SLPM yields a line having an R-squared value of at least about 0.7, such as, e.g., at least about 0.75, at least about 0.8, at least about 0.85, at least about 0.9, or, e.g., at least about 0.95.

In aspects, the average airflow rate through an inhalation device, e.g., either increased or decreased depending on how the airflow control mechanism is manipulated, by an amount of between about 1% and about 20% with each single airflow control setting adjustment. That is, in aspects, with each incremental increase or incremental decrease of the airflow control setting, the average airflow rate is increased or decreased by ~2%-~20%, ~3%-~20%, ~4%-~20%, ~5%-~20%, ~6%-~20%, ~7%-~20%, ~8%-~20%, ~9%-~20%, or, e.g., ~10%-~20%, e.g., ~1%-~19%, ~1%-~18%, ~1%-~17%, ~1%-~16%, ~1%-~15%, ~1%-~14%, ~1%-~13%, ~1%-~12%, ~1%-~11%, or, e.g., ~1%-~10%, such as, for example, ~2%-~19%, ~3%-~18%, ~4%-~17%, ~5%-~16%, ~6%-~15%, ~7%-~14%, ~8%-~13%, ~9%-~12%, or, e.g., ~10%-~12%, such as, e.g., by about 11%.

In aspects, with each single airflow control setting incremental adjustment, the average airflow rate is modified, e.g., either increased or decreased, by an amount representing between about 1% and about 10% (on average) of the average maximum airflow rate through the device when the airflow control mechanism is in a maximally open configuration. That is, in aspects, with each single airflow control setting incremental adjustment, the average airflow rate is either increased or decreased (depending on how the airflow control mechanism is manipulated) by an amount representing ~1%-~9%, ~1%-~8%, ~1%-~7%, ~1%-~6%, or, e.g., ~1%-~5%, such as, e.g., ~2%-~10%, ~3%-~10%, ~4%-~10%, or ~5%-~10%, such as, for example, ~2%-~9%, ~3%-~8%, ~4%-~7%, ~4%-~6%, or, e.g., in aspects, by an amount of about 5% on average.

In another aspect, the airflow control mechanism decreases the average airflow through the device by between about 20% and about 100%, on average, when modified from its maximum airflow configuration (e.g., maximally open position) to its minimum airflow configuration (maximally closed position), such as, e.g., by ~20%-~98%, ~20%-~96%, ~20%-~94%, ~20%-~92%, ~20%-~90%, ~20%-~88%, ~20%-~86%, or ~20%-~84%, e.g., ~25%-~100%, ~30%-~100%, ~35%-~100%, ~40%-~100%, ~45%-~100%, ~50%-~100%, ~55%-~100%, ~60%-~100%, ~65%-~100%, ~70%-~100%, ~75%-~100%, ~80%-~100%, or ~85%-~100%, such as, e.g., ~25%-~98%, ~30%-~96%, ~40%-~94%, ~45%-~92%, ~50%-~90%, ~55%-~90%, ~60%-~90%, ~70%-~90%, ~80%-~90%, ~82%-~88%, ~82%-~86%, or, e.g., by about 84%.

In aspects, airflow customization provides for an inhalation device user to modify the amount of one or more compounds received upon inhalation. In aspects, over the course of use of a single removable insert, e.g., core insert, as the amount of compound(s) available from the insert decreases, the airflow control mechanism provided by the airflow control mechanism can be adjusted. In aspects, such adjustment can provide for an at least generally consistent amount of compound being delivered over at least portion of the lifespan of the, e.g., removable insert (e.g., Core), such as, e.g., in aspects over the course of a majority of the lifespan of the removable insert (e.g., Core) insert if the insert is disposable (one-time use) or e.g., over the course of a single charge with or fill of compound(s) of an insert if such an insert is reusable.

In one specific aspect, the invention provides an inhalation device wherein the inhalation device comprises a first primary component, e.g., Body Assembly, and a second primary component, e.g., Tip Assembly, rotatable in relation to one another, wherein each of the first and second primary components having at least a portion visible on the exterior of the device, wherein the device further comprises an airflow control mechanism and further wherein the status of the airflow control mechanism (e.g., degree to which the device is open to airflow therethrough) is indicated by (a) the positioning of one or more visual indicators present on the first primary component of the device when interpreted in relationship to the positioning of one or more visual indicators on the second primary component of the device, (b) a tactile indication when the first component of the device and the second component of the device are rotated relative to one another, or (c) both (a) and (b).

In this and other component, function, or operational aspect(s) of the invention, the invention also can be characterized as comprising a "means" for controlling airflow through an inhalation device. In such a respect, any known equivalents of such airflow control mechanisms can also be, e.g., are, incorporated into devices or methods of the invention. As with other sections similarly described herein, any of the components of the invention can be, where suitable, described as means (e.g., the above-described airflow control mechanism can be described as airflow control means or means for controlling airflow).

Tactile/Audible Indicator—Airflow Control Mechanism

According to certain aspects, inhalation devices provided by the invention comprise an airflow control mechanism which is accompanied by a tactile indication associated with the modification of the airflow control and in aspects can indicate one or more settings of the airflow control mechanism. In aspects, a change between any first airflow control setting and any second airflow control setting is accompanied by a tactile indicator. Stated another way, in aspects, a change between any first airflow control setting and any second airflow control setting is accompanied by a tactile indication of such a change.

Many elements of tactile indication(s)/indicator(s) are described elsewhere herein, such as, e.g., in the detailed description of the figures and associated with the descriptions of the first and second airflow control components (see, e.g., the sections entitled, e.g., "Airflow Control First Component (Body Plug)," "Airflow Control Second Component (Barrel Plug)," and, e.g., the detailed description of figures herein). In certain aspects, one or more tactile indicators can be provided by any suitable mechanism capable of providing a tactilely detectably indication of a movement of at least two components relative to one another, such as, e.g., two components of an airflow control mechanism, such as, for example, a first airflow control component and a second airflow control component. In aspects, such a tactile indicator can be, e.g., generated by the changing interaction between two components interfacing with one another over the course of an at least 360-degree rotation in relation to one another; a single element on a first component interacting with or interfacing with a series of components on a second component (e.g., a flexible element, tab, or other suitable pointer interacting with a series of pegs or other suitable elements spaced apart over the course of 360 degrees), similar to a traditional game spinning wheel), a gear mechanism comprising two or more interfacing gears capable of providing, designed to provide, or which provide a tactile indication when a tooth of one gear interfaces with a space between teeth of a second gear, or other similar or suitable mechanism.

In specific embodiments, e.g., the degree of interface between (a) an airflow control second component, e.g., Barrel Plug, such as, e.g., specific features of such a component such as, e.g., a fan-like feature comprising alternating ridges/recessions, and (b) an airflow control first component, e.g., Body Plug, such as, e.g., specific features of such a component such as, e.g., a fan-like feature comprising alternating ridges/recessions, is established by the rotation of a first device primary component, e.g., a Body Assembly (201), comprising a first airflow control component, e.g., Body Plug which can comprise, e.g., a Body Plug fan feature and associated alternating ridges/recessions, relative to a Tip Assembly (202), comprising a second airflow control component, e.g., Barrel Plug which can comprise a fan feature and associated alternating ridges/recessions. In aspects, because the first and second primary components of the device, (e.g., Body Assembly and Tip Assembly) can be releasably engaged with one another via a selectively releasable engagement mechanism, e.g., a rapidly releasable connection mechanism, e.g., a magnetic force, in a fully assembled exemplary device, the alternating ridges/recessions of a fan-like feature of a first airflow control component, e.g., Body Plug fan ridge/recession set can be drawn to the alternating ridges/recessions of a fa-like feature of a second airflow control component, e.g., Barrel Plug fan ridge/recession set by virtue of the fact that each of such components reside in the first and second primary components, respectively, which are releasably engaged by, e.g., magnetic force. In aspects, when a first airflow control component, e.g., a Body Plug, e.g., one or more features of a Body Plug such as, e.g., alternating ridges/recessions of a fan feature, are rotated in relation to a second airflow control component, e.g., a Barrel plug, e.g., one or more features of a Barrel Plug such as, e.g., alternating ridges/recessions of a fan feature, there are positions in which one or more first airflow control component, e.g., Body Plug features, e.g., fan ridge recession(s)) are positioned around or on one or more second airflow control, e.g., Barrel Plug features, e.g., fan ridge peak(s). In such aspects, such a positioning provides a fit between the two components wherein the two components are as physically close to one another as they can be. In aspects there are further positions during such rotation in which one or more first airflow control component features, e.g., Body Plug fan-like feature recession(s) are positioned in line with one or more second airflow control component, e.g., Barrel Plug features, e.g., fan-like feature recession(s). In aspects, similarly or simultaneously, one or more first airflow control component, e.g., Body Plug features, e.g., fan-like ridge peak(s) are positioned in line with one or more second airflow control component, e.g., Barrel Plug fan ridge peak(s). In such position(s), there is a poor fit between the two components and the two components are not as physically close to one another as they could be. In such a position, the device is somewhat unstable, and the magnetic force drawing the first primary component, e.g., Body Assembly, and the second primary component, e.g., Tip Assembly together can act upon the two separated components. In aspects, the force acts to pull the two components together such that the fan-like feature ridge peak(s) of one airflow control component fit within the fan-like feature ridge recession(s) of the other airflow control component, and vice versa. Accordingly, when a user rotates the second primary component, e.g., Tip Assembly, in relation to the first primary component, e.g., Body Assembly, the two components slightly separate from one another as the components of the fan-like feature ridge sets of the first and second airflow control components alternatingly "fit" together and alternatingly "do not fit" together, e.g., "misalign" (in terms of fit). Shifting from a position of non-fit to a position of fit, an e.g., a first airflow control component, e.g., Body Plug, and a second airflow control component, e.g., Barrel Plug "snap", or "click," back together (e.g., are pulled back together by the magnetic force of the device) as the rotation continues. Thus, rotation of a second primary device component, e.g., Tip Assembly, relative to a first primary component, e.g., Body Assembly, (or vice versa) can provide an audible clicking sound and, e.g., a tactile indication of the movement as features of each of the first and second airflow control components, e.g., ridges and recessions of each, interface with one another, e.g., ride over and about each other.

In this and other component, function, or operational aspect(s) of the invention, the invention also can be characterized as comprising a "means" for providing an audible, tactile, or audible and tactile indication of one or more device operational statuses, such as, e.g., the status of the airflow control mechanism (e.g., the degree to which the device is open to airflow therethrough; e.g., how "open" or how "closed" the device is.) In such a respect, any known equivalents of such named tactile or audible indicators can also be, e.g., are, incorporated into devices or methods of the invention. As with other sections similarly described herein, any of the components of the invention can be, where suitable, described as means (e.g., the above-described tactile/audible indicators can be described as tactile/audible indicator means or means for providing tactile and/or audible indication of one or more component operational statuses, e.g., the operational status of an airflow control mechanism).

Fidgetability

In aspects, inhalation devices herein provide a manually focused experience characterizable as a "fidget" experience, e.g., an entertainment experience or, e.g., an experience which alleviates a craving, negative mental state. This is described further below.

In aspects, manual manipulation of a device herein detectably or significantly reduces one or more non-inhalation smoking habit-related craving(s). In aspects, rotation of a first primary component of the device, e.g., a Body Assembly, relative to a second primary component, e.g., a Tip Assembly (or, e.g., vice versa—herein any described rotation of a first component relative to a second component should be interpreted as also referring to a rotation of the second component relative to the first component), provides a detectable audible, detectable tactile, or both detectable audible and detectable indication of such movement, such as, e.g., snapping or clicking sound(s). In aspects, selective disengagement and reengagement of first and second primary components of the device can provide, e.g., similar sound(s) or tactile sensations(s). This is described elsewhere herein. In aspects, such manipulation of the device provides a playful or toy-like nature to the device.

In aspects, rotation of a first primary component of the device, e.g., a Body Assembly, relative to a second primary component, e.g., a Tip Assembly, selective disengagement and reengagement of first and second primary components of the device (a) provides entertainment to a device user; (b) detectably or significantly increases the ability of a user to tolerate anxiety; (c) detectably or significantly increases the ability of a user to tolerate frustration; (d) detectably or significantly increases the ability of a user to tolerate agitation; (e) detectably or significantly increases the ability of a user to tolerate stress; (f) detectably or significantly increases the ability of a user to tolerate boredom; (g) detectably or significantly increases the ability of a user to tolerate excitement; (h) detectably or significantly increased the ability of a user to tolerate sensory challenges such as sensory overload or sensitivity to a particular sensory input, (i) detectably or significantly reduces a smoking-habit related craving (such as, e.g., to hold, manipulate, or smoke a cigarette, vaping device, etc.) or (i) any combination of any or all of (a)-(h).

Solid Material Device Maintaining/Releasing Compound(s) (Core)

In aspects, the invention provides a means of maintaining, delivering, or maintaining or delivering one or more volatile compounds for inhalation. In aspects, the invention provides a means of maintaining, delivering, or maintaining or delivering one or more volatile compounds for inhalation via an inhalation device such as an inhalation device described herein, e.g., a device having any one or more of the characteristics of inhalation device(s) described herein.

In aspects, the volatile compound delivery means (means of delivering volatile compound(s)) can be any means capable of maintaining, designed to maintain, or which maintain(s), e.g., until a suitable environment is presented for the release of one or more volatile compounds contained therein (then releasing when such a suitable environment is presented) one or more volatile compounds. In aspects, such a volatile compound deliver means can be, e.g., any suitable volatile compound delivery means known in the art, such as e.g., container, compartment, or other holding device capable of containing a liquid; a fibrous component capable of holding within its structure a fluid containing one or more volatile compounds; an at least partially porous material capable of holding within its structure a fluid containing one or more volatile compounds, etc. In aspects the means can be characterized as a spongy material. In aspects, the means can be characterized as an infusible material. In aspects the means can be an absorbent material. In aspects, a fibrous material can be a synthetic or natural material, an organic or an inorganic material, capable of holding a fluid or a solid such as an oil, liquid, gas, or powder. In aspects a fibrous material can comprise woven fibers, non-woven fibers, or both. In aspects, the fibrous material can comprise an organic mousse having open cells. In aspects, a fibrous material can be a natural pulp, cotton, vegetable sponge, or spongy wood. In aspects, the fibrous material serves as a volatile substance support allowing for the retention, preservation, and release of volatile compound(s). In aspects, a porous material can also serve as a volatile substance support, allowing for the retention, preservation, and release of volatile compound(s). In aspects, a porous material can be a semi-solid or solid material. In aspects, a porous material can be a synthetic or natural material, an organic or an inorganic porous material, capable of holding or designed to hold a fluid or a solid such as an oil, liquid, gas, or powder. In certain aspects, a fibrous material can be a cellulose-based material, an acetate material, or a polyester material, such as, e.g., a medical grade polyester material. In aspects a porous material can be a ceramic material, such as, e.g., an alumina ceramic or a zirconia ceramic. In aspects, a removable insert is characterizable as at least partially solid, at least mostly solid, or solid material device which can comprise or incorporate any solid material described above, such as, e.g., a fibrous material, a ceramic material, etc. In certain aspects herein, use of the word "solid" in reference to a solid material device for maintaining, releasing, delivering, etc. one or more volatile compound(s) can be interpreted to incorporate, e.g., a more flexible or porous device, such as, e.g., a fibrous device and can be interpreted to further incorporate a more semi-solid or solid material device, such as, e.g., a ceramic device.

In aspects, a means of maintaining, delivering, or maintaining and delivering one or more volatile compounds is capable of being inserted or is designed suitably for insertion into and removed from an inhalation device. In aspects, the means is characterizable as a removable insert. In aspects, the means is embodied as a Core. In aspects, the means of maintaining, delivering, or maintaining and delivering one or more volatile compounds (volatile compound delivery means) is a removable insert having any one or more of the characteristics of a Core described in the figures or the detailed description of figures provided herein.

In aspects, the invention provides a removable insert which is fibrous. In aspects, the fibrous removable insert is made of a polyester material, such as, e.g., a medical grade polyester. In aspects, the removable insert is a semi-solid or solid material. In aspects, a semi-solid or solid material is at least partially porous. In aspects, the porous material is a ceramic material. In aspects, the ceramic is an alumina ceramic, a zirconia ceramic, or a combination thereof.

In certain aspects, the removable insert is an insert suitable for use in, e.g., capable of being used in, or, e.g., which can be used in conjunction with (is compatible with), an electronic inhalation device. In aspects, the removable insert is an insert suitable for use in, e.g., capable of being used in, or, e.g., which can be used in conjunction with (is compatible with), an inhalation device comprising a heating mechanism. In aspects, the removable insert is an insert suitable for use in, e.g., capable of being used in or, e.g., which can be used in conjunction with (is compatible with), a device which does not comprise an electronic component, does not comprise a heating component, or does not comprise either an electronic component or a heating component.

In certain aspects, the removable insert is a disposable insert. In aspects, the removable insert is designed for a single use (which may comprise a plurality of uses or inhalations via an inhalation device), after which the removable insert is discarded. In aspects, with respect to a removable insert, a "single use" can be, e.g., a use of the removable insert until an insufficient amount of volatile compounds are released during an inhalation via an inhalation device in which the removable insert is contained, such that the user is unsatisfied with the experience provided, e.g., is unsatisfied with the flavor experience provided by the removable insert. In aspects, such a single use can be a period of more than 1 hour, e.g., ≥~1 day, ≥~2 days, ≥~3 days, ≥~4 days, ≥~5 days, ≥~6 days, ≥~1 week, ≥~2 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, or ≥~6 months. In aspects, such a single use can be a number of inhalations via an inhalation device comprising the removable insert, such as, e.g., at least about 10 inhalations, ≥~20 inhalations, ≥~50 inhalations, ≥~100 inhalations, ≥~200 inhalations, ≥~300 inhalations, ≥~400 inhalations, ≥~500 inhalations, ≥~600 inhalations, ≥~700 inhalations, ≥~800 inhalations, ≥~900 inhalations, or, e.g., ≥~1000 inhalations.

In alternative aspects, the removable insert is a reusable insert. In aspects, the removable insert is designed to be refilled or recharged after a single use (which again can comprise a plurality of uses or inhalations via an inhalation device). In aspects, the removable insert can be refilled or recharged with one or more volatile compounds such as by, e.g., being exposed to an oil, e.g., an essential oil, comprising such one or more compounds. In aspects, exposure can occur while the removable insert is maintained with an inhalation device. In aspects, the exposure can occur while the removable insert is outside of an inhalation device.

In aspects, a removable insert, e.g., Core, maintains a suitable amount of one or more volatile compounds for use within an inhalation device for a period of time after manufacturing when stored in airtight packaging to allow the removable insert to be stored for a period of at least about 1 week after manufacturing and prior to use (e.g., prior to the opening of its packaging and placement into an inhalation device. In aspects, a removable insert can be stored in airtight packaging for a period of at least about 2 weeks, ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, or ≥~6 months, such as ≥~7 months, ≥~8 months, ≥~9 months, ≥~10 months, ≥~11 months, or even ≥~12 months.

In aspects, a removable insert is a solid material device comprising a first end, a second end, and an outer diameter, and wherein the solid material device comprises at least one non-circuitous passageway within its outer diameter between its first and second ends allowing the passage of air through the solid material device via the passageway. In aspects, a non-circuitous passageway is a passageway which a user can visibly see through. In aspects, the solid material device comprises ≥~2, ≥~3, ≥~4, ≥~5, ≥~6, ≥~7, ≥~8, ≥~9, or ≥~10 non-circuitous passageways within its outer diameter between its first and second ends, each of which allowing the passage of air therethrough. In aspects, a non-circuitous passageway is an at least generally, at least substantially, at least essentially, essentially, or is a direct passageway through the solid material device between its first and second ends.

In aspects, a non-circuitous passageway of a solid material device, or each non-circuitous passageway in embodiments where a plurality of non-circuitous passageways are present, detectably or significantly increases the surface area of the solid material device. In aspects, one or more non-circuitous passageways, alone or in combination with one or more other non-circuitous passageways, can increase the surface area of a solid material device by at least about 0.5%, ≥~1%, ≥~3%, ≥~5%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, or, e.g., by ≥~100% over that of a similar or the same solid material device lacking such non-circuitous passageway(s).

According to certain aspects, a solid material device comprises one or more passageways therethrough allowing for air to pass from a first end to a second end, e.g., from a distal end to a proximal end (e.g., the proximal end being nearest an inhalation device user's lip(s) when the solid material device is positioned within an inhalation device, wherein the one or more passageways are each circuitous. That is, in aspects, any passage of air through a solid material device is an indirect passageway, a passageway for which one cannot visibly through from a first end to a second way, or both.

In one aspect, the solid material device, e.g., removable insert, e.g., Core, comprises at least one non-circuitous passageway. In aspects, at least one of the at least one non-circuitous passageway(s) comprises a shape. In aspects, the shape of the passageway can be any shape. In aspects, the shape of the passageway is characterizable as a circular shape, a squircle, a multilobed (multi-petaled) flower shape, e.g., zygomorphic flower shape, or actinomorphic flower shape, or other geometrical shape, such as, e.g., a quadrilateral (e.g., square, rectangle) or other polygonal shape (e.g., a triangle, pentagon, hexagon, octagon, etc.), a star-like shape (having any number of points), etc. In aspects, the solid material device, e.g., removable insert, e.g., Core, comprises a plurality of non-circuitous passageways through the solid material device, wherein each of the plurality of non-circuitous passageways has at least generally the same, at least substantially the same, at least essentially the same, essentially the same, or the same cross-sectional shape. In alternative aspects, the solid material device, e.g., removable insert, e.g., Core, comprises a plurality of non-circuitous passageways through the solid material device, wherein at least one of the plurality of non-circuitous passageways has a shape which is detectably or significantly different than at least one other non-circuitous passageway.

According to certain embodiments, the solid material device, e.g., removable insert, e.g., Core has a length of between about 10 mm and about 50 mm, such as, e.g., ~15 mm-~50 mm, ~20 mm-~50 mm, ~25 mm-~50 mm, or ~30 mm-~50 mm, e.g., ~10 mm-~50 mm, ~10 mm-~45 mm, ~10 mm-~40 mm, ~10 mm-~35 mm, or ~10 mm-~30 mm, such as, for example, ~15 mm-~45 mm, ~20 mm-~40 mm, ~25 mm-~35 mm, or, e.g., about 30 mm or about 35 mm.

In aspects, the solid material device, e.g., removable insert, e.g., Core, comprises a shape having a first end and a second end, the shape characterizable as a cylinder, triangular prism, rectangular prism (cuboid), pentagonal prism, hexagonal prism, octagonal prism, or other multi-sided prism. In aspects, the solid material device, e.g., removable insert, e.g., Core has an at least generally, at least substantially, at least essentially, essentially, or has a cylindrical shape.

According to certain embodiments, the solid material device, e.g., removable insert, e.g., Core has a diameter, or widest width if non-cylindrical, of between about 2 mm and about 10 mm, such as, e.g., ~3 mm-~10 mm, ~4 mm-~10 mm, ~5 mm-~10 mm, or ~6 mm-~10 mm, e.g., ~2 mm-~9 mm, ~2 mm-~8 mm, ~2 mm-~7 mm, or ~2 mm-~6 mm, such as, for example, ~3 mm-~9 mm, ~4 mm-~8 mm, ~5 mm-~7 mm, or, e.g., about 6 mm or about 7 mm.

In certain aspects, the solid material device, e.g., removable insert, e.g., Core has a widest diameter, (e.g., thickness) which is detectably or significantly less than the depth of a removable insert housing component in which it is maintained in an inhalation device during operation of the device with the removable insert present.

According to one aspect, the invention provides a solid material device, e.g., a removable insert, e.g., a Core, having a length defined by a distance between a first end of the removable insert and a second end of the removable insert, wherein the removable insert is capable of resisting, is designed to resist, or resists a detectable or significant bending across its length when a force of between about 10 g to about 500 g is applied to one end or, e.g., to both ends of the removable insert, such as, e.g., when a force of ~20 g-~500 g, ~40 g-~500 g, ~60 g-~500 g, ~80 g-~500 g, ~100 g-~500 g, ~120 g-~500 g, ~140 g-~500 g, ~160 g-~500 g, ~180 g-~500 g, ~200 g-~500 g, ~220 g-~500 g, ~240 g-~500 g, ~260 g-~500 g, ~280 g-~500 g, or ~300 g-~500 g is applied to one or both ends of the removable insert, e.g., ~10 g-~480 g, ~10 g-~460 g, ~10 g-~440 g, ~10 g-~420 g, ~10 g-~400 g, ~10 g-~380 g, ~10 g-~360 g, ~10 g-~340 g, ~10 g-~320 g, or ~10 g-~300 g, such as, for example, ~20 g-~480 g, ~40 g-~460 g, ~60 g-~440 g, ~80 g-~420 g, ~100 g-~400 g, ~120 g-~380 g, ~140 g-~360 g, ~160 g-~340 g, ~180 g-~320 g, e.g., ~200 g, ~220 g, ~240 g, ~260 g, ~280 g, ~300 g, ~320 g, ~340 g, ~350 g, or ~360 g is applied to one end, of the removable insert or is applied to both ends of the removable insert.

In one aspect, the solid material device, e.g., removable insert, e.g., Core, when a force of about 50 g is applied to one or both ends of the removable insert, defines a minor arc subtending an angle of no less than about 170 degrees, as in, e.g., defines a minor arc subtending an angle of no less than ~171 degrees, ~172 degrees, ~173 degrees, ~174 degrees, ~175 degrees, ~176 degrees, ~177 degrees, ~178 degrees, ~179 degrees, or, e.g., no less than about 180 degrees.

According to certain aspects, the solid material device, e.g., removable insert, e.g., Core, is maintained stably in position within a removable insert housing component, e.g., internal compartment, e.g., Body Tube, of an inhalation device described herein (e.g., within a removable insert housing component, e.g., internal compartment, e.g., Body Tube, having any one or more of the characteristics of such a component described herein). In one aspect, the solid material device, e.g., removable insert, e.g., Core, is stably maintained within such a removable insert housing component, e.g., internal compartment, e.g., Body Tube, within an inhalation device described herein, when the inhalation device comprising the removable insert is dropped from a distance of between about 1" to about 10", or, e.g., when the device is dropped from a distance of between about 1" to about 20", between about 1" to about 30", between about 1" to about 40", between about 1" to about 50", between about 1" to about 60", or, e.g., when the device is dropped from a distance of 60" or more. In aspects, the solid material device, e.g., removable insert, e.g., Core, is stably maintained within a removable insert housing component, e.g., internal compartment, e.g., Body Tube, within an inhalation device described herein, such that when the component maintaining the removable insert is exposed to the outside environment, the insert is stably maintained within the component when the container is rotated 360 degrees in any direction. In aspects, a solid material device, e.g., removable insert, e.g., Core, can be removed or dislodged from a removable insert housing component, e.g., internal compartment, e.g., Body Tube, of an inhalation device using a finger access point (e.g., Finger Recess) or by tapping the device on a surface with sufficient force to dislodge the insert.

According to certain aspects, a solid material device, e.g., removable insert, e.g., Core, requires a pull force of between about −0.02 N–about −2 N, such as, e.g., ~−0.04 N to ~−2N, ~−0.06 N to ~−2N, ~−0.08 N to ~−2N, ~−0.1 N to ~−2N, ~−0.12 N to ~−2N, ~−0.14 N to ~−2N, ~−0.16 N to ~−2N, ~−0.18 N to ~−2N, or ~−0.2 N to ~−2N, e.g., ~−0.02 N to ~−1.8N, ~−0.02 N to ~−1.6N, ~−0.02 N to ~−1.4N, ~−0.02 N to ~−1.2N, ~−0.02 N to ~−1 N, or ~−0.02 N to ~−0.5 N, e.g., ~−0.04 N to ~−1.8N, ~−0.06 N to ~−1.6N, ~−0.08 N to ~−1.4N, ~−0.1 N to ~−1.2N, or, e.g., ~−0.12 N to ~−1 N, e.g., ~−0.02 N–~−0.5N to remove the removable element from the compartment.

In one specific exemplary embodiment, the invention provides a passive inhalation device for the inhalation of one or more volatile compounds, the device comprising at least a first primary component, a second primary component, and an airflow control mechanism, the first primary component comprising a storage compartment for maintaining a removable insert, e.g., a solid material device capable of maintaining, releasing, or maintaining and releasing one or more volatile compounds.

In this and other component, function, or operational aspect(s) of the invention, the invention also can be characterized as comprising a "means" for maintaining, delivering, or maintaining and delivering one or more volatile compounds. In such a respect, any known equivalents of such named volatile compound delivery components can also be, e.g., are, incorporated into devices or methods of the invention. As with other sections similarly described herein, any of the components of the invention can be, where suitable, described as means (e.g., the above-described components (e.g., devices or elements) for maintaining, delivering, or maintaining and delivering one or more volatile compounds via inhalation can be described as volatile compound delivery means or solid material device means or means for providing one or more volatile compounds to an inhalation delivery device for the delivery of the one or more volatile compounds to the inhalation delivery device user via inhalation).

Volatile Compounds

In aspects, one or more volatile compounds provided by an inhalation device, solid material device (e.g., removable insert, or Core), or, e.g., both, is/are directed to a health condition, such as, e.g., are delivered for the purpose of treating one or more conditions or states of a patient. Such a condition or state can be, e.g., a state of elevated anxiety, stress, or other similar discomfort. In aspects, such a condition can be a condition related to a craving, such as a condition of craving a cigarette or other tobacco product or nicotine product. In aspects, such a condition can be a condition related to a craving to use an electronic vaping device. In other aspects, one or more volatile compounds provided by an inhalation device, solid material device (e.g., removable insert, or Core), or, e.g., both, is/are directed to pure enjoyment or pleasure, such as, e.g., a taste experience.

In aspects, one or more volatile compound(s) is a pharmaceutically active drug compound. In other aspects, one or more volatile compound(s) is not a pharmaceutically active drug compound. In aspects, one or more volatile compound(s) is a botanical compound. In aspects, one, more, or all volatile compound(s) are compounds not characterizable as a nicotinic compound. In aspects, one, more, or all volatile compounds are compounds not characterizable as a tobacco-related compound. In aspects, the one or more volatile compounds is a volatile compound safe for mammalian inhalation.

In certain aspects, the one or more volatile compounds is/are volatile compounds maintained within a fluid. In aspects, the one or more volatile compound(s) are maintained within a gas. In aspects, the one or more volatile compound(s) are maintained within a liquid. In aspects, the one or more volatile compound(s) are maintained within a solution, suspension, dispersion, or other fluid. In aspects, the one or more volatile compound(s) are maintained within an oil. In aspects, the oil is maintained within a solid material device (e.g., a fibrous solid material device or, e.g., a ceramic solid material device), e.g., removable insert, e.g., Core, until released and becoming available for inhalation.

According to certain aspects, the invention provides a solid material device, e.g., removable insert, e.g., Core, comprising one or more volatile compounds, the solid material device being designed for use within an inhalation device for delivering the one or more volatile compounds, wherein the one or more volatile compounds are derived from one or more botanicals or are provided as an oil (e.g., essential oil) comprising an extract from botanicals belonging to, e.g., the botanical family Lamiaceae, e.g., *Mentha piperita* (peppermint), *Mentha spicata* (spearmint), *Lavandula* (lavender), *Salvia rosmarinus* (rosemary), *Origanum vulgare* (oregano), *Thymus vulgaris* (thyme), etc.; the botanical family Piperaceas, e.g., *Piper nigrum* (black pepper); the botanical family Myrtaceae, e.g., *Eucalyptus*

*radiata* (eucalyptus), *Eucalyptus globulus* (eucalyptus), *Syzygium aromaticum* (clove), *Melaleuca alternifolia* (tea tree); the botanical family Rutaceae, e.g., *Citrus limon* (lemon), *Citrus sinensis* (orange), *Aurantifolia* (lime) (or, e.g., *Citrus aurantifolia, Citrus latifolia, Citrus glauca*, and *Citrus hystrix*), *Citrus paradisi* (grapefruit), *Citrus bergamia* (bergamot orange); the botanical family Annonacca, e.g., *Cananga adorate* (ylang-ylang); the botanical family Lauraceae, e.g., *Cinnamomum verum* (cinnamon), *Ocotea quixos* (Ocotea or Ishpingo); the botanical family Myristicaceae, e.g., *Myristica fragrans* (nutmeg); the botanical family Pine, e.g., *Cedrus* (cedarwood), *Picea mariana* (black spruce); the botanical family Fabaceae, e.g., Genus *Copaifera* (copaiba); the botanical family Orchidaceae, e.g., *Vanilla planifolia* (vanilla); the botanical family Poaceae, e.g., *Cymbopogon* species (including, e.g., lemongrass); the botanical family Malvaceae, e.g., *Theobroma cacao* (cocoa); the botanical family Ericaceae, e.g., *Vaccinium macrocarpon* (cranberry); the botanical family Asteraceae, e.g., *Artemisia pallens* (davana); the botanical family Cupressaceae, e.g., *Juniperus communis* (juniper), *Cupressus* (cypress); the botanical family Burseraceae, e.g., *Boswellia sacra* (frankincense); and, e.g., the botanical family Geraniaceae, e.g., *Pelargonium graveolens* (geranium), etc.; or other such botanicals or mixes of botanicals known in the art or oils of botanicals (e.g., essential oils) known in the art, e.g., Anshen essential oil (mixture of lavender, sweet orange, sandalwood, frankincense, orange blossom, rose, and agarwood essential oil), jasmine essential oil, Hinoki cypress (*Chamaecyparis* obtuse) leaf oil, ginger essential oil, cardamom essential oil, or oils extracted from any one or more of the following plants (some of which may be repetitively provided as members of botanical families above): *Anthemis nobilis, Foeniculum vulgare, Hyssopus officinalis, Matricaria recutita, Melissa officinalis, Myrtus communis, Ocimum basilicum, Pogostemon cablin, Rosa damascena, Salvia sclarea, Santalum album*, or a combination of, e.g., 2 or more, 3 or more, 4 or more, 5 or more, 6 or more, 7 or more, 8 or more, 9 or more, or, e.g., 10 or more of thereof. In certain aspects, the one or more volatile compounds provided for inhalation which may be derived from or provided by a source listed above or otherwise known in the art is a compound which is safe for human inhalation.

Means for Performing/Accomplishing Function(s)

In aspects, devices provided by the invention comprise one or more means for performing or accomplishing one or more specific functions. In general, any element described herein as a "means" for performing a function can also, wherever suitable, serve as a "step for" performing a function in the context of methods of the invention, and vice versa. E.g., a component or mechanism described herein as a means for releasably connecting a first and second device component also simultaneously and implicitly supports a method of making such a device comprising such a component or mechanism, or, e.g., a device comprising, e.g., a means of maintaining a removable solid material insert stably in position within an inhalation device implicitly and simultaneously provides a step for, e.g., a method of using the inhalation device wherein a removable solid material insert is stably maintained in position within the inhalation device comprising the use of such removable insert (or insert) stabilization means.

In one aspect, inhalation devices provided by the invention comprise providing selectively releasable engagement, e.g., rapidly releasable engagement, of a first device component and a second device component, such means for releasable engagement providing rapid releasability of the two components ("selective releasable engagement means" or "means for selective engagement"). Support for means for selective engagement can be found in, e.g., the sections entitled, "Selective Releasable Engagement," "Selectively Releasable Engagement Mechanism (Magnet)," and, e.g., "Selectively Releasable Engagement Mechanism (Barrel Collar)."

In one aspect, inhalation devices provided by the invention comprise facilitating the inhalation of one or more volatile compounds ("inhalation facilitation means" or "means for inhalation facilitation"). Support for means for inhalation facilitation can be found in, e.g., the section entitled, "Inhalation Facilitation Component (Mouthpiece)."

In one aspect, inhalation devices provided by the invention comprise a component facilitating the protection of an inhalation facilitation component from undue wear ("inhalation facilitation component protection means" or "means for protecting the inhalation facilitation component"). Support for means for protecting the inhalation facilitation component can be found in, e.g., the section entitled, "Inhalation Facilitation Component Supplement (Mouthpiece Tube)" and, e.g., in the section entitled, "Inhalation Facilitation Component Attachment Insert (Mouthpiece Attachment Insert)."

In one aspect, inhalation devices provided by the invention comprise a component for holding, housing or otherwise stably maintaining a means for maintaining, releasing, or maintaining and releasing one or more volatile compounds, e.g., a removable insert/Core ("removable insert housing means" or "means for housing a removable insert"). Support for means for housing a removable insert can be found in, e.g., the section entitled, "Removable Insert Housing Component (Body Tube)."

In one aspect, inhalation devices provided by the invention comprise a component for stably maintaining or stabilizing a means for maintaining, releasing, or maintaining and releasing one or more volatile compounds, e.g., a removable insert/Core ("insert stabilization means," "removable insert stabilization means," or "means for stabilizing a removable insert/Core"). Support for means for stabilizing a removable insert/Core can be found in, e.g., the section entitled, "Compressible Element (Core Spring)."

In one aspect, inhalation devices provided by the invention comprise one or more components for controlling airflow through an inhalation device ("airflow control means" or "means for airflow control"). Support for means for airflow control can be found in, e.g., the sections entitled, "Airflow Control First Component (Body Plug)," "Airflow Control Second Component (Barrel Plug)," and, e.g., "Airflow Control Mechanism."

In one aspect, inhalation devices provided by the invention comprise a component for housing one or more inhalation device components required for suitable inhalation device operation or function while providing an aesthetically pleasing inhalation device appearance ("outer shell means" or "means of providing an outer shell"). Support for means of providing an outer shell can be found in, e.g., the section entitled, "Outer Shell (Barrel)."

In one aspect, inhalation devices provided by the invention comprise a component facilitating the protection of an outer shell component from undue wear or volatile compound contamination ("outer shell protection means" or "means for protecting an outer shell"). Support for means for protecting an outer shell can be found in, e.g., the section entitled, "Outer Shell Protection Mechanism (Barrel Tube)."

In one aspect, inhalation devices provided by the invention comprise visual indicators indicating the spatial orientation of one or more device components or indicating the operational status of an airflow control mechanism or other operational mechanism ("visual indicator means" or "means for visual indicator(s)"). Support for means for visual indicator(s) can be found in, e.g., the section entitled, "Visual Indicators."

In one aspect, inhalation devices provided by the invention comprise tactile, audible, or tactile and audible indicator(s) indicating the status of one or more operational characteristics of the inhalation device, e.g., the operational status of an airflow control component ("tactile/audible indicator means" or "means for providing tactile/audible indicator(s)"). Support for means for providing tactile/audible indicator(s) can be found in, e.g., the sections entitled, "Airflow Control First Component (Body Plug)," "Airflow Control Second Component (Barrel Plug)," and, e.g., "Airflow Control Mechanism" and its subsection, "Tactile/Audible Indicator—Airflow Control Mechanism."

In one aspect, inhalation devices provided by the invention utilize a removable component capable of maintaining, delivering, or maintaining and delivering one or more volatile compounds for inhalation, e.g., for inhalation via an inhalation device ("volatile compound delivery means" or "means for delivering volatile compound(s)"). Support for means for delivering volatile compound(s) can be found in, e.g., the section entitled, "Solid Material Device Maintaining/Releasing Volatile Compound(s) (Core)."

Washability/Durability

In aspects, inhalation device(s) described herein and components thereof are made of sufficiently durable materials so as render the device(s) reusable, such as, e.g., the devices can be used 2 or more times, ~10 or more times, ~50 or more times, ~100 or more times, ~250 or more times, ~500 or more times, or ~1000 or more times, such as, e.g., over a period of at least about 1 day, ~1 week, ~1 month, ~1 year, ~2 years, ~3 years, ~4 years, ~5 years, or, e.g., ~10 years or longer. In aspects, inhalation device(s) described herein and components thereof are made of sufficiently durable materials so as to be capable of sustaining a drop onto a hard surface from a distance of about 3 inches, ~6 inches, ~1 foot, ~18 inches, ~2 feet, ~30 inches, ~3 feet, ~4 feet, ~6 feet, ~8 feet, ~10 feet, ~12 feet, ~14 feet, ~16 feet, ~18 feet, or, e.g., ~20 feet or more without suffering damage which renders the device(s) inoperable (e.g., the device(s) remain fully operable).

According to aspects, one or more components of inhalation device(s) provided by the invention are made of a material which is washable. Therefore, in aspects, one benefit of the devices herein is the ability to maintain hygienic use of such device(s) over time. In aspects, for example, a device mouthpiece may be capable of being washed. In aspects, one or more components of inhalation device(s) described herein can be washed with typical dishwashing detergent(s), dishwashing liquid(s), soap(s), including antibacterial soap(s), common sanitizers comprising alcohols (e.g., ethanol (ethyl alcohol) or isopropyl alcohol (isopropanol or 2-propanol)), etc. In aspects, one or more components of inhalation device(s) herein can tolerate exposure to or submersion in liquid(s) such as water having a temperature typical of washing materials for sanitary purposes, such as, e.g., water at a temperature of about 50 degrees Celsius (° C.) to about 200° C., such as, e.g., ~60° C.-~200° C., ~70° C.-~200° C., ~80° C.-~200° C., ~90° C.-~200° C., ~100° C.-~200° C., ~110° C.-~200° C., ~120° C.-~200° C., such as, e.g., ~50° C.-~190° C., ~50° C.-~180° C., ~50° C.-~170° ° C., ~50° C.-~160° C., ~50° C.-~150° C., ~50° C.-~140° C., ~50° C.-~130° C., ~50° C.-~120° C., ~50° C.-~110° ° C., or, e.g., ~50° C.-~100° C., as in, for example, water having a temperature of between about ~120° C.-~180° C., which may be typical of water temperatures present in a common household dishwashing machine. Thus, in aspects, one or more components of device(s) herein may be washed in a common household dishwashing machine.

System

In aspects, the invention provides a system for providing one or more volatile compounds to a user, the system comprising an inhalation device and one or more solid material device(s) for maintaining/releasing compound(s) (Core(s)) which is/are compatible for use within the inhalation device. In aspects, the inhalation device can be any inhalation device described herein, e.g., an inhalation device comprising one or more characteristics of the inhalation device(s) described herein, such as, e.g., an inhalation device described under the broad section entitled, "Inhalation Device." In aspects, the solid material device can be any solid material device described herein capable of maintaining, releasing, or maintaining and releasing one or more volatile compounds for inhalation and which is compatible with an inhalation device provided therewith, such as, e.g., a solid material insert characterizable as a removable insert (e.g., an insert which can be selectively inserted into and removed from, e.g., repeatedly inserted into and removed from, an inhalation device, such as, e.g., a Core. In aspects, the solid material device is any solid material device described herein, e.g., a solid material device, e.g., removable insert, e.g., Core comprising one or more characteristics of such component/devices described herein, such as, e.g., a solid material device for maintaining/releasing compound(s) described within the section entitled, "Solid Material Device Maintaining/Releasing Compound(s) (Core)."

In one specific aspect, the invention provides a non-electronic, non-heating inhalation device system for the delivery of one or more volatile compounds by inhalation, the device system comprising (a) a non-electronic, non-heating inhalation device and (b) a solid material device, e.g., removable insert, e.g., Core, designed to be removably maintained therein, wherein the non-electronic, non-heating inhalation device comprises a first primary component and a second primary component releasably bound to one another by a selectively releasable force mechanism, e.g., a rapidly releasable force mechanism, e.g., a magnetic force, such that the first primary component and second primary component can be completely disengaged from one another or, alternatively, can be securely bound to one another, the inhalation device further comprising an adjustable airflow control mechanism controlled by the rotation of the first primary component and the second primary component relative to one another, and the solid material device, e.g., removable insert, is designed to maintain, release, or maintain and release the one or more volatile compounds for inhalation.

In another specific aspect, the invention provides a non-electronic, non-heating inhalation device system for the delivery of one or more volatile compounds by inhalation, the device system comprising a non-electronic, non-heating inhalation device and a solid material device, e.g., removable insert, e.g., Core, capable of being or designed to be inserted therein, the solid material device, e.g., removable insert, e.g., Core, capable of maintaining, releasing, or maintaining and releasing the one or more volatile compounds for inhalation, wherein, in use, (a) at least about one quarter (¼), e.g., ≥~½, ≥~¾, or, e.g., the entirety of, of the solid material device's, e.g., the removable insert's, e.g., the Core's, longest dimension is engaged with a first primary component of the non-electronic, non-heating inhalation device, and (b) the entirety of the solid material insert, e.g., removable insert, e.g. Core, is positioned within a second primary component of the non-electronic, non-heating inhalation device, and wherein the first and second primary components of the non-electronic, non-heating inhalation device are selectively dis-engageable, e.g., rapidly releasable, from one another.

In another specific aspect, the invention provides a non-electronic, non-heating inhalation device system for the delivery of one or more volatile compounds by inhalation, the device system comprising a non-electronic, non-heating inhalation device and a solid material device, e.g., a removable insert, e.g., a Core, capable of maintaining, releasing, or maintaining and releasing one or more volatile compounds, wherein the solid material device, e.g., removable insert, e.g., Core, comprises a first end, a second end, and at least one non-circuitous passageway passing through the solid material device from its first end to its second end.

In another specific aspect, the invention provides a non-electronic, non-heating inhalation device system for the delivery of one or more volatile compounds by inhalation, the device system comprising a non-electronic, non-heating inhalation device comprising a first primary component and a second primary component capable of rotating, designed to rotate or which rotate relative to one another and a removable solid material device capable of maintaining, releasing, or maintaining and releasing the one or more volatile compounds for inhalation, wherein the non-electronic, non-heating inhalation device comprises an airflow control mechanism adjustable in discrete increments by the rotation of the first primary component and the second primary component of the non-electronic, non-heating inhalation device in relation to one another.

Kit

In aspects, the invention provides a kit comprising an inhalation device capable of providing, designed to provide, or which provides one or more volatile compounds to an inhalation device user, such an inhalation device being any inhalation device described herein or having characteristic(s) of inhalation device(s) described herein, and one or more of the solid material device(s), e.g., removable insert(s), e.g., Core(s), capable of maintaining, releasing, or maintaining and releasing one or more volatile compounds described herein. In aspects, such a kit provides two or more such solid material devices, e.g., removable inserts, e.g., Cores, such as ≥~3, ≥~4, ≥~5, ≥~6, ≥~7, ≥~8, ≥~9, or ≥~10.

In certain aspects, within a kit comprising an inhalation device and two or more solid material devices, e.g., removable inserts, e.g., Cores, all solid material devices, e.g., removable inserts, e.g., Cores, of the kit comprise at least generally the same, at least substantially the same, at least essentially the same, essentially the same, or the same one or more volatile compounds. In aspects, within a kit comprising an inhalation device and two or more solid material devices, e.g., removable inserts, e.g., Cores, at least one of the solid material devices, e.g., removable inserts, e.g., Cores, of the kit comprise one or more volatile compounds which is detectably or significantly different from, e.g., which is at least at least generally different than, at least substantially different than, or is different from at least one other of the solid material devices, e.g., removable inserts, e.g., Cores.

In certain aspects, the invention provides a kit comprising two or more solid material device(s), e.g., removable insert(s), e.g., Core(s), capable of maintaining, releasing, or maintaining and releasing one or more volatile compounds described herein. In aspects, such a kit provides two or more such solid material devices, e.g., removable inserts, e.g., Cores, such as ≥~3, ≥~4, ≥~5, ≥~6, ≥~7, ≥~8, ≥~9, or ≥~10 such solid material devices. In aspects, a kit provides more than 10 solid material devices, e.g., removable inserts, e.g., Cores. In aspects, the kit is provided as an airtight package containing the plurality of solid material devices, e.g., removable inserts, e.g., Cores. In aspects the solid material device(s). e.g., removable insert(s), e.g., Cores of a kit are compatible for use within an inhalation device described herein, or, in aspects, e.g., having any one or more characteristics of the inhalation device described herein.

In certain aspects, within a kit comprising two or more solid material devices, e.g., removable inserts, e.g., Cores, all solid material devices, e.g., removable inserts, e.g., Cores, of the kit comprise at least generally the same, at least substantially the same, at least essentially the same, essentially the same, or the same one or more volatile compounds. In aspects, within a kit comprising an inhalation device and two or more solid material devices, e.g., removable inserts, e.g., Cores, at least one of the solid material devices, e.g., removable inserts, e.g., Cores, of the kit comprise one or more volatile compounds which is detectably or significantly different from, e.g., which is at least at least generally different than, at least substantially different than, or is different from at least one other of the solid material devices, e.g., removable inserts, e.g., Cores.

Methods

In aspects, the invention provides a method of using any one or more of the inhalation devices herein to detectably or significantly reduce a smoking habit-related craving in an individual as assessed (e.g., measured or reported) by the individual, as measured by an appropriately conducted and powered trial or survey administered or conducted by suitably trained individual(s) recognized as capable of identifying reduction in addiction-related behavior (as exemplified elsewhere herein), or both. In aspects, the inhalation device is a passive inhalation device. In aspects, the inhalation device is a non-heating inhalation device. In aspects, the inhalation device is a non-electronic inhalation device. In aspects, the inhalation device comprises heating component(s). In aspects, the inhalation device comprises electronic component(s).

In aspects, the individual is a human having previously routinely, e.g., at least once per week, ≥~2×/week, ≥~3×/week, ≥~5×/week, ≥~7×/week, ≥~2×/day, ≥~3×/day, ≥~4×/day, ≥~5×/day, ≥~6×/day, ≥~7×/day, ≥~8×/day, ≥~9×/day, ≥~10×/day, ≥~12×/day, ≥~14×/day, ≥~16×/day, ≥~18×/day, ≥~20×/day participated in a smoking habit, e.g., a tobacco-smoking-related habit, a nicotine consumption habit, a vaping habit, an e-cigarette habit, or any combination of any or all thereof, such as, e.g., for a period of a least about 1 month, ≥~2 months, ≥~3 months, ≥~6 months, ≥~9 months, ≥~12 months, ≥~18 months, ≥~24 months, ≥~30 months, ≥~36 months or more of their life. In aspects, such an individual is characterizable as having or previously suffering from an addition to a smoking habit, e.g., a tobacco-smoking-related habit, a nicotine consumption habit, a vaping habit, an e-cigarette habit, or any combination of any or all thereof. Herein, a smoking habit can comprise a habit related to any one or more of inhalation-related or manual-manipulation-related rituals associated with, e.g., tobacco-smoking, nicotine consumption, vaping, e-cigarette smoking, or, e.g., any combination thereof. Herein a smoking-habit related craving can be, e.g., as is described elsewhere herein, an oral craving, e.g., having something in their mouth, inhaling one or more compounds, e.g., inhaling a flavored inhalant, holding an object, e.g., a device to their lips, feeling the device on or between their lips, or similar such oral-fixation-related craving. In aspects a smoking-habit related craving can be a manual manipulation-related craving, such as, e.g., holding an object, e.g. device, in their hand, e.g., between two or more fingers, playing with a device with their hand(s) or fingers(s), e.g., such play characterizable as fondling, or, e.g., fidgeting, keeping their hands and or fingers occupied with such an object or device, or similar such oral-fixation-related craving.

Method of Reducing a Smoking Habit-Related Craving

According to one aspect, the invention provides a method of reducing a drug or non-drug smoking habit-related craving (e.g., a smoking habit-related craving not associated with an addiction to a drug, e.g., nicotine, such as, e.g., a craving related to the habit of holding or otherwise manually manipulating a smoking device, or, e.g., a drug addiction related habit, such as, e.g., a craving for nicotine) in an individual. In aspects, the method comprises the individual (a) holding an inhalation device described herein within their hand, between their fingers, between their lips, or any combination thereof, (b) repeatedly, e.g., at least about 2 times, rotating the first primary component of the device in relation to the second primary component of the device in any direction or combination of directions, (c) repeatedly, e.g., at least about two times, separating and allowing reattachment of the first primary device component and the second primary device component relative to one another, (d) inhaling one or more volatile compounds by placing the inhalation device to their lips or into their mouth and inhaling one or more volatile compounds available within the inhalation device by inhaling through the inhalation device, or (e) any combination of (a)-(e). In aspects, the method is applied for a sufficient period of time, or, e.g., is applied over a sufficient period of time, such that the individual experiences a detectable or significant decrease in the smoking habit-related craving as assessed by the individual, a suitably trained individual recognized as capable of identifying reduction in addiction-related behavior, or both. In certain aspects, the method is provided under the guidance of a suitably trained individual recognized as capable of identifying reduction in addiction-related behavior, such that the method comprises instructing the individual on how to conduct one or more steps of the method.

In aspects, the method is applied for a sufficient period of time, or, e.g., is applied over a sufficient period of time, such that the individual (e.g., inhalation device user) experiences a detectable or significant decrease in the smoking habit-related craving as assessed by the individual, a suitably trained individual recognized as capable of identifying reduction in addiction-related behavior, or both. In certain aspects, the method is provided under the guidance of a suitably trained individual recognized as capable of identi-fying reduction in addiction-related behavior, such that the method comprises instructing the individual on how to conduct one or more steps of the method.

In aspects, a sufficient period of time is a period of time such as, e.g. at least about 15 seconds, ~30 seconds, ~1 minute, ~2 minutes (mins), ~3 mins, ~4 mins, ~5 mins, ~10 mins, ~15 mins, ~30 mins, ~45 mins, ~1 hour, ~5 hours (hrs), ~10 hrs, ~15 hrs, ~20 hrs, or, e.g., ~24 hrs. In aspects, a sufficient period of time is a period of time greater than about 24 hours, such as, e.g., at least about 2 days, ~3 days, ~4 days, ~5 days, ~6 days, ~1 week, ~2 weeks, ~1 month, ~1.5 months, ~2 months, ~2.5 months, ~3 months, ~3.5 months, ~4 months, ~4.5 months, ~5 months, ~5.5 months, or at least about ~6 months. In aspects, a sufficient period of time is a period of time greater than about 6 months, such as, e.g., at least about 7 months, ~8 months, ~9 months, ~10 months, ~11 months, or at least about 12 months or longer. In aspects, a sufficient period of time is any amount of time required for the individual to experience a detectable or significant decrease in the smoking habit-related craving as assessed by the individual or, e.g., as assessed by a suitably trained individual recognized as capable of identifying reduction in addiction-related behavior.

In one aspect, the invention provides method(s) of detect-ably or significantly reducing a smoking habit-related craving in an individual (as assessed (e.g., measured or reported) by the individual, as measured by an appropriately con-ducted and powered trial or survey administered or con-ducted by suitably trained individual(s) recognized as capable of identifying reduction in addiction-related behav-ior, or both) by the individual inhaling via their mouth at least a partial breath inhalation through the passive inhala-tion device such that at least a detectable amount of volatile compounds available within the inhalation device (e.g., which may be provided by, e.g., a solid material device, e.g., a removable insert, e.g., a Core, therein) is delivered. In aspects, the at least partial inhalation can be repeated for as many times as needed (e.g., about 1 or more times, ≥~2 or more times, or, e.g., ≥~4, ≥~6, ≥~8, ≥~10, ≥~12, ≥~14, ≥~16, ≥~18, ≥~20, ≥~22, ≥~24, ≥~26, ≥~28, or, e.g., ≥~30 or more times) until the individual achieves a detectably, significant, or otherwise perceived or reportable reduction in the smoking habit-related craving. In certain specific aspects, such a number of inhalations is completed with a confined period of time, such as, e.g., within a period of about 1 hour, ~55 min, ~50 min, ~45 min, ~40 min, ~35 min, ~30 min, ~25 min, such as, for example, within a period about 1 minute to about 20 minutes, e.g., within a period of ~1-~18 min, ~1-~16 min, ~1-~14 min, ~1-~12 min, or ~1-~10 min, e.g., ~2 min-~20 min, ~4 min-~20 min, ~6 min-~20 min, ~8 min-~20 min, ~10 min-~20 min, such as, e.g., ~2 min-~18 min, ~4 min-~16 min, ~6 min-~14 min, or, e.g., ~8 min-~12 min.

Similar to above, according to aspects, the invention provides a method of reducing one or more smoking habit-related craving(s) in a significant number of individuals in an adequately powered population of individuals. In aspects, the method comprises providing to each individual in the population of individuals an inhalation device with or containing a removable insert, or, e.g., a system comprising an inhalation device and an insert. In aspects, each individual inhales via their mouth at least one partial or full breath through the inhalation device such that a detectable amount of volatile compounds maintained by the removable insert is delivered to each individual. In aspects, the method demonstrates a detectable or significant reduction in one or more smoking habit-related cravings in the population of individuals with a period of at least about 1 year, such as, e.g., within a period of about 12 months, ~11 months, ~10 months, ~9 months, ~8 months, ~7 months, ~6 months, ~5 months, ~4 months, ~3 months, ~2 months, or, e.g., within ~1 month, within ~3 weeks, within ~2 weeks, or, e.g., within a period of ~1 week.

In aspects, the device is used intermittently over periods of time described here, not, e.g., continuously (such as, for example, a user using the device at least about once per day or at least about once per week, such as, e.g., daily or multiple times per day.) In aspects, a sufficient period of time is a period of time is a period of time after or upon which the individual experiences a detectable or significant decrease in the non-drug, smoking habit related craving as assessed (e.g., measured or reported) by the individual, as measured by an appropriately conducted and powered trial or survey administered or conducted by suitably trained individual(s) recognized as capable of identifying reduction in addiction-related behavior, or both.

As provided elsewhere herein, in certain aspects, exemplary suitably trained individual(s) recognized as capable of identifying reduction in addiction-related behavior can be, e.g., addiction counselor(s), therapist(s), psychologist(s), medical physician(s), or other medical or non-medical personnel trained in identifying or suitably familiar with addiction related habit(s).

Method of Providing Volatile Compound(s) for Inhalation

In aspects, the invention provides a method of providing volatile compound(s) for inhalation to an individual. In aspects, the method comprises providing to the individual an inhalation device having any one or more of the characteristics described herein. In aspects, the individual is provided the device with one or more removable inserts having any one or more of the characteristics described herein. In aspects, the individual is provided a system comprising at least one inhalation device having any one or more of the characteristics described herein and at least one removable insert having any one or more of the characteristics described herein. In aspects, the method comprises the individual inhaling at least one partial or full breath through the inhalation device such that a detectable amount of volatile compound(s) maintained by the removable insert is delivered to the individual. In certain aspects, the method is provided under the guidance of a suitably trained individual recognized as capable of identifying reduction in addiction-related behavior, such that the method comprises instructing the individual on how to conduct one or more steps of the method.

Method of Providing an Olfactory Experience

In aspects, the invention provides a method of providing an olfactory experience to/for an individual. In aspects, the method comprises providing to the individual an inhalation device having any one or more of the characteristics described herein. In aspects, the individual is provided the device with one or more removable inserts having any one or more of the characteristics described herein. In aspects, the individual is provided a system comprising at least one inhalation device having any one or more of the characteristics described herein and at least one removable insert having any one or more of the characteristics described herein. In aspects, the method comprises the individual inhaling at least one partial or full breath through the inhalation device such that a detectable amount of volatile compound(s) maintained by the removable insert is delivered to the individual. In certain aspects, the method is provided under the guidance of a suitably trained individual recognized as capable of identifying reduction in addiction-related behavior, such that the method comprises instructing the individual on how to conduct one or more steps of the method. In aspects, the method is repeated for or over a sufficient period of time to provide the individual with a satisfactory olfactory experience as judged by the individual. In aspects, such a period of time can be any period of time required to satisfactorily deliver the olfactory experience, such as, e.g., a period of time of about 30 seconds, ~1 min, ~5 min, ~10 min, ~15 min, ~20 min, ~30 min, ~45 min, or, e.g., ~1 hour. In aspects, a sufficient period of time is longer than about 1 hour, such as, e.g., ~1.5 hours, ~2 hours, ~4 hours, ~6 hours, ~8 hours, ~10 hours, ~12 hours, ~14 hours, ~16 hours, ~18 hours, ~20 hours, ~22 hours, or, e.g., ~24 hours.

Method of Controlling Airflow

In aspects, the invention provides a method of controlling airflow in an inhalation device designed to deliver volatile compound(s) to a user of the inhalation device. In aspects, the method comprises moving at least two airflow control components, such at least two airflow control components having any one or more of the characteristics of the airflow control mechanism and components thereof described herein, of the inhalation device in relation to one another. In aspects, movement of the at least two airflow control components of the inhalation device relative to one another occurs only in pre-defined increments. In aspects, each movement of the two airflow control components relative to one another in a pre-defined increment provides a pre-determined increase or pre-determined decrease in airflow through the device. In aspects, the method also or alternatively comprises moving the at least two airflow control components of the inhalation device in relation to one another wherein, during normal operation of the device, at least two of the at least two airflow control components of the inhalation device are, selectively, completely separable from one another. Such functionality of airflow control components and the mechanism within which they function is described in detail elsewhere herein. In further aspects, the method also or alternatively comprises moving at least two airflow control components of the inhalation device in relation to one another, wherein movement of a first airflow control component relative to a second airflow control component comprises a rotational movement, and the rotational movement comprises movement capable of at an at least 360-degree rotation. Such functionality of airflow control components and the mechanism within which they function is described in detail elsewhere herein.

Method of Visually Identifying an Airflow Control Setting

In aspects, the invention provides a method of visually identifying an airflow control setting of an inhalation device designed to deliver volatile compound(s) to a user of the inhalation device. In aspects, the method comprises evaluating the positioning of at least one first visual indicator present on an external surface of the inhalation device. In aspects, the method comprises evaluating the positioning of at least one second visual indicator present on an external surface of the inhalation device. In aspects, the method comprises evaluating the positioning of at least one first visual indicator present on an external surface of the inhalation device relative to at least one second visual indicator present on an external surface of the inhalation device. In aspects, the relative positioning of one visual indicator to another indicates the status of the airflow control mechanism, such as, e.g., how open or how closed the airflow control mechanism of the device is (e.g., establishing an awareness for the user of the "drag" setting of the device). Such functionality of airflow control components and the mechanism within which they function, in combination with the use of visual indicators, is described in detail elsewhere herein.

Method of Determining the Spatial Positioning of an Internal Component

In aspects, the invention provides a method of determining the spatial positioning of an internal component, not externally visible, of an inhalation device designed to deliver volatile compound(s) to a user of the inhalation device. In aspects, the method comprises evaluating the positioning of at least one first visual indicator present on an external surface of the inhalation device. In aspects, the spatial positioning of at least one visual indicator indicates the spatial positioning of an otherwise externally invisible internal component, such as, e.g., in which direction certain features of such an internal component are facing, e.g., "upward" or, e.g., "downward." In aspect, the method establishes an awareness of the user of whether the device is in a desired or suitable position for conducting one or more activities, such as, e.g., separating a first primary component and a second primary component of the device to facilitate removal of a removable insert, e.g., Core. In aspects, knowing the orientation is helpful so as to reduce any risk of the removable insert, e.g., Core, falling out of the device upon separation of the first primary component from the second primary component. Such functionality of visual indicator(s), in combination with the spatial orientation of an internal, externally invisible device component, is described in detail elsewhere herein.

Method of Audibly or Tactily Determining Status of an Airflow Control Mechanism

In aspects, the invention provides a method of audibly determining the status of an airflow control setting of an inhalation device designed to deliver volatile compound(s) to a user of the inhalation device. In aspects, the invention provides a method of tactily determining the status of an airflow control setting of an inhalation device designed to deliver volatile compound(s) to a user of the inhalation device. "Tactily", as used here, means determining by receipt of a tactile indication. In aspects, the invention provides a method of audibly and tactily determining the status of an airflow control setting of an inhalation device designed to deliver volatile compound(s) to a user of the inhalation device. In aspects, the method(s) comprise moving at least two airflow control components of an inhalation device in relation to one another, such airflow control components being any airflow control components described herein. In aspects, movement of a first airflow control component relative to a second airflow control component is accompanied by an audible sound, a tactile indicator, or both. In aspects, an audible sound indicates to the user the status of the airflow control setting. In aspects, a tactile indicator indicates the status of the airflow control setting. In aspects, the combination of an audible indicator and a tactile indicator indicates the status of the airflow control setting. In aspects, particular audible sounds, particular tactile indications, or both provide an indication to the user of the airflow control setting. In aspects, particular airflow control settings provide a particular audible indication, a particular tactile indication, or both. Such audible and tactile indicators, relative to airflow control settings, are described in detail elsewhere herein.

In aspects, the invention provides such a method as disclosed in this section, wherein the inhalation device is provided with a solid material device, either individually or together, such as, e.g., as a system. In aspects, the inhalation device and a solid material device are provided as a kit. In aspects, any kit disclosed herein can be used in any method of reducing a smoking habit-related craving disclosed herein. In aspects, an inhalation device comprising any one or more characteristics of inhalation device(s) described herein are used in one or more of the methods described in this section. In aspects, a removable insert comprising any one or more characteristics of removable insert(s) described herein is used in one or more of the methods described in this section. In aspects, a system comprising any one or more of the characteristics of the system(s) described herein is used in one or more of the methods described in this section.

DETAILED DESCRIPTION OF THE DRAWINGS/FIGURES

The figures and following description of aspects of the invention provided in connection therewith are provided for the purpose of further illustrating examples of devices and related components of the invention and the operation thereof. Such embodiments provided should not be construed as limiting (e.g., figures/components may not be drawn to scale; an element may be provided primarily for illustrating operation; and several alternative embodiments are within the scope of the invention (as also described elsewhere herein).

FIGS. 1A, 1B, and 1C illustrate an exemplary device (100) provided by the invention. FIGS. 1A-1C illustrate a device when all components are assembled (e.g., the device is "fully assembled"). Within the "Detailed Description of the Drawings/Figures" section of this disclosure, discussion of the device in a "fully assembled" state references the device being in a configuration wherein all components of the device are assembled. This state of full assembly may or may not comprise a core insert. In one aspect, if the state of full assembly comprises a core insert, the device may be referred to as being in a "loaded ready-to-use" state. That is, in one aspect, herein, a "loaded ready-to-use" state is a state wherein the device is fully assembled and comprises a core insert. In an alternative aspect, if the state of full assembly does not comprise a core insert, the device may be referred to as an "unloaded ready-to-use" state, such that the device is ready for a user to insert a core insert therein.

FIG. 1A illustrates the fully assembled exemplary device (100) with the device slightly rotated to the right, so as to show a perspective wherein the opening in the body assembly (see FIG. 2A) is emphasized. FIG. 1A further illustrates a first indicator (101), here exemplified as a product logo. Such a first indicator (101) can be utilized in indicating the spatial orientation of one or more components of the device, one or more operational status(es) of the device, or both, as is described elsewhere herein. In aspects, such a first indicator (101) operates in conjunction with at least a second indicator to indicate the spatial orientation of one or more components of the device, one or more operational status(es) of the device, or both, again as is described elsewhere herein. In aspects, such a first indicator (101) operates in conjunction with at least a second indicator such as the second indicator shown in FIG. 1B (102).

FIG. 1B illustrates a straight-on side view of the fully assembled exemplary device (100). FIG. 1B further illustrates a second indicator (102), here exemplified as a groove made in an external/visible location on a device component. Such a second indicator (102) can be utilized in indicating the spatial orientation of one or more elements of the device, one or more operational status(es) of the device, or both, as is described elsewhere herein. In aspects, such a second indicator (102) operates in conjunction with at least a first indicator to indicate the spatial orientation of one or more elements of the device, one or more operational status(es) of the device, or both, as is described elsewhere herein. In aspects, such a second indicator (102) operates in conjunction with at least a first indicator such as the first indicator shown in FIG. 1A (101).

FIG. 1C illustrates the fully assembled exemplary device (100) with the device slightly rotated to the left, so as to show a perspective wherein the opening in the tip assembly (see FIG. 2B) is emphasized. In FIG. 1C, second visual indicator (102) is visible but first visual indicator (101) is not visible.

The fully assembled device of FIGS. 1A-1C illustrates that in its fully assembled state, the device is a single device with all components connected to form a single unit. Further, FIGS. 1A-1C illustrate that a plurality of indicators are visible on the external portion(s) of the fully assembled device which can, e.g., participate in establishing the spatial orientation of the device, one or more operational status(es) of the device, or both, as is described elsewhere herein.

FIGS. 2A, 2B, and 2C illustrate that at its highest level, a fully assembled device (100) is comprised of a body assembly (201), shown as the shaded element in FIG. 2A, and a tip assembly (202), shown as the shaded element in FIG. 2B. In the illustrated embodiment, the body assembly (201) connects with or attaches to the tip assembly (202) to form a fully assembled device (100). In aspects, the body assembly (201) is selectively engageable with the tip assembly (202) such that the two components can be repeatedly attached and disengaged (e.g., attached, disengaged, re-attached, disengaged, etc.) from one another. In aspects, as exemplified, the selective disengagement/re-engagement of the device provides a mechanism for providing the device with a core insert (e.g., (1800)) from a position other than the end of the device. That is, in aspects, the device can receive a core insert (e.g., (1800)) from a direction lateral to the device as opposed to receiving a core insert (e.g., (1800)) from a direction in line with the device, such as, e.g., inserted into one end of the device. In aspects, the selective disengagement/re-engagement of the device provides a mechanism for fidgeting with the device, providing the device with the ability to operate as a fidget tool/mechanism which, when in use, provides the user with a tool to help the user stay focused, stay attentive, reduce distraction, to increase level of attention, to reduce anxiety, to improve attitude, improve performance of one or more tasks, to induce calm, achieve a more relaxed state, achieve a contemplative state, achieve a mindful state, provide stimulation, improve personal/peer interaction, be entertained, or any combination of the above, or other outcomes of fidget devices known in the art.

In FIG. 2C, the tip assembly (202) is illustrated as being completely separated from the body assembly (201). Upon the complete separation of the tip assembly (202) from the body assembly (201), previously hidden component(s) of the body assembly (201) become visible. FIG. 2C, in view of FIGS. 2B and 2A, illustrates that when the body assembly (201) and the tip assembly (202) are in the fully assembled position, at least one component of the body assembly (201) resides within the tip assembly (202). This relationship is discussed further below. Further, when the body assembly (201) and the tip assembly (202) are in the fully assembled position, the tip assembly (202) and the body assembly are capable of being rotated in relation to one another. In aspects, the tip assembly (202) is capable of being rotated about at least one component of the tip assembly (201). Still further, upon such rotation of the body assembly (201) and the tip assembly (202) relative to one another, one or more visual indicators on the body assembly (201) and one or more visual indicators on the tip assembly (202) can change in orientation/positional relationship to one another. As the two components (body assembly (201) and tip assembly (202)) are rotated, a position may be reached where a visual indicator (e.g., visual indicator 101 of FIG. 1A) on the tip assembly can align with a visual indicator (e.g., visual indicator 202 of FIG. 2B) on the body assembly. In certain aspects, such an alignment can provide an indication of the spatial orientation of one or more components of the device, an indication of one or more operational status(es) of the device, or both. As the two components are further rotated, a position may be reached where a visual indicator (e.g., visual indicator 101 of FIG. 1A) on the tip assembly can be opposite or stated in another way can be 180 degrees from, a visual indicator (e.g., visual indicator 202 of FIG. 2B) on the body assembly. In certain aspects, such an orientation can provide an indication of the spatial orientation of one or more components of the device, an indication of one or more operational status(es) of the device, or both. In aspects, information related to spatial orientation of one or more components of the device, one or more operational status(es) of the device, or both may be identified by any relative positioning of one or more, e.g., two or more visual indicators.

FIGS. 3A, 3B, 3C, and 3D illustrate the complete assembly of the body assembly (201). FIG. 3A illustrates a view of the complete assembly of the body assembly (201) with the tip assembly removed. Thus, FIG. 3A does not represent a fully assembled device, but only a fully assembled single component of the device (the body assembly).

FIGS. 3A-3D illustrate that at its highest level, the body assembly (201) (see FIG. 3A) comprises at least two components; an inhalation facilitation component embodied as a mouthpiece (301), identified by shading in FIG. 3B, and a body subassembly (302) identified by shading in FIG. 3C. The body subassembly (302) is shown again in FIG. 3D, therein shown with the mouthpiece (301) of FIG. 2B removed, and with body subassembly (302) rotated such that other features of the body assembly (201) are visible. Components and features of the body assembly (201) are described in FIGS. 3B-3D, FIGS. 4A-4C, FIGS. 5A-5G, FIGS. 6A and 6B, FIG. 7, FIGS. 8A and 8B, FIGS. 9A and 9B, FIGS. 10A and 10B, FIGS. 11A and 11B, and FIGS. 12A and 12B herein. FIGS. 3A-3C illustrate that when fully assembled, the body assembly comprises a mouthpiece (301) which is attached to a body subassembly (302). In aspects, such components are not capable of being unattached by the user; that is, the body subassembly of the device in usable form is provided to the user as a single component, wherein the subcomponents of the body assembly are non dis-engageable from one another by a user or do not require disengagement in order for the user to use the device. In alternative aspects, two or more components of the body assembly, e.g., the mouthpiece (301) and the body subassembly (302) are dis-engageable from one another. This can facilitate, e.g., the exchange of a mouthpiece, such as e.g., the exchange of a mouthpiece of one material (e.g., stainless steel) to a mouthpiece of a different material (e.g., gold, platinum, titanium, plastic(s), etc.), a mouthpiece having a first color to a mouthpiece having a second color, etc. Such embodiments providing interchangeability, e.g., mouthpiece interchangeability, are one aspect of the invention.

FIGS. 4A, 4B, and 4C illustrate the body assembly (201) with a specific focus on specific components of the body subassembly. FIGS. 4A-4C illustrate that body components of the body subassembly include a magnet cover (401) shown by shading in FIG. 4A; a body tube (402) shown by shading in FIG. 4B; and a body plug (506), shown by shading in FIG. 4C. FIGS. 4A-4C illustrate that when fully assembled, the body subassembly (e.g., the body subassembly (302) of FIGS. 3C and 3D) comprises a magnet cover (401), body tube (402), and body plug (506) attached to one another to form a single body subassembly unit, which is then further attached to the mouthpiece (e.g., (301) of FIG. 3B) to form the body assembly (e.g., the body assembly (201) of FIGS. 4A-4C). In aspects, components of the body subassembly (302) are attached to one another when the device is in a ready-to-use state. In aspects, components of the body subassembly (302) are not dis-engageable from one another by a user or do not require disengagement in order for the user to use the device. One or more components of body assembly (201) are not visible in FIGS. 4A-4C, such as, e.g., magnet (502), illustrated and described below.

FIGS. 5A-5G illustrate exemplary individual components of the body assembly (201). FIG. 5A shows an exploded view (all exploded views of Figures provided within brackets) of the body assembly (201) wherein the relative positioning of each component of the body assembly (201) is discernable. FIG. 5A shows the exploded set of components slightly turned to the right (top) and to the left (bottom) in order to show the various components in the exploded view(s) from different angles, thus providing additional visibility into each component's characteristics. FIGS. 5B-5G identify each of the components of the body assembly (201) shown in the exploded view of FIG. 5A. Like FIG. 5A, components identified in FIGS. 5B-5G may be shown slightly turned to the right (top) and to the left (bottom) in order to show the various components in the exploded view(s) from different angles, thus providing additional visibility into each component's characteristics. FIG. 5B identifies a mouthpiece (301) (shaded) component of the body assembly (201). FIG. 5C identifies a magnet (502) (shaded) component of the body assembly (201). FIG. 5D identifies a magnet cover (401) (shaded) component of the body assembly (201). FIG. 5E identifies a core spring (504) (shaded) component of the body assembly (201). FIG. 5F identifies a body tube (402) (shaded) component of the body assembly (201). Finally, FIG. 5G identifies a body plug (506) (shaded) component of the body assembly (201). In aspects, FIG. 5 illustrates that devices provided by the invention, or, e.g., a component of a device of the invention, such as a body assembly component of a device, can comprise a mouthpiece (301), magnet (502), magnet cover (401), core spring (504), body tube (402), and body plug. As stated previously, in aspects, one or more, two or more, three or more, four or more, five or more, or all components of the body subassembly (302) are attached to one another when the device is in a ready-to-use state. In aspects, components of the body subassembly (302) are not dis-engageable from one another by a user or do not require disengagement in order for the user to use the device.

FIGS. 2-5 (and the sub-figures thereof) provide illustrations of the body assembly, subcomponents thereof, and their positioning relative to one another. FIGS. 6-11 (and the sub-figures thereof) provide specific embodiments of each of the components described therein.

FIGS. 6A and 6B illustrate an exemplary mouthpiece (301) of a device (e.g., device (100) as shown in FIG. 1A) provided by the invention. A mouthpiece (301) is a component of the device which typically comes into contact with the user's mouth during use. Compound-laden air for inhalation exits the device during use via the mouthpiece (301) (e.g., upon inhalation ("pulling" or "sucking") on the device by the user). The exemplary mouthpiece comprises lip groove (601), finger groove (602), ornamental feature (603), and airflow channel (604).

FIG. 6A illustrates an exemplary mouthpiece (301). As shown in FIG. 6A, features of mouthpiece (301) include lip groove (601), finger groove (602), ornamental feature (603), and airflow channel (604). In FIG. 6A, the thickness or outer diameter of lip groove (601) is shown as being, at its most narrow point, about 50%-about 70% of the largest outer diameter of the device. Lip groove (601) as exemplified in FIG. 6A is about half of the length of the mouthpiece (301) (e.g., without considering the centrally located ornamental feature (603)). Lip groove (601) receives the user's lips while the device is in use and allows the device to comfortably sit within the user's mouth. Lip groove (601) receives the user's lips while the device is in use. The shape and size of lip groove (601) can, in aspects, aid in the comfort of the user during device use and the ability of the user to maintain the device easily and comfortably in the user's mouth.

Similarly, the thickness or outer diameter of finger groove (602) illustrated in FIG. 6A is shown as being, at its most narrow point, about 50%-about 70% of the largest outer diameter of the device. Finger groove (602) as exemplified in FIG. 6A is about half of the length of the mouthpiece (301) (e.g., without considering the centrally located ornamental feature (603)). Finger groove (602) can be used by the user to hold the device, e.g., by placing two fingers on either side of the device within finger groove (602), much like a traditional smoking device, e.g., a cigarette, is held between two fingers of a user when smoking the cigarette. It should be understood that use of finger groove (602) is not mandatory for the device to operate. Finger groove (602) is provided to support user experience of the device and to aid some users in experiencing use of the device much like the experience of smoking a cigarette, which may in aspects be beneficial to users attempting to quit or reduce a cigarette smoking habit. Positioning of finger groove (602) within mouthpiece (301), within the length of the device (e.g., (100) as shown in, for example, FIG. 1A), or both, can participate in the user experience of the device by being placed at, e.g., about the center of gravity for the device (100). In aspects, the device can be at least generally, at least substantially, at least essentially, is essentially, or is balanced at the position of the finger groove (602). In aspects, the device at least generally, at least substantially, at least essentially, is essentially, or can be balanced on a user's finger when the user places a single finger beneath the device (100) at the position of finger groove (602).

FIG. 6A illustrates mouthpiece (301) as comprising an ornamental feature (603) positioned between lip groove (601) and finger groove (602). In aspects, such an ornamental feature (603) can be absent from the device. In aspects, such an ornamental feature (603) can be provided to enhance the aesthetics of the device (e.g., device (100) as shown in FIG. 1A). The ornamental feature (603) shown in FIG. 6A is a groove in the mouthpiece (301), encircling the full circumference of the device. In aspects, the groove (ornamental feature (603)) is bounded on both sides by narrow, flat surfaces (e.g., flat surface bands) which also encircle the full circumference of the device. As exemplified, ornamental feature (603) separates lip groove (601) from finger groove (602). As exemplified, ornamental feature (603) provides spacing between lip groove (601) and finger groove (602). In aspects, the size, e.g., the width of ornamental feature (603) can be adjusted such that the positioning of lip groove (601), finger groove (602), or both are located in desired position(s). For example, a wider or narrower ornamental feature (603) may provide for the shifting of the finger groove (602) to the center of gravity of the device. As described above, this may improve upon the user's pleasurable or comfortable experience in using the device. (Notably, another mechanism for shifting the center of gravity of the device can be, e.g., lengthening or shortening the portion of mouthpiece (301) identifiable as the lip groove (601), lengthening or shortening the portion of mouthpiece (301) identifiable as finger groove (602), extending or decreasing the overall length of the device (e.g., extending or decreasing the overall length of one or more components of the device other than lip groove (601) or finger groove (602)), modifying (via either increasing or decreasing) the weight of one or more components of the device, redistributing the weight of one or more components of the device, etc., or any combination thereof.

Airflow channel (604) is shown in FIG. 6A as a circular chamber passing within the mouthpiece (301). The diameter of airflow channel (604) is shown in FIG. 6A as being greater than 50%, e.g., about 50%-about 70%, of the largest outer diameter of the device. FIG. 6B illustrates mouthpiece (301) cut in half (perspective shown in the small, top figure comprising the dashed section line; Roman numerals "I" and "II" aligning/orienting the views; arrows indicating line of sight) with the upper section removed, such that the interior of mouthpiece (301) is visible. As shown in FIG. 6B, airflow channel (604) passes through (within and across) the entire length of the mouthpiece (301), from the mouthpiece inlet (607B) to the mouthpiece outlet (607A). In some aspects, airflow channel (604) has a single diameter across its length within mouthpiece (301). As exemplified in FIG. 6B, airflow channel (604) can have one or more sections or locations where the diameter is detectably or significantly different from one or more other sections or locations of the airflow channel (604). In certain aspects, when viewed alone (e.g., as a separate component, unattached to any additional component of the device), the airflow channel (604) of the mouthpiece (301) can have one or more sections or locations where the diameter is detectably or significantly different from one or more other sections or locations of the airflow channel (604); however, when the mouthpiece (301) is joined with (e.g., attached to) one or more other components of the device (e.g., device (100) of FIG. 1A) —such as, e.g., one or more other components of the body assembly (e.g., body assembly (500) shown in FIG. 5A and further exemplified in FIGS. 5B-5G) —the airflow channel (604) is at least generally, at least substantially, at least essentially, is essentially, or is uniform in its diameter across the length of the mouthpiece. That is, in aspects, the diameter of the airflow channel (604) through the mouthpiece (301) can be defined by the mouthpiece (301) alone, one or more components of the body assembly other than the mouthpiece, e.g., one or more components of the body subassembly, or both.

FIG. 6B further illustrates that the shape characteristics of each end of mouthpiece (301) can vary from one another. Lip groove (601), ornamental feature (603), finger groove (602), and airflow channel (604) are each shown in FIG. 6B. As exemplified therein, mouthpiece (301) can have a first end (605), such a first end being closest to lip groove (601). As shown, such a first end (605) can be rounded, e.g., such that the plane forming the end of a first end (605) of mouthpiece (301) does not form a right angle with the side (e.g., outer surface) of the mouthpiece (301). Lack of such a right angle can, in aspects, provide increased comfort for the user in using the device. In aspects, such a first end (605) of mouthpiece (301) can be the end of mouthpiece (301) placed in the mouth of the user. In aspects, such a rounded surface (605) can improve upon the mouth feel of mouthpiece (301), e.g., by lacking sharp edges which may irritate the, e.g., lips or tongue of a user. As further exemplified in FIG. 6B, mouthpiece (301) can have a second end (606), such a second end being closest to finger groove (602). As shown, such a second end (606) can be flat, e.g., such that the plane forming the end of a second end (606) of mouthpiece (301) forms a right angle with the side (e.g., outer surface) of mouthpiece (301). Such a right angle can, in aspects, provide for an ease of fit with one or more other components of the device, such as, e.g., one or more components of a body assembly (e.g., (201) as shown in Figure, e.g., 5A) or, more specifically, one or more components of a body subassembly (e.g., (302) of FIGS. 3C and 3D). In certain aspects as exemplified by the Figures, a second end (606) of a mouthpiece (301) contacts a surface of a magnet (502), a magnet cover (401), or both a magnet (502) and a magnet cover (401) when the device is assembled (see, e.g., FIGS. 5B-5D), such a flat second end (606) of the mouthpiece abutting the surface(s) of the magnet (502), magnet cover (401), or both sufficiently to form a smooth transition on the outer surface of the device between the mouthpiece (301) and component(s) of the body subassembly (302) (e.g., of FIGS. 3C and 3D).

In certain aspects, a mouthpiece can be made of a material such that the mouthpiece can attach to one or more other components of a device (101), such as, e.g., one or more components of a body assembly (201). In aspects for example, a mouthpiece can be made of a material such as stainless steel or a precious metal such as gold, titanium, platinum, etc. In aspects, such a material can be strong enough in nature to support the mouthpiece comprising a connection mechanism, e.g., threading, to facilitate the attachment of mouthpiece (301) to, e.g., a component of a body assembly (201) comprising corresponding threading such that the two components attach by screw fitting. In other aspects, a mouthpiece can be made of a softer material, such as, e.g., a plastic or a porous material such as ceramic or wood. In such embodiments, such a material may be insufficient for supporting the attachment of the mouthpiece to one or more other components of the device (e.g., body assembly, (201)) such that a secure, stable fit is accomplished. In such embodiments, a mouthpiece (301) can comprise a mouthpiece fit element (608) capable of receiving a mouthpiece attachment insert (not provided) or can simply comprise mouthpiece attachment insert (not provided). In aspects, the mouthpiece attachment insert (not provided) can be made of a material having a sufficient hardness to facilitate, e.g., the attachment of the mouthpiece (301) to one or more other components of the device (101), such as, e.g., a component of a body assembly (201).

A mouthpiece (301) can comprise a mouthpiece fit element (608) capable of receiving a mouthpiece attachment insert (not provided) which aids in the attachment of the mouthpiece (301) to one or more other components of the device. In aspects, a mouthpiece (301) does not comprise a mouthpiece fit element (608). In aspects, a mouthpiece (301) not comprising a mouthpiece fit element (608) comprises a mouthpiece attachment insert (not provided). In aspects, a mouthpiece fit element (608) can facilitate the manufacturing of the device. In aspects, the mouthpiece fit element (608) can facilitate the mouthpiece being fitted with/to one or more other components of the device, such as, e.g., a first magnet cover connection mechanism (815). In certain aspects, the mouthpiece fit element (608) aids in the connection of mouthpiece (301) with one or more other components, e.g., a magnet cover (401), however once the mouthpiece is engaged with such another component, the connection is made permanent such that the two components are intended to remain engaged and the two components, (e.g., the mouthpiece (301) and the magnet cover (401) are not able to be disengaged by the user; or, more specifically, the mouthpiece fit element (608) is not able to be disengaged from the first magnet cover connection mechanism (815)). This can be accomplished, e.g., by the mouthpiece fit element (608) being, e.g., a threading component, first magnet cover connection mechanism (815) being a threading mechanism capable of receiving the mouthpiece fit element (608) (threading mechanism), and, e.g., the two being further glued together when engaged.

In alternative aspects, the presence of such a mouthpiece fit element (608) can facilitate the ability of the mouthpiece to be disengaged from one or more other elements of the device, or, e.g., the entirety of the remaining structure of the device. In aspects, the ability to remove mouthpiece (301) can provide user(s) of the device with the option to change the mouthpiece or to "swap"/exchange one mouthpiece for another. This can be helpful, e.g., if for example a mouthpiece were to become damaged, in that the remaining structure of the device could be salvaged while only requiring the replacement of the single mouthpiece component. Further, the ability to remove the mouthpiece can facilitate, e.g., the ability of the user to exchange one mouthpiece for another, such as, e.g., exchanging one mouthpiece for another having a one or more different design characteristics, one or more differences in aesthetic appearance, one or more different composition materials, etc.

Mouthpiece fit element (608) is exemplified in FIG. 6B as an element capable of operating alone, e.g., as a threading element, or, e.g., is capable of receiving a mouthpiece attachment insert (not provided) or a component/portion of an inhalation facilitation component supplement (610). As stated, mouthpiece fit element (608) can, in certain embodiments, be itself a threading mechanism capable of receiving a connection element of one or more other components of the device, such as, e.g., as a first magnet cover connection mechanism (815) when, e.g., provided as a compatible threading mechanism. Mouthpiece fit element (608) can comprise, when embodied as a threading mechanism, a sufficient number of threads to ensure suitable and sufficient attachment to the one or more other components of the device. As described elsewhere herein, such a connection between the mouthpiece (301) and one or more other components of the device (e.g., magnet cover (401)) can be provided in other forms, such as, e.g., a snap fit, a magnetic fit, etc. Accordingly, in aspects, mouthpiece fit element (608) can be a fit element capable of cooperating with one or more other compatible connection mechanisms of one or more other device components (e.g., a magnet cover (401)) to form a suitably secure connection, either permanent or providing releasable engagement, with such one or more other device components.

As exemplified in FIG. 6B, mouthpiece fit element (608) is provided as a feature of the body of mouthpiece (301); that is, mouthpiece fit element (608) is made of the same material as mouthpiece (301). However, in alternative embodiments (not shown), mouthpiece fit element (608) can be comprised of a material which is different from one or more other parts of the mouthpiece (301). As one example, in aspects, mouthpiece fit element (608) can be made of metal or, e.g., ceramic, e.g., provided as a metal or ceramic component, which can be, e.g., positioned within the mouthpiece (301) which can be made of, for example, wood. Further, mouthpiece fit element (608) can in aspects be capable of receiving, e.g., maintaining, one or more components of a device which is made of a material different than that of mouthpiece (301) and which is manufactured as a separate part of the device, but which is positioned in mouthpiece fit element (608) in a fully assembled device. Such a component is exemplified in FIG. 6C. According to certain embodiments, a device may not contain a mouthpiece fit element (608).

In certain aspects, a device can comprise an inhalation facilitation component supplement (610). FIG. 6C provides an exemplary inhalation facilitation component supplement (610). Inhalation facilitation component supplement (610), exemplified here, is made of a material different from that of mouthpiece (301). Inhalation facilitation component supplement (610) can comprise mouthpiece attachment insert attachment elements (not shown), E.g., an inhalation facilitation component supplement (610) can comprise a portion having a particular shape/conformation or a portion comprising attachment elements such as threading, etc. which facilitate the attachment of the inhalation facilitation component to one or more other components of the inhalation device. In aspects, attachment element(s) of an inhalation facilitation component supplement (610), can, e.g., operate as a mouthpiece attachment insert (not provided). Inhalation facilitation component supplement (610) can further comprise an inhalation facilitation component exterior wall (614), an inhalation facilitation component interior wall (616), and, e.g., an inhalation facilitation component opening (618).

Not shown in FIG. 6C, but provided as one embodiment, mouthpiece attachment insert attachment elements (not shown) can be provided as threads/threading along a portion of the inhalation facilitation component supplement (610), allowing for the inhalation facilitation component supplement (610) to cooperatively engage with another device component comprising compatible threading, such as, e.g., an element of magnet cover (401), or, e.g., more specifically first magnet cover connection mechanism (815) of, e.g., a magnet cover (401). In aspects, the inhalation facilitation component supplement (610) is fixed in position with mouthpiece (301). That is, in aspects, the inhalation facilitation component supplement (610) is not removable from mouthpiece (301) in a fully assembled device under normal use. In certain specific embodiments, the inhalation facilitation component supplement (610) and first magnet cover connection mechanism (815) are designed to work cooperatively together, e.g., by each comprising threading compatible with the other. In aspects, the inhalation facilitation component supplement (610) and first magnet cover connection mechanism (815) are engaged with one another in a fully assembled device. In aspects, the inhalation facilitation component supplement (610) and first magnet cover connection mechanism (815) are engaged with one another in a fully assembled device such that they are not separatable from one another under conditions of normal device use. In aspects, one or more additional connection mechanisms are used to join the two components in a permanent state under normal operating conditions. In aspects, such one or more additional connection mechanisms can be, e.g., the use of a glue in addition to the, e.g., compatible/cooperative threading connective elements present in each component. In alternative aspects, the inhalation facilitation component supplement (610) and first magnet cover connection mechanism (815) are selectively engaged with one another, such that they can be selectively engaged, disengaged, and re-engaged during device operation. As described above, such selectable engagement can, in aspects, provide opportunities for a device user to remove and replace a mouthpiece at the users will and discretion. In aspects, when such selectable engagement is present, when engaged, the engagement is sufficient to provide a suitably secure and sufficient connection between the inhalation facilitation component supplement (610) and the first magnet cover connection mechanism (815) to ensure that the two components do not detectably or significantly disengage from one another during normal operation, do not detectably or significantly disengage from one another unless intentionally made to do so by the user, do not disengage to an extent which renders the device unpleasant, uncomfortable, unstable, aesthetically or tactilely displeasing (e.g., renders the device "loose" fitting with regard to the fit between components of the body assembly (201)), dysfunctional, or any combination thereof.

Further, as exemplified in FIG. 6C, the inhalation facilitation component supplement (610) comprises an inhalation facilitation component supplement exterior wall (614). In aspects, the inhalation facilitation component supplement exterior wall (614) is designed to have at least a portion of its shape complementary in fit to the interior of the mouthpiece, e.g., to be contoured to the shape of airflow channel (604) within mouthpiece (301). In aspects, the inhalation facilitation component supplement exterior wall (614) is designed to have at least a portion of its shape complementary in fit to that of mouthpiece fit element (608). That is, in aspects, an inhalation facilitation component supplement exterior wall (614) is designed to have a shape which corresponds with that of mouthpiece fit element (608) such that mouthpiece attachment insert (610) can be positioned within mouthpiece fit element (608). In certain aspects, mouthpiece fit element (608) can be a smooth, non-contoured surface defining at least part of airflow channel (604) of mouthpiece (301). In aspects, an inhalation facilitation component supplement exterior wall (614) can be a smooth, non-contoured surface complementary to that of mouthpiece fit element (608), providing for the ability of the inhalation facilitation component supplement (610) to be positioned within mouthpiece fit element (608) such that an inhalation facilitation component supplement exterior wall (614) suitably fits with mouthpiece fit element (608). In other aspects, as exemplified in the mouthpiece figures provided herein, mouthpiece fit element (608) can comprise one or more contours or comprise a conformation which requires a complementarily shaped component if such a component is to be positioned within mouthpiece fit element (608). In aspects, the inhalation facilitation component supplement exterior wall (614) comprises contouring which complements that of mouthpiece fit element (608), e.g., comprises one or more shape elements, or comprises a conformation, which complements that of mouthpiece fit element (608). In aspects, the inhalation facilitation component supplement (610) comprises an inhalation facilitation component supplement exterior wall (614) that is designed to be in contact with mouthpiece fit element (608) in an assembled device. According to alternative aspects, the inhalation facilitation component supplement does not provide attachment mechanism feature(s). In aspects, a mouthpiece attachment insert (not provided) provides such an attachment mechanism feature to aid in or otherwise facilitate in the attachment of the mouthpiece (301) to one or more other component of device(s).

Still further, as exemplified in FIG. 6C, an inhalation facilitation component supplement (610) comprises an inhalation facilitation component supplement interior wall (616) and an opening (618). In aspects, the inhalation facilitation component supplement opening (618) provides for an airflow through the inhalation facilitation component supplement (610), and, further, through mouthpiece (301), to facilitate the inhalation of compound(s) provided by a core insert, such as, e.g., core insert (1800)).

FIG. 7 illustrates an exemplary magnet (502) of a device (e.g., device (100) as shown in FIG. 1A) provided by the invention. A magnet (502) can be present in a device to provide a mechanism for connecting or otherwise maintaining reversible attachment of a body assembly (201) (see FIG. 2A) to a tip assembly (202) (see FIG. 2B). As exemplified in FIG. 5C, the magnet (502) (see FIG. 7) is a component of the body assembly (201). As exemplified, magnet (502) provides an exemplary mechanism for providing selective engageability (and, correspondingly, the selective disengage-ability) of the body assembly (201) and the tip assembly (202). Accordingly, magnet (502), as exemplified, participates in the ability of the device to be separated into at least two primary components (e.g., body assembly (201) and tip assembly (202)), allowing for a compound-laden insert providing one or more compounds for inhalation using the exemplary device (e.g., a core insert (e.g., (1800)) to be inserted from a position lateral to the device versus in-line with the device as described in detail elsewhere herein. Further, magnet (502), as exemplified, participates in the ability of the device to provide the repeated selectively engaged/dis-engaged nature of at least two components such that the device comprises a fidget-ability, e.g., providing elements of a fidget device has described herein.

The magnet (502) exemplified in FIG. 7 is a ring-shaped magnet. As exemplified, the ring-shaped magnet (502) has a magnet inner surface (701), a magnet outer surface (702), a magnet first side (703), a magnet second side (704), a magnet first inner edge (705), a corresponding magnet first outer edge (706), and a magnet second inner edge and magnet second outer edge, corresponding to the magnet first inner edge (705) and first outer edge (706) respectively but not shown. Magnet inner surface (701) is shown as running parallel to magnet outer surface (702) round the ring-shape of magnet (502). Magnet first side (703) is shown as parallel to magnet second side (704); magnet second side (704) is opposite that of magnet first side (703), facing away from the viewer. Magnet first inner edge (705) and first outer edge (706) define the inner and outer edges of magnet first side (703) as well as one edge of magnet inner surface (701) and one edge of magnet outer surface (702). Magnet second inner edge and second outer edges, not shown as they are facing away from the viewer, define the inner and outer edges of magnet second side (704), as well as one edge of magnet inner surface (701) and one edge of magnet outer surface (702).

Magnet inner surface (701) is shown in FIG. 7 as smooth, uninterrupted, and running around the inner circumference of magnet (502). Magnet inner surface (701) can contact one or more other components of the device, such as, e.g., one or more components of the body assembly (201), e.g., one or more components of the body subassembly (302), such as, e.g., specifically one or more portions of the magnet cover (401).

Magnet outer surface (702) is shown in FIG. 7 as smooth, uninterrupted, and running around the outer circumference of magnet (502). Magnet outer surface (702) is parallel to magnet inner surface (701). Magnet outer surface (702) can contact one or more other components of the device, such as, e.g., one or more components of the body assembly (201), e.g., one or more components of the body subassembly (302), such as, e.g., specifically one or more portions of the magnet cover (401).

Magnet first side (703) is shown in FIG. 7 as a flat, smooth surface. Magnet first side (703) is shown as perpendicular to both magnet inner surface (701) and magnet outer surface (702). Magnet first side (703) is parallel to magnet second side (704) (not visible to the reader). Magnet first side (703) can contact one or more other components of the device, such as, e.g., one or more components of the body assembly (201), e.g., mouthpiece (301).

Magnet second side (704) faces away from the reader in FIG. 7 but is the same as magnet first side (703) but on the opposite side of the magnet. Magnet second side (704) is perpendicular to both magnet inner surface (702) and magnet outer surface (702). Magnet second side (704) is parallel to magnet first side (703). Magnet second side (704) can contact one or more other components of the device, such as, e.g., one or more components of the body assembly, such as, e.g., one or more components of the body subassembly (302), e.g., specifically, one or more portions of magnet cover (401).

Magnet first inner edge (705) and magnet first outer edge (706) each define the interface with magnet first side (703) with magnet inner surface (701) and magnet outer surface (702), respectively. Magnet first inner edge (705) defines where magnet first side (703) meets magnet inner surface (701). Magnet first inner edge (705) can form a right angle between the two surfaces; however, as exemplified in FIG. 7, magnet first inner edge (705) can also be a surface in and of itself, such as magnet first inner edge (705) being an angled plane (relative to magnet first side (703) and magnet inner surface (701)), separating the magnet first side (703) and magnet inner surface (701) providing an angled transition between the two surfaces. Magnet first inner edge (705) in FIG. 7 is shown as a smooth surface, encircling the inner diameter of the magnet between the magnet first side (703) and magnet inner surface (701), such that the angle formed by the magnet first side (703) and magnet first inner edge (705) is about 135°, the angle formed by the magnet first inner edge (705) and magnet inner surface (701) is about 135°, or both.

Magnet first outer edge (706) defines where magnet first side (703) meets magnet outer surface (702). Magnet first outer edge (706) can form a right angle between the two surfaces; however, as exemplified in FIG. 7, magnet first outer edge (706) can also be a surface in and of itself, such as magnet first outer edge (706) being an angled plane (relative to magnet first side (703) and magnet outer surface (702)), separating the magnet first side (703) and magnet outer surface (702) providing an angled transition between the two surfaces. Magnet first outer edge (706) in FIG. 7 is shown as a smooth surface, encircling the outer diameter of the magnet between the magnet first side (703) and magnet outer surface (702), such that the angle formed by the magnet first side (703) and the magnet first outer edge (706) is about 135°, the angle formed by the magnet first outer edge (706) and magnet outer surface (702) is about 135°, or both.

As described above, a magnet second inner edge and a magnet second outer edge are also present. Magnet second inner edge (not shown) and second outer edge (not shown) are positioned similarly to magnet first inner edge (705) and magnet first outer edge (706) but are positioned on the opposite side of the magnet. That is, magnet second inner edge defines where magnet inner surface (701) meets magnet second side (704), and magnet second outer edge defines where magnet second side (704) meets magnet outer surface (702). Magnet second inner and outer edges can take on the characteristic(s) of magnet first inner and outer edges ((705) and (706)).

The magnet (502) of FIG. 7, as shown in FIG. 5C, can be positioned in an assembled device at least partially within (e.g., at least partially nested within) magnet cover (401) (see FIG. 5D). Accordingly, in this embodiment, magnet (502) is not visible on the exterior of an assembled device. When fully assembled, in this embodiment, the magnet is protected from the exterior environment by magnet cover (401). In this environment, it is the magnet that serves to maintain the fully assembled device as a single unit while also providing selectable disengagement between the body assembly (201) and the tip assembly (202). Magnet (502) is exemplified here as shaped as a ring (e.g., comprising an annular shape), with the ability to provide an airflow path through the center of magnet (502) (e.g., allow air to pass through the interior of the ring formed by magnet (502). Thus magnet (502) aids in the establishment of an airflow path through the device, e.g., specifically being continuous with both the airflow path through the mouthpiece (301) and through the magnet cover (401). The magnet (507) can be attracted to one or more other components of the device. In certain aspects, the magnet (507) is attracted to only a single component of the device. In aspects, the magnet (507) is attracted to a single component of the tip assembly (202). In aspects, the only component of the device magnet (507) is attracted to is barrel collar (1302).

FIG. 8A and FIG. 8B illustrate an exemplary mechanism for (a) holding magnet (502) in place, (b) protecting magnet (502) from the external environment, or (c) both (a) and (b). As illustrated, exemplary magnet cover (401) of a device (e.g., device (100) as shown in FIG. 1A) provided by the invention provides such features. FIG. 8A and FIG. 8B each show an exemplary magnet cover (401) from a slightly different perspective such that different components of magnet cover (401) become visible. Magnet cover (401) is embodied as comprising an interior magnet cover surface (802), exterior magnet cover surface (803), magnet cover encompassing surface thickness (804), magnet cover exterior surface first edge (805), magnet cover exterior surface second edge (806), magnet cover interior wall (807), magnet cover exterior wall (808), first magnet cover extension (809), first magnet cover extension first outer surface (810), first magnet cover extension second outer surface (811), first magnet cover extension first inner surface (812), first magnet cover extension thickness (813), first magnet cover extension interior (814), first magnet cover connection mechanism (815), second magnet cover extension component (816), second magnet cover extension first portion (817), second magnet cover extension second portion (818), second magnet cover extension edge (819), second magnet cover extension thickness (820), second magnet cover extension interior surface (821), and, e.g., second magnet cover extension interior (822). Each exemplary component of magnet cover (401) is described below. Magnet cover (401) serves in this embodiment to protect magnet (502). In this embodiment, magnet cover (401) is designed to hold, e.g., in a nested fashion, magnet (502), and to maintain magnet (502) within the device when fully assembled such that magnet (502) is not exposed to the exterior environment. In this embodiment, magnet cover (401) is designed to attach body subassembly (302) (see, e.g., FIG. 3C) to mouthpiece (301) (see, e.g., FIG. 3C). Further, in aspects, magnet cover (401) provides an externally visible indicator, e.g., second indicator (102), which, either alone or in combination with one or more other visual indicators (e.g., first indicator (101)), indicates the spatial orientation of one or more components of the device, one or more operational status(es) of the device, or both.

FIG. 8A illustrates magnet cover (401) comprising an interior magnet cover surface (802). Interior magnet cover surface (802) is exemplified as a smooth surface encompassing the inner circumference of magnet cover (401). In aspects, interior magnet cover surface (802) contacts magnet outer surface (702) (see FIG. 7) when magnet (502) is positioned within magnet cover (401). In aspects, the width of the interior magnet cover surface is at least generally, at least substantially, at least essentially, essentially, or is the same width as magnet outer surface (702). As exemplified in FIG. 8A, interior magnet cover surface (802) meets the magnet cover interior wall (807) at a right angle. Exterior magnet cover surface (803) is exemplified as a smooth surface having a single interruption, the single interruption being an indicator (second indicator (102)) which is discussed further below. Interior magnet cover surface (802) is shown as running in parallel to exterior magnet cover surface (803), separated from one another by magnet cover encompassing surface thickness (804). The magnet cover encompassing surface thickness (804) defines the distance interior magnet cover surface (802) is from exterior magnet cover surface (803). The plane defining the magnet cover encompassing surface thickness (804) (e.g., the surface defined by this thickness) can meet the interior magnet cover surface (802), exterior magnet cover surface (803), both at a right angle or an angle different from 90°. As shown, the surface defined by the magnet cover encompassing surface thickness (804) meets the interior magnet cover surface (802) at a right angle. However, as shown, the surface defined by the magnet cover encompassing surface thickness (804) meets the exterior magnet cover surface (803) at an angle differing from 90°. Therein, magnet cover exterior surface first edge (805) defines the interface between the surface defined by the magnet cover encompassing surface thickness (804) and the exterior magnet cover surface (803). This magnet cover exterior surface first edge (805) is shown as forming a surface in and of itself, such as magnet cover exterior surface first edge (805) being an angled plane (relative to the surface defined by the magnet cover encompassing surface thickness (804) and exterior magnet cover surface (803)), separating the surface defined by the magnet cover encompassing surface thickness (804) and exterior magnet cover surface (803) and providing an angled transition between the two surfaces. Magnet cover exterior surface first edge (805) in FIG. 8A is shown as a smooth surface, encircling the circumference of the magnet cover (401) between the surface defined by the magnet cover encompassing surface thickness (804) and the exterior magnet cover surface (803), such that the angle formed by the surface defined by the magnet cover encompassing surface thickness (804) and the magnet cover exterior surface first edge (805) is about 135°, the angle formed by the magnet cover exterior surface first edge (805) and the exterior magnet cover surface (803) is about 135°, or both. FIG. 8B shows a magnet cover exterior surface second edge (806), which, like magnet cover exterior surface first edge (805), encircles the circumference of the magnet cover (401), and forms a similar interface between planes of the magnet cover (401), but on the opposing side of the exterior magnet cover surface (803). For sake of brevity, this specific interface is not repeated here, but should be understood by the reader to share corresponding characteristics of magnet cover exterior surface first edge (805) described above.

FIG. 8A further illustrates magnet cover (401) comprising a magnet cover interior wall (807). Magnet cover interior wall (807) forms the back side of magnet cover exterior wall (808) shown in FIG. 8B, and vice versa. Magnet cover interior wall (401) is shown as a smooth surface on the interior of magnet cover (401), forming the inner-most wall of the magnet cover (401). As exemplified, magnet cover interior wall (807) can contact magnet (502), such as, e.g., specifically magnet second side (704) (as shown in FIG. 7) when magnet (502) is held within magnet cover (401) and the exemplary device (100) is fully assembled. Accordingly, magnet cover interior wall (807) aids in maintaining magnet (502) in place within the exemplary, fully assembled device (100).

Continuing with the description of FIG. 8A, magnet cover (401) is illustrated as comprising a first magnet cover extension component (809), extending to the left from the main body of magnet cover (401) as viewed in FIG. 8A. First magnet cover extension component (809) is shown with the following exemplary characteristics: first magnet cover extension first outer surface (810), first magnet cover extension second outer surface (811), first magnet cover extension first inner surface (812), first magnet cover extension thickness (813), first magnet cover extension interior (814), and first magnet cover connection mechanism (815). First magnet cover extension first outer surface (810) is shown as a smooth surface, opposed by first magnet cover extension first inner surface (812), and separated therefrom by a thickness which is defined by the first magnet cover extension thickness (813) and the surface associated therewith. Each of first magnet cover extension first outer surface (810) and the magnet cover extension first inner surface (812) encompass first magnet cover extension interior (814). As shown, first magnet cover extension first outer surface (810) forms a non-90° angle with the surface formed by the first magnet cover extension thickness (813). As exemplified, this angle is greater than 90°. As shown, first magnet cover extension first inner surface (812) also forms a non-90° angle with the surface formed by the first magnet cover extension thickness (813). As exemplified, this angle is less than 90°. In embodiments (all not shown) either such angle can be greater than, equal to, or less than 90°. First magnet cover connection mechanism (815) is exemplified as a threaded attachment mechanism such that magnet cover (401) can be attached to another component of exemplary device (100) by screwing magnet cover (401) onto/into such another component. As illustrated, such another component can be mouthpiece (301). In aspects, such another component can more specifically be a mouthpiece fit element (608) of a mouthpiece (301). Accordingly, as exemplified, elements (810), (812), (813), and at least a portion of (814) can be positioned within, in a fully assembled device, attached to, or both, a portion of mouthpiece (301). As described above relevant to the description of mouthpiece (301) and not repeated here, such an attachment/connection can, in some aspects be permanent (e.g., not reversible by a user). In alternative aspects, such a connection can be reversible (e.g., the two components can be disengaged by a user). Further, first magnet cover connection mechanism (815) can, as is described elsewhere, be provided in an alternative form, such as, e.g., a snap fit, magnet, etc. First magnet cover extension second outer surface (811) can be positioned within the interior of the ring formed by a ring-shaped magnet (502) (See, e.g., FIG. 7). That is, magnet (502) can be placed over/around first magnet cover extension component (809) and ultimately positioned around first magnet cover extension second outer surface (811), with magnet cover inner surface (701) making at least partial contact with first magnet cover extension second outer surface (811), and magnet second side (704) making at least partial contact with magnet cover interior wall (807). When fully assembled, interior magnet cover surface (802), exterior magnet cover surface (803), the surface formed by magnet cover encompassing surface thickness (804), magnet cover exterior surface first edge (805), magnet cover exterior surface second edge (806), or any combination thereof can be positioned outside of mouthpiece (301).

In aspects, the positioning of a magnet (502) within a magnet cover (401) is facilitated by the use of one or more magnet fit elements (not shown). In aspects, a magnet fit element can be any element facilitating the maintenance of the magnet in position within a device (401) during manufacturing, during use, or both. In aspects, such a fit element can be a glue, e.g., an epoxy glue, one or more O-rings, or both. In aspects, one or more O-rings can reduce detectable or significant shaking of a magnet. In aspects, use of a glue, e.g., epoxy, can be used to maintain secure positioning.

FIG. 8B illustrates an alternative view of magnet cover (401), wherein additional elements of magnet cover (401) are visible. As shown in FIG. 8B, magnet cover (401) further comprises a magnet cover exterior surface second edge (806), magnet cover exterior wall (808), and a second magnet cover extension component (816), which comprises a second magnet cover extension first portion (817), a second magnet cover extension second portion (818), a second magnet cover extension edge (819), a second magnet cover extension thickness (820), a second magnet cover extension interior surface (821), and a second magnet cover extension interior (822). Also shown in FIG. 8B is an indicator, e.g., a visual indicator, exemplified as second indicator (102) of exemplary device (100), which is embodied as a groove carved within exterior magnet surface (803).

As described above, magnet cover exterior surface second edge (806) is much like that of magnet cover exterior surface first edge (805) shown in FIG. 8A, exemplified as having a smooth surface, encircling the circumference of the magnet cover (401). As shown in FIG. 8B, magnet cover exterior surface second edge (806) forms the interface between exterior magnet cover surface (803) and magnet cover exterior wall (808). As exemplified, the angle formed by the exterior magnet cover surface (803) and the magnet cover exterior surface second edge (806) is about 135°, and, similarly, the angle formed by the magnet cover exterior surface second edge (806) and magnet cover exterior wall (808) is also about 135°. Magnet cover exterior wall (808) is shown as a smooth surface opposite that of magnet cover interior wall (807) (see FIG. 8A). Magnet cover exterior wall (808) may in embodiments contact at least a portion of core spring (504), at least a portion of body tube (402), at least a portion of barrel collar (1302), barrel tube (1304), or any combination thereof. In certain aspects, magnet cover exterior wall (808) does not contact a portion of core spring (504). In certain specific aspects, magnet cover (401), and specifically the magnet cover exterior wall (808), does not contact barrel collar (1302). In aspects, there is a detectable space or gap between magnet cover (401), and, e.g., in specific embodiments, between magnet cover exterior wall (808), and barrel collar (1302). In aspects, such a gap is present to ensure a suitable fit ("mating") between elements of body plug (506) and elements of barrel plug (1306), such that the two components can effectively cooperate to control airflow through the device as is described elsewhere herein. In aspects, such a detectable space can account for variance in manufacturing, e.g., manufacturing tolerances.

Second magnet cover extension first portion (817) can be distinct from second magnet cover extension second portion (818) in that it may form a different plane than second magnet cover extension second portion (818), e.g., forming an angle with second magnet cover extension second portion (818). Second magnet cover extension second portion (818) is shown as comprising a smooth surface separating second magnet cover extension first portion (817) from second magnet cover extension edge (819). As with other edge components described above, second magnet cover extension edge (819) forms a surface in and of itself, separating second magnet cover extension second portion (818) from the surface formed by second magnet cover extension thickness (820). In the exemplary embodiment shown in FIG. 8B, the angle formed by the interface of second magnet cover extension second portion (818) and the second magnet cover extension edge (819) is similar to the angle formed by the interface of second magnet cover extension edge (819) and the surface formed by second magnet cover extension thickness (820). Such angles can be, e.g., about 135° each. In aspects, second magnet cover extension first portion (817) is present to ensure that no material inadvertently remaining from a manufacturing process interferes with the mating between, contact between, or functionality of two or more components of the system, e.g., the body tube (402) and the magnet cover (401). Second magnet cover extension first portion (817), second magnet cover extension second portion (818), second magnet cover extension edge (819), or any combination thereof can, in aspects, contact core spring (504). In a fully assembled exemplary device (e.g., exemplary device (100)), core spring (504) can be positioned around at least a portion second magnet cover extension component (816). In certain embodiments, in a fully assembled exemplary device (e.g., (100)) core spring (504) can be positioned on (e.g., in contact with) second magnet cover extension second portion (818), second magnet cover extension edge (819), or both. In an exemplary fully assembled device, the surface formed by the second magnet cover extension thickness (820) can contact at least a portion of core spring (504). Second magnet cover extension component (816) comprises an interior (822). This interior (802) establishes an airflow path through magnet cover (401). Accordingly, magnet cover (401) aids in the establishment of an airflow path through the device. Specifically, airflow through magnet cover (401) is continuous with the airflow path through magnet (502) and through body tube (402). In aspects, the opening to second magnet cover extension interior (822) can be any suitable size. In aspects, the opening to second magnet cover extension interior (822) can be any size which is not detectably or significantly smaller than the largest opening established by any stage of cooperation between body plug (506) and barrel plug (1306).

Finally with regard to FIG. 8B, indicator (102) (specifically in this illustrated embodiment, second indicator (102)) is embodied as a groove in exterior magnet cover surface (803). As described previously, indicator (e.g., second indicator) (102) can inform the user by providing an indication of the spatial orientation of one or more device components, one or more operational status(es) of the device, or both. As illustrated in the exemplary embodiment, second indicator (102) spans the entire width of exterior magnet cover surface (803), including crossing magnet cover exterior surface first and second edges (805) and (806). In certain embodiments such an indicator may be smaller and may not span the entirety of any entire single dimension of the magnet cover (401) or any other component on/in which the indicator is present.

In aspects, magnet cover (401) is made of a material which is not magnetic. That is, magnet cover (401) is made of a nonmagnetic material and not capable of being magnetized. Thus, in aspects, magnet (502) is not magnetically attracted to magnet cover (401).

FIGS. 9A and 9B illustrate an exemplary component to aid in the stable maintenance of a compound laden element present to provide one or more compounds for inhalation, e.g., a core insert (e.g., (1800)). FIG. 9A exemplifies this component as a core spring (504). As shown in FIG. 9A, core spring (504) is exemplified as comprising two major elements: a core spring band (901) and a core spring flex element (902).

Elements of core spring band (901) are illustrated in FIG. 9A (with many also shown in FIG. 9B). Core spring band (901) is illustrated as comprising: a core spring band interior (903); a core spring band first interior surface (904); a core spring band second interior surface (905); a core spring band exterior surface (906); a core spring band thickness (907); a core spring band clip (908), the core spring band clip (908) comprising a core spring band clip angle (909) and a core spring band clip tab (910); and a core spring band gap (911). Core spring band interior (903) can receive one or more other components of an exemplary device (e.g., exemplary device (100)), such as, for example, a portion of a magnet cover, e.g., second magnet cover extension component (816). In certain aspects, core spring band interior (903) does not receive any significant portion of any other device (100) component. Core spring band interior (903) can be bounded at least in part by inner surface(s) of core spring band (901), such as, e.g., core spring band first interior surface (904) and core spring band second interior surface (905). As illustrated, a first interior surface (904) can form a flat plane. Further, a second interior surface (905) can form a rounded surface. In such a configuration, core spring band (901) may not form an (incomplete) circular shape, but rather, form an (incomplete) circular shape with one flat section. As shown, inner surfaces (e.g., first and second core spring band interior surfaces (904) and (905)) have an opposing core spring band exterior surface (906). Core spring band exterior surface (906) is shown as having a smooth surface. Core spring band (901) is exemplified as having a core spring band thickness (907). In aspects, core spring (504) is held in place within a device (100) by spring tension. In aspects, core spring (504) resides within a portion of body tube (402) in a fully assembled device. In aspects, core spring (504) is maintained within body tube (402) by spring force, e.g., spring tension, whereby in its relaxed state (e.g., manufactured "open" state), core spring (504) has a distance across its interior space which is greater than the diameter of body tube (402); thus, when compressed and fed or placed into the interior of body tube (402), the natural desire is for the core spring to expand to its relaxed state, creating a spring tension which maintains the core spring (504) in place within the body tube (402).

FIG. 9A illustrates the core spring band clip (908) element of core spring band (901). Therein, core spring band clip (908) is shown as comprising a bent or angled portion (core spring band clip angle (909)), and a core spring band clip tab (910). The width of core spring band clip (908) is shown as being wider than the width of the remaining portions of core spring band (901). This difference in size is best visible in FIG. 9B, wherein dashed line A illustrates the width of core spring band clip tab (910), and dashed line B illustrates the width of other portion(s) of core spring band (901). In aspects, this difference in width prevents the over-flexing of the spring tab (902). Core spring band (901) as exemplified does not form a complete ring. Core spring band (901) as exemplified comprises a break, or a gap (911). This gap allows for core spring band (901) to flex. The core spring band thickness (907) also aids in the ability of core spring band (901) to flex. Core spring band clip (908)

Turning to FIG. 9B, elements (903), (904), (905), (906), (907), core spring band clip (908), unlabeled; see FIG. 9A), (910), and (911) are repeated from FIG. 9A. FIG. 9A illustrates the connection of core spring band (901) to core spring flex element (902). This connection is illustrated as being facilitated by core spring flex element hinge (912). Core spring flex element hinge (912) is illustrated as a continuous part of the core spring band (901) and core spring flex element (902) but provides a measurable separation between the two core spring (504) components (core spring band (901) and core spring flex element (902)). Core spring flex element hinge (912) is connected to the flat portion of the core spring band (901) identified as core spring band first interior surface (904). The difference in presentation of core spring band first interior surface (904) from core spring band second interior surface (905) facilitates the attachment of core spring flex element hinge (912) thereto. Providing core spring band first interior surface (904) as a flat surface as opposed to a curved surface like that of core spring band second interior surface (905) facilitates the provision of core spring flex element hinge (912). For example, if core spring band first interior surface (904) were rounded, functionality of core spring flex element hinge could, e.g., be negatively impacted. A rounding of the side of core spring band first interior surface (904) could, in aspects, be presented as being rounded while maintaining a more flat or straight edge of core spring band first interior surface (904) connecting to the core spring flex element hinge (912). While more challenging to manufacture, such an embodiment is considered an element of the invention herein. Core spring flex element hinge (912) can be made of the same material as the core spring band (901) and core spring flex element (902), and in such cases is structurally flexible enough to allow core spring flex element (902) to flex closer to and further away from core spring band (901). Core spring flex element (902) in its natural, unencumbered state, is separated from and angled away core spring band (901) by core spring flex element hinge (912) as shown in FIGS. 9A and 9B. In operation, one or more components of a device, such as, e.g., a core insert (e.g., (1800)), can press against core spring flex element (902), forcing core spring flex element (902) to move toward core spring band (901) via the flexing of core spring flex element hinge (912). Because this force acts against the natural positioning/configuration of core spring flex element (902), core spring flex element (902) can naturally exert a counter force against, e.g., the core insert (e.g., (1800)), aiding in maintaining the positioning of the core insert (e.g., (1800)) within the device. In this sense, to aid in the understanding of the core spring (504), it can be thought of as operating similarly to a spring in a traditional/common battery compartment of an electronic device, where the spring provides tension and allows for the maintenance of a battery in position within a battery compartment.

Continuing with the description of FIG. 9B, are elements of core spring flex element (902), comprising core spring flex element interior (913), core spring flex element first surface (914), core spring flex element second surface (915), core spring flex element width interior surface (916), and core spring flex element width exterior surface (917). (913), (914), (915) (hidden but labeled), and (917) are also shown in FIG. 9A. Core spring flex element (902) is exemplified as shaped as a disc with a hole in its center, e.g., shaped like a flat ring, which in aspects provides a reduced inner diameter (918A) of an airflow channel (shown in, e.g., FIG. 17B). Core spring flex element interior (913) represents the interior of this ring. Core spring flex element first surface (914) and second surface (915) form the first and second sides, respectively, of the ring portion of the core spring flex element (902). Each is exemplified as a flat surface, separated from one another by a core spring flex element width, the width visible as, and forming, the core spring flex element width interior surface (916), and core spring flex element width exterior surface (917). Core spring flex element second surface (915) can contact one or more components of a device, such as, e.g., a core insert (e.g., (1800)), when such a core insert (1800) is inserted. As described above, a portion of a core insert (e.g., (1800)) can make contact with core spring flex element second surface (915) to aid in stabilizing core insert (e.g., (1800)) within the exemplary device, with the thickness of the core spring flex element (902), the thickness of the core spring flex element hinge (912), or both the thickness of the core sprig flex element (902) and the thickness of the core spring flex element hinge (912) contributing to the flexibility of the core spring flex element (902), and thus how much force it takes to flex core spring flex element (902) (e.g., how much force it takes a core insert (e.g., (1800)) to move core spring flex element (902)), and further, how much counter force core spring flex element exerts on, e.g., a core insert (e.g., (1800)).

FIG. 10A and FIG. 10B illustrate an exemplary component of a device provided by the invention which is capable of receiving an element capable of holding (e.g., at least in one state, comprising) one or more compounds for inhalation by a user. In aspects, FIGS. 10A and 10B illustrate an exemplary component capable of receiving an element capable of holding at least one or more compounds for inhalation by a user from a position lateral to the component. As exemplified, the exemplary component is a body tube (402).

In the exemplary embodiment provided by FIGS. 10A and 10B, body tube (402) comprises a body tube first end (1002) comprising a body tube outlet (1003B) and a body tube second end (1004) comprising a body tube inlet (1003A), and an airflow channel (1024) (FIG. 10B) therebetween. In aspects, body tube (402) can comprise one or more features which allow it to engage with one or more other components of a device. In aspects (e.g., as exemplified), an end. e.g., second end (1004) can comprise one or more distinct features which differentiate it from another end, e.g., first end (1002). In aspects, body tube (402) can comprise one or more features which allow it to engage with one or more other components of a device such that it maintains at least one or more other components of the device in a stationary position as one or more yet further components of the device move, e.g., rotate, in relation to the component. For example, as exemplified, body tube second end (1004) comprises a first portion which extends beyond that of a second portion, e.g., body tube second end extension (1006) extends beyond body tube second end recession (1008). In certain embodiments, e.g., in the exemplary embodiment, such feature(s) (e.g., body tube second end extension (1006) and body tube second end recession (1008)) provide body tube (402) with a mechanism for engaging body plug (506). In aspects, body tube (402) is capable of engaging body plug (506) and maintaining body plug (506) in place (e.g., maintaining body plug in a stationary position) while one or more other device components move, e.g., rotate, about it.

Body tube (402) of FIG. 10A is illustrated as having a body tube upper half (1010) and a body tube lower half (1012). Body tube lower half (1012) is shown alone in FIG. 10B (again, with body tube first end (1002) and body tube second end (1004) labeled). FIG. 10A further identifies the section perspective of FIG. 10B via the dashed section line; Roman numerals "I" and "II" aligning/orienting the views of FIGS. 10A and 10B; arrows indicating line of sight) Body tube (402), as shown in both FIGS. 10A and 10B comprises a body tube exterior surface (1014) and a body tube interior surface (1016), separated by a body tube wall width (1018). Further, body tube (402) forms at least in part an interior compartment (1022). As illustrated in the illustrative embodiment of FIGS. 10A and 10B, body tube upper half (1010) and body tube lower half (1012) differ from one another in that body tube upper half (1010) has a portion of its defining wall removed, forming an open portion (1020) of the body tube (402) such that the body tube interior compartment (1022) is accessible/exposed. In the provided embodiment, body tube interior compartment (1022) is capable of receiving one or more other components of a device of the invention, such as, e.g., a component capable of holding one or more compounds for inhalation, such as, e.g., a core insert (e.g., (1800)). As illustrated, the design of body tube (402) provides for a component capable of comprising one or more compounds for inhalation (e.g., core insert (1800)) to be inserted into the device from a position lateral to the device, e.g., into the open portion of the body tube (1020), instead of, e.g., through an end of the device.

As illustrated, body tube (402) can be in contact with one or more components of the exemplary device when the device is fully assembled. For example, body tube (402) can be in contact with one or more of, e.g., magnet cover (401), core spring (504), body plug (506), barrel collar (1302), barrel tube (1304), or, e.g., a combination thereof. In aspects, when the exemplary device is fully assembled, at least a portion of magnet cover (401), e.g., second magnet cover extension component (816) is positioned within the interior of body tube (402).

In aspects, body tube (402) is capable of both receiving a core insert (e.g., (1800)) and making such a core insert (e.g., (1800)) accessible for removal. In aspects, body tube (402) is capable of, alone or in conjunction with one or more other components, such as, e.g., core spring (504) and at least a portion of body plug (506) maintaining a core insert (e.g., (1800)) stably in position while the device is in use. In aspects, in a fully assembled device, core spring (504) and body plug (506) are positioned within body tube (402). In aspects, in a fully assembled device, body tube (402) is positioned within barrel tube (1304). In aspects, body tube (402) is not externally visible when the device is fully assembled, and only becomes visible when tip assembly (202) is separated from body assembly (201) (See FIGS. 2A and 2B). In aspects, to use the device, a user intentionally separates tip assembly (202) from body assembly (201), the two components held together by magnetic force provided by magnet (502), to expose body tube (402). Upon exposure of body tube (402), user can insert a core insert (e.g., (1800)) laden with compound(s) for inhalation. Upon the secure placement of core insert (e.g., (1800)) within body tube (402), the user can reunite the tip assembly (202) with the body assembly (201), placing the device in a state ready for use. In aspects a similar process can be repeated for the removal or replacement of a core insert (e.g., (1800)).

FIGS. 11A and 11B illustrate an exemplary device with certain elements removed (1100) such that the internal space within body tube (402) is visible. On a first end of the interior of body tube (402), core spring (504) is visible. On a second end of the interior of body tube (402), body plug (506) is visible. As provided, when a core insert (1800) is inserted into body tube (402), maintained within body tube (402), or both, a first end of core insert (1800) contacts core spring (504). Upon inserting a core insert (1800) into body tube (402), a first end of core insert (1800) can, e.g., be pressed up against core spring (504) such that the core spring is made to flex. Upon flexion of the core spring, the second end of core insert (1800) can be lowered into body tube (402) such that the second end of core insert (1800) contacts the end of body plug (506). Upon placement, core spring (504) places pressure on the first end of core insert (1800), applying a force which attempts to push core insert (1800) in the opposite direction, toward body plug (506). However, the second end of core insert (1800) contacts the end of body plug (506), preventing movement of core insert (1800) in such direction. Because the end of core insert (1800) stops at the edge of body plug (506), a gap is formed between the end of body plug (506) and the end of the opening to body tube (402). Such a gap is identified in FIGS. 11A and 11B as access gap (1102). In FIG. 11B, dashed line (A) illustrates where the second end of an inserted core insert (1800) would be positioned, as it rests up against the end of body plug (506). As shown, access gap (1102) is the distance between the end of core insert (1800) and the opening within body tube (402). Because the opening in body tube (402) is such that a wall of body tube (402) is lower than or recessed from the height of a core insert (1800), an access gap (1102) is created within which a user can insert their finger or other removal instrument into such an access gap (1102). Such an ability to insert, e.g., a finger, into access gap (1102) facilitates the removal of core insert (1800) when such a need arises (e.g., to facilitate replacement of a core insert (1800)).

FIGS. 12A and 12B provide an exemplary embodiment of at least a portion of an airflow control unit. In aspects, devices provided by the invention comprise an airflow control unit comprising a first component and a second component that coordinate/interface to control airflow, e.g., control drag, during device use. As provided in the exemplary embodiment(s) of the device shown in the Figures, an airflow control unit can comprise a first component, e.g., a body plug (506), and a second component, e.g., a barrel plug (1306). In this exemplary embodiment, body plug (506) and barrel plug (1306) work together to control airflow when the two components are rotated and positioned in various positions relative to one another. The operation of the device relative to these two components is described in detail elsewhere herein.

FIGS. 12A and 12B provide an exemplary embodiment of a body plug (506). Body plug (506) comprises two primary features: a body plug body (1202), which in aspects by its positioning within a device provides a reduced inner diameter (918B) of an airflow channel, and a body plug fan (1204). Starting with body plug body (1202), body plug body (1202) is illustrated in FIG. 12A as comprising a body plug body exterior surface (1206), a body plug body interior surface (1208), and a body plug body wall thickness (1210) separating body plug body exterior surface (1206) from body plug body interior surfaces (1208). As exemplified, the surface defined by body plug body wall thickness (1210) can comprise an edge, e.g., body plug body interior wall edge (1212), which in and of itself forms a surface. Like other edge features described above, this surface can form a non-right angle with an interior surface. That is, as exemplified, body plug body interior wall edge (1212) meets body plug body interior surface (1208) at an angle which is not 90 degrees. Similarly, as exemplified, body plug interior wall edge (1212) meets the surface formed by body plug body wall thickness (1210) at an angle which is not 90 degrees. In aspects, such an edge, as defined in this position of this particular component or an edge positioned in this particular component or another component (either shown or not specifically illustrated) can aid in the fit of one or more components with one or more other components of a device, can aid in facilitating suitable operation of the device, can aid in facilitating the assembly of the device, or any combination thereof.

In aspects, in a fully assembled exemplary device, body plug body (1202) is positioned within body tube (402). In aspects, in a fully assembled device, body plug body exterior surface (1206) contacts body tube interior surface (1016). As shown in FIG. 12A, the wall of body plug (506) (comprising body plug exterior surface (1206), body plug body interior surface (1208), body plug body wall thickness (1210), and body plug body interior wall edge (1212)) define a body plug body interior (1214). As shown in FIG. 12A, the wall of body plug (506) (comprising body plug exterior surface (1206), body plug body interior surface (1208), body plug body wall thickness (1210), and body plug body interior wall edge (1212)) can comprise a shape feature (1216), or, e.g., one or more, e.g., two such shape features (1216). For example, FIG. 12A exemplifies body plug body (506) comprising two such body plug body shape features (1216). In aspects, such a feature or features aid in the positioning, alignment, fit, or any combination thereof of the body plug (506) with one or more other components of an exemplary device, or, e.g., aid in facilitating suitable operation of the device, aid in facilitating the assembly of the device, or any combination thereof. In aspects, one or both of body plug shape features (1216) allow for the ease of positioning or placement body plug (506) into or with one or more other components of the device during assembly. For example, in aspects, body plug shape features (1216) facilitate the fitting of body plug (503) into body tube (402). In aspects, the rounded shape of one or more body plug shape features (1216) allows for the body plug (506) to be "slid" or easily guided into place within body tube (402), such that it can, in aspects, slide, fall, or follow contour(s) of body tube (402) into place with limited guidance required. In aspects, one or more of body plug shape features (1216) provide for limiting detectable or significant damage to a core insert (1800). In aspects, one or more of body plug shape features (1216) provide for limiting detectable or significant damage to a core insert (1800) when such a core insert (1800) is made of a fragile material, e.g., a material capable of being caught on, or, e.g., scratched by, or, e.g., capable of experiencing flaking when, contacted by a suitably shaped or sharp surface. For example, a core insert (1800) can be, e.g., made of a ceramic material which, if contacted by a suitably shaped or sharp surface, such as, e.g., one or more body plug shape features (1216) which is in the form of, e.g., a 90 degree angle, can be scratched such that at least a portion of the core is worn or, e.g., powderized (scratched to an extent to which at least a portion of the ceramic core is turned into a powder). In aspects, one or more body plug shape features (1216), such as rounded features as exemplified in FIG. 12A, prevents detectable or significant wear on a core insert (1800). In one aspect, a core insert may be a polyester core, wherein the shape of one or more body plug shape features (1216) prevents detectable or significant catching, fraying, or both of the polyester core insert. In aspects, any one or more component(s), features of component(s) (e.g., elements of component(s)), or combination thereof of the device provided by the invention can comprise a shape which prevents the detectable or significant wear of any one or more other component(s), features of component(s) (e.g., elements of component(s)) or combination thereof of the device (including, e.g., a core insert for use in the device). In aspects, the result of such forethought with regard to component design, e.g., shape, size, fit, or combination thereof, is an element of the invention.

Exemplary body plug (506), as shown in FIG. 12A and in more detail in FIG. 12B, can comprise a body plug fan (1204). Body plug fan (1204) comprises a semi-circle (or, e.g., half disk) shape. The size and shape of body plug fan (1204) is sufficient to fill approximately half of the body tube. This size and shape feature of body plug fan (1204) is, in certain aspects, an important feature of body plug fan (1204) in that it aids in defining the interaction between body plug fan (1204) and barrel plug fan (1604) and, together, the mechanism by which the two components together operate as an air control component of an exemplary device. This is discussed further in the description of barrel plug fan (1604) elsewhere herein.

Body plug fan (1204) can comprise a body plug fan fit feature (1218), a body plug fan ridge set (1220), and a body plug fan protrusion (1226). The function of body plug fan protrusion (1226) is discussed in more detail in conjunction with the discussion of barrel plug fan protrusion (1614) of FIG. 16. As shown in FIG. 12B, body plug fan fit feature (1218) is a feature having a dimension wider than body plug body (1202). In the exemplified embodiment of the device, this allows for body plug body (1202) to be positioned within body tube (402), while the body plug fan (1204) remains outside of body tube (402). Such differences in dimension of body plug (506) can aid in the positioning, alignment, fit, or any combination thereof of body plug (506) with one or more other components of an exemplary device, or, e.g., aid in facilitating suitable operation of the device, aid in facilitating the assembly of the device, or any combination thereof. As shown, body plug fan fit feature (1218) can have a plurality of surfaces, e.g., one or more surfaces at a variety of angles relative to one another, having a variety of surfaces (e.g., planar surface, rounded surface, etc.), or both. Such a plurality of surfaces is shown as features (1218-A)-(1218-F) (e.g., 1218-A, 1218-B, 1218-C, 1218-D, 1218-E, and 1218-F) in FIG. 12B. Such differences in shape/surfaces of body plug fan fit feature (1218) (e.g., (1218-A)-(1218-F)) can aid in the positioning, alignment, fit, or any combination thereof of body plug (506) with one or more other components of an exemplary device, or, e.g., aid in facilitating suitable operation of the device, aid in facilitating the assembly of the device, or any combination thereof. In aspects, in a fully assembled device, body plug fan fit feature (1218) and its associated surface(s) contacts one or more fit features of barrel plug (1306) (e.g., one or more of barrel plug fan fit features A-C ((1606)-(1610)). In aspects, as exemplified, the outward face of body plug (1204) (e.g., the face of body plug (1204) presented in FIG. 12B) interfaces with, interacts with, or otherwise contacts the inward face of the barrel plug (1306) (e.g., the face of barrel plug (1306) presented in FIG. 16).

Further shown in FIG. 12B are particular exemplary features of body plug fan (1204), in particular exemplary features of body plug fan ridge set (1220). Body plug fan ridge set (1220) is exemplified as comprising a series of ridges formed by alternating body plug fan ridge recession(s) (1222) and body plug fan ridge peak(s) (1224). A plurality of alternating body plug fan ridge recession(s) (1222) and body plug fan ridge peak(s) (1224) can be present in a body plug fan ridge set (1220). About 15 recessions (1222) and 16 peaks (1224) are exemplified in FIG. 12B. As shown, each recession is between about 11 degrees and about 13 degrees apart, such as each recession being about 12 degrees apart. The number of body plug fan ridge recessions (1220) and peaks (1224) present in a body plug fan ridge set (1220) can, in aspects, contribute to the specificity with which airflow through the device can be controlled. For example, an increased number of such features (recessions (1220) and peaks (1224) of a body plug fan ridge set (1220)) can increase the level of fine tuning a user can accomplish to control airflow (e.g., drag) when using the device, while a decreased number of such features can decrease the level of fine tuning a user can accomplish to control airflow during device use.

In aspects, in a fully assembled device, a body plug fan ridge set (1220) can contact one or more other components of the device. In aspects, in a fully assembled device, a body plug fan ridge set (1220) can contact one or more features of a barrel plug (1306), e.g., a portion or all of a barrel plug fan ridge set (1612). In one exemplary embodiment provided by the Figures, body plug fan ridge set (1220) can contact a portion or all of a barrel plug fan ridge set (1612), the two components together operating as an airflow control mechanism for the device. The degree of contact, e.g., the amount of overlap of or interface between) the two components establishes the drag provided by the device upon inhalation: the more overlap, e.g., the more interface (e.g., the higher the degree of contact, e.g., overlap) between the body plug fan ridge set (1220) and the barrel plug fan ridge set (1612), the less drag provided by the device, while the less interface (e.g., the lower the degree of contact, e.g., overlap) between the body plug fan ridge set (1220) and the barrel plug fan ridge set (1612), the higher the drag provided by the device. In such an exemplary operation, complete overlap, e.g., complete interface, of body plug fan ridge set (1220) and barrel plug fan ridge set (1612), establishes the device in a "maximally open" position, such that the device is in a configuration providing the lowest amount of drag and the highest level of possible airflow. Further, a lack of any overlap, e.g., a lack of significant interface, of body plug fan ridge set (1220) and barrel plug fan ridge set (1612), establishes the device in a "maximally closed" position, such that the device is in a configuration providing the highest amount of drag. Any overlap of the two components between these two extreme positions modulates the airflow (and, e.g., drag), accordingly. In certain aspects, a sufficient amount of air can still be drawn through the device upon inhalation by a user to render the device still operable when the device is in such a maximally closed position. That is, in certain aspects, even with the device is in a maximally closed position, establishing the device in the position providing the highest amount of drag, some users of the device may still receive an amount of one or more compounds upon inhalation which the user considers effective, pleasurable, or both. In certain aspects, a device in such a setting may consider the amount of air capable of being drawn through the device is insufficient to provide an amount of one or more compounds upon inhalation which is considered by the user to be effective, pleasurable, or both. This is also true of the device in a maximally open position; some users may consider the amount of one or more compounds received upon inhalation when the device is in a maximally open position to be undesirable, while other users may find such a setting suitable or, e.g., preferred. Thus, in aspects, a benefit of the airflow control mechanism of the device is to provide a mechanism for customizing the airflow through the device according to the preference of the device user. In aspects, such airflow customization provides for a user to modify the amount of one or more compounds received upon inhalation. In aspects, over the course of use of a single core insert, as the amount of compound(s) available from the insert decreases, the airflow control mechanism provided by the body plug (506) and the barrel plug (1306) can be adjusted. In aspects, such adjustment can provide for an at least generally consistent amount of compound being delivered over at least a majority of the lifespan of the core insert if the insert is disposable (one-time use) or e.g., over the course of a single charge with or fill of compound(s) of an insert if such an insert is reusable.

The degree of interface between body plug fan ridge set (1220) and barrel plug fan ridge set (1612) is established by the rotation of tip assembly relative to the body assembly. The specific interaction of these two components during such rotation is described below as part of the description of the tip assembly which follows.

As stated previously, an exemplary device provided by the invention can be comprised of two main parts which during one or more stages of operation of the device, can be separated from one another: the body assembly (201), components of which have been described above and are exemplified in detail in FIGS. 3-12, and the tip assembly (202) which is described here.

FIG. 13, encompassing FIGS. 13A-13E, illustrates the individual components of the tip assembly (202), shown in FIG. 2B. FIG. 13A shows an exploded view of the tip assembly (202) wherein the relative positioning of each component of the tip assembly (202) is discernable. FIG. 13A shows the exploded set of components slightly turned to the left. FIGS. 13B-13E identify each of the components of the tip assembly (202) shown in the exploded view of FIG. 13A. Notably, as shown in the embodiment of the device illustrated in FIG. 13A, in an assembled device, certain features of barrel plug (1306), specifically barrel plug fan protrusion (1614) (described in detail below), is aligned with a first indicator (101), exemplified here as a logo, on barrel (1308). This feature is relevant to the determination by a user of the spatial orientation of one or more components of the device, one or more operational status(es) of the device, or both, as is described elsewhere herein. In aspects, this alignment provides a mechanism for indicating to the device user that the device is in a maximally closed position (device is in a setting allowing for the lowest level of airflow through the device (highest drag setting)), and when in such position is accompanied by the user receiving an enhanced tactile indication (larger "snap" or "click"); however, if the tip assembly (202) were rotated relative to body assembly (201) by the user such that the first indicator (101) is then positioned 180 degrees from where the enhanced tactile indication (larger "click") was received, the device would then be in in a maximally open position (device would be in a setting allowing for the lowest level of airflow through the device (highest drag setting)). In such orientation, the first and second visual indicators ((101) and (102), respectively) are positioned on opposite sides of the inhalation device. In aspects, the alignment of barrel plug fan protrusion (1614) with a first indicator (101) is established during manufacturing of the device.

FIG. 13B identifies a barrel collar (1302) (shaded) component of the tip assembly (202). FIG. 13C identifies a barrel tube (1304) (shaded) component of the tip assembly (202). FIG. 13D identifies a barrel plug (1306) (shaded) component of the tip assembly (202). FIG. 13E identifies a barrel (1308) (shaded) component of the tip assembly (202). In aspects, FIG. 13 illustrates that devices provided by the invention, or, e.g., a component of a device of the invention, such as a tip assembly (202) component of a device, can comprise a barrel collar (1302), a barrel tube (1304), a barrel plug (1306), and a barrel (1308). As stated previously, in aspects, one or more, two or more, three or more, or all components of the tip assembly are attached to one another when the device is in a ready-to-use state. In aspects, components of the tip assembly are not dis-engageable from one another by a user or do not require disengagement in order for the user to use the device.

FIGS. 14-17 provide illustrations of each specifically exemplified tip assembly component.

FIG. 14 illustrates an exemplary embodiment of a mechanism for tip assembly (202) to attach to body assembly (201). As previously described, in the exemplified embodiment of a device provided by the invention, body assembly (201) (e.g., specifically body subassembly (302) comprises a magnet (502). In the provided embodiment of FIG. 14, barrel collar (1302) provides an attractive target element for the magnet (502), providing a mechanism for body assembly (201) to releasably connect to, binding with, or otherwise be maintained in contact with tip assembly (202) through magnetic attraction. In the exemplified embodiment, barrel collar (1302) is attracted by the magnet (502).

As shown in FIG. 14, barrel collar (1302) can be a ring-shaped component. Barrel collar (1302) is exemplified as comprising a barrel collar exterior surface (1402), a barrel collar interior surface (1404), a barrel collar first edge surface (1406), a barrel collar second edge surface (1408), a barrel collar opposing first edge surface (1410) (e.g., along the opposing edge of barrel collar exterior surface (1402)), a barrel collar third edge surface (1412), and a barrel collar interior (1414). In aspects, the thickness of the ring formed by barrel collar (1302) is defined by the thickness of the wall formed by the depth of the wall formed by the barrel collar exterior surface (1402), barrel collar interior surface (1404), barrel collar first edge surface (1406), barrel collar second edge surface (1408), and the barrel collar third edge surface (1412).

Specific note to the reader: thickness of walls of component(s) described herein should, when described by reference to a specifically defined surface, be understood to be inclusive of consideration of any surface defined by an angled edge having its own defined surface. That is, for example, if wall (A) comprises a surface (B) and, e.g., a surface (C), wall (A) has a thickness which takes into consideration surface (B) as well as depth provided in part by surface (C). Where the thickness of a wall of component(s) herein is described as the thickness represented by the surface (B), it should be understood that such a thickness should take into consideration any edge component (C) which may optionally be present.

Barrel collar exterior surface (1402) is exemplified as a smooth surface encompassing the outer circumference of barrel collar (1302). Similarly, barrel collar interior surface (1404) is exemplified as a smooth surface encircling barrel collar interior (1414), e.g., establishing the inner circumference of barrel collar (1302). Finally, barrel collar (1302) comprises an interior, (1414). In an exemplary embodiment, barrel collar interior surface (1404) can, in an assembled device, contacts the exterior surface of barrel tube (1304) (specifically, (1502)). That is, in embodiments, e.g., as exemplified, in a fully assembled device, barrel collar (1302) is positioned around barrel tube (1304) (such that barrel tube (1304) resides within barrel collar interior (1414)), barrel tube (1304) is positioned over/around body tube (402), and body tube (402) is positioned around second magnet cover extension component (816). Further, in the embodiment exemplified, an edge of each of body tube (402), barrel collar (1302), and barrel tube (1304) each make contact in a fully assembled device with magnet cover exterior wall (808). In certain aspects, one or both of the barrel collar (1302) or barrel tube (1304) do not contact magnet cover (401) or any element of magnet cover (401). In aspects, such lack of contact is established to ensure that within all manufacturing tolerances there is an accompanying tactile indication of a change in the airflow control setting when rotating the body assembly (201) and tip assembly (202) relative to one another. In aspects where such a tactile feature is not embodied, in certain aspects one or both of the barrel collar (1302) or barrel tube (1304) could potentially contact magnet cover (401).

In aspects, barrel collar (1302) is made of a magnetic material. That is, in aspects, barrel collar (1302) is made of a material which is capable of being magnetized. Thus, in aspects, magnet (502) is magnetically attracted to barrel collar (1302). In certain aspects, barrel collar (1302) is the only component of the device which is capable of being detectably or significantly attracted by magnet (502). In aspects, it is the magnetic attraction between magnet (502) and barrel collar (1302) which facilitates the engagement of the body assembly (201) and the tip assembly (202).

FIG. 15 illustrates an exemplary component protecting barrel (1308), which may, in aspects, be made of detectably or significantly moisture-sensitive material, from heat and moisture created during device use. In aspects, such a component prevents a significant amount of one or more volatile compounds present in or provided by a core insert (1800), when present in the device, to get into the material of barrel (1308). That is, in aspects, barrel (1308) can be made of (e.g., composed of or comprise at least in part) a porous material such as, e.g., wood, and thus when exposed to one or more volatile compounds, such one or more volatile compounds can seep into or enter and be maintained by barrel (1308). When such volatile compounds are flavored or scented, such compounds can provide a scent or flavor which is not desired. As an example, if a core insert (1800) is provided comprising a peppermint essential oil, one or more volatile compounds related to the peppermint scent/flavor may seep into or enter and be maintained by barrel (1308). If a user then changes core insert (1800) to a core insert comprising, e.g., a cinnamon scent/flavor, the user may experience lingering peppermint scent/flavor which interferes with the experience of the cinnamon. In aspects, the presence of such a component prevents the seeping, leaking, entering, and/or undesirable maintenance of such compounds into/within the material of barrel (1308). FIG. 15 illustrates such an exemplary component in the form of barrel tube (1304). Barrel tube (1304) is illustrated as a cylinder. As illustrated, exemplary barrel tube (1304) comprises a barrel tube exterior surface (1502), barrel tube interior surface (1504), and a barrel tube wall thickness (1506), which together surround at least in part a barrel tube interior (1508). Barrel tube exterior surface (1502) is embodied as a smooth surface. Barrel tube interior surface (1504) is embodied as a smooth surface. Barrel tube thickness is embodied as separating barrel tube exterior surface (1502) and barrel tube interior surface (1504). Barrel tube (1304) is illustrated as an uninterrupted, hollow cylinder, unlike, for example, body tube (402) which comprises an open section (e.g., a section cut out of its cylindrical wall), exemplified as open portion of body tube (1020) in FIG. 10A. In aspects, within a fully assembled device, barrel tube (1304) can be at least partially surrounded by barrel collar (1302), with barrel tube (1304) and barrel collar (1302) positioned within barrel (1308). Further, in the embodiment exemplified, an edge of barrel tube (1304) can be in contact in a fully assembled device with magnet cover exterior wall (808). In certain aspects, barrel tube (1304) does not contact magnet cover (401) or any component thereof, such as, e.g., magnet cover exterior wall (808).

In certain aspects, barrel tube (1304) is made of a material which is not magnetic. That is, barrel tube (1304) is made of a nonmagnetic material and not capable of being magnetized. Thus, in aspects, magnet (502) is not magnetically attracted to barrel tube (1304).

As described in the discussion of FIGS. 12A and 12B (describing body plug (506)), in aspects, devices provided by the invention comprise an airflow control unit comprising a first component and a second component that coordinate/interface to control airflow, e.g., control drag, during device use. As described, an airflow control unit can comprise a first component, e.g., a body plug (506), exemplified in FIGS. 12A and 12B, and a second component, e.g., a barrel plug (1306). In one exemplary embodiment, one or more elements of body plug (506) and one or more elements of barrel plug (1306) work together to control airflow when the two components are rotated and positioned in various positions relative to one another.

Exemplary barrel plug (1306), as shown in FIG. 16, can comprise a barrel plug cap (1602) and a barrel plug fan (1604). Barrel plug fan (1604) can comprise barrel plug fan fit features (1606), (1608), and (1610), a barrel plug fan ridge set (1612), and a barrel plug fan protrusion (1614), exemplified as a double protrusion.

Barrel plug cap (1602) of barrel plug (1306) can comprise a barrel plug cap outer lip (1616) comprising a barrel plug cap outer lip first surface (1620), a barrel plug cap outer lip second surface (not shown; opposite that of barrel plug cap outer lip first surface (1620)), wherein the first and second barrel plug cap outer lip surfaces separated by barrel plug cap outer lip thickness (1618), and further comprising a barrel plug cap exterior surface (1622), a barrel plug cap interior surface (1624), and a barrel plug interior (1626).

In aspects, the barrel plug cap (1602) can operate as a fit feature which allows suitable positioning of barrel plug (1306) within an exemplary device. For example, a portion of barrel plug cap (1602) can be positioned, in a fully assembled device, within barrel tube (1304) while a portion of barrel plug cap (1602), e.g., barrel plug cap outer lip (1616) can be positioned outside of barrel tube (1304). FIG.

16 illustrates barrel plug cap outer lip (1616), comprising barrel plug cap outer lip exterior edge (1618) and barrel plug cap outer lip first surface (1620) extending beyond, e.g., having a width which is wider than, the width of remaining components of barrel plug (1306). In aspects, in a fully assembled exemplary device, barrel plug cap exterior surface (1622) contacts barrel tube interior surface (1504). In aspects, barrel plug cap outer lip first surface (1620) contacts an end of barrel tube (1304).

As exemplified in FIG. 16, barrel plug (1306) further comprises a barrel plug fan (1604). Barrel plug fan (1604) comprises fit features embodied as barrel plug fan fit feature A (1606), barrel plug fan fit feature B (1608), and barrel plug fan fit feature C (1610). Barrel plug fan fit features A-C ((1606)-(1610)) are illustrated as a series of surfaces at non-90° angles relative to one another. Such surfaces of barrel plug (1306) can aid in the positioning, alignment, fit, or any combination thereof of barrel plug (1306) with one or more other components of an exemplary device, or, e.g., aid in facilitating suitable operation of the device, aid in facilitating the assembly of the device, or any combination thereof. For example, one or more of such barrel plug fit features A-C ((1606)-(1610)) can interface with one or more of body plug fan fit features (1218-A)-(1218-F) (e.g., (1218-A), (1218-B), (1218-C), (1218-D), (1218-E), or (1218-F)) shown in FIG. 12B. In aspects, in a fully assembled device, one or more barrel plug fan fit features (1606)-(1610) contact a portion of body plug (506).

Further shown in FIG. 16 are particular exemplary features of barrel plug fan (1604). Barrel plug fan (1604) comprises a semi-circle (or, e.g., half disk) shape. The size and shape of barrel plug fan (1604) is sufficient to fill approximately half of the barrel tube. This size and shape feature of barrel plug fan (1604) is, in certain aspects, an important feature of barrel plug fan (1604) in that it aids in defining the interaction between barrel plug fan (1604) and body plug fan (1204) and, together, the mechanism by which the two components together operate as an air control component of an exemplary device. This is discussed in detail below. FIG. 16 illustrates barrel plug fan ridge set (1612). Barrel plug fan ridge set (1612) is exemplified as comprising a series of ridges formed by alternating barrel plug fan ridge recession(s) (1628) and barrel plug fan ridge peak(s) (1630). A plurality of alternating barrel plug fan ridge recession(s) (1628) and barrel plug fan ridge peak(s) (1630) can be present in a barrel plug fan ridge set (1612). About 16 sets of such recessions (1628) and peaks (1630) are exemplified in FIG. 16. The number of barrel plug fan ridge recessions (1628) and peaks (1630) present in a barrel plug fan ridge set (1612) can, in aspects, contribute to the specificity with which airflow through the device can be controlled. For example, an increased number of such features (recessions (1628) and peaks (1630) of a barrel plug fan ridge set (1612)) can increase the level of fine tuning a user can accomplish to control airflow (e.g., drag) when using the device, while a decreased number of such features can decrease the level of fine tuning a user can accomplish to control airflow during device use.

In aspects, in a fully assembled device, a barrel plug fan ridge set (1612) can contact one or more other components of the device. In aspects, in a fully assembled device, a barrel plug fan ridge set (1612) can contact one or more features of a body plug (506), e.g., a portion or all of a body plug fan ridge set (1220). In one exemplary embodiment provided by the Figures, barrel plug fan ridge set (1612) can contact a portion or all of a body plug fan ridge set (1220), the two components together operating as an airflow control mechanism for the device. As previously stated, both the body plug fan (1204) and the barrel plug fan (1604) are shaped as semi-circles or half-disks, each residing within cylindrical components such that each is capable of taking up, or blocking, one-half of an available airflow pathway. The degree of contact, e.g., the amount of overlap of or interface between) the two components establishes the amount of an airflow pathway is available for airflow. That is, the degree of contact, e.g., the amount of overlap of or interface) between the two components establishes the drag provided by the device upon inhalation. As exemplified, the more overlap, e.g., the more interface (e.g., the higher the degree of contact, e.g., overlap) between the barrel plug fan ridge set (1612) and the body plug fan ridge set (1220), the less drag provided by the device. That is, when the two semi-circular components completely overlap, one-half of the cylindrical airflow space is open and available for airflow. In such an exemplary operation, complete overlap, e.g., complete interface, of barrel plug fan ridge set (1612) and barrel plug fan ridge set (1220), establishes the device in a "maximally open" position, such that the device is in a configuration providing the lowest amount of drag and the highest level of possible airflow. Alternatively, the less interface (e.g., the lower the degree of contact, e.g., overlap) between the barrel plug fan ridge set (1612) and the body plug fan ridge set (1220), the higher the drag provided by the device. That is, when the two semi-circular components overlap to a lesser extent, a reduced area of the cylindrical airflow space is available for airflow. When the two semi-circular components do not overlap at all, each of the two semi-circular shaped components block a respective half of the cylindrical airflow path available for airflow, and thus airflow is blocked. Specifically, a lack of any overlap, e.g., a lack of significant interface, of barrel plug fan ridge set (1612) and body plug fan ridge set (1220), establishes the device in a "maximally closed" position, such that the device is in a configuration providing the highest amount of drag, e.g., rendering the device functionally inoperable by preventing sufficient airflow through the device to provide the user with an ability to inhale air through the device in an amount sufficient to deliver an effective or pleasurable amount of one or more compounds. Any overlap of the two components between these two extreme positions modulates the airflow (and, e.g., drag), accordingly.

The degree of interface between barrel plug fan ridge set (1612) and body plug fan ridge set (1220) is established by the rotation of the body assembly (201), comprising the body plug (506) which comprises the body plug fan (1204) and associated ridge set (1220), relative to the tip assembly (202), comprising the barrel plug (1306) which comprises the barrel plug fan (1604) and associated barrel plug fan ridge set (1612). Keeping in mind that tip assembly (202) and body assembly (201) are held together in the provided embodiment of the exemplary device by magnetic force, it can be appreciated that in a fully assembled exemplary device, body plug fan ridge set (1220) is drawn to barrel plug fan ridge set (1612) by virtue of the fact that the components of the device in which each reside are drawn together by magnetic force. When body plug fan ridge set (1220) is rotated in relation to barrel plug fan ridge set (1612), there are positions in which one or more body plug fan ridge recession(s) (1222) are positioned around or on one or more barrel plug fan ridge peak(s) (1630), providing a fit between the two components wherein the two components are as physically close to one another as they can be. However, there are positions during such rotation in which one or more body plug fan ridge recession(s) (1222) are positioned in line with one or more barrel plug fan ridge recession(s) (1228), one or more body plug fan ridge peak(s) (1224) are positioned in line with one or more barrel plug fan ridge peak(s) (1630), or both. In such position(s), there is a poor fit between the two components and the two components are not as physically close to one another as they could be. In such a position, the device is somewhat unstable, and the magnetic force drawing body assembly (201) and tip assembly (202) together acts upon the two separated components. The force acts to pull the two components together such that the plug fan ridge peak(s) of one fit within the plug fan ridge recession(s) of the other, and vice versa. Accordingly, when a user rotates tip assembly (202) in relation to body assembly (201), the two components slightly separate from one another as the components of the body plug fan ridge set (1220) and the components of the barrel plug fan ridge set (1612) mis-align, and then "snap" back together (e.g., are pulled back together by the magnetic force of the device) as the rotation continues and the components of the body plug fan ridge set (1220) and the components of the barrel plug fan ridge set (1612) align/re-align (e.g., ridge peaks of one align with ridge recessions of the other). Thus, rotation of tip assembly (202) relative to body assembly (101) can provide an audible clicking sound and, e.g., a tactile indication of the movement as the ridges and recessions of the two plug fan ridge sets ride over and about each other. Further, rotation of tip assembly (202) relative to body assembly (101) provides a "fidget" nature to the device, such that there is a playfulness of the rotation, e.g., as provided by both the clicking sound and the tactilely detectable tension and magnetic attraction caused by the repeated separation of the two components and the reunification of the two components during rotation.

The audible clicking caused by the interface of the body plug fan ridge set (1220) and the barrel plug fan ridge set (1612) provides an audible indication of the changing airflow condition(s) within the device. Further, returning to the illustrated embodiment of the barrel plug (1306) in FIG. 12, barrel plug (1306) comprises a barrel plug fan protrusion (1614). Barrel plug fan protrusion (1614) in aspects, e.g., as embodied, can be a part of barrel plug fan component (1604). As exemplified, barrel plug fan protrusion (1614) comprises a double protrusion (e.g., two distinct rounded protrusions). Notably, barrel plug fan protrusion (1614) is positioned on the opposite side of barrel plug (1306) from the barrel plug fan ridge set (1612). Further, barrel plug fan protrusion (1614) extends significantly further away from the barrel plug (1306) than any individual barrel plug fan ridge peak(s) (1630). Returning to the illustration of body plug (1204) in FIG. 12B, body plug fan protrusion (1226), embodied as a single protrusion, is positioned directly adjacent to body plug fan ridge set (1220). Further, body plug fan protrusion (1226) extends significantly further away from the body plug (506) than any individual body plug fan ridge peak(s) (1224). Upon the rotation of barrel plug fan (1604) relative to body plug fan (1204), it can be appreciated that once in every full 360° rotation, the barrel plug fan protrusion (1614) will contact body plug fan protrusion (1226). While small audible clicks, and small, tactilely sensible "snaps" are detectably during most of a 360° rotation of one component relative to the other, when the two protrusions (body plug fan protrusion (1226) and barrel plug fan protrusion (1614) meet at the single point in the rotation, there is a detectably larger forced separation of the two device components by virtue of the size of the respective protrusion elements. Thus, when the two components come back together (e.g., when body plug fan protrusion (1226) is positioned between the two bumps of the barrel plug fan protrusion (1614) and, further when body plug fan protrusion (1226) is positioned immediately after the second of the two bumps of the barrel plug fan protrusion (1614) in the direction of rotation), there is an audibly louder or bigger "snap", "click", or otherwise audible indication, in addition to an enhanced (e.g., bigger) tactile indication/sensation of such a snap/click. Further, when the body plug fan protrusion (1226) and the barrel plug fan protrusion (1614) meet or encounter one another during or upon the rotation of the tip assembly (202) and body assembly (101) relative to one another, the rotation becomes detectably or significantly more difficult. That is, when the body plug fan protrusion (1226) and the barrel plug fan protrusion (1614) encounter one another, more force is required to continue to rotate the tip assembly (202) and body assembly (101) relative to one another. This is due to the fact that the protrusions (body plug fan protrusion (1226) and the barrel plug fan protrusion (1614)) are larger than the peaks of the body plug (506) ((body plug fan ridge peaks (1224)) and barrel plug (1306) (barrel plug fan ridge peaks (1630)) which encounter one other during all other degrees of rotation. During all other degrees of rotation of the tip assembly (202) and body assembly (101) relative to one another, the body plug fan protrusion (1226) and the barrel plug fan protrusion (1614) do not contact one another. Upon encountering one another, their increased size, and the detectably or significantly increased amount of frictional force between them due to their increased size, an increased amount of force or energy is required to allow for the respective protrusions to interface or pass one another during the rotation of the tip assembly (202) and body assembly (101) relative to one another than if the protrusions were smaller (e.g., the size of body plug fan ridge peaks (1224) or barrel plug fan ridge peaks (1630)).

When the two plug fan protrusion components (1226) and (1614) align, e.g., body plug fan protrusion (1226) is position between the two bumps of barrel plug fan protrusion (1614), body plug fan ridge set (1220) and barrel plug fan ridge set (1612) do not overlap, and the device is in its maximally closed position as described above. This is one mechanism for determining the airflow control status of the device.

Returning briefly to Figures, e.g., 1A and 1B, the relevance of first indicator (101), exemplified as a product logo, and second indicator (102) (exemplified as a groove on magnet cover (401)) can now be further appreciated. As described above, the audible and tactile indicators present upon rotation of tip assembly (202) relative to body assembly (201) provide an indication of the airflow status of the exemplary device, wherein a detectably different (e.g., larger) audible indication, tactile indication, or both indicate that the device is in a maximally closed state. With regard to the indicators shown in FIGS. 1A and 1B, when first indicator (101), present on tip assembly (202), is aligned with second indicator (102), present on body assembly (201), this provides a visual indication that the device is in a maximally open position. Further, when second indicator (102) is facing in an upward direction, this is an indication that body tube (402) is in a position wherein the open portion of body tube (1020) is facing upward. Thus, in this position, if tip assembly (202) is removed, there is little risk of a core insert (e.g., (1800)), if present in body tube (402) inadvertently falling out of body tube (402), as the open portion of body tube (1020) is facing upward and body tube (402) can continue to safely hold (e.g., by tight fit or, e.g., by cradling) a core insert (e.g., (1800)). Finally, one further mechanism is available for determining the air control status of the device. In a fully assembled state, a user can view the device from the tip-assembly or barrel end of the device (opposite the mouthpiece) and see the state of overlap between the body plug fan ridge set (1220) and the barrel plug fan ridge set (1612).

FIGS. 17A and 17B illustrate an exemplary outer cover or shell of tip assembly (202), visible to the user upon use. As illustrated, this component is embodied in FIGS. 17A and 17B as a barrel (1308). Barrel (1308) is embodied as a cylindrical component capable of housing within it one or more other components of an exemplary device when fully assembled, such as one or more of a barrel collar (1302), barrel tube (1304), and barrel plug (1306). In certain aspects as described above, in a fully assembled exemplary device, barrel collar (1302) can be positioned around barrel tube (1304), with both barrel tube (1304) and barrel collar (1302) positioned within barrel (1308). In such embodiments, barrel tube (1304) can, in aspects, serve as a lining of the interior of barrel (1308). In aspects, barrel (1308) is the exterior device component which the user contacts to remove the tip assembly (202) from the body assembly (201) when the user wishes to access the interior of body assembly (201) so as to insert or remove a component comprising (or having comprised) compounds for inhalation, such as, e.g., a core insert (e.g., (1800)).

As illustrated in FIG. 17A, barrel (1308) can comprise a barrel first or engagement end (1702) comprising an engagement end opening (1703) and a barrel second or inlet end (1704) comprising an inlet end opening (1705) (not visible), wherein the barrel first or engagement end (1702) and the barrel second or inlet end (1704) are connected by a channel for air passage (1701); a barrel exterior surface (1706); a barrel interior surface (1708); a barrel wall thickness (1710); and a barrel interior (1712). Barrel first or engagement end (1702) can, in a fully assembled device, contact magnet cover (401). Barrel second end (1704) as shown is on the opposite end of barrel (1308) from barrel first or engagement end (1702), and effectively marks the end of the device. As barrel (1308) is provided as an open-ended cylinder, a user may peer into barrel second end (1704) when a device is fully assembled and can, in some aspects, see the status of the airflow control mechanism of the device; e.g., discerning the amount of airflow being allowed or restricted (e.g., determine the drag setting/status) of the device. Thus, in aspects, one or more portions of body plug fan ridge set (1220), one or more portions of barrel plug fan ridge set (1612), or both, can be visible via the opening in barrel second end (1704).

The shape of barrel first or engagement end (1702) can, in aspects, differ from the shape of barrel second end (1704). For example, as shown in FIG. 17A, barrel first or engagement end (1702) can be flat, such that the first end of barrel (1308) ends at a 90° angle. In aspects, this can facilitate a fit with one or more components of the device in fully assembled form, such as, e.g., the close fit of barrel (1308) with magnet cover (401). Barrel first or engagement end (1702) may, in a fully assembled device, contact magnet cover exterior wall (808). Further, as shown in FIG. 17A, barrel second end (1704) can be rounded (e.g., not ending at a 90° angle). Such rounding can, in aspects, aid in providing a pleasing aesthetic nature of the device, reduce or eliminate sharp edges on the exterior of the device, or both, making the device pleasing to look at, hold, or use.

FIG. 17A further illustrates barrel (1308) as comprising a barrel exterior surface (1706). Barrel exterior surface (1706) is provided as a smooth surface. Barrel exterior surface (1706) can comprise one or more visual indicators (not shown in FIG. 17A) visible to the user when using the device. For example, barrel exterior surface (1706) can comprise a first indicator (101) as visible in FIG. 1A (embodied as a product logo). As previously described, such an indicator can participate in establishing the spatial orientation of the device, one or more operational status(es) of the device, or both. Barrel (1308) further comprises a barrel interior surface (1708). Barrel interior surface (1708) can be a smooth surface which receives or, e.g., contacts one or more other components of an exemplary device when a device is fully assembled, such as, e.g., barrel tube (1304). In certain aspects, barrel tube exterior surface (1502) contacts barrel interior surface (1708) in a fully assembled device. In certain aspects, barrel collar exterior surface (1402) contacts barrel interior surface (1708) in a fully assembled device. In aspects, both barrel tube exterior surface (1502) and barrel collar exterior surface (1402) contact barrel interior surface (1708) in a fully assembled device. Barrel (1308) has a barrel wall thickness (1710). As barrel (1308) is provided as a cylinder, barrel (1308) comprises an interior (1712). Barrel interior (1712) can receive one or more other components of an exemplary device in fully assembled form as is described above.

FIG. 17B illustrates the relationship of body assembly (201) with tip assembly (202), with the exterior of tip assembly being barrel (1308). Thus, as shown, barrel (1308) serves as the contact point for the user to remove tip assembly (202) from body assembly (201) when the user requires access to body tube (402) of body assembly (201) (see FIGS. 10A and 10B and related discussion herein). Further 17B illustrates that one or more components are visible via barrel second end (1704), such as one or more components of the airflow control mechanism being visible (1714). An area of reduced inner diameter (918A) and an area of reduced inner diameter (918B) of an airflow channel (1024) is further visible in FIG. 17B.

FIGS. 18A, 18B, and 18C provide an illustration of an exemplary component, embodied as core insert (1800), provided by the invention capable of being used in an inhalation device for the delivery of one or more volatile compounds for inhalation. FIGS. 18A and 18B illustrate exemplary core insert (1800) from different angles to illustrate the air passage (1810) as being continuous through core insert (1800) and maintaining the same shape through the insert. FIG. 18C provides an end-view of core insert (1800). Core insert (1800) is illustrated in each of FIGS. 18A, 18B, and 18C as having a cylindrical shape. Exemplary cylindrical core insert (1800) is illustrated as comprising an air passage (1810). In the illustrated embodiment, core insert (1800) is made of either (a) a sufficiently hard or dense material such that the positioning of the core insert (1800) can be facilitated by use of the core spring (504) and body plug (506) to "squeeze" the core insert (1800) to hold it in place (as described elsewhere herein) or (b) a hard material, e.g., a ceramic material, such that core insert (1800) is at least generally, at least substantially, at least essentially, is essentially, or is, inflexible, yet is capable of maintaining a suitable volume of volatile-compound-containing material to facilitate inhalation of such compounds by the user when core insert (1800) is present within an exemplary device (and, clearly, when core insert (1800) is charged with such a material, recognizing that over time such a core insert will lose its volatile compound content to an extent at which core insert (1800) will require recharging with such a material/compound(s) or replacement). Having an at least substantially, at least essentially, essentially, or completely inflexible nature, core insert (1800) is embodied as being capable of being inserted into body tube (402) much like a common battery is placed into a standard battery compartment of an electronic device. Core insert (1800), as shown in FIGS. 18A and 18B, comprises a core insert first end (1802) and a core insert second end (1804). Accordingly, one end. e.g., core insert first end (1802) can be inserted at an angle into body tube (402) and pressed or pushed against core spring (504), pushing against core spring flex element (902), e.g., pushing against core spring flex element second surface (915) and causing core spring flex element hinge (912) to flex. Once the core spring (504) is sufficiently flexed, the core insert second end (1804) can be placed into body tube (402). Once within the body tube (402), core insert (1800) is maintained in place by the core spring flex element (902) pushing against core insert first end (1802) forcing core insert second end (1804) to push against body plug (506), or, e.g., specifically, one end of body plug (506), e.g., the end of body plug (506) closest to shape features (1216). Upon placement of the second end (1804) of the core insert into the body tube, body plug (506) shape features (1216) can, e.g., prevent scratching, catching, or other interference with the structural integrity of the core insert (1800) —e.g., such a body plug shape feature (1216), as shown in FIG. 12A, can be a rounding of the body plug to facilitate the placement of the core insert (1800) into body tube (402) without causing significant damage to the core insert (1800).

The resulting squeezing of core insert (1800), e.g., between core spring (504) and body plug (506), and, e.g., the force(s) being applied to each end of core insert (1800) within body tube (402), maintain(s) core insert (402) in place. Such placement is exemplified in FIG. 19 and is discussed below.

Core insert (1800) further comprises an exterior surface (1806) as shown in FIGS. 18A and 18B. Core insert exterior surface (1806) is exemplified as being a visually smooth surface. It should be appreciated that because core insert (1800) is present for the maintenance of one or more volatile compounds until such compounds are release, e.g., by inhalation during device use, the actual material forming core insert exterior surface (1806) may be detectably or significantly porous.

The exemplified embodiment of core insert (1800) shown in FIGS. 18A-18C further comprises a core insert air passage (1808). Core insert air passage (1808) is embodied as comprising one or more core insert air passage shape feature(s) (1810). As illustrated, core insert air passage (1808) has a "flower" shape. The flower-shaped air passage (1808) increased the surface area of air passage (1808) over that which would be present if a similarly sized air passage were present as a single, circle-shaped passage. Such an alternative embodiment of a single, e.g., circular shaped air-passage (1902) is provided in FIG. 19, illustrating an alternative embodiment of a core insert (1900) as viewed from one end. FIG. 20 provides another alternative embodiment of a core insert (2000) comprising a smaller single air passage (2002) as viewed from one end of a core insert. FIG. 21 provides a still further alternative embodiment of a core insert (2100) viewed from one end, the core insert (2100) comprising a plurality of air passages (2102) (e.g., exemplified as comprising 6 individual airflow passages). The reader can appreciate that many further alternative embodiments of a mechanism for air passage through a core insert exist, either providing a single airflow passage of various sizes and shapes, each with or without one or more shape features, or providing multiple airflow passages, each being similar, the same, or different in size, shape, or both, and each comprising or not comprising one or more shape features, etc. The design of airflow passage through a core insert can be selected, at least in part, according to the amount of restriction or lack thereof of airflow through the core insert is desired/desirable, the amount of drag desired to be provided by the device, the volume of volatile compound(s) suitable or desirable for delivery to the user by inhalation, or any combination of any or all thereof.

Finally, FIG. 22, encompassing FIGS. 22A and 22B, illustrates the device with a partially inserted exemplary core insert (FIG. 22A), and completely inserted exemplary core insert (FIG. 22B). In FIG. 22A, body assembly (201) is shown with tip assembly (202) removed. Exemplary core insert (1800) is shown as being inserted into body tube (402). The core spring flex element (902) is visible. In FIG. 22B, body assembly (201) is again shown with tip assembly (202) removed. Exemplary core insert (1800) is shown as being completed inserted into body assembly (201). Tip assembly (202) is ready to be united with body assembly (201) to place the exemplary device in a ready to use state.

Description of FIGS. 23 and 24 are described in conjunction with the Examples presented below.

EXAMPLES

The following detailed Examples of certain aspects of the invention are provided to assist readers in further understanding aspects of the invention or principles related to practicing aspects of the invention. Any particular materials, methods, steps, and conditions employed/described in the following Examples, and any results thereof, are intended to further illustrate aspects of the invention. These Examples reflect exemplary embodiments of the invention, and the specific methods, findings, principles of such Examples, and the general implications thereof, can be combined with any other aspect of the invention. However, readers should understand that the invention is not limited by or to any part of the Examples.

Example 1 (Airflow Control Test)

An airflow control test was performed to assess the average airflow through the device in liters per minute at a variety of device settings according to the airflow control setting of an exemplary device provided by the invention.

A test apparatus was established comprising:
a. a connection mechanism ("adapter") for connecting a flow meter to the device;
b. a high precision, medical grade, Sensirion SFM-3000 flow meter ("flow meter") capable of connecting to the adapter and thus associating the flow meter with the device;
c. a user interface comprising a mouthpiece for the user to use to breathe through the device; and
d. a data collection computer interface.

With no device attached to the adapter of the test apparatus, a test subject was asked to place their mouth on the apparatus mouthpiece and to breath normally through the test apparatus.

The flow meter captured the airflow through the device. FIG. 23 illustrates the average flow rate of air in standard liters per minute (SLPM) through the test apparatus with no device attached. Four breaths of the user are provided (each breath measured once). The graph provided in FIG. 23 validates the use of the apparatus as a reliable mechanism for assessing flow rate, as it (a) demonstrates the relative consistency of the airflow rate across breaths of the test subject (e.g., peak airflow rate ranges between about 15 SLPM and about 27 SLPM across the 4 breaths and, specifically, between about 15 and about 20 SLPM across the final 3 breaths of the test subject) and, (b) establishes that the flow meter is capable of detecting changes in flow rate across a spectrum ranging from 0 SLPM to at least about 27 SLPM.

A device comprising an airflow control mechanism comprising a first airflow control component illustrated in FIGS. 12A and 12B and a second airflow control component illustrated in FIG. 16, and operating according to the descriptions provided therein thereof, was obtained and attached to the adapter of the test apparatus. The device comprised a core insert according to the embodiment exemplified in FIG. 18C, made of ceramic.

The airflow control mechanism of the device, established by the barrel plug and the body plug as described herein ("airflow control mechanism"), which, when in various configurations, establish positions ranging from a "maximally open" position (maximally open aperture; wherein about ½ of a circular airflow path through the device is open to airflow) to a "maximally closed" position (no opening/closed aperture), was set to its maximally open position.

The test subject was again asked to place their mouth on the apparatus mouthpiece and to breathe through the mouthpiece. After each breath, the aperture was adjusted by a single "click". As described elsewhere herein, a single "click" represented the interface of body plug peaks/recessions being adjusted relative to the barrel plug fan peaks/recession by a single peak/recession. Each "click" represented an adjustment to the size of the aperture. In the device utilized, each "click" represented an adjustment of the aperture by about 12 degrees. The test was performed over a span of 180 degrees of rotation of the body assembly and tip assembly relative to one another, as, in the test device, 0 degrees (starting position) represented a maximally open aperture (the device being in a maximally open position, providing the least amount of drag and highest level of airflow) and 180 degrees (final position) represented a maximally closed device or closed aperture (the device providing the highest amount of drag and the lowest level of airflow). Flow rates at each aperture setting were captured from the starting, maximally open position up to and including the point at which the aperture was maximally closed. This established a first set of test results.

Upon completion of the first test and the collection of the first set of test results, the device was returned to its starting configuration of the aperture being in a maximally open position.

The test was then repeated using the same test subject. This established a second set of test results.

Upon completion of the second test and the collection of the second set of test results, the device was again returned to its starting configuration of the aperture being in a maximally open position.

The test was then repeated a third time using the same test subject. This established a third and final set of test results.

The three sets of test results were then combined and averaged. The average flow rates at each of the aperture settings are provided in Table 1 below. Again, the aperture angle of zero (0) degrees represented the device being in a maximally open position and the aperture angle of 180 degrees represented the device being in a maximally closed position. FIG. 24 provides a graph of the averaged data provided in Table 1 below.

TABLE 1

Average Device Flow Rate During Inhalation at Various Aperture Positions

| Click position | Aperture angle (degrees) | Average flow (SLPM) | Average change in flow from previous aperture setting (SLPM) | Average change in flow from previous aperture setting (%) |
|---|---|---|---|---|
| 1 | 0 | 3.8 | — | — |
| 2 | 12 | 3.6 | −0.2 | 5% |
| 3 | 24 | 3.25 | −0.35 | 10% |
| 4 | 36 | 2.8 | −0.45 | 14% |
| 5 | 48 | 2.7 | −0.1 | 4% |
| 6 | 60 | 2.2 | −0.5 | 19% |
| 7 | 72 | 2 | −0.2 | 9% |
| 8 | 84 | 2 | 0 | 0% |
| 9 | 96 | 1.9 | −0.1 | 5% |
| 10 | 108 | 1.8 | −0.1 | 5% |
| 11 | 120 | 1.5 | −0.3 | 17% |
| 12 | 132 | 1.1 | −0.4 | 27% |
| 13 | 144 | 1 | −0.1 | 9% |
| 14 | 156 | 0.95 | −0.05 | 5% |
| 15 | 168 | 0.7 | −0.25 | 26% |
| 16 | 180 | 0.6 | −0.1 | 14% |
| | | Average: | −0.21 | 11% |
| | | STDEV: | 0.16 | 0.08 |

As shown in the graph of FIG. 24, the various aperture settings are capable of incrementally modifying, e.g., achieve the incremental adjustment of the flow rate of air through the device in a very consistent manner. On average, each setting decreased the airflow by about 11%, with a standard deviation of about 0.08. Further, each setting decreased the airflow by about 0.21 SLPM, with a standard deviation of about 0.16. The airflow control mechanism is capable of decreasing, or demonstrating a decrease of, the airflow from a maximum of almost 4 SLPM to less than 1 SLPM, e.g., to at least about 0.6 SLPM. Specifically, the airflow control mechanism decreased the airflow through the device via pre-determined, selectable, and distinct airflow settings by about 84%. The airflow test conducted here demonstrates the flexibility and customizability of the device(s) provided by the invention in/of airflow (drag) control.

This experiment was conducted utilizing a device comprising a ceramic core insert as described above. It can be noted that the profile of the average flow rate across device aperture settings is expected to be at least substantially the same for the device regardless of whether or not the device comprises a core insert, regardless of use of core inserts made of a different material, regardless of use of core inserts having a different design, or any combination thereof. In such circumstances, the actual airflow rates at each setting may vary, however they are expected to vary similarly across the various aperture angles and thus only the airflow rate magnitude is expected to change, while the profile of the airflow rate across the aperture angle settings of 0 degrees to 180 degrees is expected to remain at least substantially the same.

The data provided in Example 1 describe the relative changes in airflow between and across airflow control settings (aperture settings) and, thus, reflect the impact of the airflow control system. Example 1 demonstrates that the incrementally adjusted airflow control system herein provides a highly consistent decrease (or, e.g., correspondingly, a highly consistent increase) of airflow through the device as the airflow control mechanism is incrementally adjusted. Variation in breath strength, e.g., differences between inhalation device users, could, in theory, change the raw results in terms of flow rate (SLPM). Flow rate data (SLPM) demonstrated here could be different if tested in a population of users from which average flow rates at each control setting is/are obtained. However, it is expected that a pattern which is at least generally the same as, at least substantially the same as, at least substantially similar to, similar to, or e.g., which is the same as that demonstrated here will be obtained in such varied circumstances. That is, it is expected that the airflow control mechanism demonstrated here will demonstrate a highly consistent decrease (or, e.g., correspondingly, a highly consistent increase) of airflow through the device as the airflow control mechanism is incrementally adjusted as has been demonstrated in this Example.

What is claimed is:

1. An unpowered, handheld device for delivering volatile flavored compounds to the mouth of an individual, the device comprising:
   (1) a body component comprising
      (a) a mouthpiece component comprising (I) a mouthpiece component outer surface that is mostly or entirely composed of a metallic material, (II) a mouthpiece component inner surface that is mostly or entirely composed of a metallic material, (III) a mouthpiece component outlet, (IV) a mouthpiece component inlet, and (V) a mouthpiece component airflow channel positioned between the mouthpiece component inlet and mouthpiece component outlet, and
      (b) a body tube component comprising (I) a tube-forming wall that is composed of a metallic material, (II) a body tube inlet, (III) a body tube outlet, (IV) a body tube airflow channel positioned between the body tube inlet and the body tube outlet, wherein the body tube airflow channel is in airflow communication with the mouthpiece component airflow channel, and (V) an insert compartment comprising (A) an insert compartment first end positioned proximally to the body tube inlet where the tube-forming wall forms a complete tubular structure around the insert compartment first end, (B) an insert compartment second end positioned proximally to the body tube outlet where the tube-forming wall forms a complete tubular structure around the insert compartment second end, and (C) a central area positioned between the insert compartment first end and second end, wherein the central area of the insert compartment is positioned within a portion of the body tube wherein the body tube wall does not form a complete tubular structure so as to form an insert compartment opening in the body tube wall,
   (2) a barrel component that selectively releasably engages the body component to form the device, the barrel component comprising (a) a barrel component outer surface that is composed of wood or other porous organic material, (b) an engagement end that comprises a barrel component engagement end opening, (c) a barrel component inlet end that comprises a barrel component inlet end opening, and (d) a barrel component channel which is positioned between barrel component engagement end opening and the barrel component inlet end opening,
wherein when the barrel component and the body component are engaged, the body tube component is positioned within the barrel component channel, the body tube inlet is positioned within the barrel component inlet end opening, and the barrel component covers the insert compartment opening forming an enclosed continuous interior airflow channel that is positioned between and permits airflow between the body tube inlet and the mouthpiece component outlet.

2. The device of claim 1, wherein the opening to the enclosed continuous interior airflow channel is at least about 25% blocked by one or more components of the device.

3. The device of claim 2, wherein the engagement of the barrel component and the body component allows for the rotation of the barrel component and the body component relative to one another while the barrel component and body component are in contact.

4. The device of claim 3, wherein the outer surface of the barrel component is longer than the outer surface of the mouthpiece component.

5. The device of claim 4, wherein the mouthpiece component comprises two separate reduced diameter areas, each reduced diameter area having a first end and a second end, that are each positioned between the mouthpiece component inlet and the mouthpiece component outlet, each of the reduced diameter areas having an outer diameter at their narrowest point that is between about 45% and about 85% of that of the maximum outer diameter of the mouthpiece component.

6. The device of claim 5, wherein the outer surface of the mouthpiece component comprises a grooved area located near an end of one of the two reduced diameter areas.

7. The device of claim 6, wherein the metallic material of the mouthpiece component is stainless steel.

8. The device of claim 7, wherein between about 40% and about 75% of the perimeter of the tube-forming wall is missing at the insert compartment opening.

9. The device of claim 8, wherein the body tube component comprises a component positioned within the body tube airflow channel of the body tube component such that the component establishes a reduced diameter of the body tube airflow channel but allows airflow communication between the insert compartment and the mouthpiece component airflow channel.

10. A system comprising (1) the device of claim 1 and (2) a removable insert that (a) is sized to fit within the insert compartment and (b) comprises flavored volatile compounds.

11. A system comprising (1) the device of claim 9 and (2) a removable insert that (a) is sized to fit within the insert compartment and (b) comprises flavored volatile compounds.

12. The device of claim 1, wherein the releasable engagement of the barrel component and the body component allows for the rotation of the barrel component and the body component relative to one another.

13. The device of claim 1, wherein the outer surface of the barrel component is longer than the outer surface of the mouthpiece component.

14. The device of claim 1, wherein the mouthpiece component comprises two separate reduced diameter areas, each reduced diameter area having a first end and a second end, that are each positioned between the mouthpiece component inlet and the mouthpiece component outlet, each of the reduced diameter areas having an outer diameter at their narrowest point that is between about 45% and about 85% of that of the maximum outer diameter of the mouthpiece component.

15. The device of claim 1, wherein the outer surface of the mouthpiece component comprises a grooved area located near an end of one of the two reduced diameter areas.

16. The device of claim 1, wherein the metallic material of the mouthpiece component is stainless steel.

17. The device of claim 1, wherein between about 40% and about 75% of the perimeter of the tube-forming wall is missing at the insert compartment opening.

18. The device of claim 1, wherein the body tube component comprises a component positioned within the body tube airflow channel of the body tube component such that the component establishes a reduced diameter of the body tube airflow channel but allows airflow communication between the insert compartment and the mouthpiece component airflow channel.

19. A system comprising (1) the device of claim 12 and (2) a removable insert that (a) is sized to fit within the insert compartment and (b) comprises flavored volatile compounds.

20. A system comprising (1) the device of claim 17 and (2) a removable insert that (a) is sized to fit within the insert compartment and (b) comprises flavored volatile compounds.

21. The device of claim 1, wherein the barrel component selectively releasably engages the body component via a barrel collar.

* * * * *